US007202250B2

(12) United States Patent
Yoon et al.

(10) Patent No.: US 7,202,250 B2
(45) **Date of Patent: *Apr. 10, 2007**

(54) SUBSTITUTED ARYLPYRAZINES

(75) Inventors: Taeyoung Yoon, Guilford, CT (US); Ping Ge, Durham, CT (US); Raymond F. Horvath, Guilford, CT (US); Stèphane DeLombaert, Madison, CT (US); Kevin J. Hodgetts, Killingworth, CT (US); Dario Doller, Wallingford, CT (US); Cunyu Zhang, Morrisville, NC (US)

(73) Assignee: Neurogen Corporation, Branford, CT (US)

( * ) Notice: Subject to any disclaimer, the term of this patent is extended or adjusted under 35 U.S.C. 154(b) by 35 days.

This patent is subject to a terminal disclaimer.

(21) Appl. No.: 11/107,148

(22) Filed: Apr. 15, 2005

(65) Prior Publication Data

US 2005/0215559 A1 Sep. 29, 2005

Related U.S. Application Data

(62) Division of application No. 09/788,315, filed on Feb. 16, 2001, now Pat. No. 6,995,161.

(60) Provisional application No. 60/206,455, filed on May 22, 2000, provisional application No. 60/182,934, filed on Feb. 16, 2000.

(51) Int. Cl.

| | |
|---|---|
| *A61K 31/4965* | (2006.01) |
| *C07D 401/00* | (2006.01) |
| *C07D 403/00* | (2006.01) |
| *C07D 405/00* | (2006.01) |
| *C07D 409/00* | (2006.01) |

(52) U.S. Cl. ................................. 514/255.05; 544/405

(58) Field of Classification Search ..................... None
See application file for complete search history.

(56) References Cited

U.S. PATENT DOCUMENTS

| | | | |
|---|---|---|---|
| 4,211,870 | A | 7/1980 | Barnett et al. |
| 4,293,552 | A | 10/1981 | Miesel |
| 4,788,197 | A | 11/1988 | Wakabayashi et al. |

FOREIGN PATENT DOCUMENTS

| | | |
|---|---|---|
| GB | 1499768 | 5/1975 |
| JP | 3048666 | 3/1991 |
| WO | WO 95/10506 | 4/1995 |
| WO | WO 99/38829 | 1/1998 |
| WO | WO 98/11075 | 3/1998 |
| WO | WO 98/38174 | 9/1998 |
| WO | WO 98/43641 | 10/1998 |
| WO | WO 00/12488 | 3/2000 |
| WO | WO 00/45800 | 8/2000 |

OTHER PUBLICATIONS

Thompson et al, "An Efficient Synthesis of Arylpyrazines and Bipyridines" Journal of Organic Chemistry, vol. 53(9), pp. 2052-2055 (1988).*

Nakamura et al, "Synthesis of 5- and 3-,5-disubstituted 2-aminopyrazines by Pd Mediated Stille Coupling" SYNLETT, vol. 12, pp. 1227-1228 (1995).*

The Merck Index, 13th Ed., p. 1082, Entry # 6088: "Methylene Chloride." Merck & Co., Inc. Whitehouse Station, NJ © 2001.*

Akita et al., "Cross-Coupling Reaction of Chloropyrazines with Acetylenes," *Chem. Pharm. Bull.* 34(4), 1447-1458(1986).

Alvernhe et al., "Action de L'acide Fluorhydrique Sure Les Azirines: Synthese D'a-fluorectones et de Difluoramines—Etude De L'orientation de la Reaction," *Tetrahedron Letters*, vol. 21, 1437-1440, (1980).

Badiger et al., "Oxidative Cyclization Using Fetizone's Reagent," *Indian J. of Chem.*, vol. 16B, 71-75, (1978).

Benincori et al., "Studies on the Fischer Indole Synthesis: Rearrangements of Five-Six- and Seven-membered Cyclic Hydrazones of Pyrazoline, Tetrahydropyridazine and Tetrahydro-1,2-diazepin Series in Polyphosphoric Acid," *J. Chem. Soc. Perkin Trans.*, 2139-2145, (1991).

Bremner et al., "Elevated CSF Corticotropin-Releasing Factor Concentrations in Posttraumatic Stress Disorder," *Am. J. of Psychiatry*, vol. 154(5), 624-629, (1997).

Chellappa et al., "PMR Spectra of Some Substituted Pyrazines & 2,3-Dihydropyrazines," *Indian J. of Chem.*, vol. 21B, 778-779, (1982).

Heinrichs et al., "Anti-Stress Action of a Corticotropin-Releasing Factor Antagonist on Behavioral Reactivity to Stressors of Varying Type and Intensity," *Neuropsychopharmacology*, vol. 11(3), 179-186, (1994).

Iredale et al., "Differential Regulation of Corticotropin-Releasing Factor Receptor Expression by Stress and Agonist Treatments in Brain and Cultured Cells," *Mol. Pharm.*, vol. 50, 1103-1110, (1996).

Kalin et al., "Restraint stress increases corticotropin-releasing hormone mRNA content in the amygdala and paraventricular nucleus," *Brain Res.*, vol. 656, 182-186, (1994).

Menzaghi et al., "Characterization of a Novel and Potent Corticotropin-Releasing Factor Antagonist in Rats," *J. of Pharm. And Exp. Therapeutics*, vol. 269(1), 564-572, (1994).

Mitchell et al., "The Role of Corticotropin Releasing Factor in Depressive Illness: a Critical Review," *Neuroscience and Biobehavioral Reviews*, vol. 22(5), 635-651, (1998).

Ohta et al., "Anti-Platelet Aggregation Activity of Some Pyrazines," *Biol. Pharm. Bull.*, vol. 20(10), 1076-1081, (1997).

Ohta et al., "Coupling Reaction of Chloropyrazines and their N-Oxides with Tetraphenyltin," *Heterocycles*, vol. 24(3), 785-792, (1986).

(Continued)

*Primary Examiner*—Zachary C. Tucker
(74) *Attorney, Agent, or Firm*—Edwards Angell Palmer & Dodge LLP; Peter F. Corless; Dwight D. Kim

(57) ABSTRACT

Arylpyrazine compounds are provided, including arylpyrazines that can bind with high affinity and high selectivity to $CRF_1$ receptors, including human $CRF_1$ receptors. The invention thus includes methods for treatment of disorders and diseases associated with $CRF_1$ receptors, including CNS-related disorders and diseases, particularly affective disorders and diseases, and acute and chronic neurological disorders and diseases.

16 Claims, No Drawings

OTHER PUBLICATIONS

Schulz et al., "CP-14,26: A Potent and Selective Nonpeptide Antagonist of Corticotropin releasing factor Receptors," *Proc. Natl. Acad. Sci. USA*, vol. 93, 10477-10482, (1996).

Smagin et al., "Corticotropin-Releasing Factor Receptor Antagonist infused into the locus coeruleus attenuates immobilization stress-induced defensive withdrawal in rats," *Neuroscience Letters*, vol. 220, 167-170, (1996).

Smagin et al., "CRF Receptor Antagonists Attenuates Immobilization Stress-Induced Norepinephrine Release in the Prefrontal Cortex in Rats," *Brain Res. Bull.*, vol. 42(6), 431-434, (1997).

Taylor et al., "Intramolecular Diels-Alder Reactions of 1,2,4-Triazines. Route to Condensed Pyrazines via Cycloaddition of Nitrile Dienophiles," *J. Org. Chem.*, vol. 54, 1245-1249, (1989).

Taylor et al., "Synthesis of Pyridines by Diels-Alder Reactions of Hetero-Substituted 1,2,4-Triazines with Enamines and an Enaminone," *J. Org. Chem.*, vol. 54, 1249-1256, (1989).

Vinot and Pinson, "No. 797.—Synthese de pyrazines," *Bulletin de la Société Chimique de France*, No. 12, 4970-4974, (1968).

Yamagami et al. "Measurement and Prediction of Hydrophobicity Parameters for Highly Lipophilic Compounds: Application of the HPLC Colum-Switching Technique to Measurement of log P of Diarylpyrazines," *J. of Pharm. Sciences*, vol. 88(12), 1299-1304, (1999).

CAS Printout of Hamazaki et al., Chem. Abs. 100:5477, (1984).

CAS Printout of Hori et al., Chem. Abs. 80:890, (1974).

CAS Printout of McCapra et al., Chem. Abs. 79:125387, (1973).

CAS Printout of Miesel et al., Chem. Abs. 96:35307, (1982).

CAS Printout of Rees et al. (WO 98/43641), (1998).

CAS Printout of Teranishi et al. (JP 10077286) (1998).

CAS Printout of Teranishi et al., (JP 1998-184331), (1998).

CAS Printout of Teranishi et al., Chem. Abs. 114:101506, (1991).

* cited by examiner

SUBSTITUTED ARYLPYRAZINES

CROSS-REFERENCE TO RELATED APPLICATION(S)

This application is a divisional of patent application U.S. Ser. No. 09/788,315, now U.S. Pat. No. 6,995,161 filed Feb. 16, 2004, on which claims priority from U.S. Provisional Application Ser. No. 60/182,934 filed Feb. 16, 2000 and of U.S. Provisional Application Ser. No. 60/206,455 filed May 22, 2000, each of which is incorporated by reference.

FIELD OF THE INVENTION

The present invention relates to novel arylpyrazine compounds that have useful pharmacological properties in that they bind to cellular receptors, including CRF receptors. Certain of these compounds can bind to and modulate the activity of such receptors. Importantly, the compounds of the invention include compounds that bind with high selectivity and/or high affinity to CRF1 receptors (Corticotropin Releasing Factor type 1 Receptors). This invention also relates to pharmaceutical compositions comprising such compounds and to the use of such compounds as pharmaceutical agents, e.g., in treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. Additionally this invention relates to the use such compounds as probes for the localization of cellular receptors in tissue sections.

BACKGROUND OF THE INVENTION

Corticotropin releasing factor (CRF), a 41 amino acid peptide, is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain. There is also evidence that CRF plays a significant role in integrating the response of the immune system to physiological, psychological, and immunological stressors.

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system.

In affective disorder, or major depression, the concentration of CRF is significantly increased in the cerebral spinal fluid (CSF) of drug-free individuals. Furthermore, the density of CRF receptors is significantly decreased in the frontal cortex of suicide victims, consistent with a hypersecretion of CRF. In addition, there is a blunted adrenocorticotropin (ACTH) response to CRF (i.v. administered) observed in depressed patients. Preclinical studies in rats and non-human primates provide additional support for the hypothesis that hypersecretion of CRF may be involved in the symptoms seen in human depression. There is also preliminary evidence that tricyclic antidepressants can alter CRF levels and thus modulate the numbers of CRF receptors in brain.

CRF has also been implicated in the etiology of anxiety-related disorders. CRF produces anxiogenic effects in animals and interactions between benzodiazepine/non-benzodiazepine anxiolytics and CRF have been demonstrated in a variety of behavioral anxiety models. Preliminary studies using the putative CRF receptor antagonist □-helical ovine CRF (9-41) in a variety of behavioral paradigms demonstrate that the antagonist produces "anxiolytic-like" effects that are qualitatively similar to the benzodiazepines. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test and in the acoustic startle test in rats. The benzodiazepine receptor antagonist Ro 15-1788, which was without behavioral activity alone in the operant conflict test, reversed the effects of CRF in a dose-dependent manner, while the benzodiazepine inverse agonist FG 7142 enhanced the actions of CRF.

CRF has also been implicated in the pathogeneisis of certain immunological, cardiovascular or heart-related diseases such as hypertension, tachycardia and congestive heart failure, stroke and osteoporosis, as well as in premature birth, psychosocial dwarfism, stress-induced fever, ulcer, diarrhea, post-operative ileus and colonic hypersensitivity associated with psychopathological disturbance and stress.

The mechanisms and sites of action through which conventional anxiolytics and antidepressants produce their therapeutic effects remain to be fully elucidated. It has been hypothesized however, that they are involved in the suppression of CRF hypersecretion that is observed in these disorders. Of particular interest are that preliminary studies examining the effects of a CRF receptor antagonist peptide ($\alpha$-helical $CRF_{9-41}$) in a variety of behavioral paradigms have demonstrated that the CRF antagonist produces "anxiolytic-like" effects qualitatively similar to the benzodiazepines.

Certain small molecule compounds for the treatment of CRF related disorders have been disclosed in the literature [for a review see J. McCarthy et al. *Curr. Pharm. Des.* 5: 289 (1999)]. However, none of these compounds has an arylpyrazine structure.

Cox et al. (WO 98/38174) have disclosed certain aryl pyrazine derivatives for use as sodium channel blockers in the treatment of central nervous system disorders. The Cox application requires that the arylpyrazine compounds be substituted with two-amino or amido groups.

SUMMARY OF THE INVENTION

We have now discovered novel arylpyrazine compounds, including arylpyrazines that can bind with high affinity and high selectivity to $CRF_1$ receptors, including human $CRF_1$ receptors. The invention thus includes methods for treatment of disorders and diseases associated with $CRF_1$ receptors, including CNS-related disorders and diseases, particularly affective disorders and diseases, and acute and chronic neurological disorders and diseases.

Arylpyrazine compounds of the invention are preferably substituted at the 2-ring position by a carbocyclic aryl group such as phenyl, naphthyl and the like, or a heteroaromatic group, particularly a heteroaromatic having a nitrogen ring member such as pyridyl, pyrimidinyl and the like. Arylpyrazine compounds of the invention also are preferably substituted at the 5-ring position (para with respect to the aryl substituent) by a non-hydrogen substituent, particularly a non-aromatic group such as alkyl, alkenyl, alkynyl, heteroalkyl and the like, preferably aminoalkyl and alkoxy. Preferably the 3-ring position of pyrazine compounds of the invention is unsubstituted (i.e. hydrogen) or substituted by other than amino ($-NH_2$) or alkylamide ($-NHC(=O)$ alkyl, particularly $-NHC(=O)C_{1-4}$alkyl or $-NHC(=O)$ $C_{3-7}$cycloalkyl), and/or the 5-ring position of pyrazine compounds of the invention are other than hydrogen, alkyl, aminoalkyl or a nitrogen-containing heteroalicyclic compound.

Typically preferred compounds of the invention include those of the following

I

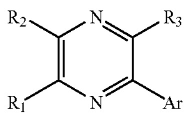

wherein:

Ar is substituted phenyl, optionally substituted napthyl, or an optionally substituted heterocyclic group having from 1 to 3 rings, and 3 to 8 ring members in each ring and 1 to about 3 hetero atoms;

$R_1$ and $R_3$ are each independently hydrogen, halogen, cyano, nitro, amino, optionally substituted alkyl, optionally substituted alkenyl, optionally substituted alkynyl, optionally substituted mono or dialkylamino, optionally substituted alkoxy, optionally substituted alkylthio, optionally substituted alkylsulfinyl, or optionally substituted alkylsulfonyl; and $R_2$ is halogen, cyano, nitro, amino, optionally substituted alkyl, optionally substituted alkenyl, optionally substituted alkynyl, optionally substituted alkylamino, optionally substituted alkoxy, optionally substituted alkylthio, optionally substituted alkylsulfinyl, or optionally substituted alkylsulfonyl;

with the proviso that if Ar is phenyl substituted with halogen, napthyl, or naphthyl substituted with halogen, then the compounds where $R_3$ is hydrogen or amino are excluded.

Preferred compounds of the invention also include those of the following Formula IA:

Formula IA

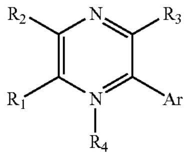

or a pharmaceutically acceptable salt thereof, wherein:

$R_1$ is selected from H, $C_{1-4}$ alkyl, $C_{2-4}$ alkenyl, $C_{2-4}$ alkynyl, halogen, CN, $C_{1-4}$ haloalkyl, trifluoromethyl, trifluoromethoxy, $-NH(C_{1-4}$ alkyl), $-N(C_{1-4}$ alkyl)($C_{1-4}$ alkyl), $-O(C_{1-4}$ alkyl), and $S(O)_n(C_{1-4}$ alkyl);

$R_2$ is selected from the group consisting of $-XR_A$ and Y, wherein $-X$, $R_A$, and Y are defined below; and $R_3$ is selected from the group consisting of hydrogen, halogen, $C_{1-4}$ alkyl, $-O(C_{1-4}$ alkyl), $-NH(C_{1-4}$ alkyl), $-N(C_{1-4}$ alkyl)($C_{1-4}$ alkyl), and $-S(O)_n(C_{1-4}$ alkyl), haloalkyl, trifluoromethyl, trifluoromethoxy, $-XR_A$ and Y;

$R_4$ is absent or an oxygen atom;

Ar is phenyl, mono-, di-, or tri-substituted with $R_C$, or

Ar is selected from the group consisting of:

naphthyl, pyridyl, pyridonyl, pyrimidinyl, and thiophenyl, each of which is unsubstituted or mono-, di-, or tri-substituted with $R_C$;

with the proviso that if Ar is phenyl substituted with halogen, napthyl, or naphthyl substituted with halogen, then the compounds where $R_3$ is hydrogen are excluded;

$R_A$ and $R_B$, which may be the same or different, are independently selected at each occurrence from the group consisting of: hydrogen and straight, branched, or cyclic alkyl groups consisting of 1 to 8 carbon atoms, which may contain one or more double or triple bonds, each of which may be further substituted with one or more substituent(s) selected from oxo, hydroxy, halogen, $-O(C_{1-4}$ alkyl), $-NH(C_{1-4}$ alkyl), $-N(C_{1-4}$ alkyl)($C_{1-4}$ alkyl), $-NHC(O)$ ($C_{1-4}$ alkyl), $-N(C_{1-4}$ alkyl)$C(=O)(C_{1-4}$ alkyl), $-NHS(O)_n(C_{1-4}$ alkyl), $-S(O)_n(C_{1-4}$ alkyl), $-S(O)_nNH(C_{1-4}$ alkyl), $-S(O)_nN(C_{1-4}$ alkyl)($C_{1-4}$ alkyl), and Z;

$R_C$ is independently selected at each occurrence from the group consisting of halogen, cyano, haloalkyl, trifluoromethyl, trifluoromethoxy, hydroxy, amino, and $C_{1-6}$alkyl optionally substituted with 0–2 $R_D$, $C_{2-6}$ alkenyl substituted with 0–2 $R_D$, $C_{1-4}$ alkynyl substituted with 0–2 $R_D$, $C_{3-7}$ cycloalkyl substituted with 0–2 $R_D$, ($C_{3-7}$ cycloalkyl) $C_{1-4}$ alkyl substituted with 0–2 $R_D$, $-O(C_{1-4}$ alkyl) substituted with 0–2 $R_D$, $-NH(C_{1-4}$ alkyl) substituted with 0–2 $R_D$, $-N(C_{1-4}$ alkyl)($C_{1-4}$ alkyl) each independently substituted with 0–2 $R_D$, $-XR_A$, and Y;

$R_D$ is independently selected at each occurrence the group consisting of halogen, hydroxy, cyano, $C_{1-4}$alkyl, $-O(C_{1-4}$ alkyl), $-NH(C_{1-4}$alkyl), $-N(C_{1-4}$alkyl)($C_{1-4}$ alkyl), morpholino, pyrrolidino, piperidino, thiomorpholino, piperazino, 4-hydroxypiperidino, $-S(O)_n(C_{1-4}$ alkyl), trifluoromethyl, trifluoromethoxy, $CO(C_{1-4}$alkyl), $CONH(C_{1-4}$alkyl), $CON(C_{1-4}$alkyl)($C_{1-4}$alkyl), $-XR_A$, and Y;

X is independently selected at each occurrence from the group consisting of $-CH_2-$, $-CHR_B-$, $-O-$, $-C(=O)-$, $-C(=O)O-$, $-S(O)_n-$, $-NH-$, $-NR_B-$, $-C(=O)NH-$, $-C(=O)NR_B-$, $-S(O)_nNH-$, $-S(O)_nNR_B-$, $-OC(=S)S-$, $-NHC(=O)-$, $-NR_BC(=O)-$, $-NHS(O)_n-$, $-OSiH_n(C_{1-4}alkyl)_{2-n}-$, and $-NR_BS(O)_n-$; and Y and Z are independently selected at each occurrence from the group consisting of: 3- to 7-membered carbocyclic and heterocyclic groups, which are saturated, unsaturated, or aromatic, which may be substituted with one or more substituents selected from halogen, haloalkyl, oxo, hydroxy, amino, $C_{1-4}$ alkyl, $-O(C_{1-4}$ alkyl), $-NH(C_{1-4}$ alkyl), $-N(C_{1-4}$ alkyl)($C_{1-4}$ alkyl), and $-S(O)_n(C_{1-4}$ alkyl), and said 3- to 7-membered heterocyclic groups contain one or more heteroatom(s) selected from N, O, and S, with the point of attachment being either carbon or nitrogen; and n is independently selected at each occurrence from 0, 1, and 2.

Particularly preferred arylpyrazines of the invention include compounds of the following Formula IB:

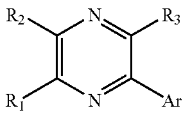

IB wherein:

Ar is selected from the group consisting of phenyl, 1- or 2-naphthyl, 2-, 3-, or 4-pyridyl, 2-, 4-, or 5-pyrimidinyl, each Ar optionally substituted with 1 to 5 with $R_6$ group, with the proviso that at least one of the positions ortho or para to the point of attachment of Ar to the pyrazine ring system is substituted;

$R_1$ is selected from H, $C_{1-4}$ alkyl, $C_{2-4}$ alkenyl, $C_{2-4}$ alkynyl, ($C_{3-6}$ cycloalkyl)$C_{1-4}$ alkyl, halogen, CN, $C_{1-4}$ haloalkyl, —NH($C_{1-4}$ alkyl), —N($C_{1-4}$ alkyl)($C_{1-4}$ alkyl), —O($C_{1-4}$ alkyl), and —$S(O)_b$($C_{1-4}$ alkyl), wherein b is 0, 1, or 2;

$R_2$ is selected from the group consisting of —$XR_4$ and Y, wherein X, $R_4$, and Y are as defined below;

X is independently selected at each occurrence from the group consisting of —$CH_2$—, —$CHR_5$—, —O—, —$S(O)_n$—, —NH—, —$NR_5$—, —C(═O)NH—, —C(═O)$NR_5$—, —$S(O)_n$NH—, —$S(O)_nNR_5$—, —NHC(═O)—, —$NR_5$C(═O)—, —NHS$(O)_n$—, and —$NR_5S(O)_n$— (where n is 0, 1, or 2);

Y and Z are independently selected at each occurrence from the group consisting of: 3- to 7-membered heterocycles, saturated or unsaturated, containing one or more heteroatom(s) selected from N, O, and S, with the point of attachment being either carbon or nitrogen (where applicable), and which may be further substituted with one or more substituents selected from halogen, oxo, hydroxy, amino, $C_{1-4}$ alkyl, —O($C_{1-4}$ alkyl),
—NH($C_{1-4}$ alkyl), —N($C_{1-4}$ alkyl)($C_{1-4}$ alkyl), and —$S(O)_a$($C_{1-4}$ alkyl) (wherein a is 0, 1, or 2);

$R_3$ is selected from the group consisting of hydrogen, halogen,
$C_{1-4}$ alkyl, —O($C_{1-4}$ alkyl), —NH($C_{1-4}$ alkyl), —N($C_{1-4}$ alkyl)($C_{1-4}$ alkyl), and —$S(O)_c$($C_{1-4}$ alkyl) (wherein c is0, 1, or 2), trifluoromethyl, trifluoromethoxy, —$XR_4$, and Y, where —X, $R_4$, and Y are as defined above.

$R_4$ and $R_5$, which may be the same or different, are independently selected at each occurrence from the group consisting of:
hydrogen, straight, branched, or cyclic alkyl groups consisting of 1 to 8 carbon atoms, which may contain one or more double or triple bonds, each of which may optionally be further substituted with one or more substituent(s) selected from oxo, hydroxy, —O($C_{1-4}$ alkyl), —NH($C_{1-4}$ alkyl), —N($C_{1-4}$ alkyl)($C_{1-4}$ alkyl), —NHC(O)($C_{1-4}$ alkyl), —N($C_{1-4}$ alkyl)C(O)($C_{1-4}$ alkyl), —NHS$(O)_m$($C_{1-4}$ alkyl), —$S(O)_m$($C_{1-4}$ alkyl), —$S(O)_m$NH($C_{1-4}$ alkyl), —$S(O)_m$N($C_{1-4}$ alkyl)($C_{1-4}$ alkyl), (where m is 0, 1, or 2), and Z, wherein Z is as defined above;

$R_6$ is independently selected at each occurrence from halogen, trifluoromethyl, trifluoromethoxy, hydroxy, amino, and $C_1$-$C_6$ alkyl (optionally substituted with 0–2 $R_7$, $C_{2-6}$ alkenyl substituted with 0–2 $R_7$, $C_{1-4}$ alkynyl substituted with 0–2 $R_7$, $C_{3-6}$ cycloalkyl substituted with 0–2 $R_7$, ($C_{3-6}$ cycloalkyl)$C_{1-4}$ alkyl substituted with 0–2 $R_7$, O($C_{1-4}$ alkyl) substituted with 0–2 $R_7$, —NH($C_{1-4}$ alkyl) substituted with 0–2 $R_7$, —N($C_{1-4}$ alkyl)($C_{1-4}$ alkyl) each independently substituted with 0–2 $R_7$, —$XR_4$, cyano, and Y; and $R_7$ is independently selected at each occurrence the group consisting of halogen, $C_{1-4}$ alkyl, —O($C_{1-4}$ alkyl), —NH($C_{1-4}$ alkyl), —N($C_{1-4}$ alkyl)($C_{1-4}$ alkyl), morpholino, pyrrolidino, piperidino, thiomorpholino, piperazino, 4-hydroxypiperidino, —$S(O)_p$($C_{1-4}$ alkyl), trifluoromethyl, trifluoromethoxy, CO($C_{1-4}$alkyl), CONH($C_{1-4}$ alkyl), CON($C_{1-4}$ alkyl)($C_{1-4}$ alkyl), —$XR_4$, and Y, wherein X, $R_4$ and Y are defined as above and p is 0, 1 or 2;

and pharmaceutically acceptable salts thereof;

and preferably if Ar is phenyl substituted with halogen, naphthyl, or naphthyl substituted with halogen, then the exclusion of compounds where 1) $R_3$ being hydrogen, amino (—$NH_2$) or alkylamide particularly —NHC(═O)$C_{1-4}$alkyl or —NHC(═O)$C_{3-7}$cycloalkyl, and/or 2) $R_2$ being hydrogen, alkylamide particularly —NHC(═O)$C_{1-4}$alkyl or —NHC(═O)$C_{3-7}$cycloalkyl, amino substituted by one or two alkyl particularly $C_{1-4}$ alkyl, or a nitrogen-containing 6-membered ring.

In the above Formulae I, IA, and IB, as well as below-specified Formulae Ia through Ie, II, IIa through IIi, III, IIIa through IIIe and IV, preferred Ar groups include 2,4-dichlorophenyl, 2,4-dimethoxyphenyl, 4-methoxy-2-methylphenyl, 2,4,6-trimethylphenyl, 4-methoxy-2,6-dimethylphenyl, 4-cyano-2,6-dimethylphenyl, 2-methoxy-4,6-dimethylphenyl, 2-methoxy4,6-bis(trifluoromethyl)phenyl, 2,6-dichloro-4-methoxyphenyl, 2-(2-(1-morpholino)ethoxy)-4,6-dimethylphenyl, 2-(2-(4-hydroxy-1-piperidino)ethoxy)-4,6-dimethylphenyl, 2-methyl4-(dimethylamino)-3-pyridyl, and 2-chloro4-dimethylamino-3-pyridyl, 2-methoxy-4,6-dimethyl-3-pyridyl.

In the above Formulae I, IA, and IB, as well as below-specified Formulae Ia through Ie, II, IIa through IIi, III, IIIa through IIIe and IV, preferred $R_1$ groups include methyl, ethyl, chloro, bromo, iodo, trifluoromethyl, methoxy, dimethylamino, and thiomethoxy.

In the above Formulae I, IA, and IB, as well as below-specified Formulae Ia through Ie, II, IIa through IIi, III, IIIa through IIIe and IV, preferred $R_2$ groups include dipropylamino, bis(2-methoxyethyl)amino, 4-methyl-1-piperazino, 3-pentylamino, 4-heptylamino, 1,3-dimethoxy-2-propylamino, 1-(dimethylamino)-2-pentylamino, 1-(3-pyridyl)-2-butylamino, (2-methoxy-5-pyridine)amino, 3-pentyloxy, 4-heptyloxy, 1-methoxy-2-butyloxy, and 1,3-dimethoxy-2-propyloxy.

In the above Formulae I, IA, and IB, as well as below-specified Formulae Ia through Ie, II, IIa through IIi, III, IIIa through IIIe and IV, preferred $R_3$ groups include methyl, ethyl, chloro, trifluoromethyl, methoxy, dimethylamino, thiomethoxy, methanesulfonyl, (1-morpholino)methyl, 2-(1-pyrrolidino)ethyl, and (2-methoxy)ethoxy.

Preferred arylpyrazines of the invention exhibit good activity in a standard in vitro CRF receptor binding assays, specifically the assay as specified in Example 96 which follows. Particularly preferred arylpyrazines of the invention have an $IC_{50}$ in such a defined standard in vitro CRF receptor binding assay of about 1.5 micromolar or less, still more preferably an $IC_{50}$ of about 100 nanomolar or less, or even more preferably an $IC_{50}$ of about 10 nanomolar or less or even 1 nanomolar or less in a such a defined standard in vitro CRF receptor binding assay.

Preferred arylpyrazines of the invention do not show activity in a standard in vitro Na channel functional assay, specifically the assay as specified in Example 99 which follows. Particularly preferred arylpyrazines of the invention do not show any statistically significant activity in a defined standard in vitro Na channel functional assay 0 at the $p<0.05$ level of significance.

The invention further comprises methods of treating patients suffering from or susceptible to (i.e. prophylactic treatment) certain disorders or diseases with an effective amount of a compound of the invention. The patient may be a human or other mammal such as other primates. Treatment of humans, domesticated companion animals (pet) or livestock animals suffering from certain with an effective amount of a compound of the invention is encompassed by the invention.

Additionally this invention relates to the use of the CRF1 compounds of the invention as probes for the localization of receptors in tissue sections.

The compounds of the present invention are useful for the treatment of CNS disorders particularly affective disorders, anxiety disorders, stress-related disorders, eating disorders and substance abuse. Affective disorders include all types of depression, bipolar disorder, cyclothymia, and dysthymia. Anxiety disorders include generalized anxiety disorder, panic, phobias and obsessive-compulsive disorder. Stress-related disorders include post-traumatic stress disorder, hemorrhagic stress, stress-induced psychotic episodes, psychosocial dwarfism, stress headaches, stress-induced immune systems disorders such as stress-induced fever, and stress-related sleep disorders. Eating disorders include anorexia nervosa, bulimia nervosa, and obesity. These conditions are herein after referred to as the primary CRF-related CNS disorders.

Arylpyrazine compounds of the invention (which includes compounds of the Formulae I, IA, and IB, as well as below-specified Formulae Ia through Ie, II, IIa through IIi, III, IIIa through IIIe and IV,) are also useful in the treatment of a variety of neurological disorders including supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, disorders of pain perception such as fibromyalgia and epilepsy. These conditions are hereinafter referred to as the secondary CRF-related CNS disorders.

Arylpyrazine compounds of the invention are useful as modulators of the G-protein coupled receptor function.

Additionally, arylpyrazine compounds of the invention are useful as modulators of the CRF receptor in the treatment of a number of gastrointestinal, cardiovascular, hormonal, autoimmune and inflammatory conditions. Such conditions include irritable bowel syndrome, ulcers, Crohn's disease, spastic colon, diarrhea, post operative ilius and colonic hypersensitivity associated with psychopathological disturbances or stress, hypertension, tachycardia, congestive heart failure, infertility, euthyroid sick syndrome, inflammatory conditions effected by rheumatoid arthritis and osteoarthritis, pain, asthma, psoriasis and allergies. These conditions are referred to hereinafter as the non-CNS CRF-related disorders.

Arylpyrazine compounds of the invention are also useful as modulators of the $CRF_1$ receptor in the treatment of animal conditions associated with aberrant CRF levels. These conditions include porcine stress syndrome, bovine shipping fever, equine paroxysmal fibrillation, and dysfunctions induced by confinement in chickens, sheering stress in sheep or human-animal interaction related stress in dogs, psychosocial dwarfism and hypoglycemia. These animal conditions are referred to hereinafter as the CRF-related animal disorders.

According to yet another aspect, the present invention provides pharmaceutical compositions comprising one or more aryl pyrazine compound of the invention of a pharmaceutically acceptable salt thereof, particularly for use in the treatment of any of the primary CNS disorders, secondary CNS disorders, non-CNS CRF-related disorders, or CRF-related animal disorders.

According to a still further aspect of the invention, arylpyrazine compounds of the invention (and especially labeled compounds of this invention) are useful as standards and reagents in determining the ability of a potential pharmaceutical to bind to the CRF receptor.

Other aspects of the invention are disclosed infra.

DETAILED DESCRIPTION OF THE INVENTION

The invention provides compounds of Formula I shown above. Preferred compound of the invention include those of the following Formula Ia:

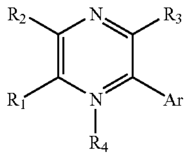

Ia or a pharmaceutically acceptable salt thereof, wherein:

$R_1$ is selected from H, $C_{1-4}$ alkyl, $C_{2-4}$ alkenyl, $C_{2-4}$ alkynyl, halogen, CN, $C_{1-4}$ haloalkyl, trifluoromethyl, trifluoromethoxy, —NH($C_{1-4}$ alkyl), —N($C_{1-4}$ alkyl)($C_{1-4}$ alkyl), —O($C_{1-4}$ alkyl), and $S(O)_n(C_{1-4}$ alkyl);

$R_2$ is selected from the group consisting of —$XR_A$ and Y, wherein —X, $R_A$, and Y are defined below; and $R_3$ is selected from the group consisting of hydrogen, halogen, $C_{1-4}$ alkyl, —O($C_{1-4}$ alkyl), —NH($C_{1-4}$ alkyl), —N($C_{1-4}$ alkyl)($C_{1-4}$ alkyl), and —$S(O)_n(C_{1-4}$ alkyl), haloalkyl, trifluoromethyl, trifluoromethoxy, —$XR_A$ and Y;

$R_4$ is absent or an oxygen atom;

Ar is phenyl, mono-, di-, or tri-substituted with $R_C$, or

Ar is selected from the group consisting of:

naphthyl, pyridyl, pyridonyl, pyrimidinyl, and thiophenyl, each of which is unsubstituted or mono-, di-, or tri-substituted with $R_C$;

with the proviso that if Ar is phenyl substituted with halogen, napthyl, or naphthyl substituted with halogen, then the compounds where $R_3$ is hydrogen are excluded;

$R_A$ and $R_B$, which may be the same or different, are independently selected at each occurrence from the group consisting of: hydrogen and straight, branched, or cyclic alkyl groups consisting of 1 to 8 carbon atoms, which may contain one or more double or triple bonds, each of which may be further substituted with one or more substituent(s) selected from oxo, hydroxy, halogen, —O($C_{1-4}$ alkyl), —NH($C_{1-4}$ alkyl), —N($C_{1-4}$ alkyl)($C_{1-4}$ alkyl), —NHC(O)($C_{1-4}$ alkyl), —N($C_{1-4}$ alkyl)C(=O)($C_{1-4}$ alkyl), —NHS(O)$_n$($C_{1-4}$ alkyl), —$S(O)_n(C_{1-4}$ alkyl), —$S(O)_n$NH($C_{1-4}$ alkyl), —$S(O)_n$N($C_{1-4}$ alkyl)($C_{1-4}$ alkyl), and Z;

$R_C$ is independently selected at each occurrence from the group consisting of halogen, cyano, haloalkyl, trifluoromethyl, trifluoromethoxy, hydroxy, amino, and $C_{1-6}$ alkyl optionally substituted with 0–2 $R_D$, $C_{2-6}$ alkenyl substituted with 0–2 $R_D$, $C_{1-4}$ alkynyl substituted with 0–2 $R_D$, $C_{3-7}$ cycloalkyl substituted with 0–2 $R_D$, ($C_{3-7}$ cycloalkyl) $C_{1-4}$ alkyl substituted with 0–2 $R_D$, —O($C_{1-4}$ alkyl) substituted with 0–2 $R_D$, —NH($C_{1-4}$ alkyl) substituted with 0–2 $R_D$, —N($C_{1-4}$ alkyl)($C_{1-4}$ alkyl) each independently substituted with 0–2 $R_D$, —$XR_A$, and Y;

$R_D$ is independently selected at each occurrence the group consisting of halogen, hydroxy, cyano, $C_{1-4}$alkyl, —O($C_{1-4}$ alkyl), —NH($C_{1-4}$alkyl), —N($C_{1-4}$alkyl)($C_{1-4}$ alkyl), morpholino, pyrrolidino, piperidino, thiomorpholino, piperazino, 4-hydroxypiperidino, —$S(O)_n$($C_{1-4}$ alkyl), trifluoromethyl, trifluoromethoxy, CO($C_{1-4}$alkyl), CONH($C_{1-4}$alkyl), CON($C_{1-4}$alkyl)($C_{1-4}$alkyl), —$XR_A$, and Y;

X is independently selected at each occurrence from the group consisting of —$CH_2$—, —$CHR_B$—, —O—, —C(=O)—, —C(=O)O—, —$S(O)_n$—, —NH—, —$NR_B$—, —C(=O)NH—, —C(=O)$NR_B$—, —$S(O)_n$NH—, —$S(O)_n NR_B$—, —OC(=S)S—, —NHC(=O)—, —$NR_B$C(=O)—, —NHS$(O)_n$—, —$OSiH_n$($C_{1-4}$alkyl)$_{2-n}$—, and —$NR_B S(O)_n$—; and Y and Z are independently selected at each occurrence from the group consisting of: 3- to 7-membered carbocyclic and heterocyclic groups, which are saturated, unsaturated, or aromatic, which may be substituted with one or more substituents selected from halogen, haloalkyl, oxo, hydroxy, amino, $C_{1-4}$ alkyl, —O($C_{1-4}$ alkyl), —NH($C_{1-4}$ alkyl), —N($C_{1-4}$ alkyl)($C_{1-4}$ alkyl), and —$S(O)_n$($C_{1-4}$ alkyl), and said 3- to 7-membered heterocyclic groups contain one or more heteroatom(s) selected from N, O, and S, with the point of attachment being either carbon or nitrogen; and n is independently selected at each occurrence from 0, 1, and 2.

Preferred compounds of general Formula Ia are those where:

$R_4$ is absent and Ar is phenyl, mono-, di-, or tri-substituted with $R_C$, and $R_1$ and $R_3$ are independently selected from the group consisting of hydrogen, halogen, methyl, ethyl, ethoxy and methoxy.

Such compounds are referred to herein as compounds of general Formula Ib.

More preferred compounds of the invention are those of general Formula Ia where:

$R_4$ is absent and Ar is phenyl, mono-, di-, or tri-substituted with $R_C$; and $R_A$ and $R_B$, which may be the same or different, are independently straight, branched, or cyclic alkyl groups having from 1 to 8 carbon atoms, which may contain one or more double or triple bonds.

Such compounds are referred to as compounds of Formula Ic.

Particularly preferred are compounds of general Formula Ia are those where:

$R_4$ is absent and Ar is phenyl mono-, di-, or tri-substituted with $R_C$; $R_A$ and $R_B$, which may be the same or different, are independently selected at each occurrence from the group consisting of: straight, branched, and cyclic alkyl groups having from 1 to 8 carbon atoms, which may contain one or more double or triple bonds; and $R_1$ and $R_3$ are independently selected from the group consisting of hydrogen, halogen, methyl, ethyl, ethoxy, and methoxy.

Such compounds are referred to herein as compounds of general Formula Id.

Particularly preferred are compounds of general Formula Ia are those where:

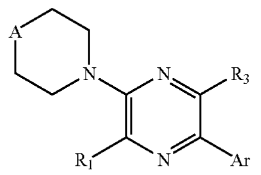

wherein A is $NR_A$ or O.

Such compounds are referred to herein as compounds of general Formula Ie.

Even more preferred compounds of the invention are those of general Formula II:

Formula II

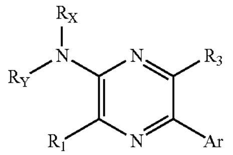

wherein $R_X$ and $R_Y$ are the same or different and are independently selected straight, branched, or cyclic alkyl groups having from 1 to 8 carbon atoms, which may contain one or more double or triple bonds, each of which may be further substituted with one or more substituent(s) independently selected from hydroxy, halogen, —O($C_{1-4}$ alkyl), —NH($C_{1-4}$ alkyl), —N($C_{1-4}$ alkyl)($C_{1-4}$ alkyl), and optionally substituted phenyl.

Other preferred compounds of the invention include those of general Formula II (above) and pharmaceutically acceptable salts thereof, wherein:

Ar is phenyl, mono-, di-, or tri-substituted with $R_C$; and $R_1$ and $R_3$ are independently selected from the group consisting of hydrogen, halogen, methyl, ethyl, ethoxy and methoxy.

Such compounds are referred to herein as compounds of general Formula IIa.

Other preferred compounds of the invention include those of general Formula II (above) and pharmaceutically acceptable salts thereof, wherein:

$R_1$ and $R_3$ are independently chosen from halogen, $C_{1-4}$ alkyl, —O($C_{1-4}$ alkyl), —NH($C_{1-4}$ alkyl), —N($C_{1-4}$ alkyl)($C_{1-4}$ alkyl), haloalkyl, trifluoromethyl, and trifluoromethoxy; and Ar is phenyl, which is mono-, di-, or trisubstituted with one or more substituent(s) independently selected from:

halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$ alkoxy), and mono- or di($C_{1-4}$alkyl)amino.

Such compounds are referred to herein as compounds of general Formula IIb.

Other preferred compounds of the invention include those of general Formula II (above) and pharmaceutically acceptable salts thereof, wherein:

$R_X$ is hydrogen;

$R_Y$ is chosen from the group consisting of:

straight, branched, or cyclic alkyl groups having from 1 to 8 carbon atoms, which may contain one or more double or triple bonds;

$R_1$ and $R_3$ are independently chosen from halogen, $C_{1-4}$ alkyl, —O($C_{1-4}$ alkyl), —NH($C_{1-4}$ alkyl), —N($C_{1-4}$ alkyl)($C_{1-4}$ alkyl), haloalkyl, trifluoromethyl, and trifluoromethoxy; and Ar is phenyl, which is mono-, di-, or trisubstituted with substituent(s) independently selected from:

halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$ alkoxy), and mono- or di($C_{1-4}$ alkyl)amino.

Such compounds are referred to herein as compounds of general Formula IIc.

Other preferred compounds of the invention include those of general Formula II (above) and pharmaceutically acceptable salts thereof, wherein:

$R_X$ is hydrogen;

$R_Y$ is chosen from the group consisting of:

straight, branched, or cyclic alkyl groups having from 1 to 8 carbon atoms, which may contain one or more double or triple bonds;

$R_1$ and $R_3$ are independently chosen from halogen, $C_{1-4}$ alkyl —O($C_{1-4}$ alkyl), —NH($C_{1-4}$ alkyl), —N($C_{1-4}$ alkyl)($C_{1-4}$ alkyl), haloalkyl, trifluoromethyl, and trifluoromethoxy; and Ar is a phenyl group of the formula:

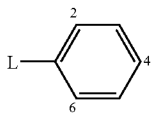

wherein L indicates a bond to the pyrazine ring in Formula A;

and the phenyl group is substituted at one, two or three of positions 2, 4, and 6 with substituent(s) independently selected from:

halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$ alkoxy), and mono- or di($C_{1-4}$ alkyl)amino.

Such compounds are referred to herein as compounds of general Formula IId.

Other preferred compounds of the invention include those of general Formula II (above) and pharmaceutically acceptable salts thereof, wherein:

$R_X$ is hydrogen;

$R_Y$ is chosen from the group consisting of:

straight, branched, or cyclic alkyl groups having from 1 to 8 carbon atoms, which may contain one or more double or triple bonds;

$R_1$ and $R_3$ are independently chosen from halogen, $C_{1-4}$ alkyl, —O($C_{1-4}$ alkyl), —NH($C_{1-4}$ alkyl), —N($C_{1-4}$ alkyl)($C_{1-4}$ alkyl), haloalkyl, trifluoromethyl, and trifluoromethoxy; and Ar is a phenyl group of the formula:

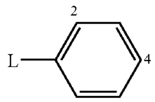

wherein L indicates a bond to the pyrazine ring in Formula A;

and the phenyl group is substituted at positions 2 and 4 with substituents independently selected from:

halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$alkoxy), and mono- or di($C_{1-4}$ alkyl)amino.

Such compounds are referred to herein as compounds of general Formula IIe.

Other preferred compounds of the invention include those of general Formula II (above) and pharmaceutically acceptable salts thereof, wherein:

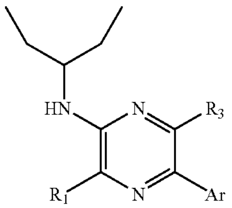

wherein:

$R_1$ and $R_3$ are independently chosen at each occurrence from halogen, $C_{1-4}$ alkyl, —O($C_{1-4}$ alkyl), —NH($C_{1-4}$ alkyl), —N($C_{1-4}$ alkyl)($C_{1-4}$ alkyl), haloalkyl, trifluoromethyl, and trifluoromethoxy; and Ar is a phenyl group of the formula:

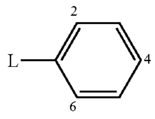

wherein L indicates a bond to the pyrazine ring in Formula A;

and the phenyl group is substituted at one, two or three of positions 2, 4, and 6 with substituent(s) independently selected from:

halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$ alkoxy), and mono- or di($C_{1-4}$ alkyl)amino.

Such compounds are referred to herein as compounds of general Formula IIf.

Other preferred compounds of the invention include those of general Formula II (above) and pharmaceutically acceptable salts thereof, wherein:

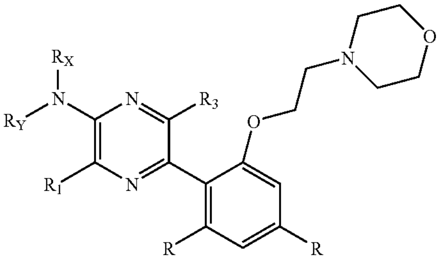

wherein

R is independently selected at each occurrence from the group consisting of: hydrogen, halogen, cyano, haloalkyl, trifluoromethyl, trifluoromethoxy, hydroxy, amino, $C_{1-6}$alkyl, $C_{1-4}$alkoxy, $C_{1-4}$alkoxy($C_{1-4}$alkoxy), mono- or di($C_{1-4}$)amino($C_{1-4}$alkoxy), and mono- or di($C_{1-4}$ alkyl) amino; and $R_1$ and $R_3$ are independently chosen from halogen, $C_{1-4}$ alkyl, —O($C_{1-4}$ alkyl), —NH($C_{1-4}$ alkyl), —N($C_{1-4}$ alkyl) ($C_{1-4}$ alkyl), haloalkyl, trifluoromethyl, and trifluoromethoxy.

Such compounds are referred to herein as compounds of general Formula IIg.

Other preferred compounds of the invention include those of general Formula II (above) and pharmaceutically acceptable salts thereof, wherein:

Ar is phenyl, which is mono-, di-, or tri-substituted with $R_C$;

$R_X$ and $R_Y$, which may be the same or different, are independently selected at each occurrence from the group consisting of: straight, branched, and cyclic alkyl groups having from 1 to 8 carbon atoms, which may contain one or more double or triple bonds; and $R_1$ and $R_3$ are independently selected from the group consisting of hydrogen, halogen, methyl, ethyl, ethoxy, and methoxy.

Such compounds are referred to herein as compounds of general Formula IIh.

Other preferred compounds of the invention include those of general Formula II (above) and pharmaceutically acceptable salts thereof, wherein:

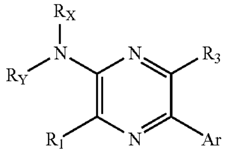

wherein $R_X$ and $R_Y$ are independently hydrogen or $C_{1-8}$ alkyl; or $NR_XR_Y$ is:

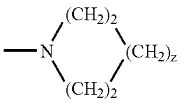

wherein z is 0 or 1.

Such compounds are referred to herein as compounds of general Formula IIi.

Other highly preferred compounds are those of general Formula III:

III

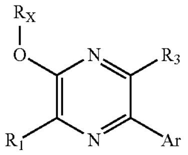

wherein:

$R_X$ is chosen from the group consisting of:

straight, branched, or cyclic alkyl groups, including (cycloalkyl)alkyl groups, having from 1 to 8 carbon atoms, which may contain one or more double or triple bonds, each of which may be further substituted with one or more substituent(s) independently selected from (a) hydroxy, halogen, —O($C_{1-4}$ alkyl), —NH($C_{1-4}$ alkyl), —N($C_{1-4}$ alkyl)($C_{1-4}$ alkyl), and (b) 3- to 7-membered carbocyclic and heterocyclic groups, which are saturated, unsaturated, or aromatic, which may be substituted with one or more substituents selected from halogen, haloalkyl, oxo, hydroxy, amino, $C_{1-4}$ alkyl, —O($C_{1-4}$ alkyl), —NH($C_{1-4}$ alkyl), and —N($C_{1-4}$ alkyl)($C_{1-4}$ alkyl)and wherein said 3- to 7-membered heterocyclic groups contain one or more heteroatom(s) selected from N, O, and S, with the point of attachment being either carbon or nitrogen.

Other preferred compounds of the invention include those of general Formula III (above) and pharmaceutically acceptable salts thereof, wherein:

$R_X$ is selected from straight, branched, or cyclic alkyl groups containing of 1 to 8 carbon atoms, which may contain one or more double or triple bonds; and;

$R_1$ and $R_3$ are independently chosen from halogen, $C_{1-4}$ alkyl, —O($C_{1-4}$ alkyl), —NH($C_{1-4}$ alkyl), —N($C_{1-4}$ alkyl) ($C_{1-4}$ alkyl), haloalkyl, trifluoromethyl, and trifluoromethoxy; and Ar is phenyl, which is mono-, di-, or trisubstituted with one or more substituent(s) independently selected from:

halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$alkoxy), and mono- or di($C_{1-4}$ alkyl)amino.

Such compounds are referred to herein as compounds of general Formula IIIa.

Other preferred compounds of the invention include those of general Formula III (above) and pharmaceutically acceptable salts thereof, wherein:

Ar is a phenyl group of the formula:

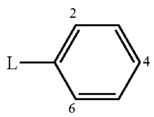

wherein L indicates a bond to the pyrazine ring in Formula III;

and the phenyl group is substituted at one, two, or three of positions 2, 4, and 6 with substituent(s)independently selected from:

halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$ alkoxy), and mono- or di($C_{1-4}$ alkyl)amino.

Such compounds are referred to herein as compounds of general Formula IIIb.

Other preferred compounds of the invention include those of general Formula III (above) and pharmaceutically acceptable salts thereof, wherein:

Ar is a phenyl group of the formula:

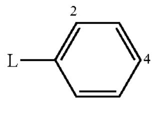

wherein L indicates a bond to the pyrazine ring in Formula III;

and the phenyl group is substituted at positions 2 and 4 with substitutuents independently selected from halogen, cyano, haloalkyl, trifluoromethyl, trifluoromethoxy, hydroxy, amino, $C_{1-6}$ alkyl, $C_{1-4}$alkoxy, $C_{1-4}$alkoxy($C_{1-4}$ alkoxy), mono- or di($C_{1-4}$)amino($C_{1-4}$alkoxy), and mono- or di($C_{1-4}$ alkyl)amino.

Such compounds are referred to herein as compounds of general Formula IIIc.

Other preferred compounds of the invention include those of general Formula III (above) and pharmaceutically acceptable salts thereof, wherein:

IIIc

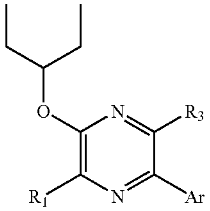

$R_1$ and $R_3$ are independently chosen from halogen, $C_{1-4}$ alkyl, —O($C_{1-4}$ alkyl), —NH($C_{1-4}$ alkyl), —N($C_{1-4}$ alkyl) ($C_{1-4}$ alkyl), haloalkyl, trifluoromethyl, and trifluoromethoxy; and Ar is a phenyl group of the formula:

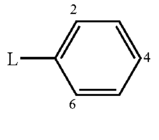

wherein L indicates a bond to the pyrazine ring in Formula B;

and the phenyl group is substituted at one, two, or three of positions 2, 4, and 6 with substituent(s)independently selected from: halogen, cyano, haloalkyl, trifluoromethyl, trifluoromethoxy, hydroxy, amino, $C_{1-6}$ alkyl, $C_{1-4}$alkoxy, $C_{1-4}$alkoxy($C_{1-4}$alkoxy), mono- or di($C_{1-4}$)amino($C_{1-4}$ alkoxy), and mono- or di($C_{1-4}$ alkyl)amino.

Such compounds are referred to herein as compounds of general Formula IIId.

Other preferred compounds of the invention include those of general Formula III (above) and pharmaceutically acceptable salts thereof, wherein:

$R_1$ and $R_3$ are independently selected from the group consisting of hydrogen, halogen, methyl, ethyl, ethoxy and methoxy.

Such compounds are referred to herein as compounds of general Formula IIIe.

Another preferred compound of the invention include 2-(2-methoxy-5-triflurormethoxyphenyl)-3-ethyl-6-methylamino-5-(1-ethylpropoxy)-pyrazine. and pharmaceutically acceptable salts thereof, the compound structure is:

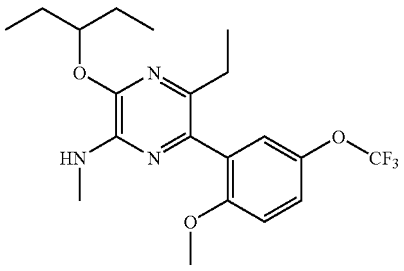

DEFINITIONS

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The CRF antagonist compounds provided by this invention and labeled derivatives thereof are also useful as standards and reagents in determining the ability of a potential pharmaceutical to bind to the CRF receptor.

Labeled derivatives the CRF antagonist compounds provided by this invention are also useful as radiotracers for positron emission tomography (PET) imaging or for single photon emission computerized tomography (SPECT).

The term "substituted," as used herein, means that any one or more hydrogens on the designated atom is replaced with a selection from the indicated group, provided that the designated atom's normal valence is not exceeded, and that the substitution results in a stable compound. When a substituent is keto (i.e., =0), then 2 hydrogens on the atom are replaced. Keto substituents are not present on aromatic moieties. The present invention is intended to include all isotopes of atoms occurring in the present compounds.

Isotopes include those atoms having the same atomic number but different mass numbers, By way of general example and without limitation, isotopes of hydrogen include tritium and deuterium. Isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

As indicated above, various substituents of the various formulae are "optionally substituted", including Ar, $R_1$, $R_2$, and $R_3$ of Formula I, and such substituents as recited in the sub-formulae such as Formulae Ia and the like. When substituted, those substituents (Ar, $R_1$, $R_2$, and $R_3$) may be substituted by other than hydrogen at one or more available positions, typically 1 to 3 or 4 positions, by one or more suitable groups such as those disclosed herein. Suitable groups that may be present on a "substituted" Ar, $R_1$, $R_2$, and $R_3$ group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an Ar group being a substituted or unsubstituted biphenyl moiety); aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

As used herein, the substitution position of a substituent on a phenyl ring is dependent on the point of attachment of the substitutent to the phenyl ring relative to the point of attachment of the phenyl group to the remainder of the chemical compound. For example, L indicates the point of attachment of the phenyl ring to the remainder of the chemical compound. The numbers 2, 3, 4, 5 and 6 identify the individual ring atoms to which substituents can be attached.

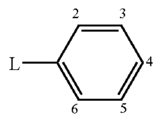

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Alkyl groups typically have 1 to about 16 carbon atoms, more typically 1 to about 12 carbon atoms. Preferred alkyl groups are $C_1$–$C_6$ alkyl groups. Especially preferred alkyl groups are methyl, ethyl, propyl, butyl, 3-pentyl.

As used herein, "cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl, cyclohexylmethyl.

As used here, "alkenyl" is intended to include hydrocarbon chains of either a straight or branched configuration and one or more unsaturated carbon-carbon bonds which may occur in any stable point along the chain, such as ethenyl and propenyl. Alkenyl groups typically will have 2 to about 12 carbon atoms, more typically 2 to about 12 carbon atoms.

As used herein, "alkynyl" is intended to include hydrocarbon chains of either a straight or branched configuration and one or more triple carbon-carbon bonds which may occur in any stable point along the chain, such as ethynyl and propynyl. Alkynyl groups typically will have 2 to about 16 carbon atoms, more typically 2 to about 12 carbon atoms.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Typical haloalkyl groups will have 1 to about 16 carbon atoms, more typically 1 to about 12 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 16 carbon atoms, more typically 1 to about 12 carbon atoms.

As used herein, the term "alkylthio" includes those groups having one or more thioether linkages and suitably from 1 to about 16 carbon atoms, more typically 1 to about 12 carbon atoms, still more typically 1 to about 6 or 8 carbon atoms.

As used herein, the term "alkylsulfinyl" includes those groups having one or more sulfoxide (SO) linkage groups and suitably from 1 to about 16 carbon atoms, more typically 1 to about 12 carbon atoms, still more typically 1 to about 6 or 8 carbon atoms.

As used herein, the term "alkylsulfonyl" includes those groups having one or more sulfonyl ($SO_2$) linkage groups and suitably from 1 to about 16 carbon atoms, more typically 1 to about 12 carbon atoms, still more typically 1 to about 6 or 8 carbon atoms.

As used herein, the term "alkylamino" includes those groups having one or more primary, secondary and/or tertiary amine groups and suitably from 1 to about 16 carbon atoms, more typically 1 to about 12 carbon atoms, still more typically 1 to about 6 or 8 carbon atoms.

As used herein, "halo" or "halogen" as used herein refers to fluoro, chloro, bromo, and iodo; and "counter-ion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7-to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl; adamantyl, and tetrahydronaphthyl.

As used herein, the term "heterocycle" or "heterocycloalkyl" is intended to mean a stable 5-to 7-membered monocyclic or bicyclic or 7-to 10-membered bicyclic heterocyclic ring which is saturated partially unsaturated or unsaturated (aromatic), and which consists of carbon atoms and from 1 to 4 heteroatoms independently selected from the group consisting of N, 0 and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and 0 atoms in the heterocycle exceeds 1, then these heteroatoms are not adjacent to one another. It is preferred that the total number of S and 0 atoms in the heterocycle is not more than 1. As used herein, the term "aromatic heterocyclic system" or similar term such as "heteroaryl" is intended to mean a stable 5-to 7-membered monocyclic or bicyclic or 7-to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1. Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobeniofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;- 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

As used herein, the term "carbocyclic aryl" includes groups that contain 1 to 3 separate or fused rings and from 6 to about 18 ring atoms, without hetero atoms as ring members. Specifically preferred carbocyclic aryl groups include phenyl, and naphthyl including 1-napthyl and 2-naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, HOOC—$(CH_2)n$—COOH where n is 0–4, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

"Prodrugs" are intended to include any covalently bonded carriers which release the active parent drug according to formula I in vivo when such prodrug is administered to a mammalian subject. Prodrugs of a compound of formula I are prepared by modifying functional groups present in the compound in such a way that the modifications are cleaved, either in routine manipulation or in vivo, to the parent compound. Prodrugs include compounds of formula I wherein a hydroxy, amino, or sulfhydryl group is bonded to any group that, when the prodrug or compound of formula I is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula I, and the like.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent. The term "therapeutically effective amount" of a compound of this invention means an amount effective to antagonize abnormal level of CRF or treat the symptoms of affective disorder, anxiety or depression in a host.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

Dosage levels of the order of from about 0.1 mg to about 140 mg of a compound of the invention per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most CNS disorders, a dosage regimen of 4 times daily or less is preferred. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127). Alternatively, compound half-life may be predicted from an in vitro microsomal assay such as the assay given in example 99b.

The present invention also pertains to methods for altering the activity of CRF receptors, said method comprising exposing cells expressing such receptors to an effective amount of a compound of the invention, wherein the compound is present in the solution at a concentration sufficient to specifically alter the signal transduction activity in response to CRF in cells expressing high levels of CRF1 receptors in vitro. This method includes altering the signal transduction activity of CRF receptors in vivo, e.g., in a patient given an amount of a compound of Formula I that would be sufficient to alter the signal transduction activity in response to CRF in cells expressing high levels of CRF1 in vitro. The amount of a compound that would be sufficient to alter the signal transduction activity in response to CRF receptors may be determined via an assay of CRF receptor mediated signal transduction, such as an assay wherein the binding of CRF to a cell surface CRF receptor effects a changes in reporter gene expression.

The present invention also pertains to packaged pharmaceutical compositions for treating disorders responsive to C5a receptor modulation, e.g., eating disorders, depression or stress. The packaged pharmaceutical compositions include a container holding a therapeutically effective amount of at least one CRF1 receptor modulator as described supra and instructions for using the treating disorder responsive to CRF1 receptor modulation in the patient.

Preparation of Arylpyranzines

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. Preferred methods for the preparation of compounds of the present invention include, but are not limited to, those described in Scheme I, Scheme II, and Scheme III. Those who are skilled in the art will recognize that the starting materials may be varied and additional steps employed to produce compounds encompassed by the present invention. All references cited herein are hereby incorporated in their entirety herein by reference. The following abbreviations are used herein:

| | |
|---|---|
| AcOH | acetic acid |
| DMF | N,N-dimethylformamide |
| $Et_2O$ | diethyl ether |
| EtOAc | ethyl acetate |
| EtOH | ethanol |
| NaH | sodium hydride |
| NaHMDS | sodium bis(trimethylsilyl)amide |
| THF | tetrahydrofuran |

Scheme I (Method A)

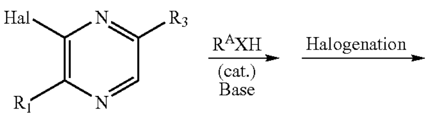

VI

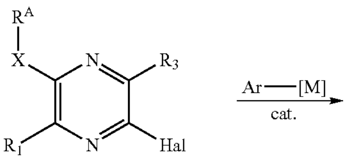

(X = NH, $NR_B$, O, S)

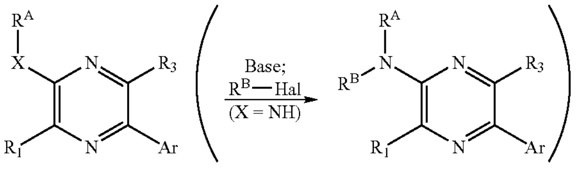

VII II

According to the general method A, wherein $R_1$ and $R_3$ are as defined for formula I and Hal represents a halogen atom, suitably chloride or bromide, the halide in VI can be displaced by an amine or (thio)alkoxide nucleophile. Thus, aminopyrazine can be prepared from VI and an amine in the presence of a suitable transition metal catalyst such as but not limited to palladium(II) acetate or tris(dibenzylideneacetone)dipalladium(0), a ligand such as but not limited to 1,1'-bis(diphenylphosphine)ferrocene, 2,2'-bis(diphenylphosphine)-1,1'-binaphthyl, dicyclohexyl(2-biphenyl) phosphine, tricyclohexylphosphine, or tri-tert-butylphosphine, and a base such as sodium or potassium tert-butoxide in inert solvents such as but not limited to toluene, ethyleneglycol dimethyl ether, diglyme, DMF, or N-methylpyrrolidinone at temperatures ranging from ambient to 100° C. (Thio)alkoxypyrazines can be prepared by treating VI with a sodium or potassium salt of an alcohol or thiol in an inert solvent such as THF, DMF, N-methylpyrrolidinone, or methyl sulfoxide at ambient temperature or at elevated temperature up to the boiling point of the solvent employed. Halogenation may be accomplished by a variety of methods known in the art, including treatment with N-chlorosuccinimide, bromine, N-bromosuccinimide, pyridinium tribromide, triphenylphosphine dibromide, iodine, and N-iodosuccinimide in solvents such as but not limited to dichloromethane, acetic acid, or methyl sulfoxide. The bromopyrazine can be converted to arylpyrazine VII by a transition metal-catalyzed coupling reaction with a metalloaryl reagent (Ar-[M]). More commonly employed reagent/catalyst pairs include aryl boronic acid/palladium(0) (Suzuki reaction; N. Miyaura and A. Suzuki, Chemical Review 1995, 95, 2457), aryl trialkylstannane/palladium(0) (Stille reaction; T. N. Mitchell, Synthesis 1992, 803), arylzinc/palladium(0) and aryl Grignard/nickel(II). Palladium(0) represents a catalytic system made of a various combination of metal/ligand pair which includes, but not limited to, tetrakis (triphenylphosphine)palladium(0), palladium(II) acetate/tri (o-tolyl)phosphine, tris(dibenzylideneacetone)dipalladium (0)/tri-tert-butylphosphine and dichloro[1,1'-bis (diphenylphosphine)ferrocene]palladium(0). Nickel(II) represents a nickel-containing catalyst such as [1,2-bis (diphenylphosphino)ethane]dichloronickel(II) and [1,3-bis (diphenylphosphino)propane]dichloronickel(II). The arylpyrazine VII, when X is NH, may be further transformed to VIII by N-alkylation. The N—H group is deprotonated by a strong base such as but not limited to alkali metal hydride, alkali metal amide, or alkali metal alkoxide in inert solvents such as but not limited to THF, DMF, or methyl sulfoxide. Alkylation may be conducted using alkyl halide, suitably bromide or iodide, at temperatures ranging from 0° C. to 100° C.

Scheme II (Method B)

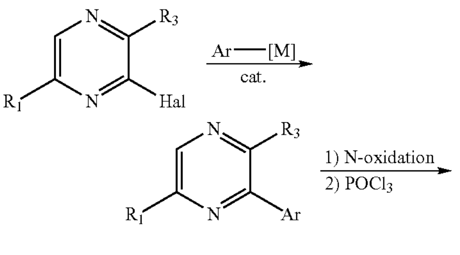

VIII

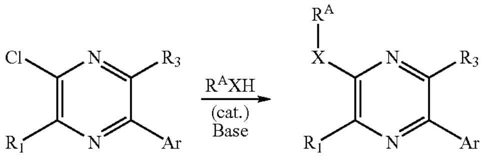

IX VII ( X = NH, $NR^B$, O, S)

In an alternative way, compounds of Formula VII can be prepared as outlined in Scheme II. Transition metal-catalyzed coupling of the halo pyrazine VI as described in the Method A can provide the intermediate VIII. Oxidation of sterically less hindered nitrogen can be effected by using a variety of oxidizing agents known in the art, which includes m-chloroperoxybenzoic acid, trifluoroperacetic acid, hydrogen peroxide, and monoperoxyphthalic acid. The N-oxide can undergo rearrangement to give chloropyrazine IX upon the action of phosphorus oxychloride at temperatures ranging from ambient to 100° C. Displacement of the chloride with a nitrogen, oxygen, or sulfur nucleophile as described in the Method A can furnish the compounds of Formula VII.

Scheme III (Method C)

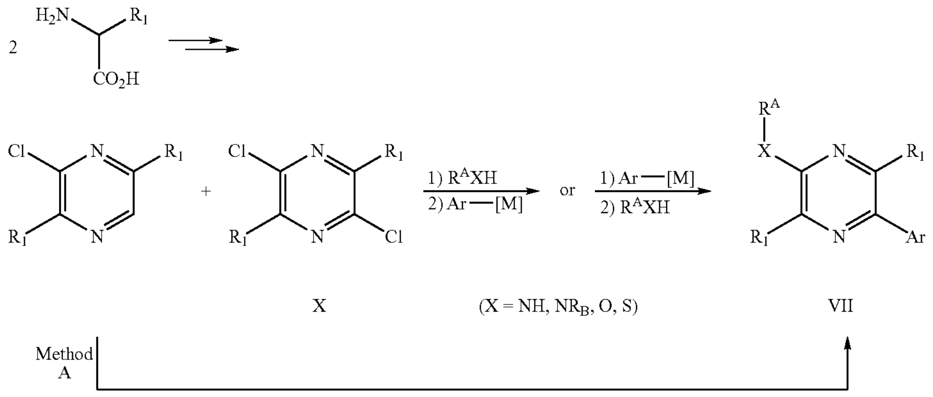

Yet another way of preparing compounds of formula VII is illustrated in the Scheme III. Compounds of formula X, 3,6-dialkyl-2,5-dichloropyrazines, can be prepared from 2-alkylglycine according to a known literature procedure (Ref: *Chemical and Pharmaceutical Bulletin of Japan* 1979, 27, 2027). Nucleophilic displacement of one chloride followed by Suzuki-type coupling at the other, as described in the Method A, can furnish the compounds of formula VII. of the solvent. In addition, X may react with a sodium or potassium (thio)alkoxide in inert solvents such as but not limited to THF, DMF, N-methylpyrrolidinone, or methyl sulfoxide at temperatures ranging from 0° C. to ambient temperature. Resulting monochloropyrazine XI can be halogenated by using the conditions described in the Method A to give a mixture of regioisomeric bromides XIIa and XIIb. Transition metal-catalyzed (hetero)aryl-aryl coupling of Scheme IV (Method D)

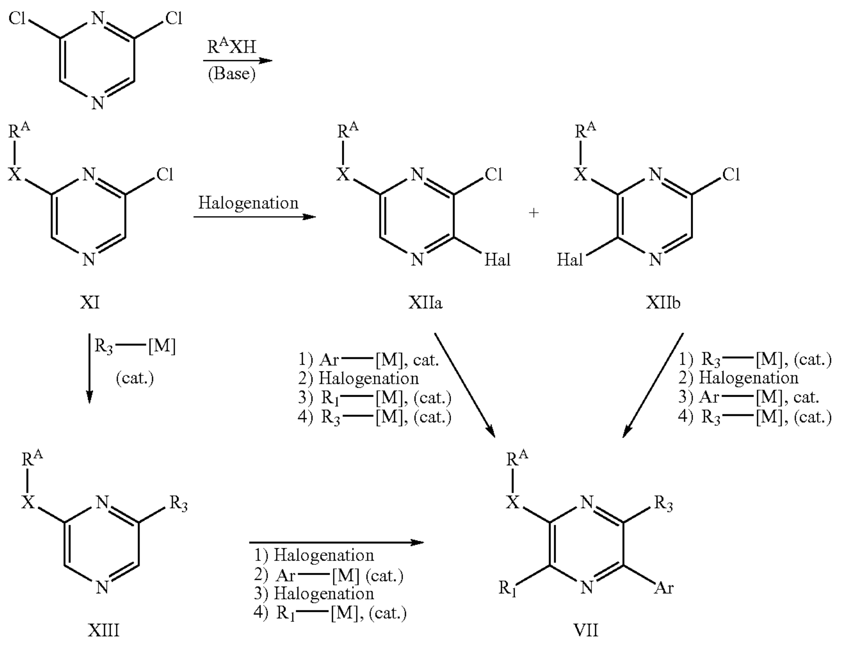

Still another way of preparing compounds of formula VII is illustrated in Scheme IV. Commercially available 2,6-Dichloropyrazine can undergo monosubstitution with nitrogen, oxygen, or sulfur nucleophile to give XI. Thus, X may react with an amine in solvents such as but not limited to dichloromethane, acetonitrile, THF, DMF, N-methylpyrrolidinone, methyl sulfoxide, methanol, ethanol, and isopropanol at temperatures ranging from 0° C. to the boiling point XIIa, as described in the Method A, followed by another halogenation can provide VII ($R_1$=Hal, $R_3$=Cl) which can be further converted to VII by displacing one or both of the halogen atoms, either sequentially or simultaneously, with a variety of nucleophiles ($R_1$-[M] and $R_3$-[M]), same or different, in the presence or absence of a transition metal catalyst. The aforementioned nucleophiles may include sodium or potassium (thio)alkoxide, alkylamine, and organometallic reagent such as but not limited to alkyl Grignard reagents, alkylboronic acids or its ester, or alkylstannanes. The aforementioned transition metal catalyst may represent palladium or nickel catalysts described in the Method A. The other regioisomeric bromide XIIb can also be converted to VII by changing the order of the transformation sequence. Those who are skilled in the art will also recognize that one can further change the order of transformations to prepare the compounds of Formula VII by way of the intermediate XIII.

As discussed above, preferred arylpyrazines of the invention exhibit good activity in standard in vitro CRF receptor binding assays, specifically the assay as specified in Example 96, which follows. References herein to "standard in vitro receptor binding assay" are intended to refer to that protocol as defined in Example 96 which follows. Generally preferred compounds preferred arylpyrimidines of the invention have an $IC_{50}$ of about 10 micromolar or less, still more preferably and $IC_{50}$ of about 100 nanomolar or less even more preferably an $IC_{50}$ of about 10 nanomolar or less or even 1 nanomolar or less in such a defined standard in vitro CRF receptor binding assay as exemplified by Example 96 which follows.

EXAMPLES

The preparation of the compounds of the present invention is illustrated further by the following examples, which are not to be construed as limiting the invention in scope or spirit to the specific procedures and compounds described in them.

Commercial reagents were used without further purification. room or ambient temperature refers to 20 to 25° C. Concentration in vacuo implies the use of a rotary evaporator. TLC refers to thin layer chromatography. Proton nuclear magnetic resonance ($^1$H NMR) spectral data were obtained at 300 or 400 MHz. Mass spectral data were obtained either by CI or APCI methods.

Example 1

[N-(1-ethyl)propyl]-5-(2,4-dimethoxyphenyl)-3,6-dimethylpyrazine-2-amine [Formula I: Ar=2,4-dimethoxyphenyl; $R_2$=—N-(1-ethyl)propyl; $R_1$=$R_3$=$CH_3$]

A. To a mixture of 2-chloro-3,6-dimethylpyrazine (0.83 mmol), tris(dibenzylideneacetone)dipalladium(0) (2 mol %), and BINAP (6 mol %) in ethyleneglycol dimethyl ether (2 mL) under nitrogen is added 1-ethylpropylamine (1.0 mmol) followed by sodium tert-butoxide (1.25 mmol). The mixture is stirred at 70–80° C. for 2.5 h, diluted with aqueous ammonium chloride, and extracted 1:1 hexane-$Et_2O$. Combined extracts are dried (sodium sulfate), filtered, concentrated, and chromatographed on silica gel (10:1 to 4:1 hexane-EtOAc eluent) to give the aminopyrazine.

B. A solution of N-(1-ethyl)propyl-3,6-dimethylpyrazine-2-amine (0.72 g; 3.7 mmol) in dichloromethane (20 mL) is cooled to 0° C. and N-bromosuccinimide (0.72 g; 4.1 mmol) is added in portions. After the addition, the mixture is further stirred for 1 h while being allowed to warm to room temperature. The mixture is then concentrated to a small volume in vacuo, triturated with hexane, filtered, washed with hexane, and the filtrate is concentrated and chromatographed on silica gel to give the bromide (1.07 g).

C. A mixed solution of 5-bromo-[N-(1-ethyl)propyl]-3,6-dimethylpyrazine-2-amine (0.40 g; 1.47 mmol) and tetrakis (triphenylphosphine)palladium(0) (33 mg; 2 mol %) in ethyleneglycol dimethyl ether (8 mL) is stirred at room temperature for 15 min, when 2,4-dimethoxybenzeneboronic acid (1.76 mmol) and an aqueous solution of sodium carbonate (1.0M, 4 mL) are added sequentially. The mixture is heated to 75° C. with stirring for 1.5 h, then diluted with 0.1N sodium hydroxide and extracted twice with 1:1 hexane-ethyl ether. Combined extracts are dried (sodium sulfate), filtered, concentrated, and chromatographed on silica (4:1 to 1:1 hexane-EtOAc) to give the title compound (0.50 g): 1H NMR (CDCl3, 400 MHz) δ 0.95 (t, 6H), 1.6 (m, 4H), 2.2 (s, 3H), 2.4 (s, 3H), 3.75 (s, 3H), 3.85 (s, 3H), 3.95 (br d, 1H), 4.1 (br q, 1H), 6.5 (s, 1H), 6.55 (d, 1H) 7.2 (d, 1H); MS (CI) 330.

Examples 2–20a

In the Table I may be Prepared Following the Methods Described in Example 1.

TABLE I

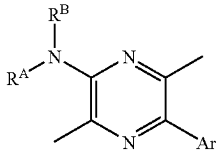

| EX# | $R_A$ | $R_B$ | Ar | 1H NMR (CDCl3) | MS (Cl) | Name |
|---|---|---|---|---|---|---|
| 2 | H | 1-ethylpropyl | 2,4-dichlorophenyl | 1.0 (t, 6H), 1.6 (m, 4H), 2.2 (s, 3H), 2.4 (s, 3H), 4.05 (br, 2H), 7.25 (d, 1H), 7.3 (d, 1 H), 7.45 (s, 1 H) | 338 | 3,6-dimethyl-N-(1-ethylpropyl)-5-(2,4-dichlorophenyl)pyrazin-2-amine |
| 3 | H | 1-ethylpropyl | 4-methoxy-2-methylphenyl | 1.0 (t, 6H), 1.5–1.7 (m, 4H), 2.1 (s, 3H), 2.2 (s, 3H), 2.4 (s, 3H), 3.8 (s, 3H, 4.0 (br, 1H), 4.1 (br, 1H), 6.75 (d, 1H), 6.8 (s, 1H), 7.1 (s, 1H) | 326 | 3,6-dimethyl-N-(1-ethylpropyl)-5-(2-methyl-4-methoxyphenyl)pyrazin-2-amine |

TABLE I-continued

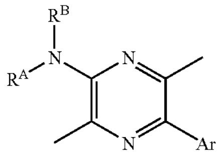

| EX# | $R_A$ | $R_B$ | Ar | 1H NMR (CDCl3) | MS (Cl) | Name |
|---|---|---|---|---|---|---|
| 4 | H | 1-ethylpropyl | 3-cyanophenyl | 0.95 (t, 6H), 1.6 (m, 4H), 2.4 (s, 3H), 2.45 (s, 3H), 4.1 (br, 2H), 7.5 (t, 1 H), 7.6 (d, 1H), 7.75 (d, 1H), 7.85 (s, 1H) | 295 | 3,6-dimethyl-N-(1-ethylpropyl)-5-(3-cyanophenyl)pyrazin-2-amine |
| 5 | H | 1-methoxy-2-butyl | 2,4-dichlorophenyl | 1.0 (t, 3H), 1.7 (m, 2H), 2.2 (s, 3H), 2.4 (s, 3H), 3.4 (s, 3H), 3.55 (m, 2H), 4.25 (br, 1H), 4.55 (d, 1H), 7.25 (d, 1H), 7.3 (d, 1H), 7.45 (s, 1H) | 354 | 3,6-dimethyl-N-(1-methoxy-2-butyl)-5-(2,4-dichlorophenyl)pyrazin-2-amine |
| 6 | H | 1-methoxy-2-butyl | 2,4-dimethoxyphenyl | 1.0 (t, 3H), 1.7 (m, 2H), 2.2 (s, 3H), 2.4 (s, 3H), 3.4 (s, 3H), 3.55 (m 2H), 3.75 (s, 3H), 3.85 (s, 3H), 4.25 (br, 1H), 4.4 (d, 1H), 6.5 (s, 1H), 6.6 (d, 1H), 7.2 (d, 1H) | 346 | 3,6-dimethyl-N-(1-methoxy-2-butyl)-5-(2,4-dimethoxyphenyl)pyrazin-2-amine |
| 7 | | 2-methoxymethyl-1-pyrrolidine | 2,4-dichlorophenyl | 1.9 (m, 4H), 2.2 (s, 3H), 2.6 (s, 3H), 3.3 (dd, 1H), 3.35 (s, 3H), 3.4 (br, 1H), 3.6 (dd, 1H), 3.8 (m, 1H), 4.6 (m, 1H), 7.3 (s, 2H), 7.5 (s, 1H) | 366 | 2-(2,4-dichlorophenyl)-5-[2-(methoxymethyl)pyrrolidin-1-yl]-3,6-dimethylpyrazine |
| 8 | | 2-methoxymethyl-1-pyrrolidine | 2,4-dimethoxyphenyl | 1.9 (m, 4H), 2.2 (s, 3H), 2.6 (s, 3H), 3.3 (dd, 1H), 3.4 (s, 3H), 3.6 (dd, 1H), 3.75 (s, 3H), 3.85 (s, 3H), 4.6 (m, 1H), 6.5 (s, 1H), 6.6 (d, 1H), 7.2 (d, 1H) | 358 | 2-(2,4-dimethoxyphenyl)-5-[2-(methoxymethyl) pyrrolidin-1-yl]-3,6-dimethylpyrazine |
| 9 | H | 1-propylbutyl | 2,4-dichlorophenyl | 1.0 (t, 6H), 1.3–1.6 (m, 8H), 2.2 (s, 3H), 2.35 (s, 3H), 4.0 (d, 1H), 4.25 (m, 1H), 7.25 (m, 2H), 7.45 (s, 1H) | 366 | 3,6-dimethyl-N-(1-propylbutyl)-5-(2,4-dichlorophenyl)pyrazin-2-amine |
| 10 | H | 1-propylbutyl | 4-methoxy-2-methylphenyl | 1.0 (t, 6H), 1.3–1.6 (m, 8H), 2.1 (s, 3H), 2.2 (s, 3H), 2.35 (s, 3H), 3.8 (s, 3H), 3.9 (d, 1H), 4.25 (m, 1H), 6.8 (m, 2H), 7.1 (d, 1H) | 342 | 3,6-dimethyl-N-(1-propylbutyl)-5-(2-methyl-4-methoxyphenyl)pyrazin-2-amine |
| 11 | H | 1-propylbutyl | 4-chloro-2-methylphenyl | 1.0 (t, 6H), 1.3–1.6 (m, 8H), 2.15 (s, 3H), 2.2 (s, 3H), 2.35 (s, 3H), 4.0 (d, 1H), 4.25 (br, 1H), 7.1 (d, 1H), 7.2 (d, 1H), 7.25 (s, 1H) | 346 | 3,6-dimethyl-N-(1-propylbutyl)-5-(2-methyl-4-chlorophenyl)pyrazin-2-amine |
| 12 | H | 1-propylbutyl | 4-dimethylamino-2-trifluoromethylphenyl | 1.0 (t, 6H), 1.3–1.6 (m, 8H), 2.1 (s, 3H), 2.3 (s, 3H), 3.0 (s, 6H), 3.9 (d, 1H), 4.25 (m, 1H), 6.8 (d, 1H), 7.0 (s, 1H), 7.1 (d, 1H) | 409 | 3,6-dimethyl-N-(1-propylbutyl)-5-(2-trifluoromethyl-4-dimethylaminophenyl)pyrazin-2-amine |
| 13 | H | 1-phenylpropyl | 2,4-dichlorophenyl | 1.0 (t, 3H), 1.9–2.1 (m, 2H), 2.2 (s, 3H), 2.4 (s, 3H), 4.6 (d, 1H), 5.15 (q, 1H), 7.2–7.4 (m, 8H) | 386 | 3,6-dimethyl-N-(3-phenylpropyl)-5-(2,4-dichlorophenyl)pyrazin-2-amine |
| 14 | H | 1-phenylpropyl | 4-methoxy-2-methylphenyl | 1.0 (t, 3H), 1.9–2.1 (m, 2H), 2.05 (s, 3H), 2.1 (s, 3H), 2.4 (s, 3H), 3.8 (s, 3H), 4.5 (d, 1H), 5.15 (q, 1H), 6.8 (m, 2H), 7.0 (d, 1H), 7.2–7.4 (m, 5H) | 362 | 3,6-dimethyl-N-(3-phenylpropyl)-5-(2-methyl-4-methoxyphenyl)pyrazin-2-amine |
| 15 | H | 1-phenylpropyl | 4-chloro-2-methylphenyl | 1.0 (t, 3H), 1.9–2.1 (m, 2H), 2.05 (s, 3H), 2.1 (s, 3H), 2.4 (s, 3H), 3.8 (s, 3H), 4.5 (d, 1H), 5.15 (q, 1H), 7.0 (d, 1H), 7.2–7.4 (m, 7H) | 366 | 3,6-dimethyl-N-(3-phenylpropyl)-5-(2-chloro-4-methylphenyl)pyrazin-2-amine |

TABLE I-continued

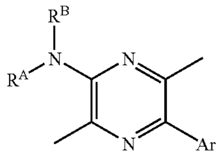

| EX# | $R_A$ | $R_B$ | Ar | 1H NMR (CDCl3) | MS (Cl) | Name |
|---|---|---|---|---|---|---|
| 16 | H | 1-phenylpropyl | 4-dimethylamino-2-trifluoromethylphenyl | 1.0 (t, 3H), 1.8–2.1 (m, 2H), 2.1 (s, 3H), 2.4 (s, 3H), 3.0 (s, 6H), 4.5 (d, 1H), 5.15 (q, 1H), 6.8 (d, 1H), 7.0 (s, 1H), 7.1 (d, 1H), 7.2–7.4 (m, 5H) | 429 | 3,6-dimethyl-N-(3-phenylpropyl)-5-(2-trifluoromethyl-4-dimethylaminophenyl)pyrazin-2-amine |
| 17 | H | 1-propylbutyl | 2,4-dimethoxyphenyl | 1.0 (t, 6H), 1.3–1.6 (m, 8H), 2.2 (s, 3H), 2.35 (s, 3H), 3.75 (s, 3H), 3.85 (s, 3H), 3.9 (d, 1H), 4.25 (br, 1H), 6.5 (s, 1H), 6.55 (d, 1H), 7.2 (d, 1H) | 358 | 3,6-dimethyl-N-(1-propylbutyl)-5-(2,4-dimethoxyphenyl)pyrazin-2-amine |
| 18 | H | 1-phenylpropyl | 2,4-dimethoxyphenyl | 1.0 (t, 3H), 1.9–2.1 (m, 2H), 2.2 (s, 3H), 2.4 (s, 3H), 3.7 (s, 3H), 3.8 (s, 3H), 4.5 (d, 1H), 5.15 (q, 1H), 6.5 (s, 1H), 6.55 (d, 1H), 7.1 (d, 1H), 7.2–7.4 (m, 5H) | 378 | 3,6-dimethyl-N-(3-phenylpropyl)-5-(2,4-dimethoxyphenyl)pyrazin-2-amine |
| 19 | H | 1-ethylpropyl | 4-chloro-2-methylphenyl | 1.0 (t, 6H), 1.4–1.6 (m, 4H), 2.1 (s, 3H), 2.15 (s, 3H), 2.4 (s, 3H), 4.0–4.1 (br, 2H), 7.1 (d, 1H), 7.2 (d, 1H), 7.25 (s, 1H) | 318 | 3,6-dimethyl-N-(1-ethylpropyl)-5-(2-methyl-4-chlorophenyl)pyrazin-2-amine |
| 20 | H | 1-ethylpropyl | 4-dimethylamino-2-trifluoromethylphenyl | 11.0 (t, 6H), 1.4–1.6 (m, 4H), 2.15 (s, 3H), 2.35 (s, 3H), 3.0 (s, 6H), 4.0 (d, 1H), 4.1 (m, 1H), 6.8 (d, 1H), 7.0 (s, 1H), 7.1 (d, 1H) | 381 | 3,6-dimethyl-N-(1-ethylpropyl)-5-(2-trifluoromethyl-4-dimethylaminophenyl)pyrazin-2-amine |
| 20a | H | 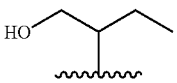 | 2,4-dichlorophenyl | 0.89 (t, 3H), 1.6 (m, 2H), 2.14 (s, 3H), 2.42 (s, 3H), 3.44 (m, 2H), 4.16 (m, 1H), 7.43 (d, 1H), 7.50 (d, 1H0, 7.72 (s, 1H); HCl salt | 340, | 2-{[5-(2,4-dimethylphenyl)-3,6-dimethylpyrazin-2-yl]amino}butan-1-ol |

Example 21

[N-(1-ethyl)propyl]-3,6-dimethyl-5-(2,4,6-trimethylphenyl) pyrazine-2-amine [Formula I: Ar=2,4,6-trimethylphenyl; $R_2$=—N-(1-ethyl)propyl; $R_1=R_3=CH_3$]

To a solution of 5-bromo-[N-(1-ethyl)propyl]-3,6-dimethylpyrazine-2-amine (200 mg) obtained as in Example 1B in THF (4 mL) at room temperature is added [1,3-bis(diphenylphosphino)propane]dichloronickel(II) (40 mg). After 10 min, 2,4,6-trimethylphenylmagnesium bromide (1.0M in THF, 4 mL) is added slowly dropwise. The mixture is stirred at room temperature for 1 day, then refluxed overnight. The resulting dark solution is poured into aqueous ammonium chloride and extracted twice with ether. Combined extracts are dried (sodium sulfate), filtered, concentrated, and chromatographed to give the desired product (87 mg): $^1$H NMR ($CDCl_3$, 400 MHz) δ 1.0 (t, 6H), 1.5–1.7 (m, 4H), 1.95 (s, 3H), 2.1 (s, 3H), 2.3 (s, 3H), 2.35 (s, 3H), 3.95 (br, 1H), 4.1 (br, 1H), 6.9 (s, 2H).

Example 22

3-ethyl-[N-(1-ethyl)propyl]-6-methyl-5-(2,4,6-trimethylphenyl) pyrazine-2-amine [Formula I: Ar=2,4,6-trimethylphenyl; $R_2$=—N(1-ethyl)propyl; $R_1=CH_2CH_3$; $R_3=CH_3$]

To a solution of [N-(1-ethyl)propyl]-3,6-dimethyl-5-(2,4,6-trimethylphenyl)pyrazine-2-amine (74 mg; 0.24 mmol) in THF (2 mL) at 0° C. is added n-butyllithium (2.5M in hexane, 0.24 mL). After 10 min at 0° C., iodomethane (0.020 mL) is added. The mixture is stirred at 0° C. for 10 min before being poured into aqueous ammonium chloride and extracted with $Et_2O$. The extract is dried (sodium sulfate), filtered, concentrated and the residue is purified by preparative TLC (10% EtOAc in hexane, developed 3 times) to give the title compound (17 mg): $^1$H NMR ($CDCl_3$, 400 MHz) δ 1.0 (t, 6H), 1.25 (t. 3H), 1.5–1.7 (m, 4H), 1.95 (s, 3H), 2.05 (s, 3H), 2.3 (s, 3H), 2.65 (q, 2H), 4.05 (m, 2H), 6.9 (s, 2H).

Example 23

3,6-diethyl-5-(2,4-dimethoxyphenyl)-[N-(1-ethylpropyl)]pyrazine-2-amine [Formula I: Ar=2,4-dimethoxyphenyl; $R_2$=—N(1-ethyl)propyl; $R_1$=$R_3$=$CH_2CH_3$]

2-Chloro-3,6-diethylpyrazine (*Chem. Pharm. Bull. Jap.*, 27, 2027 (1979)) is converted to the desired product following the procedures described in Example 1: $^1H$ NMR ($CDCl_3$, 300 MHz) δ 0.95 (t, 6H), 1.15 (t, 3H), 1.25 (t, 3H), 1.5–1.7 (m, 4H), 2.45 (q, 2H), 2.65 (q, 2H), 3.75 (s, 3H), 3.85 (s, 3H), 4.0–4.2 (br, 2H), 6.5 (s, 1H), 6.55 (d, 1H), 7.2 (d, 1H).LC-MS: 358

Examples 24–48

In the Table II may be Prepared Following the General Procedure Described in Example 23

TABLE II

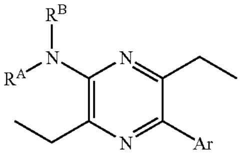

| EX# | $R_A$ | $R_B$ | Ar | 1HNMR ($CDCl_3$) | MS (Cl) | Name |
|---|---|---|---|---|---|---|
| 23a | H | 1-ethylpropyl | 2-methoxy-4-trifluoro-methoxyphenyl | 0.96(t, 6H), 1.15(t, 3H), 1.28(t, 3H), 1.57(m, 2H), 1.67(m, 2H), 2.42(m, 2H), 2.66(q, 2H), 3.78(s, 3H), 4.10(br. 2H), 6.77(s, 1H), 6.89(d, 1H), 7.27(d, 1H) | 412 | 3,6-diethyl-N-(1-ethylpropyl)-5-(2-methoxy-4-trifluoromethoxyphenyl) pyrazin-2-amine |
| 23b | H | 1-ethylpropyl | 4-methoxy-2-trifluoro-methoxyphenyl | 0.96(t, 6H), 1.15(t, 3H), 1.27(t, 3H), 1.57(m, 2H), 1.67(m, 2H), 2.45(q, 2H), 2.63(q, 2H), 3.85(s, 3H), 4.10(br. 2H), 6.86(brs, 1H), 6.89(dd, 1H), 7.29(d, 1H) | 412 | 3,6-diethyl-N-(1-ethylpropyl)-5-(2-trifluoromethoxy-4-methoxyphenyl)pyrazin-2-amine |
| 23c | H | 1-ethylpropyl | 2-methoxy-4-trifluoro-methylphenyl | 0.96(t, 6H), 1.15(t, 3H), 1.28(t, 3H), 1.57(m, 2H), 1.67(m, 2H), 2.42(m, 2H), 2.63(q, 2H), 3.82(s, 3H), 4.10(m, 2H), 7.14(s, 1H), 7.28(d, 1H), 7.38(d, 1H) | 396 | 3,6-diethyl-N-(1-ethylpropyl)-5-(2-methoxy-4-trifluoromethylphenyl) pyrazin-2-amine |
| 23d | H | 1-ethylpropyl | 4-methoxy-2-trifluoro-methylphenyl | 0.96(t, 6H), 1.31(t, 3H), 1.24(t, 3H), 1.57(m, 2H), 1.67(m, 2H), 2.34(q, 2H), 2.63(q, 2H), 3.87(s, 3H), 4.10(m, 2H), 7.07(dd, 1H), 7.24(d, 1H), 7.25(s, 1H) | 396 | 3,6-diethyl-N-(1-ethylpropyl)-5-(2-trifluoromethyl-4-methoxyphenyl)pyrazin-2-amine |
| 23e | H | 1-ethylpropyl | 2-methoxy-4-methyl-phenyl | 0.95(t, 6H), 1.14(t, 3H), 1.28(t, 3H), 1.55(m, 2H), 1.67(m, 2H), 2.38(s, 3H), 2.46(m, 2H), 2.64(q, 2H), 3.75(s, 3H), 4.10(m, 2H), 6.74(s, 1H), 6.82(d, 1H), 7.14(d, 1H) | 342 | 3,6-diethyl-N-(1-ethylpropyl)-5-(2-methoxy-4-methylphenyl)pyrazin-2-amine |
| 23f | H | 1-ethylpropyl | 2,4-ditrifluoro-methoxyphenyl | 0.96(t, 6H), 1.17(t, 3H), 1.27(t, 3H), 1.57(m, 2H), 1.69(m, 2H), 2.44(m, 2H), 2.64(q, 2H), 4.10(m, 2H), 7.20(s, 1H), 7.22(d, 1H), 7.44(d, 1H) | 466 | 3,6-diethyl-N-(1-ethylpropyl)-5-(2,4-bis-trifluoro-methoxyphenyl) pyrazin-2-amine |
| 23g | H | 1-ethylpropyl | 2,4-dichlorophenyl | 0.96(t, 6H), 1.14(t, 3H), 1.28(t, 3H), 1.57(m, 2H), 1.67(m, 2H), 2.43(m, 2H), 2.64(q, 2H), 4.12(m, 2H), 7.25(d, 1H), 7.30(dd, 1H), 7.46(d, 1H) | 366 | 3,6-diethyl-N-(1-ethylpropyl)-5-(2,4-dichlorophenyl) pyrazin-2-amine |
| 24 | H | 1-methoxy-2-butyl | 2,4-dichlorophenyl | | 382 | 3,6-diethyl-N-(1-methoxy-2-butyl)-5-(2,4-dichlorophenyl) pyrazin-2-amine |
| 25 | H | 1-methylpropyl | 2,4-dichlorophenyl | | 352 | 3,6-diethyl-N-(1-methylpropyl)-5-(2,4-dichlorophenyl) pyrazin-2-amine |

TABLE II-continued

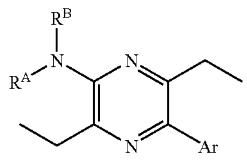

| EX# | $R_A$ | $R_B$ | Ar | 1HNMR ($CDCl_3$) | MS (Cl) | Name |
|---|---|---|---|---|---|---|
| 26 | H | 1-phenylethyl | 2,4-dichlorophenyl | | 400 | 3,6-diethyl-N-(2-phenylethyl)-5-(2-methyl-4-chlorophenyl) pyrazin-2-amine |
| 27 | H | 1-propylbutyl | 4-chloro-2-methylphenyl | | 374 | 3,6-diethyl-N-(1-propylbutyl)-5-(2-methyl-4-chlorophenyl) pyrazin-2-amine |
| 28 | H | 1-methoxy-2-butyl | 4-chloro-2-methylphenyl | | 362 | 3,6-diethyl-N-(1-methoxy-2-butyl)-5-(2-methyl-4-chlorophenyl) pyrazin-2-amine |
| 29 | H | 1-methylpropyl | 4-chloro-2-methylphenyl | | 332 | 3,6-diethyl-N-(1-methylpropyl)-5-(2-methyl-4-chlorophenyl) pyrazin-2-amine |
| 30 | H | 1-phenylethyl | 4-chloro-2-methylphenyl | | 380 | 3,6-diethyl-N-(2-phenylethyl)-5-(2-methyl-4-chlorophenyl) pyrazin-2-amine |
| 31 | H | 1-propylbutyl | 4-methoxy-2-methylphenyl | | 370 | 3,6-diethyl-N-(1-propylbutyl)-5-(2-methyl-4-chlorophenyl) pyrazin-2-amine |
| 32 | H | 1-methoxy-2-butyl | 4-methoxy-2-methylphenyl | | 358 | 3,6-diethyl-N-(1-methoxy-2-butyl)-5-(2-methyl-4-methoxyphenyl) pyrazin-2-amine |
| 33 | H | 1-methylpropyl | 4-methoxy-2-methylphenyl | | 328 | 3,6-diethyl-N-(1-methylpropyl)-5-(2-methyl-4-methoxyphenyl) pyrazin-2-amine |
| 34 | H | 1-propylbutyl | 2,4-dimethoxyphenyl | | 386 | 3,6-diethyl-N-(1-propylbutyl)-5-(2,4-dimethoxyphenyl) pyrazin-2-amine |
| 35 | H | 1-methoxy-2-butyl butyl | 2,4-dimethoxyphenyl | | 374 | 3,6-diethyl-N-(1-methoxy-2-butyl)-(2,4-dimethoxyphenyl) pyrazin-2-amine |
| 36 | H | 1-methylpropyl | 2,4-dimethoxyphenyl | | 344 | 3,6-diethyl-N-(1-methylpropyl)-5-(2,4-dimethoxyphenyl) pyrazin-2-amine |
| 37 | H | 1-phenylethyl | 2,4-dimethoxyphenyl | | 392 | 3,6-diethyl-N-(2-phenylethyl)-5-(2,4-dimethoxyphenyl) pyrazin-2-amine |
| 38 | H | benzyl | 2,4-dimethoxyphenyl | | 378 | 3,6-diethyl-N-benzyl-5-(2,4-dimethoxyphenyl) pyrazin-2-amine |
| 39 | H | 2-methyl-1-phenylpropyl | 2,4-dimethoxyphenyl | | 420 | |
| 40 | H | 1-propylbutyl | 2-chloro-4-(dimethylamino) phenyl | | 403 | 3,6-diethyl-N-(1-propylbutyl)-5-(2-chloro-4-dimethylaminophenyl) pyrazin-2-amine |
| 41 | H | 1-methoxy-2-butyl | 2-chloro-4-(dimethylamino) phenyl | | 391 | 3,6-diethyl-N-(1-methoxy-2-butyl)-5-(2-chloro-4-dimethylaminophenyl) pyrazin-2-amine |

TABLE II-continued

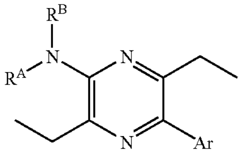

| EX# | $R_A$ | $R_B$ | Ar | 1HNMR ($CDCl_3$) | MS (Cl) | Name |
|---|---|---|---|---|---|---|
| 42 | H | 1-methylpropyl | 2-chloro-4-(dimethylamino) phenyl | | 361 | 3,6-diethyl-N-(1-methylpropyl)-5-(2-chloro-4-dimethylaminophenyl) pyrazin-2-amine |
| 43 | H | 2-methylpropyl | 2-chloro-4-(dimethylamino) phenyl | | 361 | 3,6-diethyl-N-(2-methylpropyl)-5-(2-chloro-4-dimethylaminophenyl) pyrazin-2-amine |
| 44 | H | 1-phenylethyl | 2-chloro-4-(dimethylamino) phenyl | | 409 | 3,6-diethyl-N-(2-phenylethyl)-5-(2-chloro-4-dimethylphenyl) pyrazin-2-amine |
| 45 | H | 1-propylbutyl | 4-dimethylamino-2-(trifluoromethyl) phenyl | | 437 | 3,6-diethyl-N-(1-propylbutyl)-5-(2-trifluoromethyl-4-dimethylaminophenyl) pyrazin-2-amine |
| 46 | H | 1-methoxy-2-butyl | 4-dimethylamino-2-(trifluoromethyl) phenyl | | 425 | 3,6-diethyl-N-(1-methoxy-2-butyl)-5-(2-trifluoromethyl-4-dimethylaminophenyl) pyrazin-2-amine |
| 46a | H | 1-ethylpropyl | 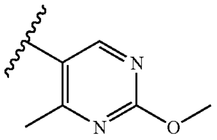 | | | 5-(2-methoxy-4-methylpyrimidin-5-yl)-3,6-diethyl-N-(1-ethylpropyl) pyrazin-2-amine |
| 46b | H | 1-ethylpropyl | 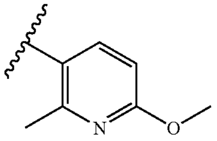 | | | 5-(2-methyl-6-methoxypyridin-3-yl)-3,6-diethyl-N-(1-ethylpropyl) pyrazin-2-amine |
| 46c | H | 1-ethylpropyl | 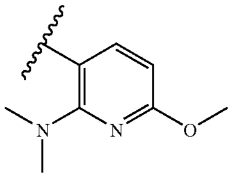 | | | 5-(2-dimethylamino-6-methoxypyridin-3-yl)-3,6-diethyl-N-(1-ethylpropyl) pyrazin-2-amine |
| 46d | H | 1-ethylpropyl | 5-chloro-2,4-dimethylphenyl | | | 3,6-diethyl-N-(1-ethylpropyl)-5-(2,4-dimethyl-5-chlorophenyl) pyrazin-2-amine |
| 46e | H | 1-ethylpropyl | 2,4-dichloro-5-methylphenyl | | | 3,6-diethyl-N-(1-ethylpropyl)-5-(2,4-dimethyl-5-methylphenyl) pyrazin-2-amine |
| 46f | H | 1-ethylpropyl | 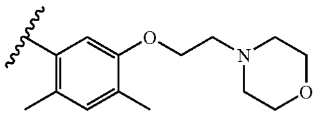 | | | 5-[2,4-dimethyl-5-(2-morpholin-4-ylethoxy) phenyl]-3,6-diethyl-N-(1-ethylpropyl) pyrazin-2-amine |

TABLE II-continued

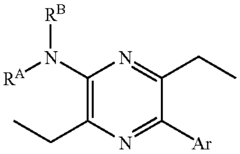

| EX# | $R_A$ | $R_B$ | Ar | 1HNMR ($CDCl_3$) | MS (Cl) | Name |
|---|---|---|---|---|---|---|
| 46g | H | 1-ethylpropyl | 2,4-dimethyl-5-methoxyphenyl | | | 3,6-diethyl-N-(1-ethylpropyl)-5-(2,4-dimethyl-5-methoxyphenyl) pyrazin-2-amine |
| 46h | H | 1-ethylpropyl | 2-methyl-4-methoxyphenyl | | 342 | 3,6-diethyl-N-(1-ethylpropyl)-5-(2-methyl-4-methoxy-phenyl)pyrazin-2-amine |
| 46i | H | 1-ethylpropyl | 2-methyl-4-chlorophenyl | | 382 | 3,6-diethyl-N-(1-ethylpropyl)-5-(2-methyl-4-chlorophenyl) pyrazin-2-amine |
| 46j | H | 1-ethylpropyl | 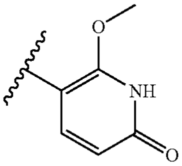 | | 345 | 5-[5-(2-ethylpropylamino)-3,6-dimethylpyrazin-2-yl]-6-methoxypyridin-2(3H)-one |
| 46k | H | 1-ethylpropyl | 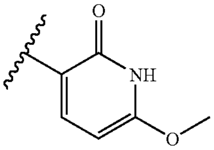 | | 345 | 3-[5-(1-ethylpropylamino)-3,6-dimethylpyrazin-2-yl]-6-methoxypyridin-2(3H)-one |
| 47 | H | 1-methylpropyl | 4-dimethylamino-2-(trifluoromethyl) phenyl | | 395 | 3,6-diethyl-N-(1-methylpropyl)-5-(2-trifluoromethyl-4-methoxyphenyl) pyrazin-2-amine |
| 47a | H | 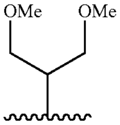 | 2-methoxy-4,6-dimethylphenyl | 1.10 (t, 3H), 1.26 (t, 3H), 1.94 (s, 3H), 2.33 (s, 3H), 2.38 (m, 2H), 2.67 (m, 2H), 3.40 (s, 3H), 3.42 (s, 3H), 3.57 (m, 2H), 3.68 (m, 2H), 3.70 (s, 3H), 4.53 (m, 1H), 4.69 (m, 1H), 6.60 (s, 1H), 6.71 (s, 1H) | 388 | 3,6-diethyl-N-[2-methoxy-1-(methoxymethyl) ethyl]-5-(2-methoxy-4,6-dimethylphenyl) pyrazin-2-amine |
| 47b | H | 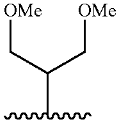 | 2,4-dimethoxyphenyl | 1.14 (t, 3H), 1.26 (t, 3H), 2.44 (m, 2H), 2.67 (m, 2H), 3.40 (s, 6H), 3.53 (m, 2H), 3.66 (m, 2H), 3.75 (s, 3H), 3.82 (s, 3H), 4.52 (m, 1H), 4.71 (m, 1H), 6.50 (s, 1H), 6.55 (d, 1H), 7.18 (d, 1H) | 390 | 3,6-diethyl-N-[2-methoxy-1-(methoxymethyl) ethyl]-5-(2,4-dimethoxyphenyl) pyrazin-2-amine |
| 47c | H | 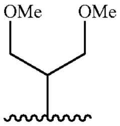 | 2,4-dichlorophenyl | 1.14 (t, 3H), 1.29 (t, 3H), 2.43 (b, 2H), 2.66 (m, 2H), 3.42 (s, 6H), 3.56 (m, 2H), 3.68 (m, 2H), 4.55 (m, 1H), 4.86 (d, 1H), 7.3 (m, 2H), 7.48 (m, 1H) | 398 | 3,6-diethyl-N-[2-methoxy-1-(methoxymethyl)ethyl]-5-(2,4-dichlorophenyl) pyrazin-2-amine |

TABLE II-continued

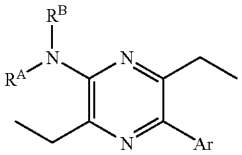

| EX# | $R_A$ | $R_B$ | Ar | 1HNMR ($CDCl_3$) | MS (Cl) | Name |
|---|---|---|---|---|---|---|
| 47d | H | 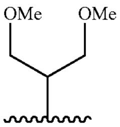 | 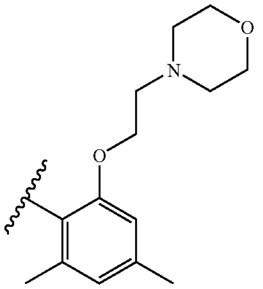 | 1.11 (t, 3H), 1.26 (t, 3H), 1.98 (s, 3H), 2.29 (m, 4H), 2.32 (s, 3H), 2.37 (m, 2H), 2.57 (m, 2H), 2.66 (m, 2H), 3.42 (s, 6H), 3.54 (m, 6H), 3.68 (m, 2H), 4.0 (m, 2H), 4.54 (m, 1H), 4.70 (d, 1H), 6.59 (s, 1H), 6.72 (s, 1H) | 487 | 3,6-diethyl-N-[2-methoxy-1-(methoxymethyl) ethyl]-5-[2,4-dimethyl-6-(2-morpholin-4-ylethoxy)phenyl]-pyrazin-2-amine |
| 47e | H | 1-ethylpropyl | 4-fluoro-2-methylphenyl | 0.98 (t, 6H), 1.12 (t, 3H), 1.28 (t, 3H), 1.57 (m, 2H), 1.71 (m, 2H), 2.13 (s, 3H), 2.40 (m, 2H), 2.66 (m, 2H), 4.1 (b, 2H), 6.93 (m, 2H), 7.15 (m, 1H) | 330 | 3,6-diethyl-N-(1-ethylpropyl)-5-(2-methyl-4-fluorophenyl) pyrazin-2-amine |
| 47f | 2-methoxy ethyl | 2-methoxyethyl | 2,4-dichlorophenyl | 1.13 (t, 3H), 1.24 (t, 3H), 2.5 (b, 2H), 2.84 (q, 2H), 3.33 (s, 6H), 3.6 (m, 8H), 7.31 (m, 2H), 7.49 (s, 1H) | 413 | 3,6-diethyl-N,N-(2-methoxyethyl)-5-(2,4-dichlorophenyl) pyrazin-2-amine |
| 47g | Propyl | Cyclopropyl methyl | 2,4-dichlorophonyl | 0.12 (m, 2H), 0.48 (m, 2H), 0.91 (t, 3H), 1.05 (m, 1H), 1.15 (m, 3H), 1.3 (m, 3H), 1.6 (m, 2H), 2.5 (b, 2H), 2.83 (m, 2H), 3.16 (m, 2H), 3..34 (m, 2H), 7.34 (s, 2H), 7.49 (s, 1H) | 391 | 3,6-diethyl-N-propyl-N-(cyclopropylmethyl)-5-(2,4-dichlorophenyl) pyrazin-2-amine |
| 47h | H | 1-ethylpropyl | 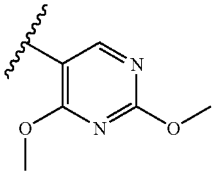 | 0.94 (t, 6H), 1.16 (t, 3H), 1.28 (t, 3H), 1.55 (m, 2H), 1.78 (m, 2H), 2.42 (q, 2H), 2.62 (q, 2H), 3.94 (s, 3H), 4.01 (s, 3H), 4.12 (m, 2H), 8.2 (s, 1H) | 361 | 5-(2,4-dimethoxypyrimidin-5-yl)-3,6-diethyl-N-(1-ethylpropyl) pyrazin-2-amine |
| 47i | H | 1-ethylpropyl | 2,4-bis(trifluoromethyl)-6-methoxyphenyl | 0.98 (t, 6H), 1.12 (t, 3H), 1.25 (t, 3H), 2.64 (m, 4H), 2.29 (q, 2H), 2.61 (q, 2H), 3.81 (s, 3H), 4.12 (m, 2H), 7.33 (s, 1H), 7.60 (s, 1H) | 464 | 3,6-diethyl-N-(1-ethylpropyl)-5-(2,4-bis-trifluoromethyl-6-methoxyphenyl)pyrazin-2-amine |
| 47j | H | 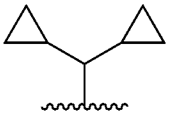 | 2,4-dichlorophenyl | 0.5 (m, 8H), 1.03 (m, 2H), 1.1 (t, 3H), 1.3 (t, 3H), 2.4 (b, 2H), 2.66 (m, 2H), 3.5 (m, 1H), 4.25 (d, 1H), 7.25 (m, 2H), 7.46 (s, 1H) | 390 | 3,6-diethyl-N-(dicyclopropylmethyl)-5-(2,4-dichlorophenyl) pyrazin-2-amine |
| 47k | H | 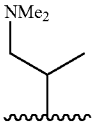 | 2,4-dichlorophenyl | 1.16 (t, 3H), 1.28 (t, 3H), 1.35 (d, 3H), 2.25 (m, 2H), 2.29 (s, 6H), 2.5 (m, 2H), 2.68 (m, 2H), 4.06 (m, 1H), 5.15 (b, 1H), 7.28 (m, 2H), 7.47 (s, 1H) | 381 | $N^2$-[3,6-diethyl-(5-2,4-dichlorophenyl) pyrazin-2-yl]-$N^1$,$N^1$-dimethylpropane-1,2-diamine |

TABLE II-continued

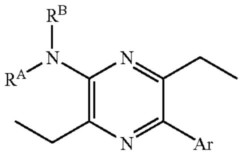

| EX# | $R_A$ | $R_B$ | Ar | 1HNMR ($CDCl_3$) | MS (Cl) | Name |
|---|---|---|---|---|---|---|
| 47l | H | 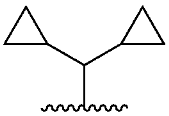 | 2,4-dimethoxyphenyl | 0.48 (m, 8H), 1.05 (m, 2H), 1.12 (t, 3H), 1.30 (t, 3H), 2.41 (q, 2H), 2.69 (q, 2H), 3.50 (m, 1H), 3.74 (s, 3H), 3.83 (s, 3H), 4.31 (d, 1H), 6.51 (s, 1H), 6.56 (d, 1H), 7.17 (d, 1H) | 382 | 3,6-diethyl-N-(dicyclopropylmethyl)-5-(2,4-dimethoxyphenyl) pyrazin-2-amine |
| 47m | H | 1-ethylpropyl | 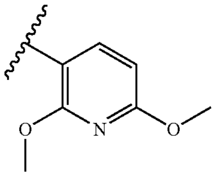 | 0.97 (t, 6H), 1.15 (t, 3H), 1.28 (t, 3H), 1.6 (m, 4H), 2.46 (q, 2H), 2.65 (q, 2H), 3.91 (s, 3H), 3.94 (s, 3H), 4.07 (m, 2H), 6.40 (d, 1H), 7.50 (d, 1H) | 359 | 3,6-diethyl-N-(1-ethylpropyl)-5-(2,6-dimethoxypyridin-3-yl)pyrazin-2-amine |
| 47n | H | 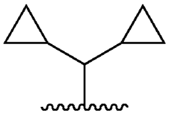 | 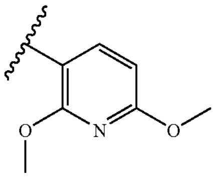 | 0.44 (m, 8H), 1.03 (m, 2H), 1.12 (t, 3H), 1.30 (t, 3H), 2.44 (q, 2H), 2.67 (q, 2H), 3.49 (m, 1H), 3.90 (s, 3H), 3.94 (s, 3H), 4.34 (d, 1H), 6.40 (d, 1H), 7.50 (d, 1H) | 383 | 3,6-diethyl-N-(dicyclopropylmethyl)-5-(2,6-dimethoxypyridin-3-yl)pyrazin-2-amine |
| 47o | Propyl | 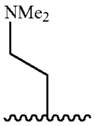 | 2,4-dichlorophenyl | 0.90 (t, 3H), 1.05 (t, 3H), 1.25 (t, 3H), 1.4 (m, 2H), 1.6 (m, 2H), 2.30 (s, 6H), 2.52 (m, 2H), 2.80 (m, 2H), 3.26 (m, 2H), 3.5 (b, 2H), 7.32 (m, 2H), 7.50 (s, 1H) | 409 | 3,6-diethyl-N-propyl-N-(2-dimethylaminoethyl)-5-(2,4-dichlorophenyl) pyrazin-2-amine |
| 47p | H | 1-ethylpropyl | 4-chloro-2-methylphenyl | | | 3,6-diethyl-N-(1-ethylpropyl)-5-(2-methyl-4-chlorophenyl) pyrazin-2-amine |
| 47q | H | 1-ethylpropyl | 2-chloro-4-methoxyphenyl | | | 3,6-diethyl-N-(1-ethylpropyl)-5-(2-methyl-4-methoxyphenyl) pyrazin-2-amine |
| 47r | H | 1-ethylpropyl | 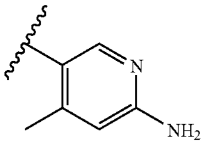 | | | 3,6-diethyl-N-(1-ethylpropyl)-5-(2-amino-4-methylpyridin-2-yl)pyrazin-2-amine |
| 47s | Ethyl | 1-ethylpropyl | 2,4-dichlorophenyl | | | 3,6-diethyl-N-(1-ethylpropyl)-5-(2,4-dichlorophenyl) pyrazin-2-amine |
| 47t | H | 1-ethylpropyl | 2-chloro-4-trifluoromethyl phenyl | | | 3,6-diethyl-N-(1-ethylpropyl)-5-(2-methyl-4-cyanophenyl) pyrazin-2-amine |
| 47u | H | 1-ethylpropyl | 4-cyano-2-methylphenyl | | | 3,6-diethyl-N-(1-ethylpropyl)-5-(2-methyl-4-chlorophenyl) pyrazin-2-amine |

TABLE II-continued

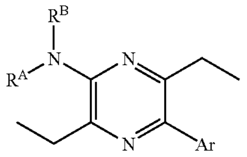

| EX# | $R_A$ | $R_B$ | Ar | 1HNMR ($CDCl_3$) | MS (Cl) | Name |
|---|---|---|---|---|---|---|
| 47v | H | 1-ethylpropyl | 4-cyano-2-trifluoromethyl phenyl | | | 3,6-diethyl-N-(1-ethylpropyl)-5-(2-trifluoromethyl-4-chlorophenyl) pyrazin-2-amine |
| 47w | H | 1-ethylpropyl | 2-cyano-4-methoxyphenyl | | | 3,6-diethyl-N-(1-ethylpropyl)-5-(2-cyano-4-methoxyphenyl) pyrazin-2-amine |
| 47x | H | 1-ethylpropyl | 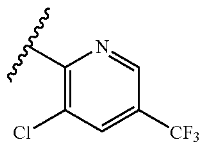 | | | 3,6-diethyl-N-(1-ethylpropyl)-5-(3 trifluoromethyl-5-chloropyridin-6-yl) pyrazin-2-amine |
| 47y | H | 1-ethylpropyl | 2-cyano-4-trifluoromethyl phenyl | | | 3,6-diethyl-N-(1-ethylpropyl)-5-(2-cyano-4-trifluoromethylphenyl) pyrazin-2-amine |
| 47z | Methyl | 1-ethylpropyl | 2-chloro-4-methoxyphenyl | | | 3,6-diethyl-N-methyl-N-(1-ethylpropyl)-5-(2-chloro-4-methoxyphenyl) pyrazin-2-amine |
| 48 | H | 1-phenylethyl | 4-dimethylamino-2-(trifluoromethyl) phenyl | | 443 | 3,6-diethyl-N-(2-phenylethyl)-5-(2-trifluoromethyl-4-dimethylaminophenyl) pyrazin-2-amine |

Example 48a

3,6-diethyl-5-(2,4-diethoxy)phenyl-[N-(1-ethylpropyl)]pyrazine-2-amine [Formula I: Ar=2,4-diethoxyphenyl; $R_2$=—N(1-ethyl)propyl; $R_1=R_3=CH_2CH_3$]

A: To a solution of 3,6-diethyl-5-(2,4-dimethoxyphenyl)-[N-(1-ethylpropyl)]pyrazine-2-amine (910 mg, 2.54 mmol) (obtained in example 23) in dichloromethane was added $BBr_3$ (1N,6 ml)at −78° C. The mixture is stirred for 10 min then gradually warmed to room temperature and stirred for 3 hr before being poured into ice-water and extracted with dichloromethane. The aqueous layer was basified with sat. $NaHCO_3$ and extracted with dichloromethane. The combined extracts were dried (sodium sulfate), filtered, concentrated and the residue is purified by column (20% EtOAc in hexane) to give 3,6-diethyl-5-(2,4-dihydroxyphenyl)-[N-(1-ethylpropyl)]pyrazine-2-amine as a yellow oil(590 mg, 71%): $^1H$ NMR ($CDCl_3$, 400 MHz) δ 0.94 (t, 6H), 1.30 (t, 3H), 1.36 (t, 3H), 1.57 (m, 2H), 1.67 (m, 2H), 2.62 (q, 2H), 2.86 (q, 2H), 4.15 (m, 2H). 6.41 (t, 1H), 6.51 (d, 1H), 7.27 (d, 1H). LC-MS: 330 (M+1).

B: The above yellow oil (60 mg, 0.182 mmol) was dissolved in DMF (2 ml) and alkylated with iodoethane (0.072 ml, 0.9 mmol) in the presence of $K_2CO_3$ (125 mg) at 75° C. for 2 hr. The reaction mixture was then diluted with water and extracted with EtOAc. The extracts were dried (sodium sulfate), filtered, concentrated and the residue is purified by column (2.5% MeOH in dichloromethane) to give the title compound as an oil (49 mg, 70%):$^1H$ NMR ($CDCl_3$, 400 MHz) δ 0.96 (t, 6H), 1.13 (t, 3H), 1.27 (m, 6H), 1.42 (t, 3H), 1.57 (m, 2H), 1.67 (m, 2H), 2.47 (m, 2H), 2.66 (q, 2H), 3.95–4.15(m, 6H), 6.49(s, 1H), 6.53 (d, 1H), 7.15 (d, 1H). LC-MS: 387 (M+1).

Examples 48b –48k

May be Prepared According to the General Procedure Described in Example 48a

TABLE IIa

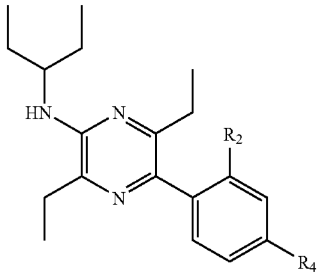

| EX# | $R_2$ | $R_4$ | 1HNMR ($CDCl_3$) | MS(Cl) | Name |
|---|---|---|---|---|---|
| 48b | OH | $OCH_3$ | 0.95 (t, 6H), 1.30(t, 3H), 1.37(t, 3H), 1.55(m, 2H), 1.67(m, 2H), 2.64(q, 2H), 2.86(q, 2H), 3.82(s, 3H), 4.15(m, 2H), 6.48(dd, 1H), 6.59(d, 1H), 7.31(d, 1H) | 344 (M + 1) | 3,6-diethyl-N-(1-ethylpropyl)-5-(2-hydroxy-4-methoxyphenyl)pyrazin-2-amine |
| 48c | OH | $OCH_2CH_3$ | 0.95(t, 6H), 1.30(t, 3H), 1.37(t, 3H), 1.42(t, 3H), 1.55(m, 2H), 1.67(m, 2H), 2.62(q, 2H), 2.87(q, 2H), 4.05(q, 2H), 4.10(m, 2H), 6.46(dd, 1H), 6.56(d, 1H), 7.30(d, 1H) | 358 (M + 1) | 3,6-diethyl-N-(1-ethylpropyl)-5-(2-hydroxy-4-ethoxyphenyl)pyrazin-2-amine |
| 48d | OH | $OCH(CH_3)_2$ | 0.95(t, 6H), 1.30(t, 3H), 1.35(d, 6H), 1.37(t, 3H), 1.55(m, 2H), 1.67(m, 2H), 2.64(q, 2H), 2.87(q, 2H), 4.11(m, 2H), 4.56(m, 1H), 6.45(dd, 1H), 6.56(d, 1H), 7.28(d, 1H) | 372 (M + 1) | 3,6-diethyl-N-(1-ethylpropyl)-5-[2-hydroxy-4-(2-propoxy)phenyl]pyrazin-2-amine |
| 48e | OH | $OCHF_2$ | 0.95 (t, 6H), 1.30(t, 3H), 1.37(t, 3H), 1.55(m, 2H), 1.69(m, 2H), 2.64(q, 2H), 2.86(q, 2H), 4.14(m, 1H), 4.18(brs. 1H), 6.54(t, J=74 Hz, 1H), 6.65(d, 1H), 6.78(s, 1H), 7.36(d, 1H) | 380 (M + 1) | 3,6-diethyl-N-(1-ethylpropyl)-5-(2-hydroxy-4-difluoromethoxyphenyl) pyrazin-2-amine |
| 48f | $OCH_3$ | OH | 0.95 (t, 6H), 1.13(t, 3H), 1.29(t, 3H), 1.55(m, 2H), 1.67(m, 2H), 2.45(q, 2H), 2.70(q, 2H), 3.68(s, 3H), 4.10(m, 2H), 6.32(d, 1H), 6.33(s, 1H), 6.99(d, 1H) | 344 (M + 1) | 3,6-diethyl-N-(1-ethylpropyl)-5-(2-methoxy-4-hydroxyphenyl)pyrazin-2-amine |
| 48g | $OCH_3$ | $OCH_2CH_3$ | 0.95 (t, 6H), 1.14(t, 3H), 1.28(t, 3H), 1.43(t, 3H), 1.55(m, 2H), 1.67(m, 2H), 2.46(q, 2H), 2.65(q, 2H), 3.74(s, 3H), 4.07(q, 2H), 4.10(m, 2H), 6.51(d, 1H), 6.54(dd, 1H), 7.15(d, 1H) | 372 (M + 1) | 3,6-diethyl-N-(1-ethylpropyl)-5-(2-methoxy-4-ethoxyphenyl)pyrazin-2-amine |
| 48h | $OCH_3$ | $OCH(CH_3)_2$ | 0.95(t, 6H), 1.14(t, 3H), 1.28(t, 3H), 1.33(d, 6H), 1.55(m, 2H), 1.67(m, 2H), 2.46(q, 2H), 2.65(q, 2H), 3.74(s, 3H), 4.02(d, 1H), 4.08(m, 1H), 4.59(m, 1H), 6.51 (d, 1H), 6.54(dd, 1H), 7.15(d, 1H) | 386 (M + 1) | 3,6-diethyl-N-(1-ethylpropyl)-5-[2-methoxy-4-(2-propoxy)phenyl]pyrazin-2-amine |
| 48i | $OCH(CH_3)_2$ | $OCH(CH_3)_2$ | 0.95(t, 6H), 1.14(t, 3H), 1.18(br. 6H), 1.28(t, 3H), 1.34(d, 6H), 1.55(m, 2H), 1.67(m, 2H), 2.46(m, 2H), 2.65(q, 2H), 4.02(br, 1H), 4.10(m, 1H), 4.84(m, 1H), 4.55(m, 1H), 6.48(d, 1H), 6.54(dd, 1H), 7.15(d, 1H) | 414 (M + 1) | 3,6-diethyl-N-(1-ethylpropyl)-5-[2,4-bis-(2-propoxy)phenyl]pyrazin-2-amine |
| 48j | $OCHF_2$ | $OCHF_2$ | 0.96(t, 6H), 1.16(t, 3H), 1.28(t, 3H), 1.57(m, 2H), 1.69(m, 2H), 2.46(q, 2H), 2.63(q, 2H), 4.15(m, 2H), 6.51(t, J=75 Hz, 1H), 6.55(t, J=74 Hz, 1H), 7.03(s, 1H), 7.04(d, 1H), 7.35(d, 1H) | 430 (M + 1) | 3,6-diethyl-N-(1-ethylpropyl)-5-(2,4-bis-difluoromethoxyphenyl) pyrazin-2-amine |
| 48k | OH | $CH_3$ | 0.95 (t, 6H), 1.14(t, 3H), 1.28(t, 3H), 1.55(m, 2H), 1.67(m, 2H), 2.38(s, 3H), 2.46(q, 2H), 2.65(q, 2H), 3.75(s, 3H), 4.02(d, 1H), 4.08(m, 1H), 6.74(s, 1H), 6.69(d, 1H), 7.13(d, 1H) | 342 (M + 1) | 3,6-diethyl-N-(1-ethylpropyl)-5-(2-hydroxy-4-methoxyphenyl)pyrazin-2-amine |
| 48l | $OCH_2CH_2OH$ | $CH_3$ | 0.95(t, 6H), 1.16(t, 3H), 1.25(t, 3H), 1.55(m, 2H), 1.67(m, 2H), 2.38(s, 3H), 2.54(q, 2H), 2.68(q, 2H), 3.74(t, 2H), 4.11(m, 2H), 4.22(m, 2H), 6.83(d, 1H), 6.87(s, 1H), 7.07(d, 1H) | 372 (M + 1) | 3,6-diethyl-N-(1-ethylpropyl)-5-(2-hydroxyethoxy-4-methylphenyl)pyrazin-2-amine |

TABLE IIa-continued

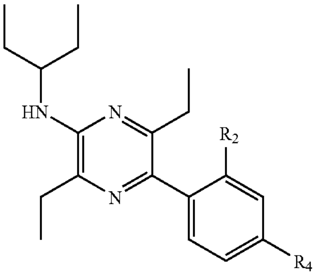

| EX# | $R_2$ | $R_4$ | 1HNMR ($CDCl_3$) | MS(Cl) | Name |
|---|---|---|---|---|---|
| 48m | $OCH_2CH_2OCH_3$ | $CH_3$ | 0.95(t, 6H), 1.12(t, 3H), 1.25(t, 3H), 1.55(m, 2H), 1.67(m, 2H), 2.36(s, 3H), 2.48(m, 2H), 2.63(q, 2H), 3.23(s, 3H), 3.58(t, 2H), 4.02(d, 1H), 4.04(t, 2H), 4.11(m, 1H), 6.76(s, 1H), 6.83(d, 1H), 7.14(d, 1H) | 386 (M + 1) | 3,6-diethyl-N-(1-ethylpropyl)-5-(2-methoxyethoxy-4-methylphenyl)pyrazin-2-amine |
| 48n | $O(CH_2)_2N(CH_3)_2$ | $CH_3$ | 0.94(t, 6H), 1.12(t, 3H), 1.25(t, 3H), 1.55(m, 2H), 1.67(m, 2H), 2.15(s, 6H), 2.36(s, 3H), 2.48(m, 2H), 258(t, 2H), 2.63(q, 2H), 4.00(t, 2H), 4.02(d, 1H), 4.11(m, 1H), 6.74(s, 1H), 6.83(d, 1H), 7.14(d, 1H) | 399 (M + 1) | 3,6-diethyl-N-(1-ethylpropyl)-5-(2-dimethylaminoethoxy-4-methylphenyl)pyrazin-2-amine |

Example 48o

[N-(1-ethyl)propyl]-5-[(2-dimethylamino-4-methyl) pyridin-5-yl]-3,6-diethylpyrazine-2-amine [Formula I: Ar=(2-dimethylamino4-methyl)pyridin-5-yl; $R_2$=—N(1-ethyl)propyl); $R_1$=$R_3$=$CH_2CH_3$]

5-Bromo-3,6-diethyl-[N-(1-ethyl)propyl]pyrazine-2-amine obtained in Example 23 reacts with [(2-dimethylamino-4-methyl)pyridin-5-yl]magnesium bromide as in Example 21 to give the title compound.

$^1$H NMR ($CDCl_3$, 400 MHz) δ 0.96 (t, 6H), 1.14 (t, 3H), 1.28 (t, 3H), 1.57 (m, 2H), 1.67 (m, 2H),2.12 (s, 3H), 2.48 (m, 2H), 2.64 (q, 2H), 3.12 (s, 6H), 4.10 (m, 2H), 6.43 (s, 1H), 7.89 (s, 1H). LC-MS: 356

Example 49

[N-(1-ethyl)propyl]-5-(2-methoxy4,6-dimethylphenyl)-3,6-dimethylpyrazine-2-amine [Formula I: Ar=2-methoxy-4,6-dimethylphenyl; $R_2$=—N(1-ethyl)propyl; $R_1$=$R_3$=$CH_3$]

A. To a solution of 2-chloro-3,6-dimethylpyrazine (0.71 g, 5.0 mmol) and tetrakis(triphenylphosphine)palladium(0) (140 mg, 2.5 mol %) in ethylene glycol dimethyl ether (30 mL) is added 2-methoxy4,6-dimethylbenzeneboronic acid (1.08 g, 6.0 mmol), followed by addition of 1 M aqueous sodium carbonate solution (15 mL). The mixture is stirred at 70–75° C. overnight, allowed to cool, diluted by saturated aqueous sodium bicarbonate solution, and extracted twice with $Et_2O$. Combined extracts are dried (sodium sulfate), filtered, and concentrated in vacuo. The residue is purified by filtration through a short pad of silica gel to give 1.4 g of crude product.

B. The crude material obtained above is dissolved in dichloromethane (20 mL), cooled to 0° C., and m-chloroperoxybenzoic acid (70%, 1.2 g) is added in portions. After 4 hours at ambient temperature, the mixture is diluted by n-hexane (20 mL) and washed with 1 M aqueous sodium hydroxide solution. The organic phase separated is dried (sodium sulfate), filtered, concentrated in vacuo, and the residue is used directly in the next step without further purification.

C. The crude N-oxide is dissolved in phosphorus oxychloride (10 mL) and the solution is heated at 80° C. overnight. Evaporation of phosphorus oxychloride and usual aqueous work-up of the residue followed by chromatography on silica yields 2-aryl-5-chloro-3,6-dimethylpyrazine as a white solid (0.76 g).

D. To a solution of the chloropyrazine obtained in C (260 mg, 0.94 mmol) and tris(dibenzylideneacetone)dipalladium (0) (11 mg) in toluene (10 mL) is added a 0.2 M solution of tri-tert-butylphosphine in toluene (0.10 mL). After 15 min at ambient temperature, 1-ethylpropylamine (0.14 mL) and potassium t-butoxide (1.0 M in THF, 1.4 mL) are added successively and the reaction mixture is heated at 80° C. for 4 hours. The mixture is allowed to cool to room temperature, diluted by ether, washed with aqueous ammonium chloride solution, dried (sodium sulfate), filtered, concentrated, and chromatographed on silica to give the desired product as a white solid (250 mg): $^1$H NMR ($CDCl_3$, 400 MHz) δ 0.95 (t, 6H), 1.5–1.7 (m, 4H), 2.0 (s, 3H), 2.1 (s, 3H), 2.4 (s, 6H), 3.7 (s, 3H), 3.95 (br d, 1H), 4.1 (br q, 1H), 6.6 (s, 1H), 6.7 (s, 1H).

Examples 50–53

May be Prepared According to the General Procedure Described in Example 49

Example 50

N-benzyl-5-(2-methoxy-4,6-dimethylphenyl)-3,6-diethylpyrazine-2-amine [Formula I: Ar=2-methoxy4,6-dimethylphenyl; $R_2$=—$NHCH_2C_6H_5$); $R_1$=$R_3$=$CH_2CH_3$] MS (CI) 376.

Example 51

5-(2-methoxy-4,6-dimethylphenyl)-3,6-diethylpyrazine-[N-(1-phenyl-2-methyl)propyl]-2-amine [Formula I: Ar=2-methoxy4,6-dimethylphenyl; $R_2$=—$NHCH(C_6H_5)CH(CH_3)CH_3$; $R_1$=$R_3$=$CH_2CH_3$] MS (CI) 418.

Example 52

5-(2-methoxy-4,6-dimethylphenyl)-3,6-diethylpyrazine-[N-(1-propyl)butyl]-2-amine [Formula I: Ar=2-methoxy4,6-dimethylphenyl; $R_2$=—$NHCH(CH_2CH_2CH_3)_2$; $R_1$=$R_3$=$CH_2CH_3$] MS (CI) 384.

Example 53

[N-(1-methoxy)-2-butyl]-5-(2-methoxy-4,6-dimethylphenyl)-3,6-diethylpyrazine-2-amine [Formula I: Ar=2-methoxy-4,6-dimethylphenyl; $R_2$=—$NCH(CH_2OCH_3)CH_2CH_3$; $R_1$=$R_3$=$CH_2CH_3$] MS (CI) 372.

Example 54

5-(2-methoxy-2,4-dimethylphenyl)-3,6-dimethyl-2-(3-pentyloxy)pyrazine [Formula I: Ar=2-methoxy-4,6-dimethylphenyl; $R_2$=—$OCH(CH_2CH_3)_2$; $R_1$=$R_3$=$CH_3$]

To an suspension of NaH (60% in mineral oil, 40 mg) in DMF (0.5 mL) is added 3-pentanol (0.1 mL). The mixture is stirred at ambient temperature until hydrogen evolution ceased. To the resulting alkoxide solution is added an N-methylpyrrolidinone solution of 2-aryl-5-chloro-3,6-dimethylpyrazine (20 mg in 0.5 mL solvent) obtained as in Example 49C. After 1 hour at room temperature, the mixture is heated to 70° C. for another hour before it being allowed to cool and diluted with aqueous ammonium chloride solution and extracted twice with $Et_2O$. Combined organics are dried (sodium sulfate), filtered, concentrated, and chromatographed on silica gel to give the title compound as a colorless oil (15 mg): $^1H$ NMR ($CDCl_3$, 400 MHz) δ 1.0 (t, 6H), 1.75 (m, 4H), 1.95 (s, 3H), 2.15 (s, 3H), 2.35 (s, 3H), 2.45 (s, 3H), 3.7 (s, 3H), 5.1 (quint, 1H)), 6.6 (s, 1H), 6.7 (s, 1H): MS (CI) 329, 259.

Examples 55–62

In Table III may be Prepared Following the General Procedure Described in Examples 54 and 63

TABLE III

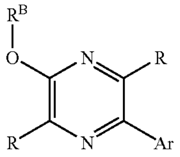

| EX# | R | $R_B$ | Ar | 1H NMR (CDCl3) | MS (CI) | NAME |
|---|---|---|---|---|---|---|
| 55 | Me | 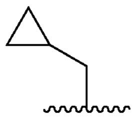 | 2-methoxy-4,6-dimethylphenyl | 0.4 (m, 2H), 0.6 (m, 2H), 1.35 (m, 1H), 1.95 (s, 3H), 2.15 (s, 3H), 2.35 (s, 3H), 2.5 (s, 3H), 3.7 (s, 3H), 4.2 (d, 2H), 6.6 (s, 1H), 6.7 (s, 1H) | 313, 259 | 3,6-dimethyl-(2-cyclopropylmethoxy)-5-(2-methoxyethoxy-4,6-dimethylphenyl)pyrazine |
| 56 | Me | 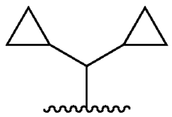 | 2,4-dichlorophenyl | 0.4 0.6 (m, 10H), 2.2 (s, 3H), 2.45 (s, 3H), 4.5 (t, 1H), 7.25 (d, 1H), 7.3 (d, 1H), 7.5 (s, 1H) | 363, 269 | 3,6-dimethyl-(2-dicyclopropylmethoxy)-5-(2,4-dichlorophenyl)pyrazine |
| 57 | Me | 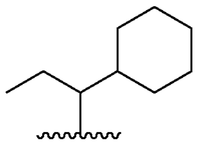 | 2,4-dichlorophenyl | | 393, 269 | 3,6-dimethyl-2-(1-cyclohexylpropoxy)-5-(2,4-dichlorophenyl)pyrazine |
| 58 | Me | 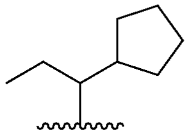 | 2,4-dichlorophenyl | | 381, 269 | 3,6-dimethyl-2-(1-cyclohexylpropoxy)-5-(2,4-dichlorophenyl)pyrazine |
| 59 | Me | 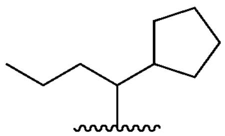 | 2,4-dichlorophenyl | | 393, 269 | 3,6-dimethyl-2-(1-cyclobutylpropoxy)-5-(2,4-dichlorophenyl)pyrazine |

TABLE III-continued

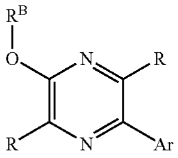

| EX# | R | $R_B$ | Ar | 1H NMR (CDCl3) | MS (Cl) | NAME |
|---|---|---|---|---|---|---|
| 60 | Me | 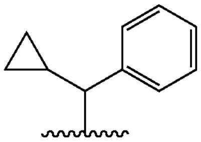 | 2,4-dichlorophenyl | | 399, 269 | 3,6-dimethyl-2-(cyclopropyl-phenylmethoxy)-5-(2,4-dichlorophenyl)pyrazine |
| 61 | Me | 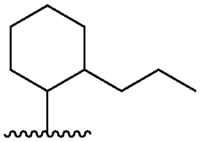 | 2,4-dichlorophenyl | | 393, 269 | 2,5-dimethyl-3-(2,4-dichlorophenyl)-6-[(2-propylcyclohexyl) oxy]pyrazine |
| 61a | Et | 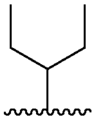 | 4-fluoro-2-methylphenyl | | 331 | 3,6-dimethyl-2-(1-ethylpropoxy)-5-(2,4-dichlorophenyl)pyrazine |
| 61b | Et | 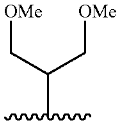 | 2,4-dichlorophenyl | | 399 | 2-[2-methoxy-1-(methoxymethyl)ethoxy]-3,6-diethyl-5-(2-methoxy-4-trifluoromethyoxyphenyl) pyrazine |
| 61b | Et | 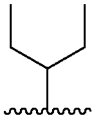 | 2-methoxy-4-trifluoromethoxy phenyl | | 413 | 3,6-diethyl-2-(1-ethylpropoxy)-5-(2-methoxy-4-trifluorophenyl)pyrazine |
| 62 | Et | 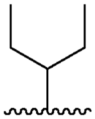 | 2,4-dimethoxyphenyl | 1.0 (t, 6H), 1.2 (t, 3H), 1.25 (t, 3H), 1.75 (quint, 4H), 2.5 (br, 2H), 2.8 (q, 2H), 3.75 (s, 3H), 3.85 (s, 3H), 5.1 (quint, 1H), 6.5 (s, 1H), 6.6 (d, 1H), 7.2 (d, 1H) | 359, 289 | 3,6-diethyl-2-(1-ethylpropoxy)-5-(2,4-dimethoxy-phenyl)pyrazine |
| 62a | Me | 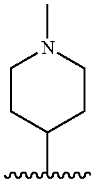 | 2,4-dichlorophenyl | 1.9 (m, 2H), 2.1 (m, 2H), 2.23 (s, 3H), 2.34 (s, 3H), 2.4 (m, 2H), 2.46 (s, 3H), 2.7 (b, 2H), 5.2 (b, 1H), 7.26 (dd, 1H), 7.33 (dd, 1 H), 7.48 (d, 1H) | 366, 269 | 2,5-dimethyl-3-(2,4-dichlorophenyl)-6-[(1-methylpiperidin-4-yl)oxy]pyrazine |
| 62b | Me | 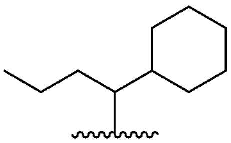 | 2,4-dichlorophenyl | | 407, 269 | 3,6-dimethyl-2-(1-cyclohexylbutoxy)-5-(2,4-dichlorophenyl)pyrazine |

TABLE III-continued

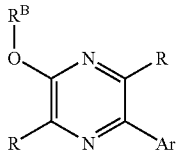

| EX# | R | $R_B$ | Ar | 1H NMR (CDCl3) | MS (Cl) | NAME |
|---|---|---|---|---|---|---|
| 62c | Me | 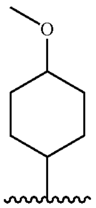 | 2,4-dichlorophenyl | | 381, 269 | 2,5-dimethyl-3-(2,4-dichlorophenyl)-6-[(4-methoxycyclohexyl) oxy]pyrazine |
| 62d | Me | 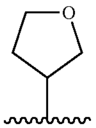 | 2,4-dichlorophenyl | 2.2 (m, 2H), 2.25 (s, 3H), 2.46 (s, 3H), 3.9–4.1 (m. 4H), 5.6 (m, 1H), 7.26 (d, 1H), 7.33 (d, 1H), 7.49 (s, 1H) | 339, 269 | 2,5-dimethyl-3-(2,4-dichlorophenyl)-6-(tetrahydrofuran-3-yl)oxy]pyrazine |
| 62e | Me | 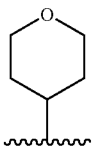 | 2,4-dichlorophenyl | | 253, 269 | 2,5-dimethyl-3-(2,4-dichlorophenyl)-6-(tetrahydro-2H-pyran-4-yloxy)pyrazine |
| 62f | Me | 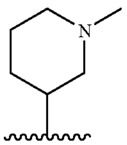 | 2,4-dichlorophenyl | 1.4–2.4 (m, 6H), 2.23 (s, 3H), 2.33 (s, 3H), 2.44 (s, 3H), 2.7 (m, 1H), 3.1 (m, 1H), 5.3 (m, 1H), 7.26 (d, 1H), 7.31 (d, 1H), 7.48 (s, 1H) | 366, 269 | 2,5-dimethyl-3-(2,4-dichlorophenyl)-6-[(1-methylpiperidin-3-yl)oxy]pyrazine |
| 62g | Me | 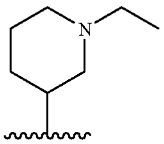 | 2,4-dichlorophenyl | | 380, 269 | 2,5-dimethyl-3-(2,4-dichlorophenyl)-6-[(1-ethylpiperidin-3-yl)oxy]pyrazine |
| 62h | Me | 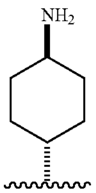 | 2,4-dichlorophenyl | | 366, 269 | 2,5-dimethyl-3-(2,4-dichlorophenyl)-6-[(1-aminopiperidin-4-yl)oxy]pyrazine |
| 62i | Me | 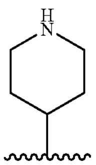 | 2,4-dichlorophenyl | | 352, 269 | 2,5-dimethyl-3-(2,4-dichlorophenyl)-6-(1-piperidin-4-yl)oxy]pyrazine |
| 62j | Me | 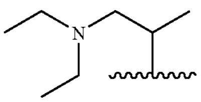 | 2,4-dichlorophenyl | | 382, 269 | 2-{(3,6-dimethyl)-[5-(2,4-dichlorophenyl) pyrazin-2-yl)oxy}-N,N-diethylpropan-1-amine |

TABLE III-continued

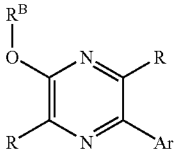

| EX# | R | $R_B$ | Ar | 1H NMR (CDCl3) | MS (Cl) | NAME |
|---|---|---|---|---|---|---|
| 62k | Me | 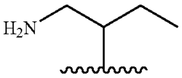 | 2,4-dichlorophenyl | | 340, 269 | 3-{[5-(2,4-dichloro-phenyl)-3,6-dimethylpyrazin-2-yl]oxy}butylamine |
| 62l | Me | 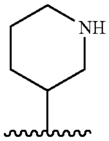 | 2,4-dichlorophenyl | | 352, 269 | 2,5-dimethyl-3-(2,4-dichlorophenyl)-6-(piperidin-3-yl)oxy]pyrazine |
| 62m | Me | 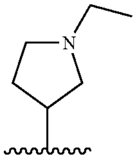 | 2,4-dichlorophenyl | 1.16(t, 3H), 2.1 (m. 1H), 2.24 (s, 3H), 2.3–2.6 (m, 4H), 2.46 (s, 3H), 2.8 (m, 2H), 3.0 (m, 1H), 5.5 (m, 1H), 7.26 (d, 1H), 7.32 (d, 1H), 7.48 (s, 1H) | 366, 269 | 2,5-dimethyl-3-(2,4-dichlorophenyl)-6-[(1-ethylpyrrolidin-3-yl)oxy]pyrazine |
| 62n | Me | 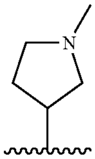 | 2,4-dichlorophenyl | | 352, 269 | 2,5-dimethyl-3-(2,4-dichlorophenyl)-6-[(1-methylpyrrolidin-3-yl)oxy]pyrazine |
| 62o | Me | 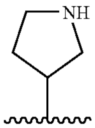 | 2,4-dichlorophenyl | | 338, 269 | 2,5-dimethyl-3-(2,4-dichlorophenyl)-6-[(pyrrolidin-3-yl)oxy]pyrazine |
| 62p | Me | 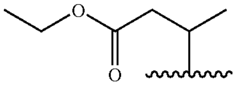 | 2,4-dichlorophenyl | | 383, 269 | ethyl 3-{[5-(2,4-dichlorophenyl)-3,6-dimethylpyrazin-2-yl]oxy}butanoate |
| 62q | Me | 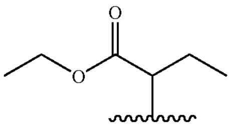 | 2,4-dichlorophenyl | 1.14(t, 3H), 1.26(t, 3H), 2.05 (q, 2H), 2.19 (s, 3H), 2.54 (s, 3H), 4.22 (q, 2H), 5.12 (t, 1H), 7.25 (d, 1H), 7.33 (d, 1H), 7.48 (s, 1H) | 383, 269 | ethyl 2-{[5-(2,4-dichlorophenyl)-3,6-dimethylpyrazin-2-yl]oxy}propanoate |
| 62r | Me | 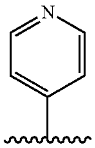 | 2,4-dichlorophenyl | 2.44 (s, 3H), 2.64 (s, 3H), 6.53 (d, 2H), 7.32 (d, 1H), 7.43 (d, 1H), 7.56 (s, 1H), 7.70 (d, 2H) | 346, 269 | 2,5-dimethyl-3-(2,4-dichlorophenyl)-6-pyridin-4-yl) oxy}pyrazine |
| 62s | Et | 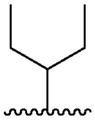 | 2-methoxy-4,6-dimethylphenyl | 0.98 (t, 6H), 1.11 (t, 3H), 1.23 (t, 3H), 1.75 (m, 4H), 1.96 (s, 3H), 2.35 (s, 3H), 2.4 (m, 2H), 2.8 (m, 2H), 3.70 (s, 3H), 5.1 (m, 1H), 6.60 (s, 1H) 6.71 (s, 1H) | 357, 287 | 3,6-diethyl-2-(1-ethylpropoxy)-5-(2-methoxy-4,6-dimethylphenyl)pyrazine |

TABLE III-continued

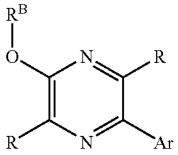

| EX# | R | $R_B$ | Ar | 1H NMR (CDCl3) | MS (Cl) | NAME |
|---|---|---|---|---|---|---|
| 62t | Me | 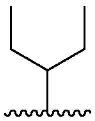 | 2,4-dichlorophenyl | 0.97 (t, 6H), , 1.74 (m, 4H), 2.24 (s, 3H), 2.44 (s, 3H), 5.11 (m, 1H), 7.28 (d, 1H), 7.32 (d, 1H), 7.48 (s, 1H) | 340, 269 | 3,6-dimethyl-2-(1-ethylpropoxy)-5-(2,4-dichlorophenyl) pyrazine |
| 62u | Et | 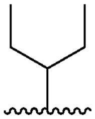 | 2-hydroxy-4,6-dimethylphenyl | 0.98(m, 6H), 1.12 (t, 3H), 1.21 (t, 3H), 2.74 (m, 4H), 2.01 (s, 3H), 2.29 (s, 3H), 2.5 (m, 2H), 2.73 (m, 2H), 5.14 (m, 1H), 6.4 (b, 1H), 6.58 (s, 1H), 6.65 (s, 1H) | 343, 273 | 3,6-diethyl-2-(1-ethylpropoxy)-5-(2-hydroxy-4,6-dimethylphenyl)pyrazine |
| 62v | Et | 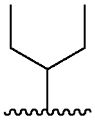 | 2,4-dichlorophenyl | 0.99 (t, 6H), 1.16 (t, 3H), 1.24 (t, 3H), 1.75 (m, 4H), 2.5 (b, 2H), 2.82 (m, 2H), 5.13 (m, 1H), 7.26 (d, 1H), 7.32 (d, 1H), 7.49 (s, 1H) | 367, 297 | 3,6-diethyl-2-(1-ethylpropoxy)-5-(2,4-dichlorophenyl)pyrazine |
| 62w | Et | 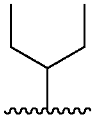 | 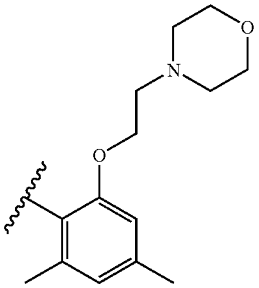 | 0.99 (t, 6H), 1.15 (t, 3H), 1.23 (t, 3H), 1.72 (m, 4H), 1.99 (s, 3H), 2.25 (m, 4H), 2.32 (s, 3H), 2.4 (m, 2H), 2.55 (m, 2H), 2.8 (m, 2H), 2.56 (m, 4H), 4.0 (m, 2H), 5.14 (m, 1H), 6.57 (s, 1H), 6.71 (s, 1H) | 456, 386 | 3,6-diethyl-2-(1-ethylpropoxy)-5-[2,4-dimethyl-6-(2-morpholin-4-ylethoxy)phenyl] pyrazine |
| 62x | Et | 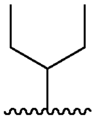 | 2,4-bis(trifluoro-methyl)phenyl | | | 3,6-diethyl-2-(1-ethylpropoxy)-5-(2,4-bis-trifluoromethylphenyl) pyrazine |
| 62y | Et | 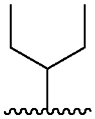 | 2-chloro-4-trifluoromethyl phenyl | | | 3,6-diethyl-2-(1-ethylpropoxy)-5-(2-chloro-4-trifluorophenyl)pyrazine |
| 62z | Et | 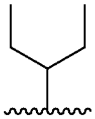 | 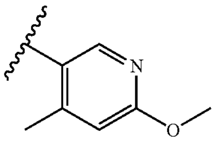 | | | 3,6-diethyl-2-(1-ethylpropoxy)-5-(2-methoxy-4-methyl-pyridin-3-yl)pyrazine |

Example 63

[N-(1-ethyl)propyl]-3,6-dimethyl-5-{2-[2-(4-morpholino)ethyl]oxy-4,6-dimethylphenyl}pyrazine-2-amine [Formula I: Ar=2-[2-(4-morpholino)ethyl]oxy-4,6-dimethylphenyl; $R_2$=—$NHCH(CH_2CH_3)_2$; $R_1$=$R_3$=$CH_3$]

A. A solution of 2-chloro-3,6-dimethyl-5-(2-methoxy-4,6-dimethylphenyl)pyrazine (180 mg) in dichloromethane was cooled to 0° C. and boron tribromide (0.1 mL) is added slowly dropwise. After the addition, the mixture is further stirred at 0° C. for 1.5 hours, diluted by $Et_2O$, washed with saturated aqueous sodium bicarbonate solution, dried (sodium sulfate), filtered, and concentrated in vacuo. The residue is used in the next step without further purification.

B. To a suspension of the crude phenol and potassium carbonate (400 mg) in DMF (4 mL) is added 4-(2-chloroethyl)morpholine hydrochloride (200 mg) in one portion and the mixture is stirred at 60° C. for 4 hours. After further stirring at room temperature overnight, the mixture is poured into aqueous sodium bicarbonate and extracted twice with Et2O-hexane. Combined extracts are dried (sodium sulfate), filtered, concentrated, and chromatographed on silica (eluent 5% triethylamine in 1:1 EtOAc-hexane) to give the product as a colorless oil (160 mg).

C. The chloropyrazine is converted to the corresponding aminopyrazine following the same procedure as in Example 49D: $^1$H NMR ($CDCl_3$, 400 MHz) δ 0.95 (m, 6H), 1.6 (m, 4H), 2.0 (s, 3H), 2.1 (s, 3H), 2.3 (m, 4H), 2.35 (s, 6H), 2.6 (m, 2H), 3.6 (m, 2H), 3.9 (d, 1H), 4.0 (m, 2H), 4.05 (m, 1H), 6.55 (s, 1H), 6.7 (s, 1H); MS (CI) 427.

Examples 64–74

In Table IV may be Prepared Following the General Procedure Described in Example 63

TABLE IV

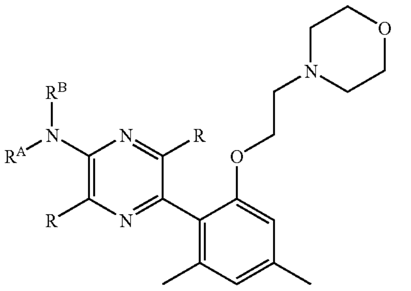

| EX# | R | $R_A$ | $R_B$ | 1H NMR (CDCl3) | MS(CI) | NAME |
|---|---|---|---|---|---|---|
| 64 | Me | H | 1-propylbutyl | 0.95 (t, 6H), 1.3–1.6 (m, 8H), 2.0 (s, 3H), 2.1 (s, 3H), 2.3 (m, 10H), 2.6 (m, 2H), 3.6 (m, 4H), 3.85 (d, 1H), 4.0 (m, 2H), 4.25 (m, 1H), 6.6 (s, 1H), 6.7 (s, 1H) | 455 | 3,6-dimethyl-N-(1-propylbutyl)-5-[2,4-dimethyl-6-(2-morpholin-4-ylethoxy)phenyl]pyrazine-2-amine |
| 65 | Me | H | 1-methoxy-2-butyl | 1.0 (t, 2H), 1.8 (m, 2H), 2.0 (s, 3H), 2.1 (s, 3H), 2.3 (m, 10H), 2.6 (br, 2H), 3.4 (s, 3H), 3.5–3.6 (m, 6H), 4.0 (br, 2H), 4.25 (br, 1H), 4.4 (d, 1H), 6.6 (s, 1H), 6.7 (s, 1H) | 443 | 3,6-dimethyl-N-(1-methoxy-2-butyl)-5-[2,4-dimethyl-6-(2-morpholin-4-ylethoxy)phenyl]pyrazine-2-amine |
| 66 | Me | propyl | propyl | 0.9 (t, 6H), 1.6 (q, 4H), 2.0 (s, 3H), 2.15 (s, 3H), 2.3 (m, 4H), 2.35 (s, 3H), 2.45 (s, 3H), 2.55 (m, 2H), 3.2 (m, 4H), 3.6 (m, 4H), 4.0 (m, 2H), 6.6 (s, 1H), 6.7 (s, 1H) | 441 | 3,6-dimethyl-N,N-dipropyl-5-[2,4-dimethyl-6-(2-morpholin-4-ylethoxy)phenyl]pyrazine-2-amine |
| 67 | Et | H | 1-ethylpropyl | 0.95 (m, 6H), 1.1 (t, 3H), 1.25 (t, 3H), 1.5–1.7 (m, 4H), 2.0 (s, 3H), 2.25 (m, 4H), 2.3 (s, 3H), 2.35 (q, 2H), 2.55 (m, 2H), 2.6 (q, 2H), 3.55 (m, 4H), 4.0 (m, 3H), 4.1 (m, 1H), 6.6 (s, 1H), 6.7 (s, 1H) | 455 | 3,6-diethyl-N-(1-ethylpropyl)-5-[2,4-dimethyl-6-(2-morpholin-4-ylethoxy)phenyl]pyrazine-2-amine |
| 68 | Et | H | 1-propylbutyl | 0.95 (t, 6H), 1.1 (t, 3H), 1.2 (t, 3H), 1.4 (br, 4H), 1.55 (br, 4H), 2.0 (s, 3H), 2.25 (m, 4H), 2.3 (s, 3H), 2.35 (q, 2H), 2.55 (br s, 2H), 2.6 (q, 2H), 3.6 (br s, 4H), 4.0 (br, 3H), 4.25 (br q, 1H), 6.6 (s, 1H), 6.7 (s, 1H) | 483 | 3,6-diethyl-N-(1-propylbutyl)-5-[2,4-dimethyl-6-(2-morpholin-4-ylethoxy)phenyl]pyrazine-2-amine |
| 69 | Et | propyl | propyl | 0.9 (t, 6H), 1.1 (t, 3H), 1.3 (t, 3H), 1.6 (m, 4H), 2.0 (s, 3H), 2.25 (br, 4H), 2.3 (s, 3H), 2.4 (m, 2H), 2.55 (br s, 2H), 2.7–2.9 (m, 2H), 3.2 (m, 4H), 3.6 (m, 4H), 4.0 (m, 2H), 6.6 (s, 3H), 6.7 (s, 1H) | 469 | 3,6-diethyl-N,N-dipropyl-5-[2,4-dimethyl-6-(2-morpholin-4-ylethoxy)phenyl]pyrazine-2-amine |
| 70 | Et | ethyl | butyl | 0.9 (t, 3H), 1.1–1.3 (m, 9H), 1.3 (m, 2H), 1.55 (m, 2H), 2.0 (s, 3H), 2.25 (br, 4H), 2.3 (s, 3H), 2.4 (m, 2H), 2.55 (br s, 2H), 2.7–2.9 (m, 2H), 3.2 (m, 4H), 3.6 (m, 4H), 4.0 (m, 2H), 6.6 (s, 3H), 6.7 (s, 1H) | 469 | 3,6-diethyl-N-ethyl-N-propyl-5-[2,4-dimethyl-6-(2-morpholin-4-ylethoxy)phenyl]pyrazine-2-amine |

TABLE IV-continued

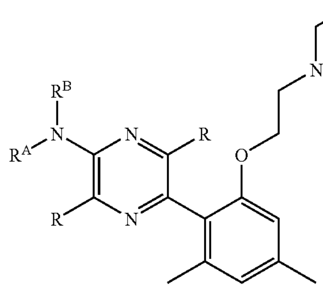

| EX# | R | $R_A$ | $R_B$ | 1H NMR (CDCl3) | MS(Cl) | NAME |
|---|---|---|---|---|---|---|
| 71 | Et | H | 1-methylpropyl | 1.0 (t, 3H), 1.1 (t, 3H), 1.2 (t + d, 6H), 1.5–1.7 (m, 2H), 2.0 (s, 3H), 2.25 (br s, 4H), 2.3 (s, 3H), 2.35 (q, 2H), 2.55 (br s, 2H), 2.6 (q, 2H), 3.55 (app t, 4H), 4.0 (m, 3H), 4.2 (m, 1H), 6.6 (s, 1H), 6.7 (s, 1H) | 441 | 3,6-diethyl-N-(1-methylpropyl)-5-[2,4-dimethyl-6-(2-morpholin-4-ylethoxy)phenyl]pyrazine-2-amine |
| 72 | Et | H | 1-methoxy-2-butyl | 1.0 (t, 3H), 1.1 (t, 3H), 1.3 (t, 3H), 1.7 (br, 2H), 2.0 (s, 3H), 2.25 (br s, 4H), 2.3 (s, 3H), 2.35 (q, 2H), 2.55 (br s, 2H), 2.6 (q, 2H), 3.4 (s, 3H), 3.6 (br s, 6H), 4.0 (br, 2H), 4.25 (br, 1H), 4.45 (d, 1H), 6.6 (s, 1H), 6.7 (s, 1H) | 471 | 3,6-diethyl-N-(1-methoxy-2-butyl)-5-[2,4-dimethyl-6-(2-morpholin-4-ylethoxy)phenyl]pyrazine-2-amine |
| 73 | Et | propyl | cyclopropane-methyl | 0.1 (app d, 2H), 0.45 (app. d, 2H), 0.9 (t, 3H), 1.05 (m, 1H), 1.1 (t, 3H), 1.2 (t, 3H), 2.0 (s, 3H), 2.25 (m, 4H), 2.3 (s, 3H), 2.4 (m, 2H), 2.55 (br s, 2H), 2.8 (m, 2H), 3.1 (d, 2H), 3.3 (m, 2H), 3.6 (br s, 4H), 4.0 (br, 2H), 6.6 (s, 1H), 6.7 (s, 1H) | 481 | 3,6-diethyl-N-(1-methoxy-2-butyl)-5-[2,4-dimethyl-6-(2-morpholin-4-ylethoxy)phenyl]pyrazine-2-amine |
| 74 | Et | ethyl | benzyl | 1.0–1.3 (m, 9H), 2.0 (s, 3H), 2.25 (br s, 4H), 2.3 (s, 3H), 2.4 (m, 2H), 2.55 (br s, 2H), 2.8 (m, 2H), 3.25 (q, 2H), 3.6 (br s, 4H), 4.0 (br, 2H), 4.45 (app q, 2H), 6.6 (s, 1H), 6.7 (s, 1H), 7.25 (m, 1H), 7.3 (t, 2H), 7.4 (d, 2H) | 503 | 3,6-diethyl-N-ethyl-N-benzyl-5-[2,4-dimethyl-6-(2-morpholin-4-ylethoxy) phenyl]pyrazine-2-amine |

Example 75

3-bromo-6-chloro-5-(2,4-dichlorophenyl)-[N-(1-ethyl)propyl]pyrazine-2-amine [Formula I: Ar=2,4-dichlorophenyl; $R_1$=Br; $R_2$=—NHCH($CH_2CH_3$)$_2$; $R_3$=Cl]

A. A solution of 2,6-dichloropyrazine (2.2 g) and 1-ethylpropylamine (5 mL) in EtOH (10 mL) is heated at 140° C. in a Teflon-sealed tube. Resulting solution is concentrated in vacuo, diluted by water, and extracted twice with hexane-ethyl ether. Combined extracts are dried (sodium sulfate), filtered, concentrated in vacuo, and the residue is filtered through a short pad of silica gel. The filtrate is concentrated to give 2-(3-pentylamino)-6-chloropyrazine as brownish oil that solidifies on standing (3.0 g).

B. A solution of the above amine (4.09 g; 20.48 mmol) in chloroform (80 ml) is cooled to 0° C. and N-bromosuccinimide (3.65 g; 20.48 mmol) is added in portions. The mixture is stirred at 0° C. for 30 min, poured into saturated aqueous $NaHCO_3$, and extracted with dichloromethane. The combined extracts are washed successively with water and brine, dried (sodium sulfate), and concentrated in vacuo. The residue is chromatographed on silica gel (6% EtOAc in hexane) to give the desired 3-bromopyrazine as a minor product (0.53 g; 9%) along with 6-chloro-5-bromo-[N-(1-ethyl)propyl]pyrazine-2-amine (4.37 g; 77%) as the major isomer.

C. 5-bromopyrazine obtained as above undergoes Suzuki coupling with 2,4-dichlorobenzeneboronic acid following the procedures in Example 1C to give 6-chloro-5-(2,4-dichlorophenyl)-[N-(1-ethyl)propyl]pyrazine-2-amine.

D. The aryl pyrazine is brominated again by using N-bromosuccinimide as described in Example 75B to give the desired product: $^1$H NMR ($CDCl_3$, 400 MHz) δ 0.97 (t, 6H), 1.58 (m, 2H), 1.70 (m, 2H), 4.00 (m, 1H), 5.20 (d, 1H), 7.30 (s, 2H), 7.50 (s, 1H); MS(CI) 422.

Example 76

6-chloro-5-(2,4-dichlorophenyl)-[N-(1-ethyl)propyl]-3-(2-propenyl)pyrazine-2-amine [Formula I: Ar=2,4-dichlorophenyl; $R_1$=$CH_2CH$=$CH_2$; $R_2$=—$NHCH(CH_2CH_3)_2$; $R_3$=Cl]

The bromopyrazine obtained in Example 75 is converted to the desired product by using alkylboronic acid following the same procedure as in Example 1C: $^1$H NMR ($CDCl_3$, 400 MHz) δ 0.93 (t, 6H), 1.50–1.71 (m, 4H), 3.50 (d, 2H), 4.05 (m, 1H), 4.55 (d, 1H), 5.22 (m, 2H), 5.92 (m, 1H), 7.34 (m, 2H), 7.48 (m, 1H); MS(CI) 384.

Example 77

6-chloro-5-(2,4-dichlorophenyl)-3-ethyl-[N-(1-ethyl)propyl]pyrazine-2-amine [Formula I: Ar=2,4-dichlorophenyl; $R_1$=$CH_2CH_3$; $R_2$=—$NHCH(CH_2CH_3)_2$; $R_3$=Cl]

The bromopyrazine obtained in Example 75 is converted to the desired product by using ethaneboronic acid following the same procedure as in Example 1C: $^1$H NMR ($CDCl_3$, 400 MHz) δ 0.96 (t, 6H), 1.30 (t, 3H), 1.56 (m, 2H), 1.70 (m, 2H), 2.65 (t, 2H), 4.08 (m, 1H), 4.35 (d, 1H), 7.32 (d, 1H), 7.33 (s, H), 7.48 (d, 1H); MS (CI) 372.

B. The above amine is brominated and coupled with 2,4-dichlorobenzeneboronic acid following the same procedure as described in Examples 75B and 75C, respectively to give the title compound: $^1$H NMR ($CDCl_3$, 400 MHz) δ 0.97 (t, 6H), 1.13 (t, 3H), 1.56 (m, 2H), 1.65 (m, 2H), 2.45 (m, 2H), 3.72 (m, 1H), 4.45 (d, 1H), 7.25 (d, 1H), 7.30 (dd, 1H), 7.48 (d, 1H), 7.74 (s, 1H); MS(CI) 338.

Example 79

3-bromo-5-(2,4-dichlorophenyl)-6-ethyl-[N-(1-ethyl)propyl]pyrazine-2-amine [Formula I: Ar=2,4-dichlorophenyl; $R_1$=Br; $R_2$=—$NHCH(CH_2CH_3)_2$; $R_3$=$CH_2CH_3$]

The product of Example 78 is brominated as in Example 75B to give the title compound: $^1$H NMR ($CDCl_3$, 400 MHz) δ 0.97 (t, 6H), 1.14 (t, 3H), 1.56 (m, 2H), 1.65 (m, 2H), 2.45 (m, 2H), 4.02 (m, 1H), 5.00 (d, 1H), 7.25 (d, 1H), 7.30 (dd, 1H), 7.46 (d, 1H); MS (CI) 416.

Examples 80–82

In Table V may be Prepared Following the General Procedure Described in Example 79 Using the Corresponding Halogenating Agent Indicated in the Table

TABLE V

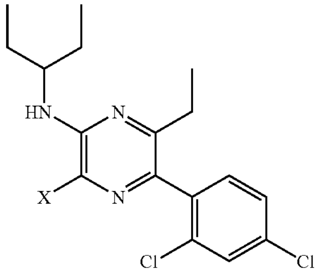

| EX# | X | Reagent | 1H NMR | MS(CI) | NAME |
|---|---|---|---|---|---|
| 80 | F | SelectFluor(TM) | 0.96 (t, 6H), 1.13 (t, 3H), 1.50–1.72 (m, 4H), 2.42 (m, 12H), 4.05 (m, 1H), 4.60 (d, 1H), 7.24 (d, 1H), 7.30 (dd, 1H), 7.48 (d, 1H). | 356 | 3-fluoro-6-ethyl-N-(1-ethylpropyl)-5-(2,4-dichlorophenyl)pyrazin-2-amine |
| 81 | Cl | N-chlorosuccinimide | 0.97 (t, 6H), 1.14 (t, 3H), 1.55 (m, 2H), 1.70 (m, 2H), 2.46 (m, 2H), 4.05 (m, 1H), 4.93 (d, 1H), 7.24 (d, 1H), 7.30 (dd, 1H), 7.47 (d, 1H). | 372 | 3-chloro-6-ethyl-N-(1-ethylpropyl)-5-(2,4-dichlorophenyl)pyrazin-2-amine |
| 82 | I | N-iodosuccinimide | 0.97 (t, 6H), 1.14 (t, 3H), 1.55 (m, 2H), 1.68 (m, 2H), 2.43 (m, 2H), 4.00 (m, 1H), 4.95 (d, 1H), 7.24 (d, 1H), 7.30 (dd, 1H), 7.46 (d, 1H). | 464 | 3-iodo-6-ethyl-N-(1-ethylpropyl)-5-(2,4-dichlorophenyl)pyrazin-2-amine |

Example 78

5-(2,4-dichlorophenyl)-6-ethyl-[N-(1-ethyl)propyl]pyrazine-2-amine [Formula I: Ar=2,4-dichlorophenyl; $R_1$=H; $R_2$=—$NHCH(CH_2CH_3)_2$; $R_3$=$CH_2CH_3$]

A. 6-chloro-[N-(1-ethyl)propyl]pyrazine-2-amine obtained in Example 75A reacts with ethylmagnesium bromide as in Example 21 to give 6-ethyl-[N-(1-ethyl)propyl]pyrazine-2-amine.

Example 83

5-(2,4-dichlorophenyl)-6-ethyl-[N-(1-ethyl)propyl]-3-methoxypyrazine2-amine [Formula I: Ar=2,4-dichlorophenyl; $R_1$=$OCH_3$; $R_2$=—NHCH $(CH_2CH_3)_2$; $R_3$=$CH_2CH_3$]

To a 1 N solution of sodium methoxide in N-methylpyrrolidinone is added 3-bromo-6-ethyl-5-(2,4-dichlorophenyl)-[N-(1-ethyl)propyl]pyrazine-2-amine obtained as in Example 79. The mixture is heated to 70° C. for 6 hr before being allowed to cool and diluted with water and the reaction mixture is extracted with 20% EtOAc in hexane. The combined extracts are washed with water, dried (sodium sulfate), filtered, concentrated in vacuo, and chromatographed on silica gel to give the title compound: $^1$H NMR ($CDCl_3$, 400 MHz) δ 0.97 (t, 6H), 1.12 (t, 3H), 1.56 (m, 2H), 1.65 (m, 2H), 2.40 (q, 2H), 3.92 (s, 3H), 4.04 (m, 1H), 4.82 (d, 1H), 7.28 (m, 2H), 7.48 (d, 1H); MS(CI) 368.

Example 84

5-(2,4-dichlorophenyl)-3-ethyl-6-methyl-[N-(1-ethyl)propyl]pyrazine-2-amine [Formula I: Ar=2,4-dichlorophenyl; $R_1$=$CH_2CH_3$; $R_2$=—NHCH$(CH_2CH_3)_2$; $R_3$=$CH_3$]

A: To a solution of 2-(3-pentylamino)-6-chloropyrazine (4.26 g, 21.3 mmol) (obtained in example 75) in THF (30 mL) at room temperature is added [1,3-bis(diphenylphosphino)propane]dichloronickel(II) (540 mg). After 10 min, methylmagnesium bromide (3.0M in diethyl ether, 15.7 mL) is added slowly dropwise at 0° C. The mixture is stirred at room temperature for 1 hr. The resulting dark solution is poured into aqueous ammonium chloride and extracted twice with ether. Combined extracts are dried (sodium sulfate), filtered, concentrated, and chromatographed to give the desired product as a light brown oil(98%).

B: A solution of the above oil in chloroform(60 mL) is cooled to 0° C. and N-bromosuccinimide (3.8 g) is added in portions. After the addition, the mixture is further stirred for 1 h while being allowed to warm to room temperature. The mixture is then concentrated to a small volume in vacuo, triturated with hexane, filtered, washed with hexane, and the filtrate is concentrated and chromatographed on silica gel (8% ethyl acetate in hexane elution) to give 5-bromo-[N-(1-ethyl)propyl]-6-methylpyrazine-2-amine (92%).

C. A mixed solution of the above bromide (1.2 g; 4.65 mmol) and tetrakis(triphenylphosphine)palladium(0) (4 mol %) in ethyleneglycol dimethyl ether (60 mL) is stirred at room temperature for 15 min, when 2,4-dichlorobenzeneboronic acid (1.3 g, 7 mmol) and an aqueous solution of sodium carbonate (1.0M, 12 mL) are added sequentially. The mixture is heated to 75° C. with stirring for 1.5 h, then diluted with 0.1N sodium hydroxide and extracted twice with 1:1 hexane-ethyl ether. Combined extracts are dried (sodium sulfate), filtered, concentrated, and chromatographed on silica (4:1 hexane-EtOAc) to give 5-(2,4-dichlorophenyl)-6-methyl-[N-(1-ethyl)propyl]pyrazine-2-amine as a yellow oil (1.46 g, 97%): $^1$H NMR (CDCl3, 400 MHz) δ 0.97 (t, 6H), 1.54 (m, 2H), 1.67 (m, 2H), 2.22 (s, 3H), 3.65 (m, 1H), 4.50 (br, 1H), 7.27 (d, 1H), 7.31 (dd, 1H), 7.48 (d, 1H), 7.76 (s, 1H).

D: A solution of the above oil (1.27 g, 3.92 mmol) in chloroform(40 mL) is cooled to 0° C. and N-bromosuccinimide (770 mg) is added in portions. After the addition, the mixture is further stirred for 1 h while being allowed to warm to room temperature. The mixture is then concentrated to a small volume in vacuo, triturated with hexane, filtered, washed with hexane, and the filtrate is concentrated and chromatographed on silica gel (3% ethyl acetate in hexane elution) to give 3-bromo-5-(2,4-dichlorophenyl)-6-methyl-[N-(1-ethyl)propyl]pyrazine-2-amine (1.56 g, 98%).

E: A mixed solution of 3-bromo-5-(2,4-dichlorophenyl)-6-methyl-[N-(1-ethyl)propyl]pyrazine-2-amine (960 mg; 2.38 mmol) and tetrakis(triphenylphosphine)palladium(0) (4 mol %) in ethyleneglycol dimethyl ether (25 mL) is stirred at room temperature for 15 min, when ethaneboronic acid (1.0 g) and an aqueous solution of sodium carbonate (1.0M, 8.5 mL) are added sequentially. The mixture is heated to 75° C. with stirring for 12 h, then diluted with 0.1N sodium hydroxide and extracted twice with 1:1 hexane-ethyl ether. Combined extracts are dried (sodium sulfate), filtered, concentrated, and chromatographed on silica (10:1 hexane-EtOAc) to give the title compound as a yellow oil (460 mg, 55%): $^1$H NMR (CDCl3, 400 MHz) δ 0.95 (t, 6H), 1.28 (t, 3H), 1.54 (m, 2H), 1.67 (m, 2H), 2.20 (s, 3H), 2.65 (q, 2H), 4.13 (m, 2H), 7.27 (d, 1H), 7.31 (d, 1H), 7.48 (s, 1H).LC-MS: 352 (M+1).

Example 84a 5-(2,4-dichlorophenyl) -3-ethoxy-6-ethyl-[N-(1-ethyl)propyl]pyrazine-2-amine [Formula I: Ar=2,4-dichlorophenyl; $R_1$=$OCH_2CH_3$; $R_2$=—NHCH$(CH_2CH_3)_2$; $R_3$=$CH_2CH_3$]

The same reaction as in Example 83 with sodium ethoxide gives the title compound: $^1$H NMR ($CDCl_3$, 400 MHz)) δ 0.95 (t, 6H), 1.10 (t, 3H), 1.37 (t, 3H), 1.55 (m, 2H), 1.68 (m, 2H), 2.36 (m, 2H), 4.05 (m, 1H), 4.33 (q, 2H), 4.81 (d, 1H), 7.24 (d, 1H), 7.26 (dd, 1H), 7.46 (d, 1H); MS(CI) 382.

Example 85

5-(2,4-dichlorophenyl)-6-ethyl-[N-(1-ethyl)propyl]-3-methylpyrazine-2-amine [Formula I: Ar=2,4-dichlorophenyl; $R_1$=$CH_3$; $R_2$=—NHCH$(CH_2CH_3)_2$; $R_3$=$CH_2CH_3$]

3-Bromo-5-(2,4-dichlorophenyl)-6-ethyl-[N-(1-ethyl)propyl]pyrazine-2-amine obtained from Example 79 is converted to the title compound by using methylmagnesium bromide according to the same procedure used in Example 21: $^1$H NMR ($CDCl_3$, 400 MHz) δ 0.97 (t, 6H), 1.12 (t, 3H), 1.56 (m, 2H), 1.65 (m, 2H), 2.35 (s, 3H), 2.42 (m, 2H), 4.04 (m, 2H), 7.25 (d, 1H), 7.29 (dd, 1H), 7.46 (d, 1H); MS (CI) 352.

Example 86

3-Bromo-5-(2,4-dichlorophenyl)-[N-(1-ethyl)propyl]-6-methoxypyrazine-2-amine [Formula I: Ar=2,4-dichlorophenyl; $R_1$=Br; $R_2$=—NHCH$(CH_2CH_3)_2$; $R_3$=$OCH_3$]

6-Chloro-5-(2,4dichlorophenyl)-[N-(1-ethyl)propyl]pyrazine-2-amine obtained in Example 75C is converted to 5-(2,4dichlorophenyl)-6-methoxy-[N-(1-ethyl)propyl]pyrazine-2-amine according to the same procedure used in Example 83, which is further converted to the title compound according to the same procedure used in Example 79: $^1$H NMR ($CDCl_3$, 400 MHz) δ 0.97 (t, 6H), 1.60 (m, 2H), 1.70 (m, 2H), 3.89 (s, 3H), 3.92 (m, 1H), 4.98 (d, 1H), 7.27 (dd, 1H), 7.34 (d, 1H), 7.44 (d, 1H); MS (CI) 418.

Example 86a 5-(2,4-Dichlorophenyl)-[N-(1-ethyl)propyl]-3,6-dimethoxypyrazine-2-amine [Formula I: Ar=2,4-dichlorophenyl; $R_1$=$R_3$=$OCH_3$, $R_2$=—NHCH$(CH_2CH_3)_2$]

To a solution of 3-bromo-5-(2,4-dichlorophenyl)-[N-(1-ethyl)propyl]-6-methoxypyrazine-2-amine (0.8 mmole, obtained in example 86) in 1-methyl-2-pyrrolidinone (5 ml) was added sodium methoxide (3.0 mmole). The resulting mixture was then heated to 80° C. for three days. The mixture was then diluted with water and extracted with ethyl acetate. The combined extracts were washed thoroughly with water, then brine and dried. After solvent removed, the crude was purified by silica gel column (eluted with 3% EtOAc in hexane) to give the title compound as a light yellow oil (65% yield). $^1$H NMR ($CDCl_3$, 400 MHz) δ 0.97 (t, 6H), 1.56 (m, 2H), 1.68 (m, 2H), 3.86 (s, 3H), 3.94 (s, 3H), 3.95 (m, 1H), 4.82 (d, 1H), 7.27 (dd, 1H), 7.40 (d, 1H), 7.44 (d, 1H). MS (CI) 370.

Example 86b

3-Ethyl-5-(2,4-dichlorophenyl)-[N-(1-ethyl)propyl]-6-methoxypyrazine-2-amine [Formula I: Ar=2,4-dichlorophenyl; $R_1$=$CH_2CH_3$; $R_3$=$OCH_3$, $R_2$=—$NHCH(CH_2CH_3)_2$]

A: To a solution of 2-(3-pentylamino)-6-chloropyrazine (3.3 g, 16.5 mmol) (obtained in example 75) in 1-methyl-2-pyrrolidinone (15 mL) at room temperature is added a solution of sodium methoxide in methanol (5.0M, 10 ml). The resulting solution was heated to 50° C. for 20 h then evaporated and poured into water and extracted twice with ethyl acetate/hexane (1:1). Combined extracts were dried (sodium sulfate), filtered, concentrated, and chromatographed to give N-(1-ethyl)propyl-6-methoxypyrazine-2-amine as a light yellow solid(98%).

B: A solution of the above solid in chloroform(60 mL) is cooled to 0° C. and N-bromosuccinimide (3.0 g) is added in portions. After the addition, the mixture is further stirred for 1 h while being allowed to warm to room temperature. The mixture is then diluted with dichloromethane, washed with saturated $NaHCO_3$, water, brine and dried, filtered. The filtrate is concentrated and chromatographed on silica gel (dichloromethane/hexane 1:1 elution) to give 3-bromo-[N-(1-ethyl)propyl]-6-methoxypyrazine-2-amine as a yellow oil(35%).$^1$H NMR ($CDCl_3$, 400 MHz) δ0 0.93 (t, 6H), 1.56 (m, 2H), 1.66 (m, 2H), 3.87 (s, 3H), 3.92 (m, 1H), 4.85 (d, 1H), 7.18 (s, 1H).

C: To a solution of above 3-bromo-[N-(1-ethyl)propyl]-6-methoxypyrazine-2-amine (1.27 g, 4.63 mmol) in THF (30 mL) is added [1,3-bis(diphenylphosphino)propane] dichloronickel(II) (125 mg). After 10 min, ethylmagnesium bromide (1.0 M in THF, 9.7 mL) is added slowly dropwise at 0° C. The mixture is stirred at room temperature for 1 hr. The resulting dark solution is poured into aqueous ammonium chloride and extracted twice with ether. Combined extracts are dried (sodium sulfate), filtered, concentrated, and chromatographed (2.5% MeOH/$CH_2Cl_2$) to give the desired product 3-ethyl-[N-(1-ethyl)propyl]-6-methoxy-pyrazine-2-amine as a light yellow oil (55%).

D: A solution of the above oil (0.55 g, 2.46 mmol) in chloroform(10 mL) is cooled to 0° C. and N-bromosuccinimide (445 mg) is added in portions. After the addition, the mixture is further stirred for 30 min while being allowed to warm to room temperature. The mixture is then concentrated to dryness in vacuo, and chromatographed on silica gel (5% ethyl acetate in hexane elution) to give 5-bromo-3-ethyl-6-methoxy-[N-(1-ethyl)propyl]pyrazine-2-amine (85%).

E. A mixed solution of the above bromide (100 mg; 0.33 mmol) and tetrakis(triphenylphosphine)palladium(0) (5 mol %) in ethyleneglycol dimethyl ether (3 mL) is stirred at room temperature for 15 min, when 2,4-dichlorobenzeneboronic acid (95 mg) and an aqueous solution of sodium carbonate (1.0M, 0.75 mL) are added sequentially. The mixture is heated to 75° C. with stirring for 15 h, then diluted with water and extracted twice with 1:1 hexane-ethyl ether. Combined extracts are dried (sodium sulfate), filtered, concentrated, and chromatographed on silica (6% ethyl acetate in hexane) to give the title compound as a yellow oil (121 mg, 99%): $^1$H NMR (CDCl3, 400 MHz) δ 0.97 (t, 6H), 1.27 (t, 3H), 1.56 (m, 2H), 1.70 (m, 2H), 2.62 (q, 2H), 3.85 (s, 3H), 4.00 (m, 1H), 4.18 (d, 1H), 7.28 (d, 1H), 7.38 (d, 1H), 7.44 (s, 1H). MS: 368.

Examples 86C–86D

In Table VI may be Prepared Following the General Procedure Described in Example 86b or Example 86e Using the Corresponding Phenylboronic Acids

TABLE VI

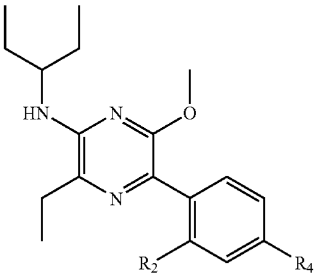

| EX# | $R_2$ | $R_4$ | $^1$H NMR | MS(CI) | NAME |
|---|---|---|---|---|---|
| 86C | $OCH_3$ | $OCH_3$ | 0.96(t, 6H), 1.27(t, 3H), 1.56(m, 2H), 1.70(m, 2H), 2.62(q, 2H), 3.78(s, 3H), 3.82(s, 3H), 3.85(s, 3H) 4.02(m, 2H), 6.54(d, 1H), 6.56(dd, 1H), 7.26(d, 1H). | 360 | 3-ethyl-6-methoxy-N-(1-ethylpropyl)-5-(2,4-dimethoxyphenyl)pyrazin-2-amine |
| 86D | $OCF_3$ | $OCH_3$ | 0.97(t, 6H), 1.27(t, 3H), 1.56(m, 2H), 1.70(m, 2H), 2.62(q, 2H), 3.83(s, 3H), 3.86(s, 3H), 4.01(m, 1H), | 414 | 3-ethyl-6-methoxy-N-(1-ethylpropyl)-5-(2- |

TABLE VI-continued

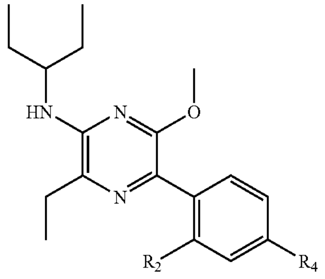

| EX# | $R_2$ | $R_4$ | $^1H$ NMR | MS(CI) | NAME |
|---|---|---|---|---|---|
| | | | 4.10(d, 1H), 6.85(s, 1H), 6.87(d, 1H), 7.43(d, 1H). | | difluoromethoxy-4-methoxyphenyl)pyrazin-2-amine |
| 86E | $OCH_3$ | $CF_3$ | 0.96(t, 6H), 1.27(t, 3H), 1.58(m, 2H), 1.70(m, 2H), 2.63(q, 2H), 3.86(s, 3H), 3.87(s, 3H), 4.01(m, 1H) 4.13(m, 1H), 7.16(s, 1H), 7.27(d, 1H), 7.47(d, 1H). | 398 | 3-ethyl-6-methoxy-N-(1-ethylpropyl)-5-(2-methoxy-4-trifluoromethylphenyl) pyrazin-2-amine |

Example 86f

3-Ethyl-5-(2-methoxy-4-trifluoromethoxyphenyl)-[N-(1-ethyl)propyl]-6-methoxypyrazine-2-amine Scheme V

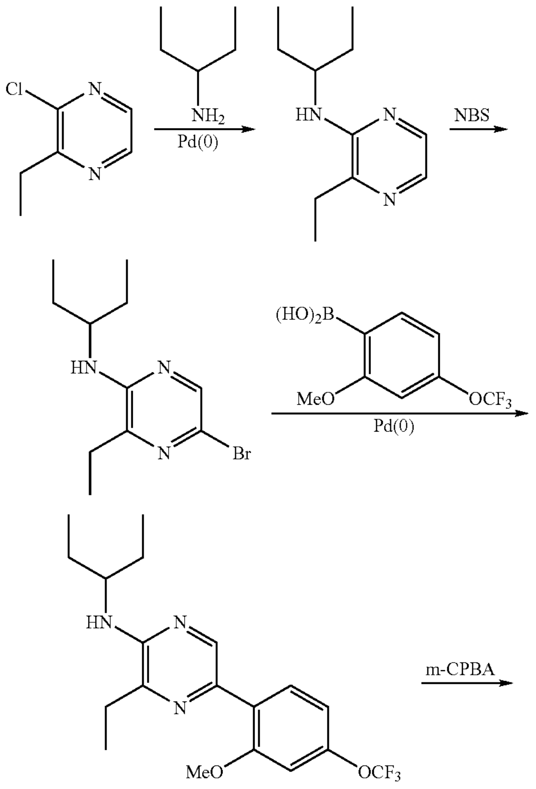

-continued

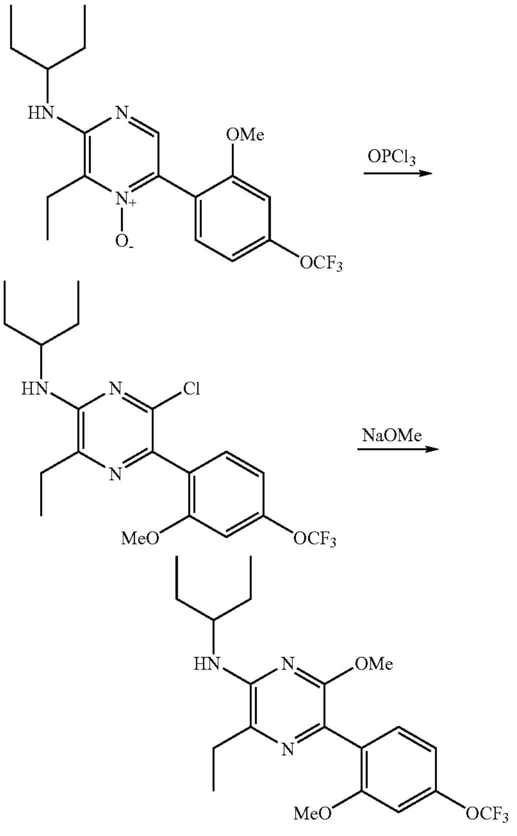

A. (1-Ethyl-propyl)-(3-ethyl-pyrazin-2-yl)-amine. In a pressure tube, 2-chloro-3-ethyl-pyrazine (1.4 g, 10 mmol), $Pd_2(dba)_3$ (229 mg, 0.25 mmol) and $P(t-Bu)_3$ (100 □L, 0.4 mmol) were dissolved in toluene (15 mL) and stirred at room temperature for 30 min. 1-Ethyl-propylamine (1.75 mL, 15 mmol) and KOt-Bu (1M in THF, 15 mmol, 15 mL) were added, and the dark solution was stirred at 55° C. (oil bath temperature) for 90 min. The reaction mixture was allowed to reach room temperature, diluted with ethyl ether (100 mL)

and washed with brine (3×100 mL). After drying with MgSO4, the solvents were removed under reduced pressure and a dark oil obtained. Flash chromatography (100% hexanes to 20% ethyl acetate in hexanes) produced the desired product (710 mg, 37%). H-1 NMR ($CDCl_3$, 300 MHz): 7.84 (1H, d, J=8.1 Hz), 7.68 (1H, d, J=9 Hz), 4.15 (br, 1H), 4.05 (quint, 1H), 2.6 (2H, q, J=7.4 Hz), 1.4–1.6 (m, 4H), 1.32 (t, 3H, J=7.4 Hz), 0.95 (t, 6H, J=7.4 Hz). MS: 194 (M+1, positive mode) and 192 (M−1, negative mode).

B. (5-Bromo-3-ethyl-pyrazin-2-yl)-(1-ethyl-propyl)-amine. The product from step 1 (650 mg, 3.4 mmol) was dissolved in chloroform (20 mL) and treated at room temperature with N-bromosuccinimide (600 mg, 3.5 mmol). After 5 min the mixture was diluted with chloroform (100 mL) and the organic solution washed with brine (3×100 mL), dried ($MgSO_4$), filtered, and the solvent removed under reduced pressure to produce 5-bromo-3-ethyl-pyrazin-2-yl)-(1-ethyl-propyl)-amine (700 mg, 77%). H-1 NMR ($CDCl_3$, 400 MHz): 7.94 (1H, s), 4.1 (br, 1H), 3.95 (quint, 1H), 2.60 (2H, q, J=7.4 Hz), 1.4–1.6 (m, 4H), 1.32 (t, 3H, J=7.4 Hz), 0.95 (t, 6H, J=7.4 Hz). MS: 274.1 (M+1, positive mode) and 270.3 (M−1, negative mode).

C. [3-Ethyl-5-(2-methoxy4-trifluoromethoxy-phenyl)-pyrazin-2-yl]-(1-ethyl-propyl)-amine. In a pressure tube, a mixture of the product from step 2 (700 mg, 2.6 mmol), 2-methoxy-4-trifluoromethoxyboronic acid (1.0 g, 4.2 mmol) and $Pd(PPh_3)_4$ (100 mg) in toluene (10 mL), ethanol (0.5 mL) and aqueous $K_2CO_3$ (2M, 5 mL) was heated in oil bath at 80° C. for 16 h. The mixture was diluted with ethyl acetate, and the organic fraction washed with NaOH (2M, 50 mL) and brine (3×50 mL), dried (MgSO4) filtered, and the solvent removed under reduced pressure. Flash chromatography of the residue (100% hexanes to 4% ethyl acetate in hexanes) provided the desired product as an oil (850 mg, 85%). H-1 NMR ($CDCl_3$, 300 MHz): 8.53 (1H, s), 7.91 (1H, d, J=8.8 Hz), 6.93 (1H, d, J=8.8 Hz), 6.80 (s, 1H), 4.18 (1H, d, J=8.2 Hz), 4.10 (quint, 1H, J=5.8 Hz), 3.88. (3H, s), 2.6 (2H, q, J=7.4 Hz), 1.4–1.6 (m, 4H), 1.37 (t, 3H, J=7.4 Hz), 0.95 (t, 6H, J=7.4 Hz). MS: 384.3 (M+1, positive mode) and 382.2 (M−1, negative mode).

D. [3-Ethyl-5-(2-methoxy4-trifluoromethoxy-phenyl)4-oxy-pyrazin-2-yl]-(1-ethyl-propyl)-amine. The aminopyrazine obtained in step 3 (370 mg, 0.97 mmol) was dissolved in dichloromethane (15 mL) and treated with solid m-chloroperoxybenzoic acid (374 mg, 1.3 eq) at room temperature. After 3 h the reaction was worked up by diluting with dichloromethane (50 mL) and washing with NaOH 2M (25 mL) and brine (3×50 mL). The organic solution was dried (MgSO4), filtered and the solvent evaporated under reduced pressure. The residue was purified by preparative thin layer chromatography, eluting with 30% ethyl acetate in hexanes), furnishing the desired product (55 mg, 14%). NMR ($CDCl_3$, 400 MHz) H-1: 7.86 (1H, s), 7.38 (1H, d, J=8.4 Hz), 6.89 (1H, d, J=7.2 Hz), 6.81 (s, 1H), 4.21 (1H, d, J=8.0 Hz), 4.08 (quint, 1H, J=6.0 Hz), 3.81 (3H, s) 2.9 (2H, q, J=7.6 Hz), 1.5–1.75 (m, 4H), 1.23 (t, 3H, J=7.2 Hz), 0.96 (t, 6H, J=7.6 Hz). C-13: 158.96, 154.43, 150.64, 142.56, 132.86, 132.47, 131.32, 119.15, 112.22, 104.58, 104.58, 56.01, 53.35, 26.96, 17.89, 10.04, 8.86. F-19 NMR: −58.04 (s). (MS: 400.3 (M+1, positive mode) and 398.3 (M−1, negative mode).

E. [6-Chloro-3-ethyl-5-(2-methoxy4-trifluoromethoxy-phenyl)-pyrazin-2-yl]-(1-ethyl-propyl)-amine. The N-oxide from step 4 (40 mg, 0.1 mmol) was dissolved in $OPCl_3$ (1.5 mL) and heated at 80° C. for 16 h. After cooling down to room temperature, the reaction mixture was diluted with ethyl ether (100 mL) and washed with NaOH (2M, 50 mL) and brine (3×50 mL), dried (MgSO4), filtered, and the solvent evaporated under reduced pressure to afford the desired chloropyrazine (40 mg, 96%). NMR ($CDCl_3$, 400 MHz) H-1: 7.32 (1H, d, J=8.4 Hz), 6.89 (1H, d, J=7.2 Hz), 6.80 (s, 1H), 4.26 (1H, d, J=8.4 Hz), 4.07 (quint, 1H, J=5.6 Hz), 3.82 (3H, s), 2.64 (2H, q, J=7.6 Hz), 1.5–1.75 (m, 4H), 1.29 (t, 3H, J=7.6 Hz), 0.96 (t, 6H, J=7.2 Hz). C-13: 158.20, 150.91, 150.14, 143.80, 140.95, 134.30, 131.94, 126.07, 112.44, 104.58, 55.78, 53.01, 26.81, 25.75, 10.80, 10.02. F-19 NMR: −58.03 (s). (MS: 418.2 (M+1, positive mode) and 416.2 (M−1, negative mode).

F. [3-Ethyl-6-methoxy-5-(2-methoxy-4-trifluoromethoxy-phenyl)-pyrazin-2-yl]-(1-ethyl-propyl)-amine. In a pressure tube, the chloropyrazine from step 5 (30 mg) was dissolved in DMF (2 mL) and treated with sodium methoxide (100 mg) at 80° C. for 120 h. The reaction mixture was diluted with ethyl ether (50 mL) and washed with brine. The residue was purified by preparative thin layer chromatography (15% ethyl acetate in hexanes to produce [3-ethyl-6-methoxy-5-(2-methoxy4-trifluoromethoxy-phenyl)-pyrazin-2-yl]-(1-ethyl-propyl)-amine (10 mg, 33%), identical by tlc and NMR with an authentic specimen.

Example 87

6-chloro-[N-(1-ethyl)propyl]-3-methoxy-5-(2,4-dichlorophenyl)pyrazine-2-amine [Formula I: Ar=2,4-dichlorophenyl; $R_1$═$OCH_3$; $R_2$═—$NHCH(CH_2CH_3)_2$; $R_3$═Cl]

A. A solution in DMF (2 mL) of 3-bromo-6-chloro-[N-(1-ethyl)propyl]pyrazine-2-amine (0.50 g; 1.8 mmol) obtained as a minor product in Example 75B is added into a solution of sodium methoxide (freshly prepared from 90 mg of sodium metal in methanol; 3.9 mmol) in DMF (3 mL). The mixture is stirred at room temperature overnight, then poured into aqueous ammonium chloride solution and extracted twice with hexane-ethyl ether. Combined extracts are dried (sodium sulfate), filtered, concentrated in vacuo, and chromatographed on silica gel to give 6-chloro-3-methoxy-[N-(1-ethyl)propyl]pyrazine-2-amine (410 mg).

B. The above material is brominated according to the same procedure used in Example 79 and further converted to the title compound according to the same Suzuki coupling procedure used in Example 1C: $^1H$ NMR ($CDCl_3$, 400 MHz) δ 0.95 (t, 6H), 1.5–1.7 (m, 4H), 2.15 (s, 3H), 3.8 (s, 3H), 3.85 (s, 3H), 3.95 (s, 3H), 4.0 (m, 1H), 4.8 (br d, 1H), 6.55 (s, 1H), 6.55 (d, 1H), 7.3 (d, 1H).

Example 88

5-(2,4-dichlorophenyl)-[N-(1-ethyl)propyl]-3-methoxy-6-methylpyrazine-2-amine [Formula I: Ar=2,4dichlorophenyl; $R_1$═$OCH_3$; $R_2$═—$NHCH(CH_2CH_3)_2$; $R_3$═$CH_3$]

A. 6-chloro-3-methoxy-[N-(1-ethyl)propyl]pyrazine-2-amine obtained in Example 87A is converted to 6-methyl derivative according to the same procedure used in Example 85 and further brominated according to the same procedure used in Example 79.

B. The 5-bromopyrazine obtained as above is converted to the title compound according to the same procedure used in Example 1C: $^1H$ NMR ($CDCl_3$, 400 MHz) δ 0.95 (t, 6H), 1.5–1.7 (m, 4H), 2.15 (s, 3H), 3.9 (s, 3H), 4.05 (m, 1H), 4.8 (br d, 1H), 7.3 (s, 2H), 7.45 (s, 1H); MS (CI) 356.

Examples 89-90

May be Prepared According to the General Procedure Described in Example 88

Example 89

[N-(1-ethyl)propyl]-3-methoxy-5-(2,4-dimethoxyphenyl)-6-methylpyrazine-2-amine [Formula I: Ar=2,4-dimethoxyphenyl; $R_1$=$OCH_3$; $R_2$=—$NHCH(CH_2CH_3)_2$; $R_3$=$CH_3$]

$^1$H NMR ($CDCl_3$, 400 MHz): δ 0.95 (t, 6H), 1.5-1.7 (m, 4H), 2.15 (s, 3H), 3.8 (s, 3H), 3.85 (s, 3H), 3.95 (s, 3H), 4.0 (m, 1H), 4.7 (br d, 1H), 6.5 (s, 1H), 6.55 (d, 1H), 7.2 (d, 1H); MS (CI) 346.

Example 90

[N-(1-ethyl)propyl]-3-methoxy-5-(4-methoxy-2-methylphenyl)-6-methylpyrazine-2-amine [Formula I: Ar=2-methyl4-methoxyphenyl; $R_1$=$OCH_3$; $R_2$=—$NHCH(CH_2CH_3)_2$; $R_3$=$CH_3$]

$^1$H NMR ($CDCl_3$, 400 MHz): δ 0.95 (t, 6H), 1.5-1.7 (m, 4H), 2.15 (s, 3H), 2.2 (s, 3H), 3.8 (s, 3H), 3.9 (s, 3H), 4.0 (m, 1H), 4.7 (br d, 1H), 6.75 (d, 1H), 6.8 (s, 1H), 7.15 (d, 1H); MS (CI) 330.

Example 91

{4-[6-Ethyl-5-(ethylpropoxy)-3-methoxypyrazin-2-yl]-3-methoxyphenoxy}trifluoromethane

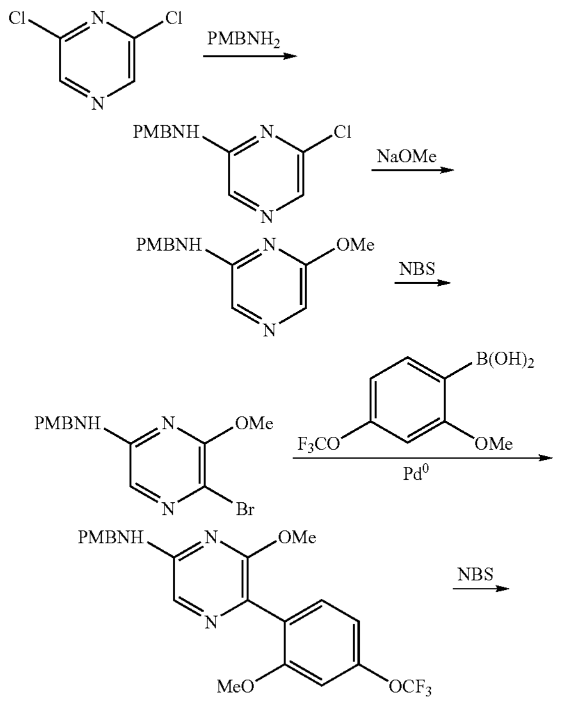

-continued

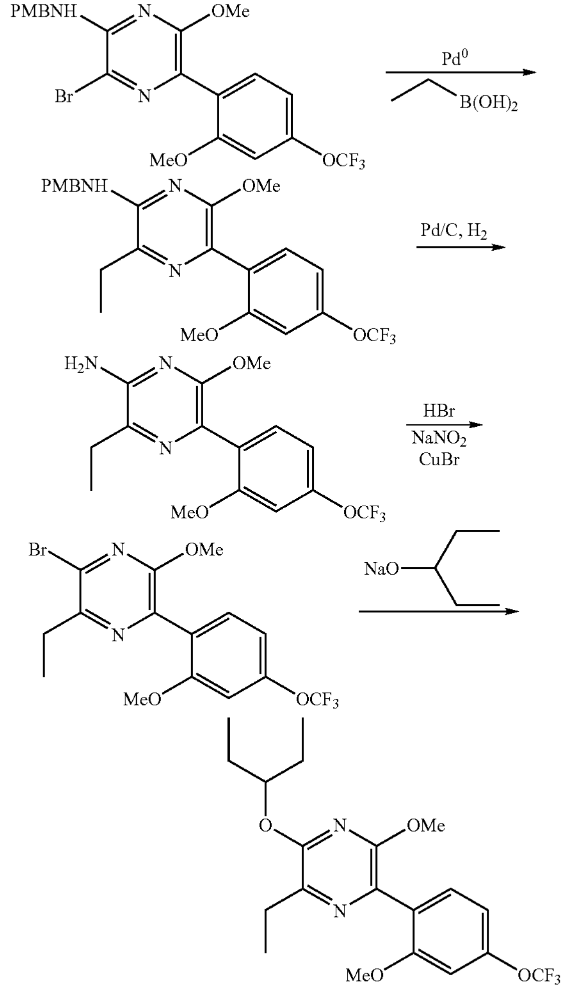

A. To a stirred solution of 2,6-dichloropyrazine (25 g, 0.167 mol) and ethanol (120 mL) in a sealed tube is added 4-methoxybenzylamine (68.6 g, 0.5 mol). The mixture is heated to 115° C. for 12 h and cooled. The white solid is removed by filtration and the filtrate evaporated. The residue is dissolved in ethyl acetate and washed successively with 2M sodium hydroxide, water and aqueous sodium chloride. The organics are dried (magnesium sulfate), filtered, and evaporated to give (6-chloropyrazin-2-yl)[(4-methoxyphenyl)methyl]amine (35.5 g), a white solid.

B. To a stirred solution of (6-chloropyrazin-2-yl)[(4-methoxyphenyl)methyl]amine (5.0 g, 20.0 mmol) in DMF (30 mL) is added sodium methoxide (7.50 g, 125.0 mmol). The mixture is heated at reflux for 12 h, cooled and partitioned between ethyl acetate (100 mL) and water (100 mL). The layers are separated and the organic layer washed with water (3×100 mL). The combined extracts are dried (magnesium sulfate), filtered, and evaporated to give [(4-methoxyphenyl)methyl](6-methoxypyrain-2-yl)amine (4.65 g), a yellow solid.

C. A solution of [(4-methoxyphenyl)methyl](6-methoxypyrain-2-yl)amine (2.45 g, 10.0 mmol) in chloroform (50 mL) is cooled to 0° C. and N-bromosuccinimide (1.8 g, 10.0 mmol) is added in portions. After the addition, the mixture is further stirred for 1 h while being allowed to warm to room temperature. The mixture is washed with saturated aqueous sodium bicarbonate, aqueous sodium chloride, dried (magnesium sulfate), filtered and evaporated. The residue is purified by flash chromatography, eluting with 20% ether in hexanes to give (5-bromo-6-methoxypyrazin-2-yl)[(4-methoxyphenyl)methyl]amine (1.1 g).

D. To a stirred solution of (5-bromo-6-methoxypyrazin-2-yl)[(4-methoxyphenyl)methyl]amine (0.80 g, 2.50 mmol) and 2-methoxy4-tritluoromethoxybenzeneboronic acid (1.75 g, 7.5 mmol) in toluene (25 mL) is added tetrakis (triphenylphosphine)palladium(0) (100 mg) and potassium carbonate (2.0 M, 2.0 mL). The mixture is heated to 85° C. for 8 h, cooled to room temperature, diluted with 2.0 M sodium hydroxide and extracted twice with 1:1 hexane-ethyl ether. The combined extracts are dried (sodium sulfate), filtered and concentrated. The residue is purified by flash chromatography, eluting with 60% hexanes in ether to give {6-methoxy-5-[2-methoxy4-(trifluoromethoxy)phenyl] pyrazin-2-yl }[(4-methoxyphenyl)methyl]amine (967 mg).

E. A solution of {6-methoxy-5-[2-methoxy4-(trifluoromethoxy)phenyl]pyrazin-2-yl }[(4-methoxyphenyl)methyl]amine (870 mg, 2.0 mmol) in chloroform (10 mL) is cooled to 0° C. and N-bromosuccinimide (356 mg, 2.0 mmol) is added in portions. After the addition, the mixture is further stirred for 1 h while being allowed to warm to room temperature. The mixture is washed with saturated aqueous sodium bicarbonate, aqueous sodium chloride, dried (magnesium sulfate), filtered, and evaporated to give {3-bromo-6-methoxy-5-[2-methoxy-4-(trifluoromethoxy) phenyl]pyrazin-2-yl }[(4-methoxyphenyl)methyl]amine (920 mg), a yellow solid.

F. To a stirred solution of {3-bromo-6-methoxy-5-[2-methoxy-4-(trifluoromethoxy)phenyl]pyrazin-2-yl }[(4-methoxyphenyl)methyl]amine (514 mg, 1.0 mmol) and ethylboronic acid (219 mg, 3.0 mmol) in toluene (8 mL) is added tetrakis(triphenylphosphine)palladium(0) (50 mg) and potassium carbonate (2.0 M, 1.0 mL). The mixture is heated to 85° C. for 8 h, cooled to room temperature, diluted with 2.0 M sodium hydroxide and extracted twice with 1:1 hexane-ethyl ether. The combined extracts are dried (sodium sulfate), filtered and concentrated. The residue is purified by flash chromatography, eluting with 20% ether in hexanes to give {3-ethyl-6-methoxy-5-[2-methoxy-4-(trifluoromethoxy)phenyl]pyrazin-2-yl }[(4-methoxyphenyl)methyl]amine (430 mg).

G. To {3-ethyl-6-methoxy-5-[2-methoxy-4-(trifluoromethoxy)phenyl]pyrazin-2-yl}[(4-methoxyphenyl)methyl]amine (115 mg, 0.25 mmol) in methanol (3 mL) under a nitrogen atmosphere is added 1M hydrochloric acid in ether (2 mL) and 10% palladium on carbon (40 mg). The mixture is then hydrogenated at 1 ATM for 18 h, filtered through Celite and evaporated to give 3-ethyl-6-methoxy-5-[2-methoxy4-(trifluoromethoxy)phenyl]pyrazin-2-ylamine (80 mg).

H. To a stirred solution of 3-ethyl-6-methoxy-5-[2-methoxy-4-(trifluoromethoxy)phenyl]pyrazin-2-ylamine (86 mg, 0.25 mmol) in 48% hydrogen bromide (0.3 mL) at 0° C. is added a solution of sodium nitrite (21 mg, 0.3 mmol) in water (1 mL). After 1.5 h copper bromide (43 mg, 0.3 mmol) is added and the mixture heated to 70° C. for 1 h. The mixture is cooled to room temperature and extracted with ether. The extracts are dried (sodium sulfate), filtered and concentrated to give [4-(5-bromo-6-ethyl-3-methoxypyrazin-2-yl)-3-methoxyphenoxy]trifluoromethane (76 mg).

I. To a stirred solution of 3-pentanol (88 mg, 1 mmol) in THF (1 mL) is added 60% sodium hydride (12 mg, 0.3 mmol) and after 0.5 h [4-(5-bromo-6-ethyl-3-methoxypyrazin-2-yl)-3-methoxyphenoxy]trifluoromethane (41 mg, 0.1 mmol) is added. The mixture is heated to 50° C. for 12 h, cooled and partitioned between ethyl acetate and water. The organic layer is washed with water, brine, dried (sodium sulfate), filtered and concentrated. The residue is purified by preparative TLC eluting with 50% ether in hexanes to give {4-[6-Ethyl-5-(ethylpropoxy)-3-methoxypyrazin-2-yl]-3-methoxyphenoxy}trifluoromethane, a colorless oil (19 mg). NMR ($CDCl_3$, 400 MHz) □0.98 (t, 6H), 1.22 (t, 3H), 1.78 (m, 4H) 2.80 (q, 2H), 3.80 (s, 3H), 3.88 (s, 3H), 5.05 (quintet, 1H), 6.8 (s, 1H), 6.90 (d, 1H), 7.37 (d, 1H); MS 345 (M+1).

Additional compounds prepared and assayed by the methods described herein are shown in Table VII.

TABLE VII

Formula I

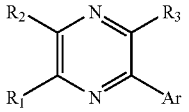

| Cpnd No. | Ar | $R_1$ | $R_2$ | $R_3$ | Synthetic Method | IMR32 Binding | Name |
|---|---|---|---|---|---|---|---|
| 91a | 2,4,6-trichlorophenyl | $CH_3$ | 3-pentyl amino | $CH_3$ | Example I | 40 nM | 3,6-dimethyl-N-(1-ethylpropyl)-5-(2,4,6-trimethylphenyl)pyrazin-2-amine |
| 91b | 2,4-dichlorophenyl | Br | 3-pentyl amino | Cl | Example I | 28 nM | 3-bromo-6-chloro-N-(1-ethylpropyl)-5-(2,4-dichlorophenyl)pyrazin-2-amine |

Example 92

Synthesis of [3-ethyl-5-(2-methoxy-4-trifluoromethoxy-phenyl)-6-methylsulfanyl-pyrazin-2-yl]-(1-ethyl-propyl)-amine

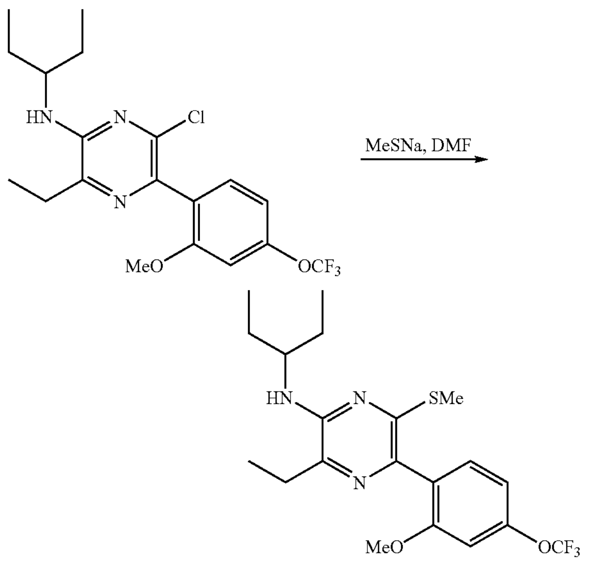

In a pressure tube equipped with Teflon O-ring were combined [6-chloro-3-ethyl-5-(2-methoxy-4-trifluoromethoxy-phenyl)-pyrazin-2-yl]-(1-ethyl-propyl)-amine (100 mg) obtained in step E of Example 86e, NaSMe (200 mg), THF (5 mL) and DMF (3 mL). 10 The mixture was heated at 80° C. (oil bath temperature) for 72 h. The crude mixture was diluted with ethyl acetate (40 mL) and water (40 mL), and the organic phase washed with brine (3×100 mL). After drying (MgSO4), filtration and elimination of solvents at reduced pressure, the title compound was isolated as a clear oil by preparative thin layer chromatography (10% EtOAc in hexanes). Yield was 50 mg (49%). NMR ($CDCl_3$, 400 MHz) H-1: 7.32 (1H, d, J=8.4 Hz), 6.88 (1H, m), 6.78 (s, 1H), 4.18 (1H, d), 4.07 (m, 1H), 3.78 (3H, s), 2.64 (2H, q), 2,24 (s, 3H), 1.5–1.75 (m, 4H), 1.25 (t, 3H), 0.96 (t, 6H), MS: 430.2 (M+1, positive mode) and 428.4 (M−1, negative mode).

Example 93

2-sec-butylsulfanyl-5-(2,4-dimethoxy-phenyl)-3,6-diethyl-pyrazine

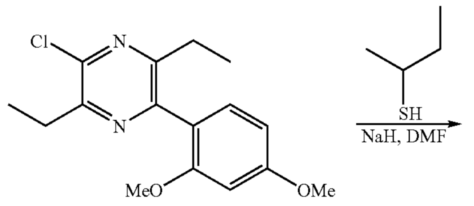

-continued

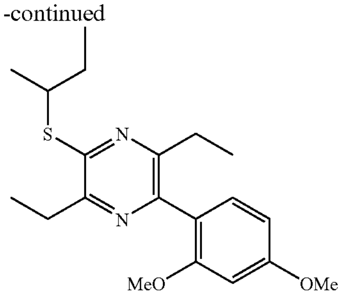

NaH (60 mg, 1.5 mmol. 60% in mineral oil) was added to a solution of butane-2-thiol (170 μL, 1.5 mmol) in THF (5 mL). After 10 minutes, 2-chloro-5-(2,4-dimethoxy-phenyl)-3,6-diethyl-pyrazine (100 mg, 0.33 mmol) obtained as in Example 45, steps A–C, in THF (1 mL) was added dropwise, and the mixture heated at 80° C. (oil bath temperature) for 16 h. After extractive work-up, preparative thin layer chromatography (hexanes) furnished the title compound as a clear oil (60 mg, 51%). NMR ($CDCl_3$, 400 MHz) H-1: 7.19 (1H, d, J=8.4 Hz), 6.58 (1H, dd, J=2.4, 8.4 Hz), 6.60 (s, 1H, J=2.4 Hz), 3.99 (sext, 1H, J=6.8 Hz), 3.85 (3H, s), 3.75 (3H, s), 2.81 (2H, q, J=7.4 Hz), 2.58 (2H, br q, J=6.8 Hz), 1.6–1.9 (m, 4H), 1.44 (3H, d, J=6.4 Hz), 1.28 (t, 3H, J=7.6 Hz), 1.19 (3H), t, J=7.6 Hz), 1.06 (t, 3H, J=7.2 Hz). C-13: 161.10, 157.86, 153.49, 151.79, 151.67, 144.47, 131.68, 121.18, 104.78, 98,60, 55.44, 55.33, 40.87, 29.65, 27.54, 27.08, 20.56, 12.43, 12.09, 11.51. MS: 414.2 (M+1, positive mode) and 412.2 (M−1, negative mode).

Example 93a

2—Sec-butylsulfanyl-5-(2,4-dichloro-phenyl)-3,6-diethyl-pyrazine

By a similar procedure, but starting from 2-chloro-5-(2,4-dichloro-phenyl)-3,6-diethyl-pyrazine obtained as in Example 49 steps A–C, was obtained 2-sec-butylsulfanyl-5-(2,4-dichloro-phenyl)-3,6-diethyl-pyrazine. NMR ($CDCl_3$, 400 MHz) H-1: 7.19 (1H, d, J=2.0 Hz), 7.26 (1H, dd, J=2.0, 8.0 Hz), 7.18 (1H, d, J=8.0 Hz), 3.92 (1H, sext, J=6.8 Hz), 2.72 (2H, q, J=7.6 Hz), 2.58 (2H, br), 1.6–1.8 (m, 4H), 1.36 (3H, d, J=6.8 Hz), 1.20 (t, 3H), J=7.6 Hz), 1.12 (3H, t, J=7.6 Hz), 0.98 (t, 3H, J=7.6 Hz). C-13: 153.93, 152.40, 152.00, 143.69, 136.46, 134.73, 134.40, 131.94, 129.48, 127.24, 41.01, 29.56, 27.40, 27.10, 20.45, 12.48, 11.86, 11.51. MS: 369.2 (M+1, positive mode).

Example 93b

2—Sec-butylsulfanyl-3-ethyl-6-methoxy-5-(2-methoxy-4-trifluoromethoxy-phenyl)-pyrazine By a similar procedure, but starting from 2-bromo-3-ethyl-6-methoxy-5-(2-methoxy4-trifluoromethoxy-phenyl)-pyrazine obtained as in Example 49 steps A–C, was obtained 2-sec-butylsulfanyl-3-ethyl-6-methoxy-5-(2-methoxy-4-trifluoromethoxy-phenyl)-pyrazine. NMR ($CDCl_3$, 400 MHz) H-1: 7.37 (1H, d, J=8.4 Hz), 6.91 (1H, m), 6.80 (1H, s), 3.94 (3H, s), 3.89 (1H, m), 3.79 (3H, s), 2.78 (2H, q, J=7.6 Hz), 1.7–1.9 (m, 4H), 1.46 (3H, d, J=6.8 Hz), 1.27 (t, 3H, J=7.2 Hz), 1.07 (3H, t, J=7.2 Hz). C-13: 158.43, 155.85, 150.32, 149.90, 146.33, 135.34, 133.73, 131.85, 124.81, 112.66, 104.85, 55.93, 53.57, 41.47, 29.61, 26.83, 20.61, 12.30, 11.54. F-19 NMR: −58.04 (s). MS: 417.2 (M+1, positive mode).

Example 94

1-[3,6-diethyl-5-(2-methylbutyl)pyrazin-2-yl]-2,4-dimethoxybenzene

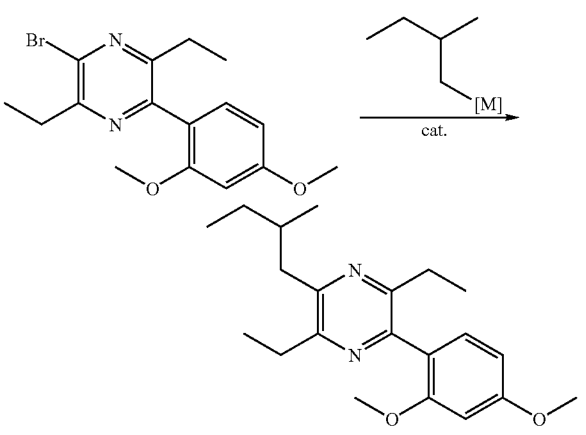

To a solution of 2-methyl-1-butene (210 mg, 3.0 mmol) in THF is added a solution of 9-BBN (9-borabicyclo[3.3.1] nonane) in T1F (0.5 M, 6.0 mL, 3.0 mmol). The mixture is heated at reflux, under a nitrogen atmosphere for 12 h and cooled. To the solution is added 1-(5-bromo-3,6-diethylpyrazin-2-yl)-2,4-dimethoxybenzene (664 mg, 2.0 mmol), obtained as in Example 49 steps A–C, tetrakis(triphenylphosphine) palladium(0) (50 mg) and sodium hydroxide (3.0 M, 3.0 mL, 3.0 mmol). The mixture is heated at 50° C. for 12 h and cooled. 30% Hydrogen peroxide (1 mL) is added, the solution stirred for 1 h and the reaction mixture extracted with ether. The combined extracts are dried (sodium sulfate), filtered and concentrated. The residue is purified by flash chromatography, eluting with 40% ether in hexanes to give 1-[3,6-diethyl-5-(2-methylbutyl)pyrazin-2-yl]-2,4-dimethoxybenzene (393 mg).

Example 95

2(2-methoxy-5-triflurormethoxyphenyl)-3-ethyl-6-methylamino-5-(1-ethylpropoxy)-pyrazine

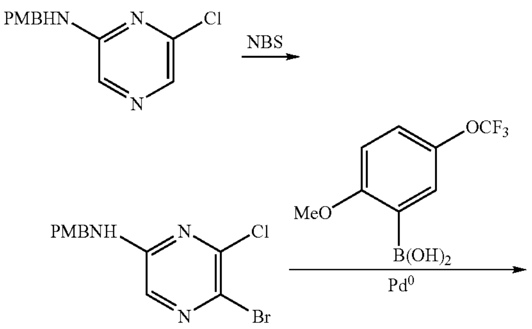

-continued

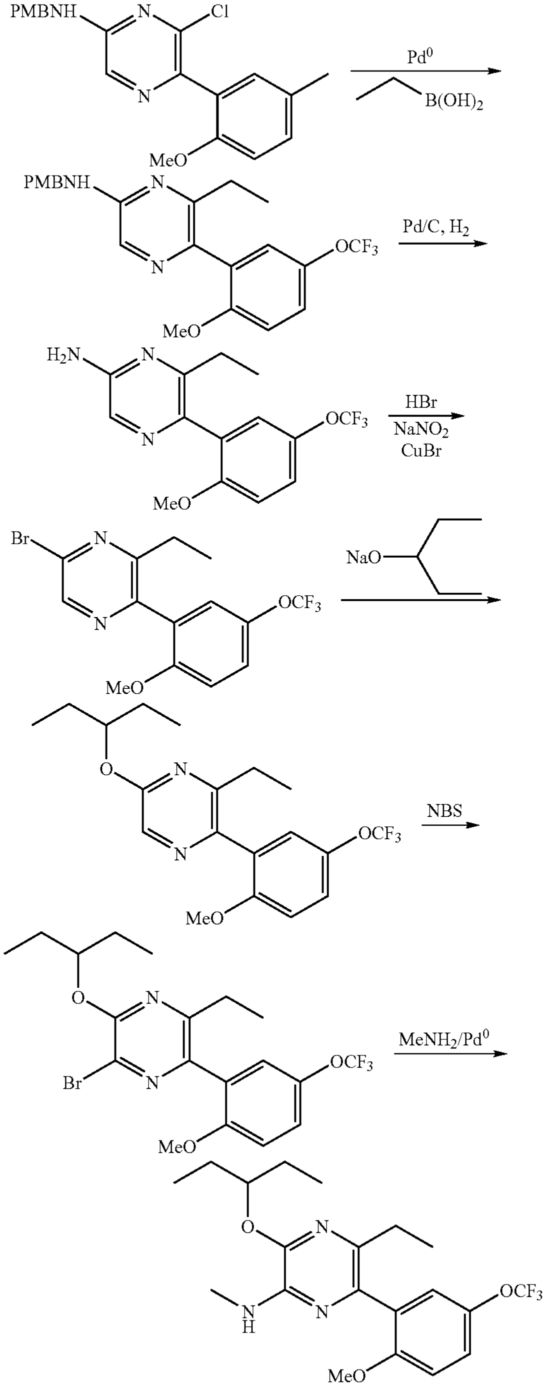

(6-Chloropyrazin-2-yl)[(4-methoxyphenyl)methyl] amine is prepared by Step A of Example 91

A. A solution of 6-(Chloropyrazin-2-yl)[(4-methoxyphenyl)methyl]amine in chloroform (4 mL/mmol NBS) is cooled to 0° C. and N-bromosuccinimide (1.05 eq) is added in portions while stirring the reaction mixture. After complete addition, the mixture is further stirred for 1 hour while being allowed to warm to room temperature. The mixture is then diluted with dichloromethane, washed with saturated $NaHCO_3$, water, brine and then dried and filtered. The filtrate is concentrated and purified by chromatography on silica gel to give (5-bromo-6-chloropyrazin-2-yl)[(4-methoxyphenyl)methyl]amine.

B. In a pressure tube, a mixture of the product from step A (1 equivalent), 2-methoxy-5-trifluoromethoxyphenylboronic acid (1.6 equivalents) and $Pd(PPh_3)_4$ (0.04 equivalents) in toluene (4 ml/mmol of product from step A), ethanol (0.2 ml/mmol of product from step A ) and aqueous $K_2CO_3$ (2M, 2 ml/mmol of product from step A) is heated to 80° C. for 16 h. The mixture was diluted with ethyl acetate, and the organic fraction washed with NaOH (2M, 20 mL/mmol of product from step A) and brine (3×20 ml/mmol of product from step A), then dried ($MgSO_4$), filtered and the solvent removed under reduced pressure. Chromatography of the residue provided (3-(2-methoxy-5-trifluoromethoxyphenyl)-6-chloropyrazin-2-yl)[(4-methoxyphenyl)methyl] amine.

C. (5-(2-methoxy-5-trifluoromethoxyphenyl)-6-ethylpyrazin-2-yl)[(4-methoxyphenyl)methyl]amine can be prepared by the method of Example 1, step A by substituting (5-(2-methoxy-5-trifluoromethoxyphenyl)-6-chloropyrazin-2-yl)[(4-methoxyphenyl)methyl]amine for 2-chloro-3,6-dimethylpyrazine.

D. (5-(2-methoxy-5-trifluoromethoxyphenyl)-6-ethylpyrazin-2-yl)amine can be prepared by the hydrogentation method of Example 91, step G by substituting (5-(2-methoxy-5-trifluoromethoxyphenyl)-6-ethylpyrazin-2-yl) [(4-methoxyphenyl)methyl]amine for {3-ethyl-6-methoxy-5-[2-methoxy4-(trifluoromethoxy)phenyl]pyrazin-2-yl }[(4-methoxyphenyl)methyl]amine.

E. 2-Bromo-5-(2-methoxy-5-trifluoromethoxyphenyl)-6-ethylpyrazine can be prepared by the halogenation method of Example 91, step H by substituting (5-(2-methoxy-5-trifluoromethoxyphenyl)-6-ethylpyrazin-2-yl)amine for {3-ethyl-6-methoxy-5-[2-methoxy4-(trifluoromethoxy)phenyl]pyrazin-2-yl }amine.

F. 2-(3-Pentoxy)-(5-(2-methoxy-5-trifluoromethoxyphenyl)-6-ethylpyrazine can be prepared by the method of Example 91, step I by substituting 2-bromo-(5-(2-methoxy-5-trifluoromethoxyphenyl)-6-ethylpyrazin-2-yl)[(4-methoxyphenyl)methyl]amine for [4-(5-bromo-6-ethyl-3-methoxypyrazin-2-yl)-3-methoxyphenoxy]trifluoromethane.

G. 2-(3-Pentoxy)-3-bromo-(5-(2-methoxy-5-trifluoromethoxyphenyl)-6-ethylpyrazine can be prepared by the method of step A of the present Example by substituting 2-(3-Pentoxy)-3-bromo-(5-(2-methoxy-5-trifluoromethoxyphenyl)-6-ethylpyrazine for (6-chloropyrazin-2-yl)[(4-methoxyphenyl)methyl]amine.

H. To a mixture of 2-(3-Pentoxy)-3-bromo-(5-(2-methoxy-5-trifluoromethoxyphenyl)-6-ethylpyrazine (1 equivalent), tris(dibenzylideneacetone)dipalladium(0) (2 mol %), and 1,1'-binaphthyl-2,2'-di(diphenylphosphine) (BINAP) (6 mol %) in ethyleneglycol dimethyl ether (2.4 mL/mmol substrate) under nitrogen is added methylamine (1.2 equivalents) followed by sodium tert-butoxide (1.5 equivalents). The mixture is stirred at 70–80° C. for about 2.5 hours, diluted with aqueous ammonium chloride, and extracted with 1:1 hexane-diethyl ether. The combined extracts are dried (sodium sulfate), filtered, concentrated and then purified by chromatography on silica gel to afford 2-(3-Pentoxy)-3-(N-methylamino)-(5-(2-methoxy-5-trifluoromethoxyphenyl)-6-ethylpyrazin

Example 96

Assay for CRF Receptor Binding Activity

As discussed above, the following assay is defined herein as a standard in vitro CRF receptor binding assay.

The pharmaceutical utility of compounds of this invention is indicated by the following assay for CRF1 receptor activity. The CRF receptor binding is performed using a modified version of the assay described by Grigoriadis and De Souza (*Methods in Neurosciences*, Vol. 5, 1991). IMR-32 human neuroblastoma cells, a cell-line that naturally expresses the CRF1 receptor, are grown to confluency in DMEM containing FBS.

To prepare receptor containing membranes cells are homogenized in wash buffer (50 mM Tris HCl, 10 mM $MgCl_2$, 2 mM EGTA, pH 7.4) and centrifuged at 48,000×g for 10 minutes at 4° C. The pellet is re-suspended in wash buffer and the homogenization and centrifugation steps are performed two additional times.

Membrane pellets containing CRF receptors are re-suspended in 50 mM Tris buffer pH 7.7 containing 10 mM $MgCl_2$ and 2 mM EDTA and centrifuged for 10 minutes at 48000 g. Membranes are washed again and brought to a final concentration of 1500 mg/ml in binding buffer (Tris buffer above with 0.1% BSA, 15 mM bacitracin and 0.01 mg/ml aprotinin.). For the binding assay, 100 ml of the membrane preparation are added to 96 well microtube plates containing 100 ml of $^{125}$I-CRF (SA 2200 Ci/mmol, final concentration of 100 pM) and 50 ml of test compound. Binding is carried out at room temperature for 2 hours. Plates are then harvested on a Brandel 96 well cell harvester and filters are counted for gamma emissions on a Wallac 1205 Betaplate liquid scintillation counter. Non specific binding is defined by 1 mM cold CRF. $IC_{50}$ values are calculated with the non-linear curve fitting program RS/1 (BBN Software Products Corp., Cambridge, Mass.). The binding affinity for the compounds of Formula I expressed as $IC_{50}$ value, generally ranges from about 0.5 nanomolar to about 10 micromolar. Preferred compounds of Formula I exhibit $IC_{50}$ values of less than or equal to 1.5 micromolar, more preferred compounds of Formula I exhibit $IC_{50}$ values of less than 500 nanomolar, still more preferred compounds of Formula I exhibit $IC_{50}$ values of less than 100 nanomolar, and most preferred compound of Formula I exhibit $IC_{50}$ values of less than 10 nanomolar. The compounds shown in Examples 1–95 and Examples 100–396 have been tested in this assay and found to exhibit $IC_{50}$ values of less than or equal to 1.5 micromolar.

Example 97

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.;

ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 98

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 99

Additional Aspects of Preferred Compounds of the Invention

The most preferred compounds of the invention are suitable for pharmaceutical use in treating human patients. Accordingly, such preferred compounds are non-toxic. They do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages.

Preferably, administration of such preferred compounds of the invention at certain doses (e.g., doses yielding therapeutically effective in vivo concentrations or preferably doses of 10, 50, 100, 150, or 200 mg/kg—preferably 150 mg/kg—administered parenterally or prefrerably orally) does not result in prolongation of heart QT intervals (i.e., as determined by electrocardiography, e.g., in guinea pigs, minipigs or dogs). When administered daily for 5 or preferably ten days, such doses of such preferred compounds also do not cause liver enlargement resulting in an increase of liver to body weight ratio of more than 100%, preferably not more than 75% and more preferably not more than 50% over matched controls in laboratory rodents (e.g., mice or rats). In another aspect such doses of such preferred compounds also preferably do not cause liver enlargement resulting in an increase of liver to body weight ratio of more than 50%, preferably preferably not more than 25%, and more preferably not more than 10% over matched untreated controls in dogs or other non-rodent animals.

In yet another aspect such doses of such preferred compounds also preferably do not promote the release of liver enzymes (e.g., ALT, LDH, or AST) from hepatocytes in vivo. Preferably such doses do not elevate such enzymes by more than 100%, preferably not by more than 75% and more preferably not by more than 50% over matched untreated controls in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause release of any of such liver enzymes from hepatocytes in vitro.

Because side effects are often due to undesirable receptor activation or antagonism, preferred compounds of the invention exert their receptor-modulatory effects with high selectivity. This means that they do not bind to certain other receptors (i.e., other than CRF receptors) with high affinity, but rather only bind to, activate, or inhibit the activity of such other receptors with affinity constants of greater than 100 nanomolar, preferably greater than 1 micromolar, more preferably greater than 10 micromolar and most preferably greater than 100 micromolar. Such receptors preferably are selected from the group including ion channel receptors, including sodium ion channel receptors, neurotransmitter receptors such as alpha- and beta-adrenergic receptors, muscarinic receptors (particularly m1, m2, and m3 receptors), dopamine receptors, and metabotropic glutamate receptors; and also include histamine receptors and cytokine receptors, e.g., interleukin receptors, particularly IL 8 receptors. The group of other receptors to which preferred compounds do not bind with high affinity also includes $GABA_A$ receptors, bioactive peptide receptors (including NPY and VIP receptors), neurokinin receptors, bradykinin receptors (e.g., BK1 receptors and BK2 receptors), and hormone receptors (including thyrotropin releasing hormone receptors and melanocyte-concentrating hormone receptors).

Example 99a

Absence of Sodium Ion Channel Activity

Preferred compounds of the invention do not exhibit activity as Sodium ion channel blockers. Sodium channel activity may be measured a standard in vitro sodium channel binding assays such as the assay given by Brown et al. (J. Neurosci. (1986) 265: 17995–18004). Preferred compounds of the invention exhibit less than 15 percent inhibition, and more preferably less than 10 percent inhibition, of sodium channel specific ligand binding when present at a concentration of 4 uM. The sodium ion channel specific ligand used may be labeled batrachotoxinin, tetrodotoxin, or saxitoxin. Such assays, including the assay of Brown referred to above, are performed as a commercial service by CEREP, INC., Redmond, Wash.

Alternatively, sodium ion channel activity may be measured in vivo in an assay of anti-epileptic activity. Anti-epileptic activity of compounds may be measured by the ability of the compounds to inhibit hind limb extension in the supra maximal electro shock model. Male Han Wistar rats (150–200 mg) are dosed i.p. with a suspension of 1 to 20 mg of test compound in 0.25% methylcellulose 2 hr. prior to test. A visual observation is carried out just prior to testing for the presence of ataxia. Using auricular electrodes a current of 200 mA, duration 200 millisec, is applied and the presence or absence of hind limb extension is noted. Preferred compounds of the invention do not exhibit significant anti-epileptic activity at the $p<0.1$ level of significance or more preferably at the $p<0.05$ level of significance as measured using a standard parametric assay of statistical significance such as a student's T test.

Example 99b

Optimal In Vitro Half-life

Compound half-life values ($t_{1/2}$ values) may be determined via the following standard liver microsomal half-life assay. Liver microsomes obtained from pooled liver samples and prepared so that the P-450 enzyme content is approximately 0.5 nmol/mg protein. Reactions are preformed in a 5 ml well deep-well plate as follows:

Phosphate buffer: 19 mL 0.1 M $NaH_2PO_4$, 81 mL 0.1 $Na_2HPO_4$, pH 7.4 with $H_3PO_4$.

CoFactor Mixture: 16.2 mg NADP, 45.4 mg Glucose-6-phosphate in 4 mL 100 mM $MgCl_2$. Glucose-6-phosphate dehydrogenase: 214.3 ul glucose-6-phosphate dehydrogenase, 1285.7 ul distilled water Starting Reaction Mixture: 3 mL CoFactor Mixture, 1.2 mL Glucose-6-phosphate dehydrogenase 6 identical samples wells each containing 25 ul microsomes, 5 ul of test compound (from a 100 uM stock), and 399 ul 0.1 M phosphate buffer, pH 7.4, are prepared. A seventh well containing 25 ul microsomes, 399 ul 0.1 M phosphate buffer, pH 7.4, and 5 ul (from a 100 uM stock) of a compound, e.g. DIAZEPAM, CLOZEPINE, with known metabolic properties is used as a positive control. Reactions are preincubated at 39° C. for 10 minutes. 71 ul Starting Reaction Mixture is added to 5 of the 6 reaction wells and to the positive control well, 71 ul 100 mM $MgCl_2$ is added to the sixth reaction well, which is used as a negative control. At each time point (0, 1, 3, 5, and 10 minutes) 75 ul reaction is pipetted into a 96-well deep-well plate reaction well containing 75 ul ice-cold acetonitrile. Samples are vortexed and centrifuged 10 minutes at 6000 rpm (Sorval T 6000D rotor). Supernatant, 75 ul from each reaction well, is transferred to a 96-well plate containing 150 ul internal standard per well. The remaining test compound is quantitated via LCMS and Compound concentration vs time is plotted and commercially available statistical software is used to extrapolate to the $t_{1/2}$ value of the test compound.

Preferred compounds of the invention exhibit in vitro $t_{1/2}$ values of greater than 10 minutes and less than 4 hours. Most preferred compounds of the invention exhibit in vitro $t_{1/2}$ values of between 30 minutes and 1 hour in human liver microsomes.

Example 99c

MDCK Toxicity

Toxicity of a test compound may be assessed by measuring the effect of the compound on ATP production by MDCK cells.

MDCK cells, product no. CCL-34, are purchased from ATCC, Manassas, Va. and maintained in sterile conditions by the methods described in the supplier's production information sheet. The PACKARD BIOSCIENCE, (Groningen, The Netherlands) ATP-LITE-M Luminescent ATP decection kit, product no. 6016941, may be used to monitor ATP production in MDCK cells.

Prior to assay 1 ul of test compound or control sample is pipetted into PACKARD (Meriden, Conn.) clear bottom 96-well plates. Test compounds and control samples are diluted in DMSO to give final concentration in the assay of 10 micromolar, 100 micromolar, or 200 micromolar. Control samples are drug compounds having known toxicity properties.

Confluent MDCK cells are trypsinized, harvested, and diluted to a concentration of $0.1\times10^6$ cells/ml with warm ATCC Eagle's Minimum Essential Medium (catalog # 30-2003). Warm Eagle's MEM without cells (100ul) is pipetted in five wells a 96-well plate. These wells are used to determine the standard curve. Cells in Eagle's MEM (100 ul or 10,000 cells) are pipetted into the remaining wells of the 96-well plates. All samples are incubated at 37° C. under carbogen (95% $O_2$, 5% $CO_2$) for 2 hours with constant shaking. After incubation 50 ul mammalian cell lysis solution is added to well of the 96-well plates, wells are covered with Packard topseal stickers, and plates are shaken at approximately 700 rpm on a microtiter shaker for 2 minutes.

During the incubation, Packard ATP Lite-M reagents are allowed to equilibrate to room temperature. Once equilibrated the lyophilized substrate solution in reconstituted in 5.5 mls of substrate buffer solution (from kit). Lyophilized ATP standard solution is reconstituted in deionized water to give a 10 mM stock. Standard (10 ul), diluted so that a 10 ul aliquot yields a final concentration of 200 nM, 100 nM, 50 nM, 25 nM, or 12.5 nM is added to each of the five standard curve wells, which do not contain cells.

Substrate solution (50 ul) is added to all wells. Wells are covered with Packard topseal stickers, and plates are shaken at approximately 700 rpm on a microtiter shaker for 2 minutes. A white Packard sticker is attached to the bottom of each plates and samples are dark adapted by wrapping plates in foil and placing in the dark for 10 minutes. Luminescence is then quantitated at 22° C. using a luminescence counter, e.g. Packard TopCount Microplate Scintillation and Luminescense Counter or Tecan Spectrafluor plus.

Luminscence values at each concentration are compared to the values computed from the standard curve for that concentration. Preferred test compounds exhibit luminescence values 80% or more of the standard, or preferably 90% or more of the standard, when 10 micromolar concentration of the test compound is used. When a 100 micromolar concentration of the test compound is used, preferred test compounds exhibit luminescence values 50% or more of the standard, or more preferably 80% or more of the standard.

Examples 100–396

Additional compounds of the invention prepared by the methods described for compounds shown in Examples 1–95 are shown in TABLE VIII

| EX# | STRUCTURE | UPAC Name |
|---|---|---|
| 100 | 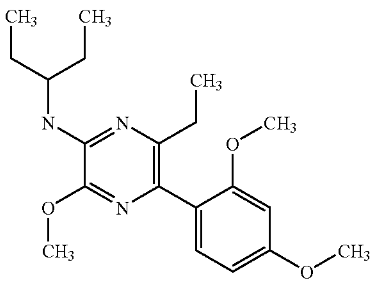 | 5-(2,4-dimethoxyphenyl)-6-ethyl-N-(1-ethylpropyl)-3-methoxypyrazin-2-amine |
| 101 | 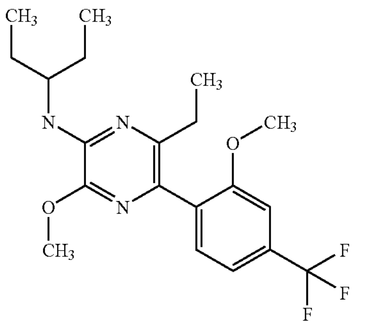 | 6-ethyl-N-(1-ethylpropyl)-3-methoxy-5-[2-methoxy-4-(trifluoromethyl)phenyl]pyrazin-2-amine |
| 102 | 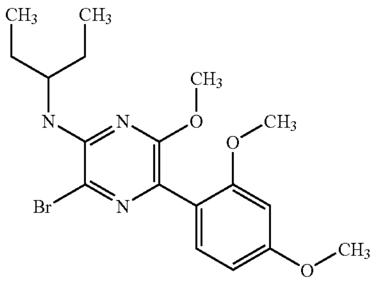 | 3-bromo-5-(2,4-dimethoxyphenyl)-N-(1-ethylpropyl)-6-methoxypyrazin-2-amine |
| 103 | 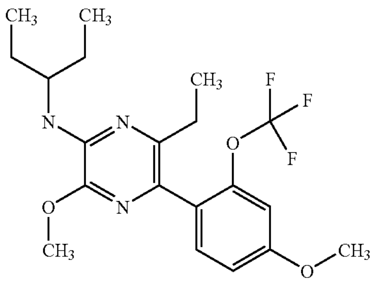 | 6-ethyl-N-(1-ethylpropyl)-3-methoxy-5-[4-methoxy-2-(trifluoromethoxy)phenyl]pyrazin-2-amine |

-continued
| EX# | STRUCTURE | UPAC Name |
| --- | --- | --- |
| 104 | 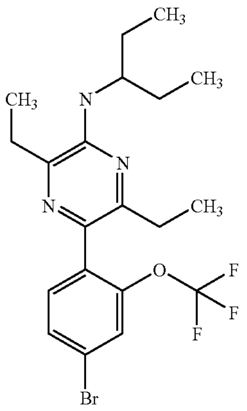 | 5-[4-bromo-2-(trifluoromethoxy)phenyl]-3,6-diethyl-N-(1-ethylpropyl)pyrazin-2-amine |
| 105 | 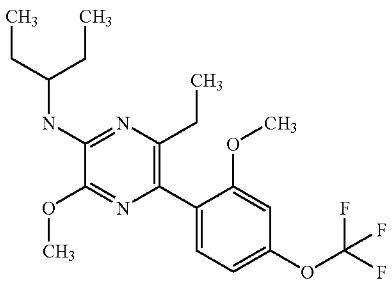 | 6-ethyl-N-(1-ethylpropyl)-3-methoxy-5-[2-methoxy-4-(trifluoromethoxy)phenyl]pyrazin-2-amine |
| 106 | 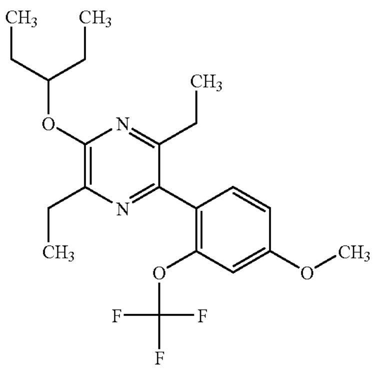 | 2,5-diethyl-3-(1-ethylpropoxy)-6-[4-methoxy-2-(trifluoromethoxy)phenyl]pyrazine |
| 107 | 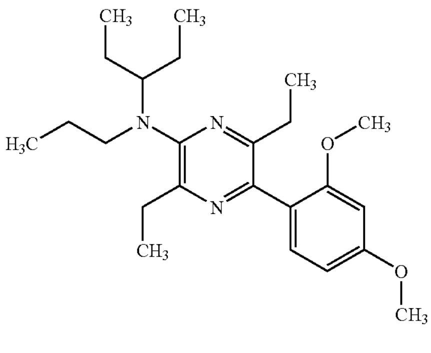 | 5-(2,4-dimethoxyphenyl)-3,6-diethyl-N-(1-ethylpropyl)-N-propylpyrazin-2-amine |

-continued
| EX# | STRUCTURE | UPAC Name |
|---|---|---|
| 108 | 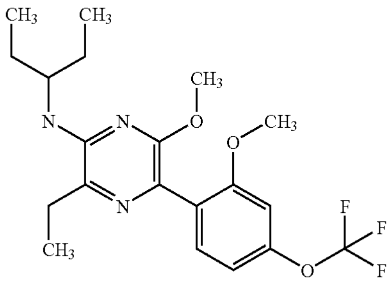 | 3-ethyl-N-(1-ethylpropyl)-6-methoxy-5-[2-methoxy-4-(trifluoromethoxy)phenyl]pyrazin-2-amine |
| 109 | 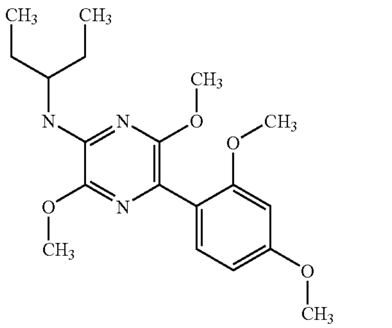 | 5-(2,4-dimethoxyphenyl)-N-(1-ethylpropyl)-3,6-dimethoxypyrazin-2-amine |
| 110 | 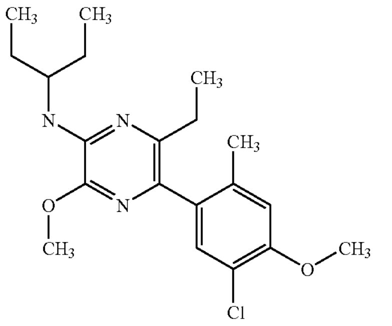 | 5-(5-chloro-4-methoxy-2-methylphenyl)-6-ethyl-N-(1-ethylpropyl)-3-methoxypyrazin-2-amine |
| 111 | 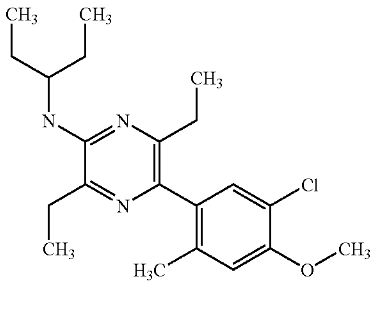 | 5-(5-chloro-4-methoxy-2-methylphenyl)-3,6-diethyl-N-(1-ethylpropyl)pyrazin-2-amine |

-continued
| EX# | STRUCTURE | UPAC Name |
|---|---|---|
| 112 | 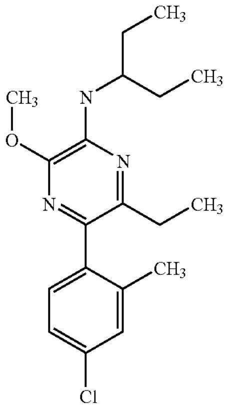 | 5-(4-chloro-2-methylphenyl)-6-ethyl-N-(1-ethylpropyl)-3-methoxypyrazin-2-amine |
| 113 | 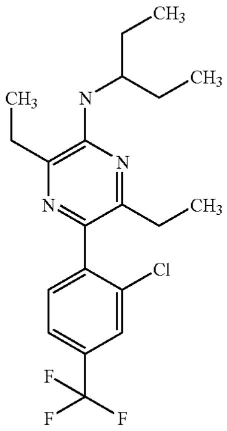 | 5-[2-chloro-4-(trifluoromethyl)phenyl]-3,6-diethyl-N-(1-ethylpropyl)pyrazin-2-amine |
| 114 | 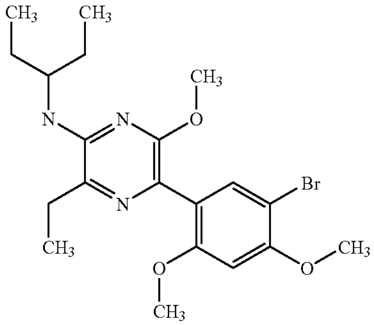 | 5-(5-bromo-2,4-dimethoxyphenyl)-3-ethyl-N-(1-ethylpropyl)-6-methoxypyrazin-2-amine |
| 115 | 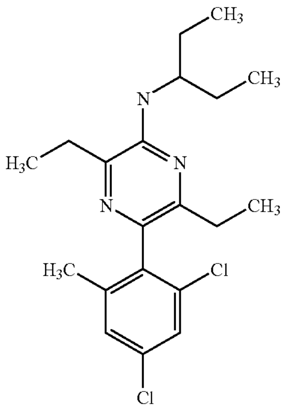 | 5-(2,4-dichloro-6-methylphenyl)-3,6-diethyl-N-(1-ethylpropyl)pyrazin-2-amine |

-continued
| EX# | STRUCTURE | UPAC Name |
| --- | --- | --- |
| 116 | 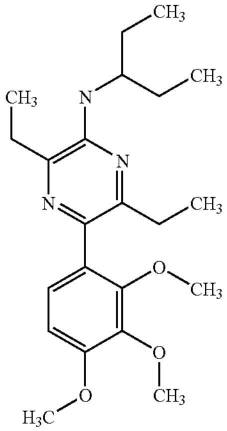 | 3,6-diethyl-N-(1-ethylpropyl)-5-(2,3,4-trimethoxyphenyl)pyrazin-2-amine |
| 117 | 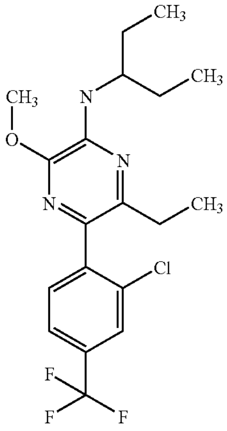 | 5-[2-chloro-4-trifluoromethyl)phenyl]-6-ethyl-N-(1-ethylpropyl)-3-methoxypyrazin-2-amine |
| 118 | 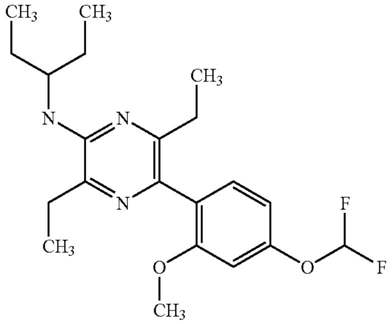 | 5-[4-(difluoromethoxy)-2-methoxyphenyl]-3,6-diethyl-N-(1-ethylpropyl)pyrazin-2-amine |
| 119 | 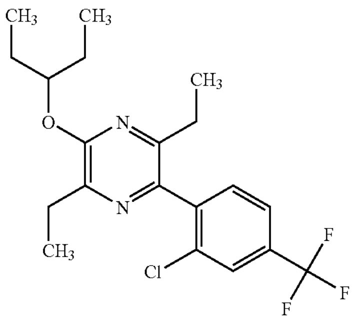 | 2-[2-chloro-4-(trifluoromethyl)phenyl]-3,6-diethyl-5-(1-ethylpropoxy)pyrazine |

-continued
| EX# | STRUCTURE | UPAC Name |
| --- | --- | --- |
| 120 | 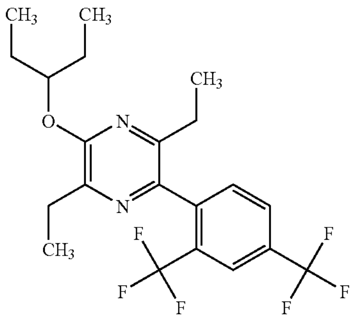 | 2-[2,4-bis(trifluoromethyl)phenyl]-3,6-diethyl-5-(1-ethylpropoxy)pyrazine |
| 121 | 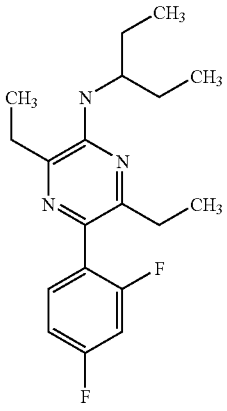 | 5-(2,4-difluorophenyl)-3,6-diethyl-N-(1-ethylpropyl)pyrazin-2-amine |
| 122 | 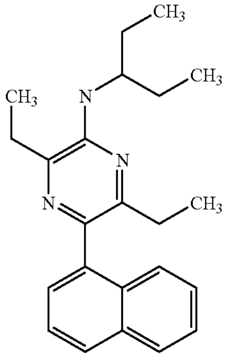 | 3,6-diethyl-N-(1-ethylpropyl)-5-(1-naphthyl)pyrazin-2-amine |
| 123 | 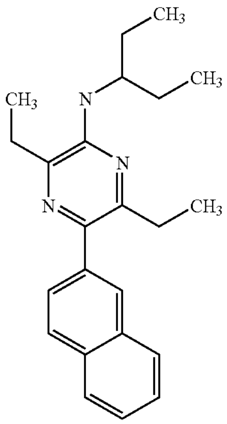 | 3,6-diethyl-N-4-ethylpropyl)-5-(2-naphthyl)pyrazin-2-amine |

-continued
| EX# | STRUCTURE | UPAC Name |
|---|---|---|
| 124 | 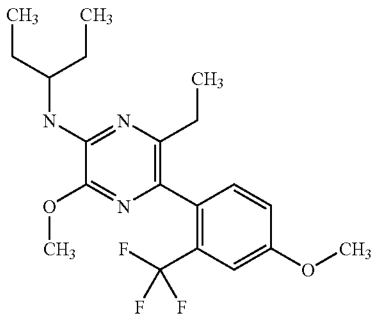 | 6-ethyl-N-(1-ethylpropyl)-3-methoxy-5-[4-methoxy-2-(trifluoromethyl)phenyl]pyrazin-2-amine |
| 125 | 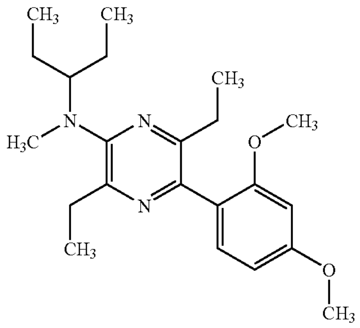 | 5-(2,4-dimethoxyphenyl)-3,6-diethyl-N-(1-ethylpropyl)-N-methylpyrazin-2-amine |
| 126 | 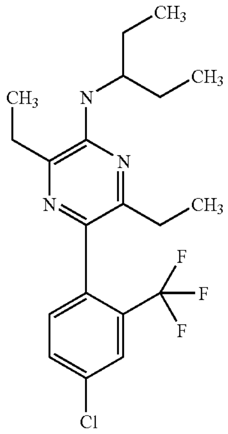 | 5-[4-chloro-2-(trifluoromethyl)phenyl]-3,6-diethyl-N-(1-ethylpropyl)pyrazin-2-amine |
| 127 | 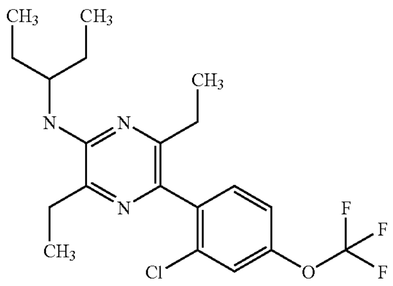 | 5-[2-chloro-4-(trifluoromethoxy)phenyl]-3,6-diethyl-N-(1-ethylpropyl)pyrazin-2-amine |

-continued
| EX# | STRUCTURE | UPAC Name |
|---|---|---|
| 128 | 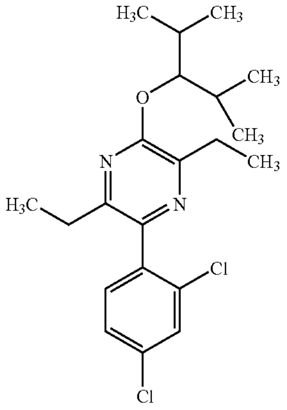 | 2-(2,4-dichlorophenyl)-3,6-diethyl-5-(1-isopropyl-2-methylpropoxy)pyrazine |
| 129 | 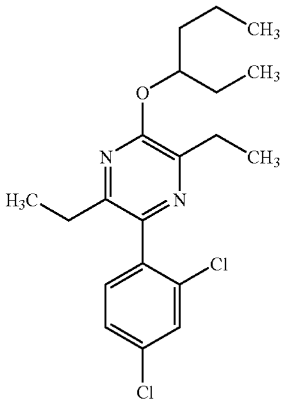 | 2-(2,4-dichlorophenyl)-3,6-diethyl-5-(1-ethylbutoxy)pyrazine |
| 130 | 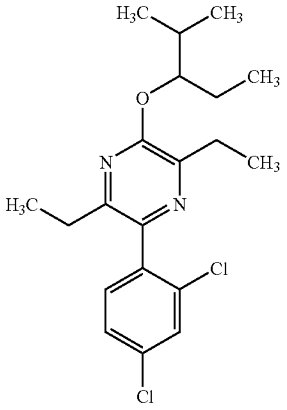 | 2-(2,4-dichlorophenyl)-3,6-diethyl-5-(1-ethyl-2-methylpropoxy)pyrazine |
| 131 | 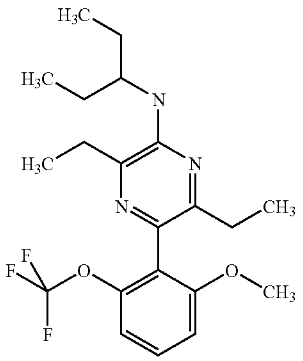 | 3,6-diethyl-N-(1-ethylpropyl)-5-[2-methoxy-6-(trifluoromethoxy)phenyl]-pyrazin-2-amine |

-continued
| EX# | STRUCTURE | UPAC Name |
|---|---|---|
| 132 | 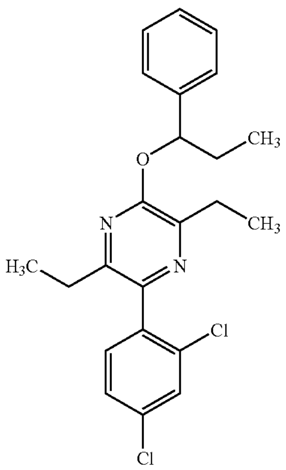 | 2-(2,4-dichlorophenyl)-3,6-diethyl-5-(1-phenylpropoxy)pyrazine |
| 133 | 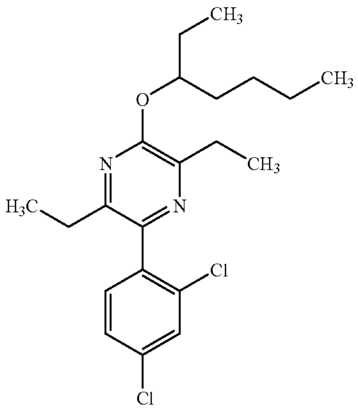 | 2-(2,4-dichlorophenyl)-3,6-diethyl-5-[(1-ethylpentyl)oxy]pyrazine |
| 134 | 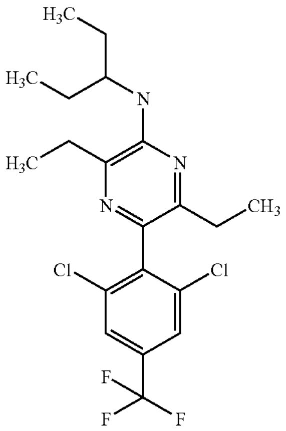 | 5-[2,6-dichloro-4-(trifluoromethyl)phenyl]-3,6-diethyl-N-(1-ethylpropyl)pyrazin-2-amine |

-continued
| EX# | STRUCTURE | UPAC Name |
| --- | --- | --- |
| 135 | 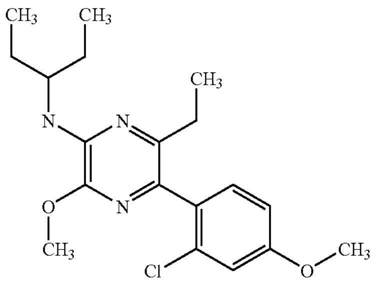 | 5-(2-chloro-methoxyphenyl)-6-ethyl-N-(1-ethylpropyl)-3-methoxypyrazin-2-amine |
| 136 | 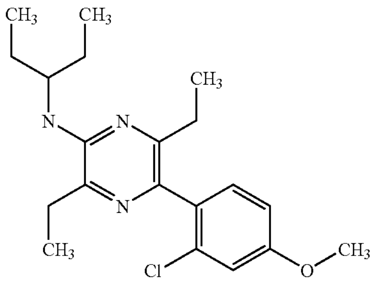 | 5-(2-chloro-4-methoxyphenyl)-3,6-diethyl-N-(1-ethylpropyl)pyrazin-2-amine |
| 137 | 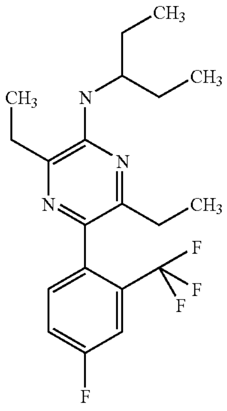 | 3,6-diethyl-N-(1-ethylpropyl)-5-[4-fluoro-2-(trifluoromethyl)phenyl]pyrazin-2-amine |
| 138 | 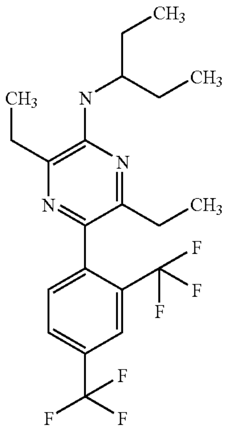 | 5-[2,4-bis(trifluoromethyl)phenyl]-3,6-diethyl-N-(1-ethylpropyl)pyrazin-2-amine |

-continued
| EX# | STRUCTURE | UPAC Name |
|---|---|---|
| 139 | 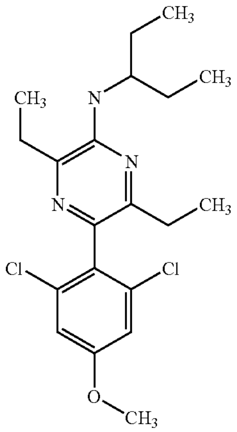 | 5-(2,6-dichloro-4-methoxyphenyl)-3,6-diethyl-N-(1-ethylpropyl)pyrazin-2-amine |
| 140 | 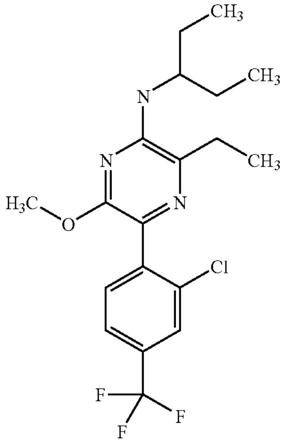 | 5-[2-chloro-4-(trifluoromethyl)pheny]-3-ethyl-N-(1-ethylpropyl)-6-methoxypyrazin-2-amine |
| 141 | 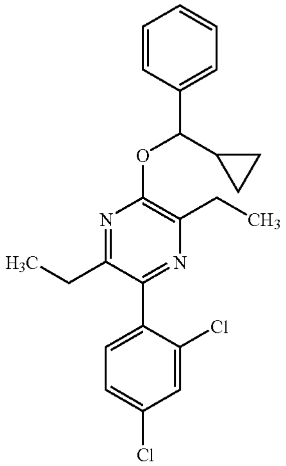 | 2-[cyclopropyl(phenyl)methoxy]-5-(2,4-dichlorophenyl)-3,6-diethylpyrazine |

-continued
| EX# | STRUCTURE | UPAC Name |
| --- | --- | --- |
| 142 | 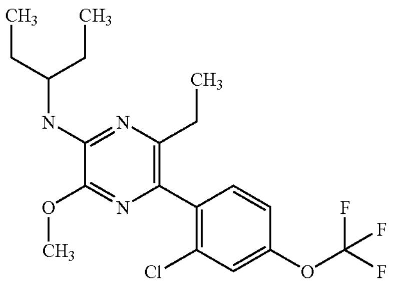 | 5-[2-chloro-4-(trifluoromethoxy)phenyl]-6-ethyl-N-(1-ethylpropyl)-3-methoxypyrazin-2-amine |
| 143 | 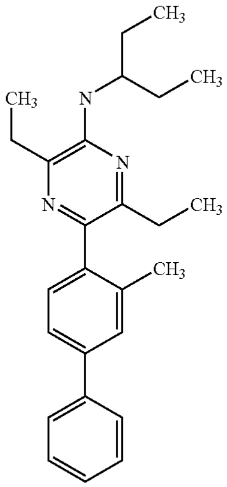 | 3,6-diethyl-N-(1-ethylpropyl)-5-(3-methyl-1,1'-biphenyl-4-yl)pyrazin-2-amine |
| 144 | 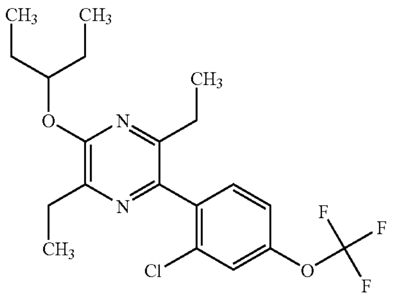 | 2-[2-chloro-4-(trifluoromethoxy)phenyl]-3,6-diethyl-5-(1-ethylpropoxy)pyrazine |
| 145 | 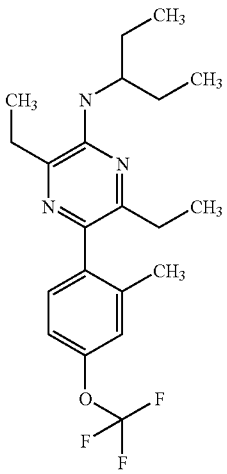 | 3,6-diethyl-N-(1-ethylpropyl)-5-[2-methyl-4-(trifluoromethoxy)phenyl]pyrazin-2-amine |

-continued
| EX# | STRUCTURE | UPAC Name |
|---|---|---|
| 146 | 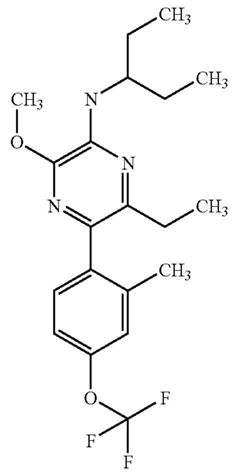 | 6-ethyl-N-(1-ethylpropyl)-3-methoxy-5-[2-methyl-4-(trifluoromethoxy)phenyl]pyrazin-2-amine |
| 147 | 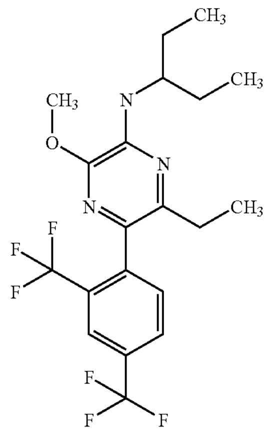 | 5-[2,4-bis(trifluoromethyl)phenyl]-6-ethyl-N-(1-ethylpropyl)-3-methoxypyrazin-2-amine |
| 148 | 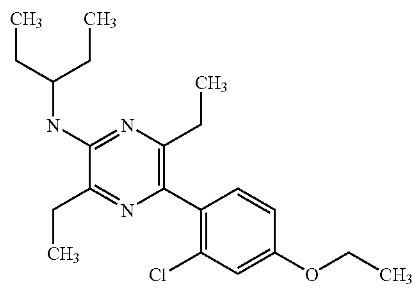 | 5-(2-chloro-4-ethoxyphenyl)-3,6-diethyl-N-(1-ethylpropyl)pyrazin-2-amine |

-continued
| EX# | STRUCTURE | UPAC Name |
| --- | --- | --- |
| 149 | 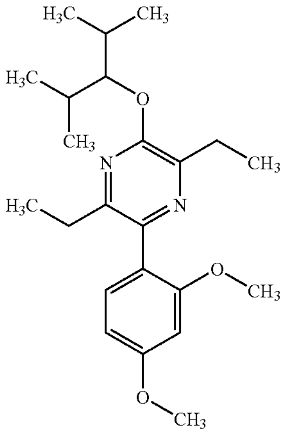 | 2-(2,4-dimethoxyphenyl)-3,6-diethyl-5-(1-isopropyl-2-methylpropoxy)pyrazine |
| 150 | 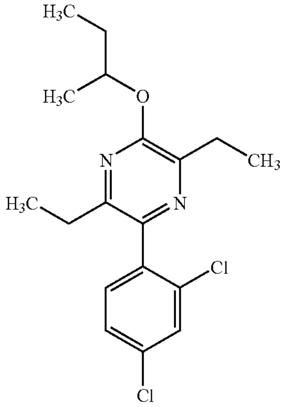 | 2-sec-butoxy-5-(2,4-dichlorophenyl)-3,6-diethylpyrazine |
| 151 | 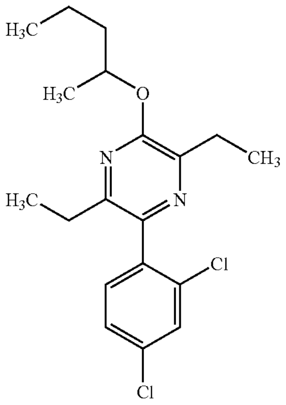 | 2-(2,4-dichlorophenyl)-3,6-diethyl-5-(1-methylbutoxy)pyrazine |

-continued
| EX# | STRUCTURE | UPAC Name |
| --- | --- | --- |
| 152 | 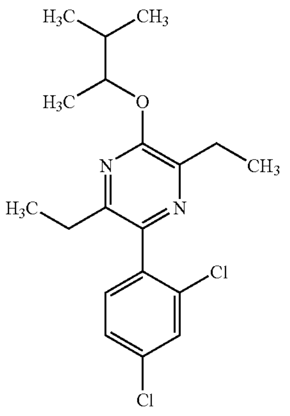 | 2-(2,4-dichlorophenyl)-5-(1,2-dimethylpropoxy)-3,6-diethylpyrazine |
| 153 | 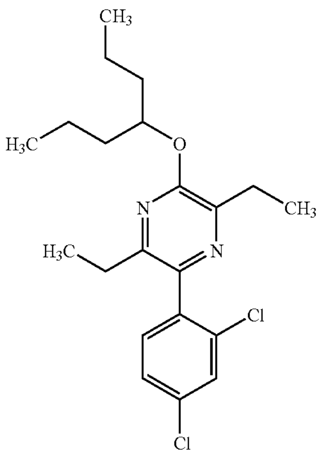 | 2-(2,4-dichlorophenyl)-3,6-diethyl-5-(1-propylbutoxy)pyrazine |
| 154 | 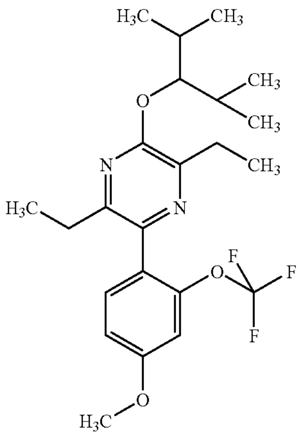 | 2,5-diethyl-3-(1-isopropyl-2-methylpropoxy)-6-[4-methoxy-2-(trifluoromethoxy)phenyl]pyrazine |

-continued
| EX# | STRUCTURE | UPAC Name |
| --- | --- | --- |
| 155 | 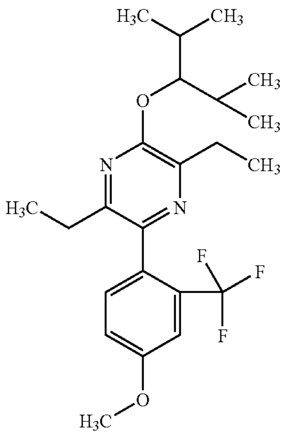 | 2,5-diethyl-3-(1-isopropyl-2-methylpropoxy)-6-[4-methoxy-2-(trifluoromethyl)phenyl]pyrazine |
| 156 | 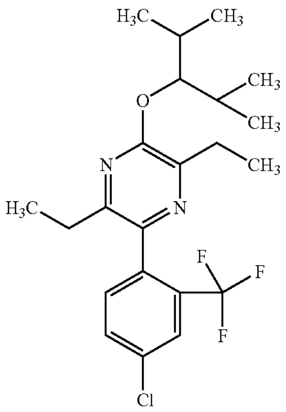 | 2-[4-chloro-2-(trifluoromethyl)phenyl]-3,6-diethyl-5-(1-isopropyl-2-methylpropoxy)pyrazine |
| 157 | 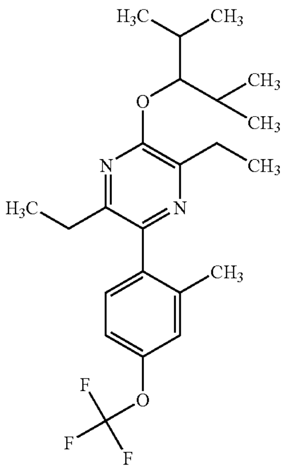 | 2,5-diethyl-3-(1-isopropyl-2-methylpropoxy)-6-[2-methyl-4-(trifluoromethoxy)phenyl]pyrazine |

-continued
| EX# | STRUCTURE | UPAC Name |
|---|---|---|
| 158 | 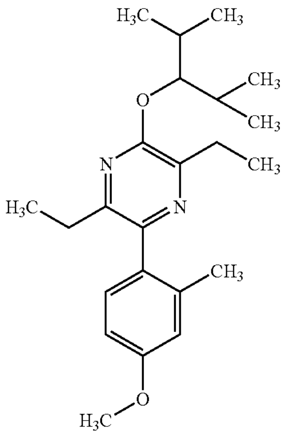 | 2,5-diethyl-3-(1-isopropyl-2-methylpropoxy)-6-(4-methoxy-2-methylphenyl)pyrazine |
| 159 | 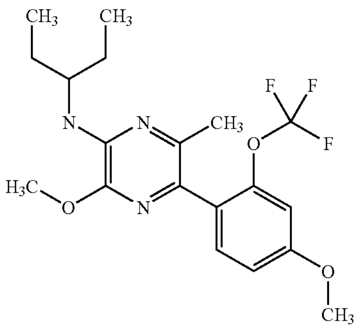 | N-(1-ethylpropyl)-3-methoxy-5-[4-methoxy-2-(trifluoromethoxy)phenyl]-6-methylpyrazin-2-amine |
| 160 | 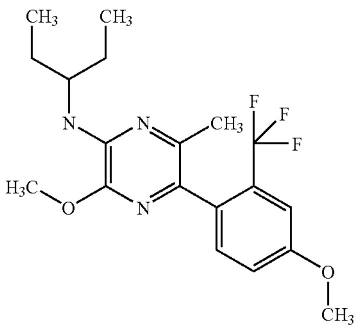 | N-(1-ethylpropyl)-3-methoxy-5-[4-methoxy-2-(trifluoromethyl)phenyl]-6-methylpyrazin-2-amine |
| 161 | 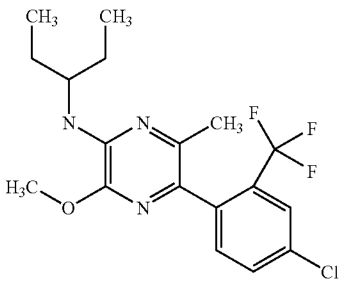 | 5-[4-chloro-2-(trifluoromethyl)phenyl]-N-(1-ethylpropyl)-3-methoxy-6-methylpyrazin-2-amine |

-continued
| EX# | STRUCTURE | UPAC Name |
| --- | --- | --- |
| 162 | 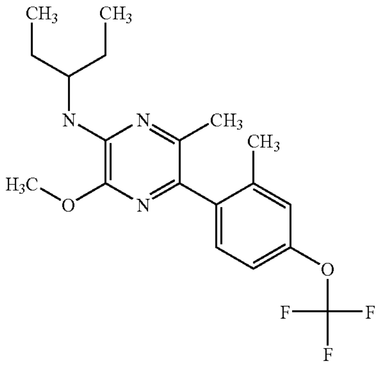 | N-(1-ethylpropyl)-3-methoxy-6-methyl-5-[2-methyl-4-(trifluoromethoxy)phenyl]pyrazin-2-amine |
| 163 | 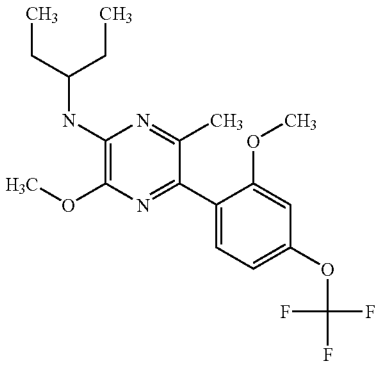 | N-(1-ethylpropyl)-3-methoxy-5-[2-methoxy-4-(trifluoromethoxy)phenyl]-6-methylpyrazin-2-amine |
| 164 | 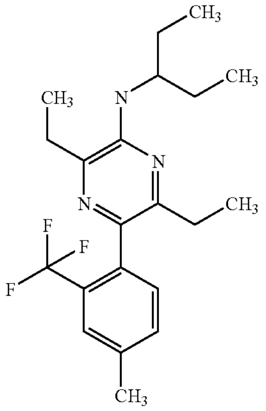 | 3,6-diethyl-N-(1-ethylpropyl)-5-[4-methyl-2-(trifluoromethyl)phenyl]pyrazin-2-amine |
| 165 | 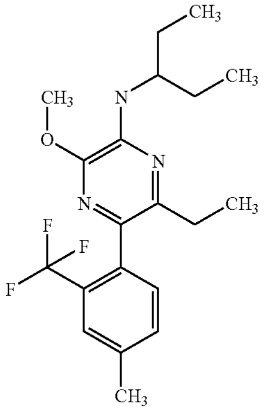 | 6-ethyl-N-(1-ethylpropyl)-3-methoxy-5-[4-methyl-2-(trifluoromethyl)phenyl]-pyrazin-2-amine |

-continued
| EX# | STRUCTURE | UPAC Name |
| --- | --- | --- |
| 166 | 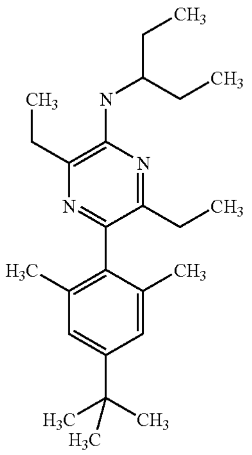 | 5-(4-tert-butyl-2,6-dimethylphenyl)-3,6-diethyl-N-(1-ethylpropyl)pyrazin-2-amine |
| 167 | 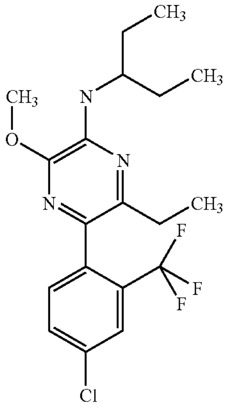 | 5-[4-chloro-2-(trifluoromethyl)phenyl]-6-ethyl-N-(1-ethylpropyl)-3-methoxypyrazin-2-amine |
| 168 | 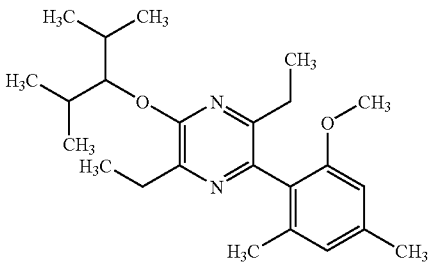 | 2,5-diethyl-3-(1-isopropyl-2-methylpropoxy)-6-(2-methoxy-4,6-dimethylphenyl)pyrazine |
| 169 | 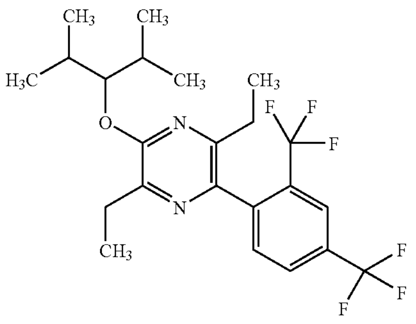 | 2-[2,4-bis(trifluoromethyl)phenyl]-3,6-diethyl-5-(1-isopropyl-2-methylpropoxy)pyrazine |

-continued

| EX# | STRUCTURE | UPAC Name |
| --- | --- | --- |
| 170 | 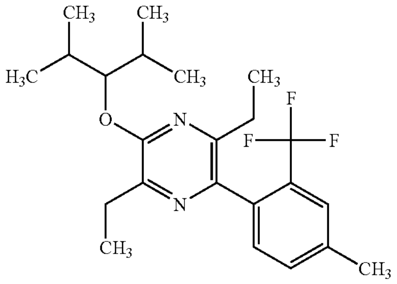 | 2,5-diethyl-3-(1-isopropyl-2-methylpropoxy)-6-[4-methyl-2-(trifluoromethyl)phenyl]pyrazine |
| 171 | 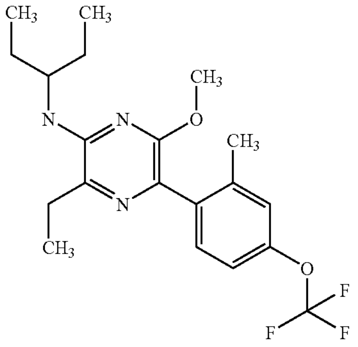 | 3-ethyl-N-(1-ethylpropyl)-6-methyl-5-[2-methyl-4-(trifluoromethoxy)phenyl]-pyrazin-2-amine |
| 172 | 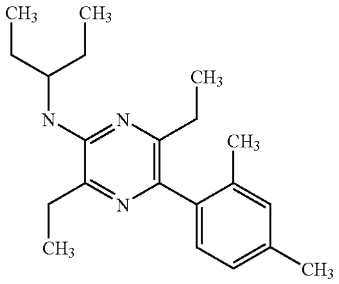 | 5-(2,4-dimethylphenyl)-3,6-diethyl-N-(1-ethylpropyl)pyrazin-2-amine |
| 173 | 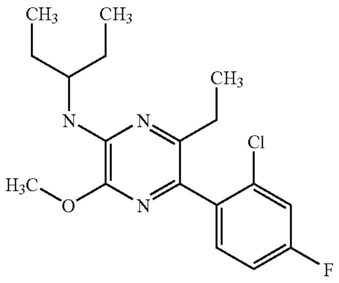 | 5-(2-chloro-4-fluorophenyl)-6-ethyl-N-(1-ethylpropyl)-3-methoxypyrazin-2-amine |
| 174 | 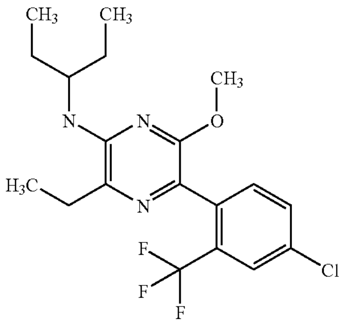 | 5-[4-chloro-2-(trifluoromethyl)phenyl]-3-ethyl-N-(1-ethylpropyl)-6-methoxypyrazin-2-amine |

-continued

| EX# | STRUCTURE | UPAC Name |
| --- | --- | --- |
| 175 | 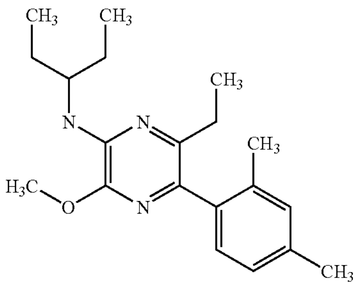 | 5-(2,4-dimethylphenyl)-6-ethyl-N-(1-ethylpropyl)-3-methoxypyrazin-2-amine |
| 176 | 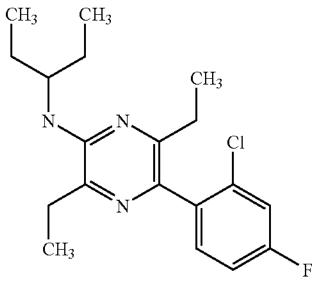 | 5-(2-chloro-4-fluorophenyl)-3,6-diethyl-N-(1-ethylpropyl)pyrazin-2-amine |
| 177 | 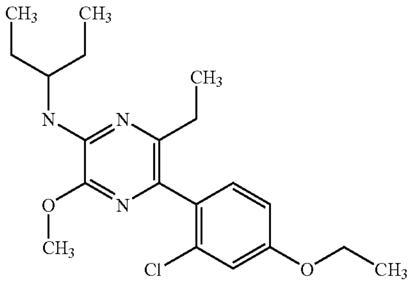 | 5-(2-chloro-4-ethoxyphenyl)-6-ethyl-N-(1-ethylpropyl)-3-methoxypyrazin-2-amine |
| 178 | 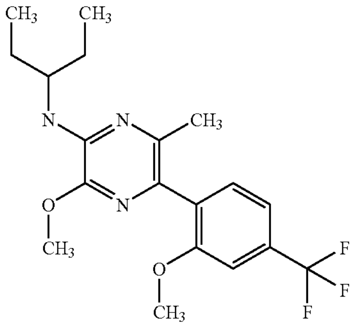 | N-(1-ethylpropyl)-3-methoxy-5-[2-methoxy-4-(trifluoromethyl)phenyl]-6-methylpyrazin-2-amine |
| 179 | 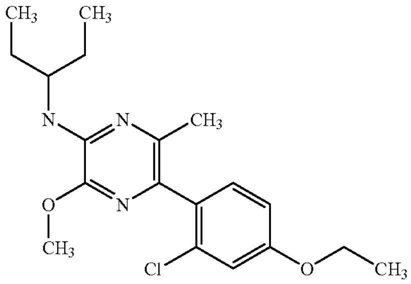 | 5-(2-chloro-4-ethoxyphenyl)-N-(1-ethylpropyl)-3-methoxy-6-methylpyrazin-2-amine |

-continued

| EX# | STRUCTURE | UPAC Name |
|---|---|---|
| 180 | 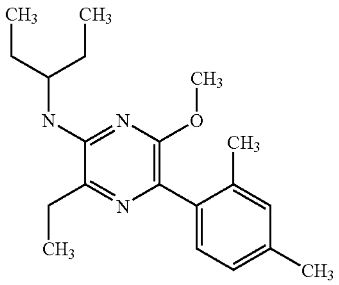 | 5-(2,4-dimethylphenyl)-3-ethyl-N-(1-ethylpropyl)-6-methoxypyrazin-2-amine |
| 181 | 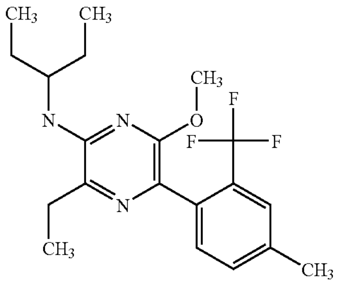 | 3-ethyl-N-(1-ethylpropyl)-6-methoxy-5-[4-methyl-2-(trifluoromethyl)phenyl]-pyrazin-2-amine |
| 182 | 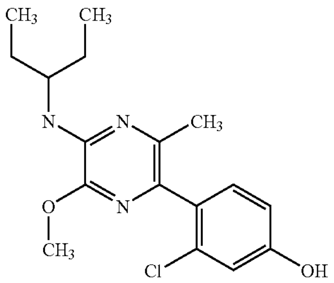 | 3-chloro-4-{5-[(1-ethylpropyl)amino]-6-methoxy-3-methylpyrazin-2-yl}phenol |
| 183 | 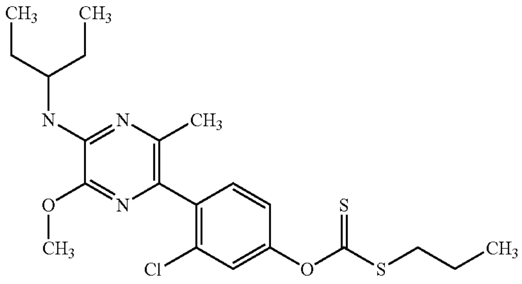 | O-(3-chloro-4-{5-[(1-ethylpropyl)amino]-6-methoxy-3-methylpyrazin-2-yl}phenyl)S-propyl(dithiocarbonate) |
| 184 | 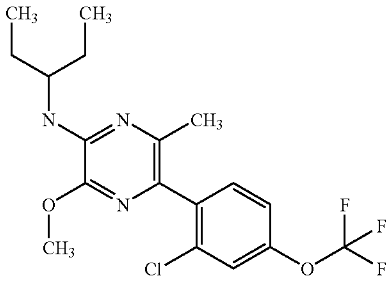 | 5-[2-chloro-4-(trifluoromethoxy)phenyl]-N-(1-ethylpropyl)-3-methoxy-6-methylpyrazin-2-amine |

-continued
| EX# | STRUCTURE | UPAC Name |
|---|---|---|
| 185 | 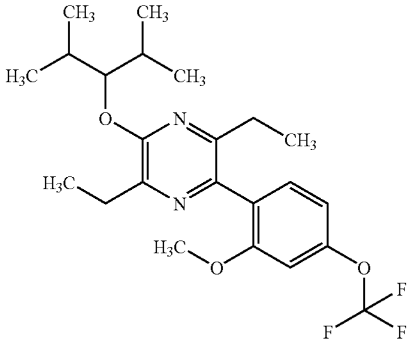 | 2,5-diethyl-3-(1-isopropyl-2-methylpropoxy)-6-[2-methoxy-4-(trifluoromethoxy)phenyl]pyrazine |
| 186 | 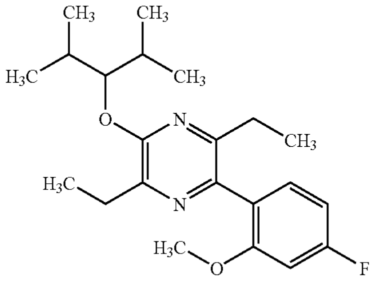 | 2,5-diethyl-3-(4-fluoro-2-methoxyphenyl)-6-(1-isopropyl-2-methylpropoxy)pyrazine |
| 187 | 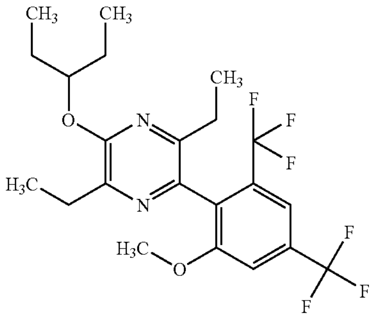 | 2,5-diethyl-3-(1-ethylpropoxy)-6-[2-methoxy-4,6-bis(trifluoromethyl)phenyl]pyrazine |
| 188 | 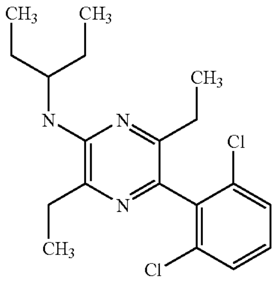 | 5-(2,6-dichlorophenyl)-3,6-diethyl-N-(1-ethylpropyl)pyrazin-2-amine |
| 189 | 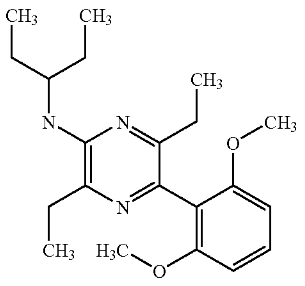 | 5-(2,6-dimethoxyphenyl)-3,6-diethyl-N-(1-ethylpropyl)pyrazin-2-amine |

-continued
| EX# | STRUCTURE | UPAC Name |
| --- | --- | --- |
| 190 | 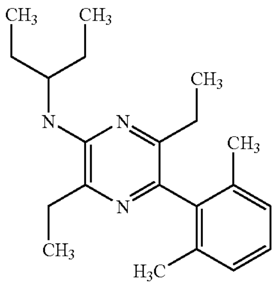 | 5-(2,6-dimethylphenyl)-3,6-diethyl-N-(1-ethylpropyl)pyrazin-2-amine |
| 191 | 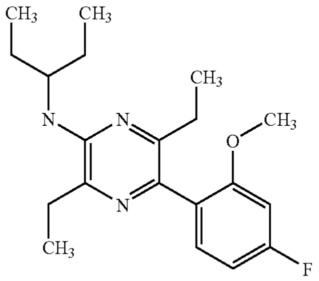 | 3,6-diethyl-N-(1-ethylpropyl)-5-(4-fluoro-2-methoxyphenyl)pyrazin-2-amine |
| 192 | 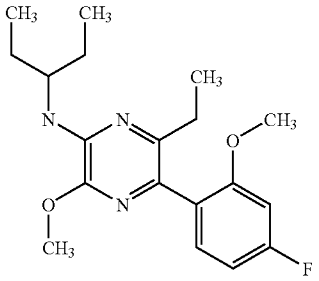 | 6-ethyl-N-(1-ethylpropyl)-5-(4-fluoro-2-methoxyphenyl)-3-methoxypyrazin-2-amine |
| 193 | 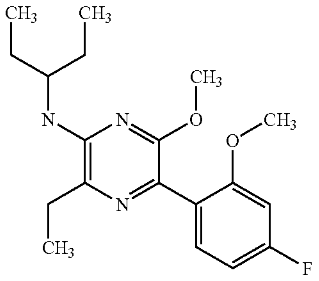 | 3-ethyl-N-(1-ethylpropyl)-5-(4-fluoro-2-methoxyphenyl)-6-methoxypyrazin-2-amine |
| 194 | 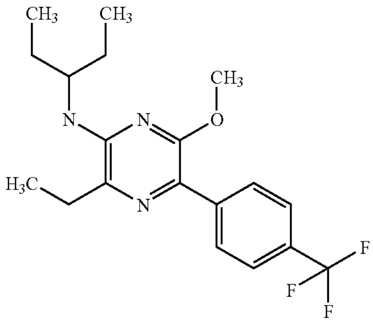 | 3-ethyl-N-(1-ethylpropyl)-6-methoxy-5-[4-(trifluoromethyl)phenyl]pyrazin-2-amine |

-continued
| EX# | STRUCTURE | UPAC Name |
|---|---|---|
| 195 | 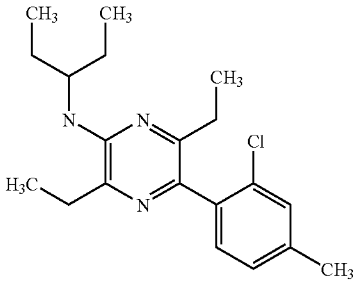 | 5-(2-chloro-4-methylphenyl)-3,6-diethyl-N-(1-ethylpropyl)pyrazin-2-amine |
| 196 | 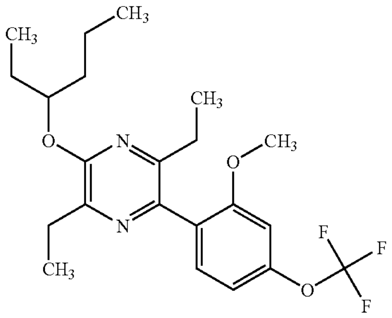 | 2,5-diethyl-3-(1-ethylbutoxy)-6-[2-methoxy-4-(trifluoromethoxy)phenyl]pyrazine |
| 197 | 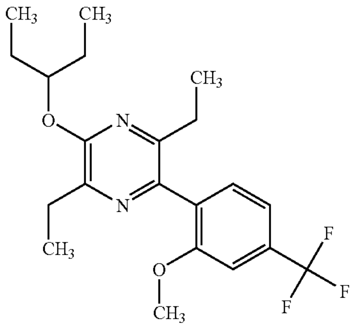 | 2,5-diethyl-3-(1-ethylpropoxy)-6-[2-methoxy-4-(trifluoromethyl)phenyl]pyrazine |
| 198 | 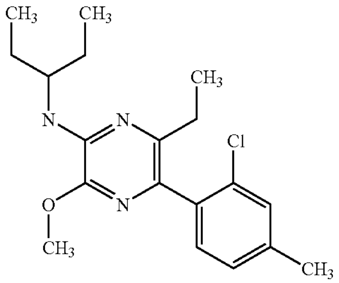 | 5-(2-chloro-4-methylphenyl)-6-ethyl-N-(1-ethylpropyl)-3-methoxypyrazin-2-amine |
| 199 | 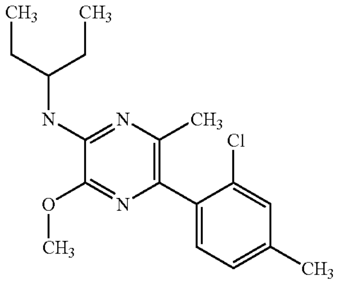 | 5-(2-chloro-4-methylphenyl)-N-(1-ethylpropyl)-3-methoxy-6-methylpyrazin-2-amine |

-continued

| EX# | STRUCTURE | UPAC Name |
| --- | --- | --- |
| 200 | 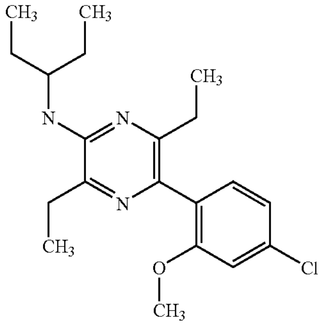 | 5-(4-chloro-2-methoxyphenyl)-3,6-diethyl-N-(1-ethylpropyl)pyrazin-2-amine |
| 201 | 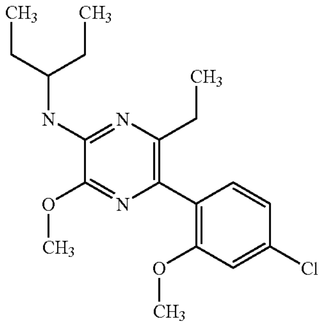 | 5-(4-chloro-2-methoxyphenyl)-6-ethyl-N-(1-ethylpropyl)-3-methoxypyrazin-2-amine |
| 202 | 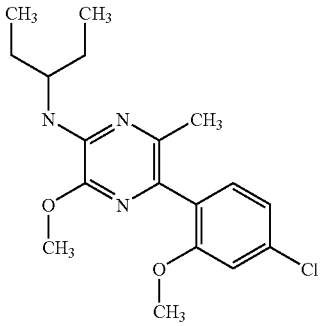 | 5-(4-chloro-2-methoxyphenyl)-N-(1-ethylpropyl)-3-methoxy-6-methylpyrazin-2-amine |
| 203 | 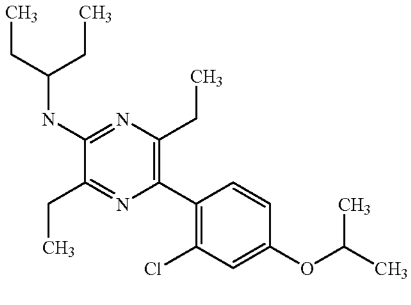 | 5-(2-chloro-4-isopropoxyphenyl)-3,6-diethyl-N-(1-ethylpropyl)pyrazin-2-amine |
| 204 | 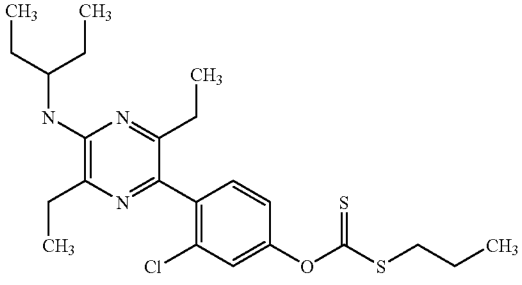 | O-(3-chloro-4-{3,6-diethyl-5-[(1-ethylpropyl)amino]pyrazin-2-yl}phenyl)S-propyl(dithiocarbonate) |

-continued
| EX# | STRUCTURE | UPAC Name |
|---|---|---|
| 205 | 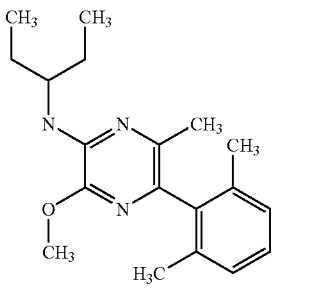 | 5-(2,6-dimethylphenyl)-N-(1-ethylpropyl)-3-methoxy-6-methylpyrazin-2-amine |
| 206 | 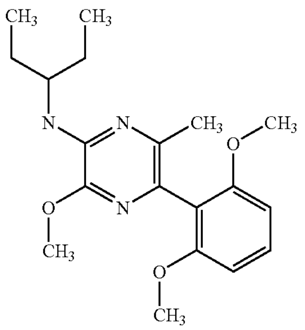 | 5-(2,6-dimethoxyphenyl)-N-(1-ethylpropyl)-3-methoxy-6-methylpyrazin-2-amine |
| 207 | 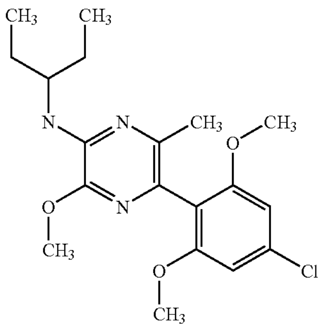 | 5-(4-chloro-2-dimethoxyphenyl)-N-(1-ethylpropyl)-3-methoxy-6-methylpyrazin-2-amine |
| 208 | 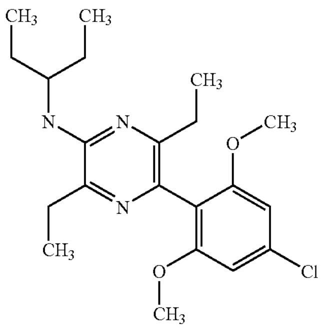 | 5-(4-chloro-2,6-dimethoxyphenyl)-3,6-diethyl-N-(1-ethylpropyl)pyrazin-2-amine |

-continued
| EX# | STRUCTURE | UPAC Name |
|---|---|---|
| 209 | 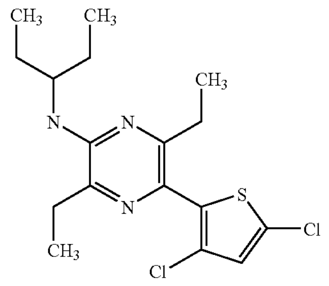 | 5-(3,5-dichlorothien-2-yl)-3,6-diethyl-N-(1-ethylpropyl)pyrazin-2-amine |
| 210 | 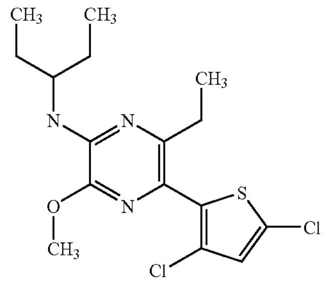 | 5-(3,5-dichlorothien-2-yl)-6-ethyl-N-(1-ethylpropyl)-3-methoxypyrazin-2-amine |
| 211 | 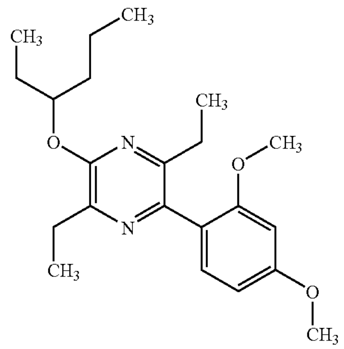 | 2-(2,4-dimethoxyphenyl)-3,6-diethyl-5-(1-ethylbutoxy)pyrazine |
| 212 | 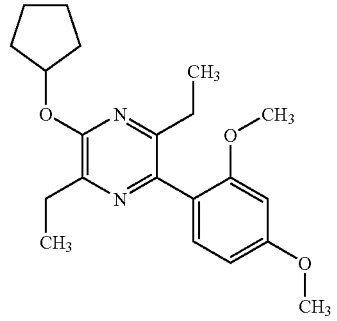 | 2-(cyclopentyloxy)-5-(2,4-dimethoxyphenyl)-3,6-diethylpyrazine |

-continued
| EX# | STRUCTURE | UPAC Name |
|---|---|---|
| 213 | 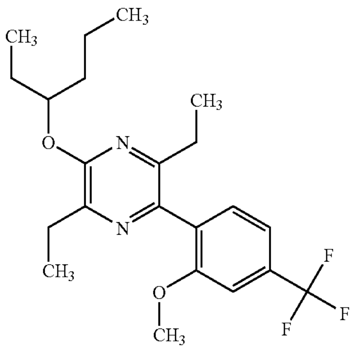 | 2,5-diethyl-3-methylbutoxy)-6-[2-methoxy-4-(trifluorornethyl)phenyl]pyrazine |
| 214 | 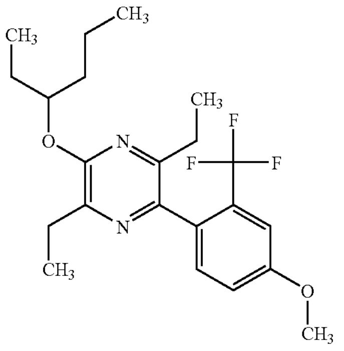 | 2,5-diethyl-3-(1-ethylbutoxy)-6-[4-methoxy-2-(trifluoromethyl)phenyl]pyrazine |
| 215 | 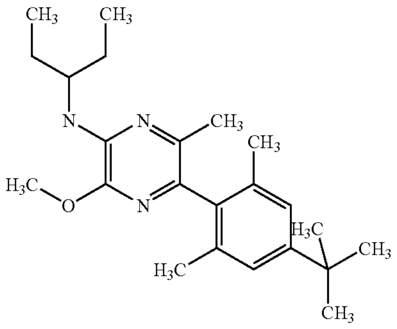 | 5-(4-tert-butyl-2,6-dimethylphenyl)-N-(1-ethylpropyl)-3-methoxy-6-methylpyrazin-2-amine |
| 216 | 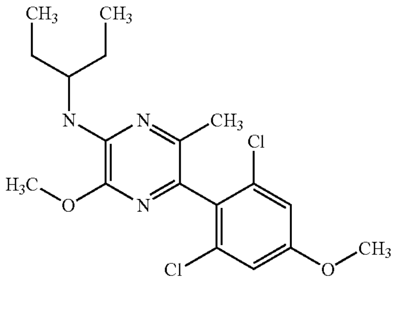 | 5-(2,6-dichloro-4-methoxyphenyl)-N-(1-ethylpropyl)-3-methoxy-6-methylpyrazin-2-amine |

-continued

| EX# | STRUCTURE | UPAC Name |
|---|---|---|
| 217 | 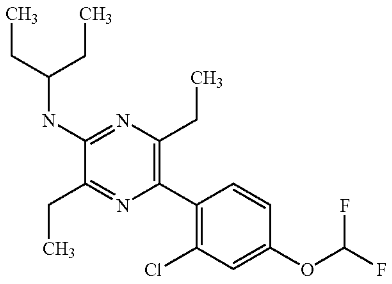 | 5-[2-chloro-4-(difluoromethoxy)phenyl]-3,6-diethyl-N-(1-ethylpropyl)pyrazin-2-amine |
| 218 | 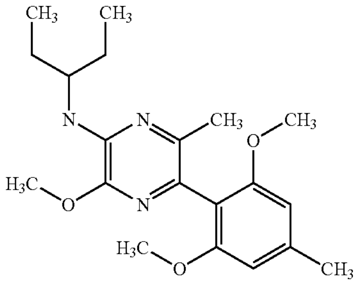 | 5-(2,6-methoxy-4-methylphenyl)-N-(1-ethylpropyl)-3-methoxy-6-methylpyrazin-2-amine |
| 219 | 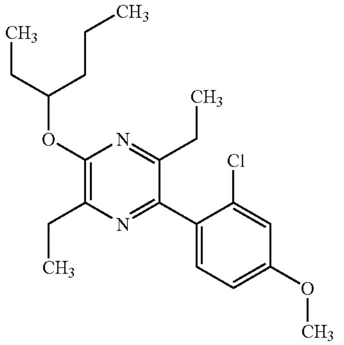 | 2-(2-chloro-4-methoxyphenyl)-3,6-diethyl-5-(1-ethylbutoxy)pyrazine |
| 220 | 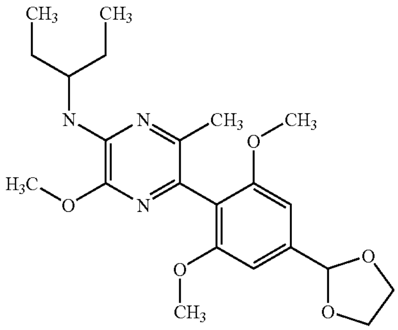 | 5-[4-(1,3-dioxolan-2-yl)-2,6-dimethoxyphenyl]-N-(1-ethylpropyl)-3-methoxy-6-methylpyrazin-2-amine |
| 221 | 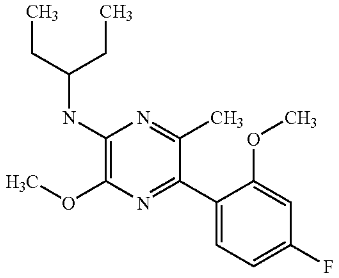 | N-(1-ethylpropyl)-5-(4-fluoro-2-methoxyphenyl)-3-methoxy-6-methylpyrazin-2-amine |

-continued

| EX# | STRUCTURE | UPAC Name |
|---|---|---|
| 222 | 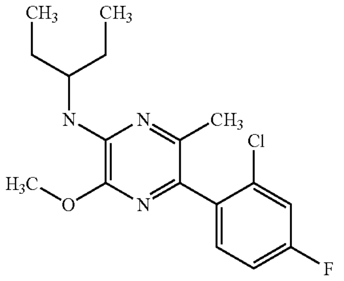 | 5-(2-chloro-4-fluorophenyl)-N-(1-ethylpropyl)-3-methoxy-6-methylpyrazin-2-amine |
| 223 | 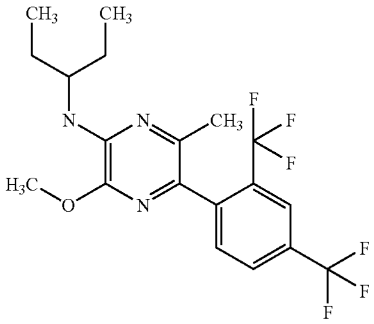 | 5-[2,4-bis(trifluoromethyl)phenyl]-N-(1-ethylpropyl)-3-methoxy-6-methylpyrazin-2-amine |
| 224 | 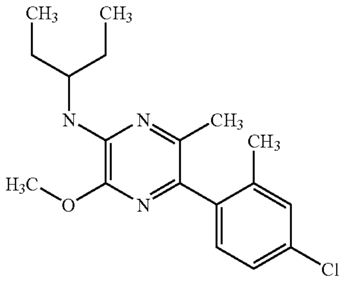 | 5-(4-chloro-2-methylphenyl)-N-(1-ethylpropyl)-3-methoxy-6-methylpyrazin-2-amine |
| 225 | 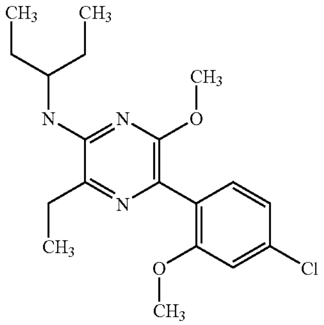 | 5-(4-chloro-2-methoxyphenyl)-3-ethyl-N-(1-ethylpropyl)-6-methoxypyrazin-2-amine |
| 226 | 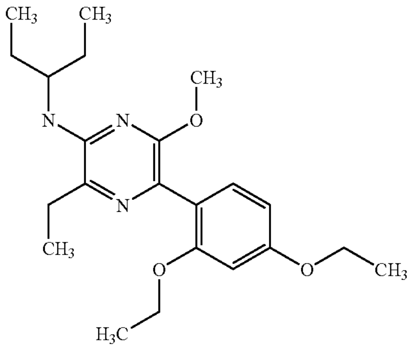 | 5-(2,4-diethoxyphenyl)-3-ethyl-N-(1-ethylpropyl)-6-methoxypyrazin-2-amine |

-continued

| EX# | STRUCTURE | UPAC Name |
| --- | --- | --- |
| 227 | 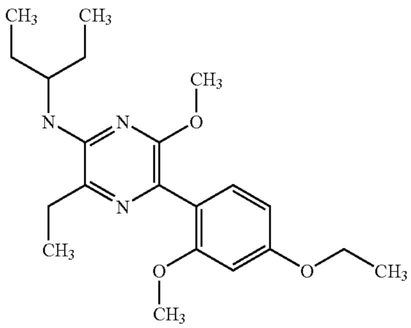 | 5-(4-ethoxy-2-methoxyphenyl)-3-ethyl-N-(1-ethylpropyl)-6-methoxypyrazin-2-amine |
| 228 | 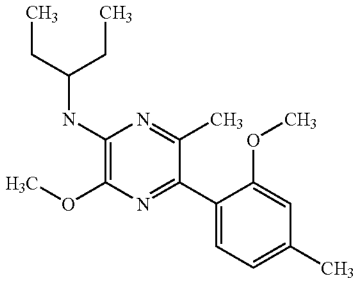 | N-(1-ethylpropyl)-3-methoxy-5-(2-methoxy-4-methylphenyl)-6-methylpyrazin-2-amine |
| 229 | 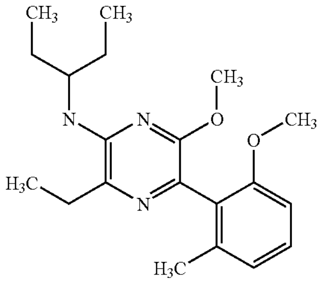 | 3-ethyl-N-(1-ethylpropyl)-6-methoxy-5-(2-methoxy-6-methylphenyl)pyrazin-2-amine |
| 230 | 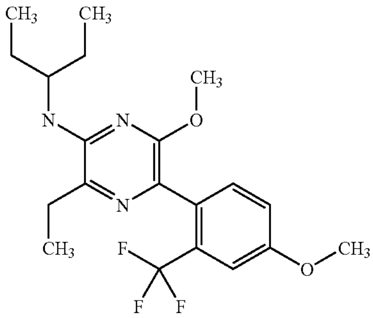 | 3-ethyl-N-(1-ethylpropyl)-6-methoxy-5-(4-methoxy-2-(trifluoromethyl)phenyl]pyrazin-2-amine |
| 231 | 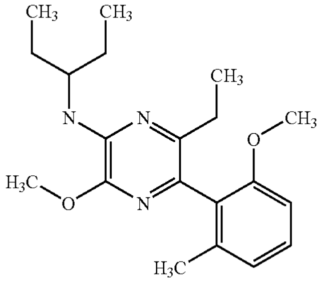 | 6-ethyl-N-(methylpropyl)-3-methoxy-5-(2-methoxy-6-methylphenyl)pyrazin-2-amine |

-continued
| EX# | STRUCTURE | UPAC Name |
| --- | --- | --- |
| 232 | 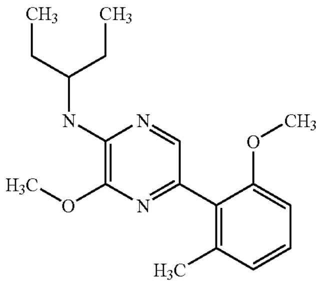 | N-(1-ethylpropyl)-3-methoxy-5-(2-methoxy-6-methylphenyl)pyrazin-2-amine |
| 233 | 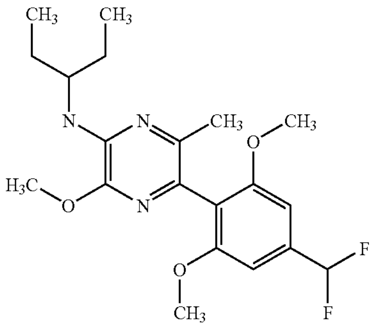 | 5-[4-(difluoromethyl)-2,6-dimethoxyphenyl]-N-(1-ethylpropyl)-3-methoxy-6-methylpyrazin-2-amine |
| 234 | 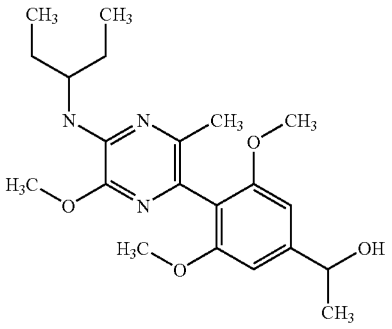 | 1-(4-{5-[(1-ethylpropyl)amino]-6-methoxy-3-methylpyrazin-2-yl}-3,5-dimethoxyphenyl)ethanol |
| 235 | 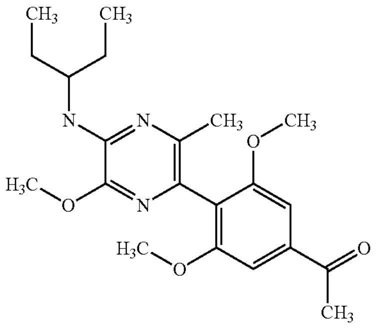 | 1-(4-{5-[(1-ethylpropyl)amino]-6-methoxy-3-methylpyrazin-2-yl}-3,5-dimethoxyphenyl)ethanone |

-continued
| EX# | STRUCTURE | UPAC Name |
| --- | --- | --- |
| 236 | 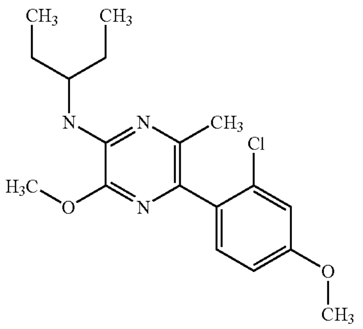 | 5-(2-chloro-4-methoxyphenyl)-N-(1-ethylpropyl)-3-methoxy-6-methylpyrazin-2-amine |
| 237 | 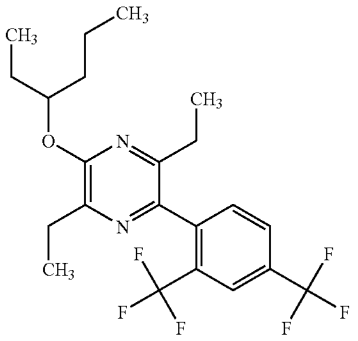 | 2-[2,4-bis(trifluoromethyl)phenyl]-3,6-diethyl-5-(1-ethylbutoxy)pyrazine |
| 238 | 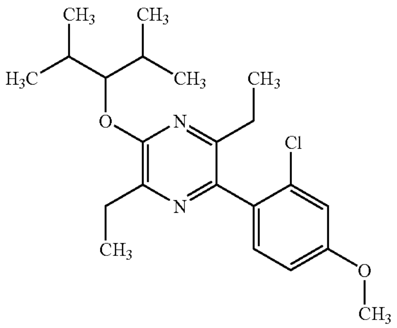 | 2-(2-chloro-4-methoxyphenyl)-3,6-diethyl-5-(1-isopropyl-2-methylpropoxy)pyrazine |
| 239 | 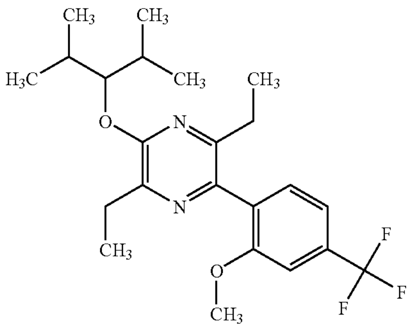 | 2,5-diethyl-3-(1-isopropyl-2-methylpropoxy)-6-[2-methoxy-4-(trifluoromethyl)phenyl]pyrazine |

-continued

| EX# | STRUCTURE | UPAC Name |
|---|---|---|
| 240 | 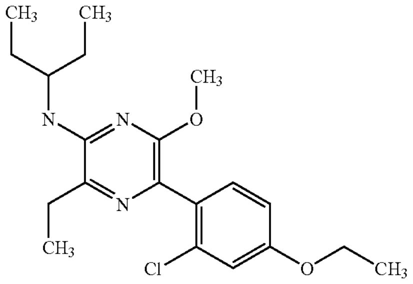 | 5-(2-chloro-4-ethoxyphenyl)-3-ethyl-N-(1-ethylpropyl)-6-methoxypyrazin-2-amine |
| 241 | 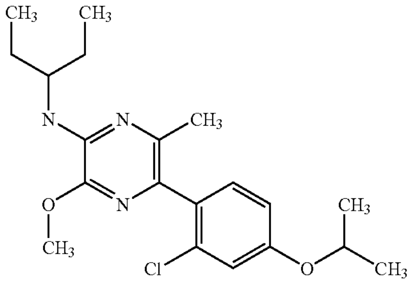 | 5-(2-chloro-4-isopropoxyphenyl)-N-(1-ethylpropyl)-3-methoxy-6-methylpyrazin-2-amine |
| 242 | 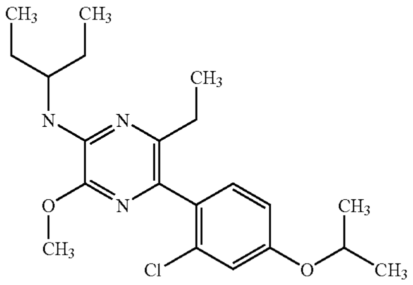 | 5-(2-chloro-4-isopropoxyphenyl)-6-ethyl-N-(1-ethylpropyl)-3-methoxypyrazin-2-amine |
| 243 | 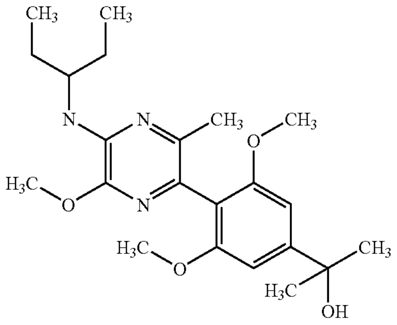 | 2-(4-{5-[(1-ethylpropyl)amino)-6-methoxy-3-methylpyrazin-2-yl}-3,5-dimethoxyphenyl)propan-2-ol |
| 244 | 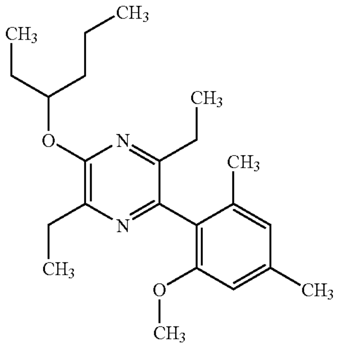 | 2,5-diethyl-3-(1-ethylbutoxy)-6-(2-methoxy-4,6-dimethylphenyl)pyrazine |

-continued
| EX# | STRUCTURE | UPAC Name |
|---|---|---|
| 245 | 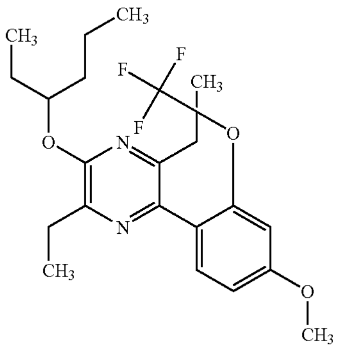 | 2,5-diethyl-3-(1-ethylbutoxy)-6-[4-methoxy-2-(trifluoromethoxy)phenyl]pyrazine |
| 246 | 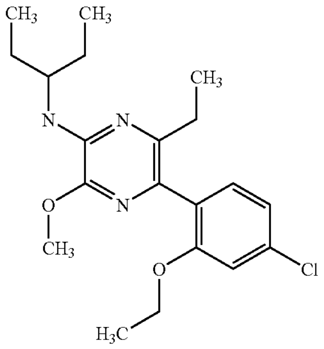 | 5-(4-chloro-2-ethoxyphenyl)-6-ethyl-N-(1-ethylpropyl)-3-methoxypyrazin-2-amine |
| 247 | 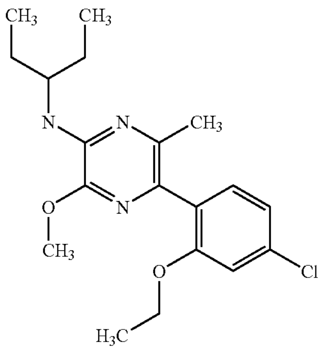 | 5-(4-chloro-2-ethoxyphenyl)-N-(1-ethylpropyl)-3-methoxy-6-methylpyrazin-2-amine |
| 248 | 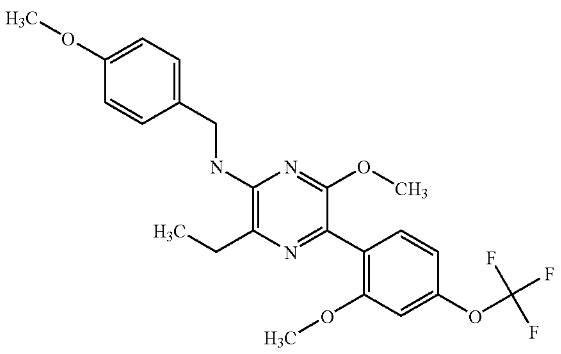 | 3-ethyl-6-methoxy-N-(4-methoxybenzyl)-5-[2-methoxy-4-(trifluoromethoxy)phenyl]-pyrazin-2-amine |

-continued
| EX# | STRUCTURE | UPAC Name |
|---|---|---|
| 249 | 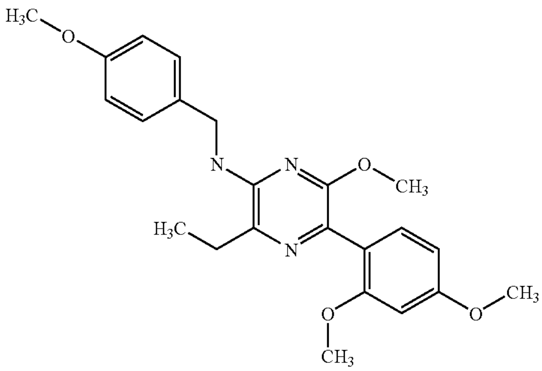 | 5-(2,4-dimethoxyphenyl)-3-ethyl-6-methoxy-N-(4-methoxybenzyl)pyrazin-2-amine |
| 250 | 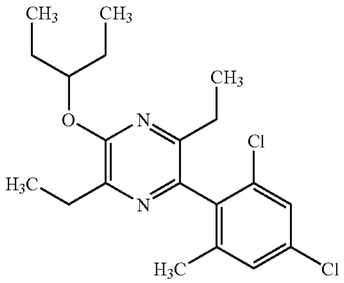 | 2-(2,4-dichloro-6-methylphenyl)-3,6-diethyl-5-(1-ethylpropoxy)pyrazine |
| 251 | 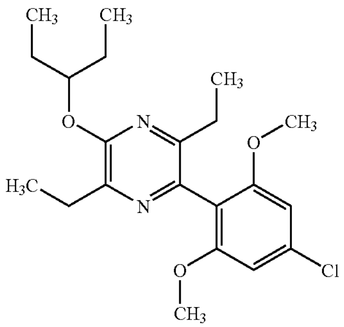 | 2-(4-chloro-2,6-dimethoxyphenyl)-3,6-diethyl-5-(1-ethylpropoxy)pyrazine |
| 252 | 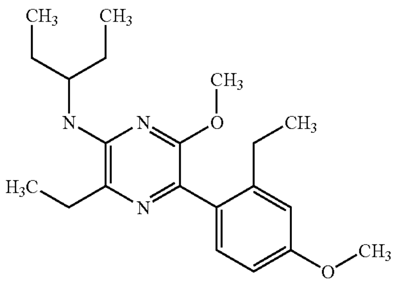 | 3-ethyl-5-(2-ethyl-4-methoxyphenyl)-N-(1-ethylpropyl)-6-methoxypyrazin-2-amine |
| 253 | 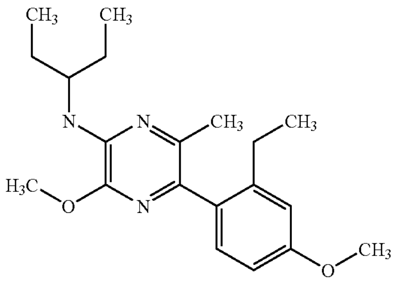 | 5-(2-ethyl-4-methoxyphenyl)-N-(1-ethylpropyl)-3-methoxy-6-methylpyrazin-2-amine |

-continued
| EX# | STRUCTURE | UPAC Name |
|---|---|---|
| 254 | 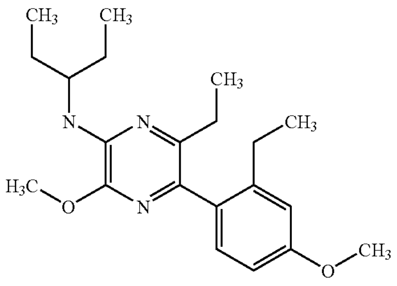 | 6-ethyl-5-(2-ethyl-4-methoxyphenyl)-N-(1-ethylpropyl)-3-methoxypyrazin-2-amine |
| 255 | 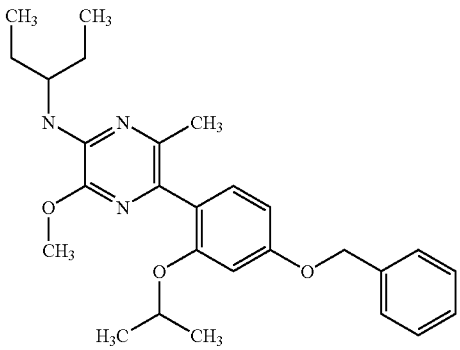 | 5-[4-(benzyloxy-2-isopropoxyphenyl]-N-(1-ethylpropyl)-3-methoxy-6-methylpyrazin-2-amine |
| 256 | 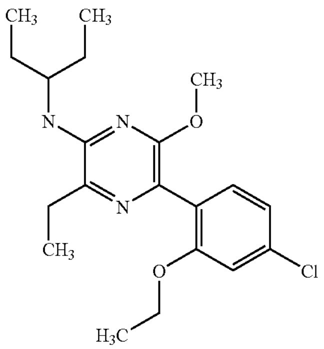 | 5-(4-chloro-2-ethoxyphenyl)-3-ethyl-N-(1-ethylpropyl)-6-methoxypyrazin-2-amine |
| 257 | 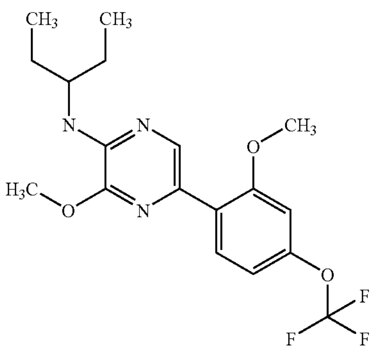 | N-(1-ethylpropyl)-3-methoxy-5-[2-methoxy-4-(trifluoromethoxy)phenyl]pyrazin-2-amine |

-continued

| EX# | STRUCTURE | UPAC Name |
| --- | --- | --- |
| 258 | 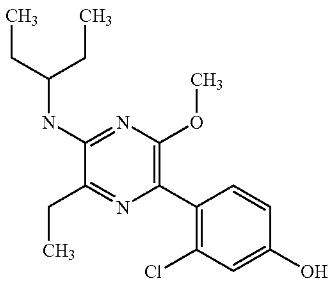 | 3-chloro-4-{6-ethyl-5-[(1-ethylpropyl)amino]-3-methoxypyrazin-2-yl}phenol |
| 259 | 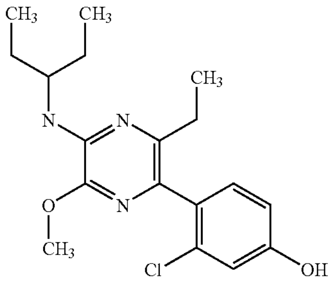 | 3-chloro-4-{3-ethyl-5-[(1-ethylpropyl)amino]-6-methoxypyrazin-2-yl}phenol |
| 260 | 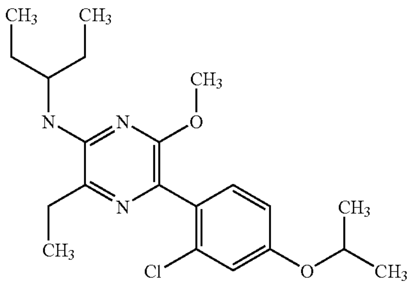 | 5-(2-chloro-4-isopropoxyphenyl)-3-ethyl-N-(1-ethylpropyl)-6-methoxypyrazin-2-amine |
| 261 | 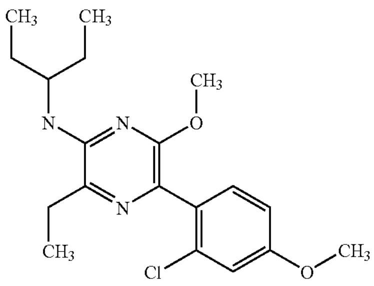 | 5-(2-chloro-4-methoxyphenyl)-3-ethyl-N-(1-ethylpropyl)-6-methoxypyrazin-2-amine |
| 262 | 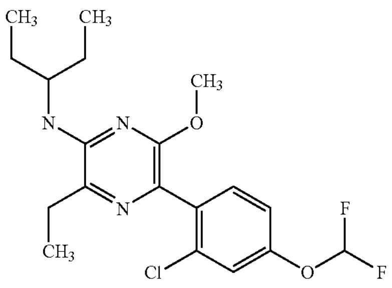 | 5-[2-chloro-4-(difluoromethoxy)phenyl]-3-ethyl-N-(1-ethylpropyl)-6-methoxypyrazin-2-amine |

-continued

| EX# | STRUCTURE | UPAC Name |
| --- | --- | --- |
| 263 | 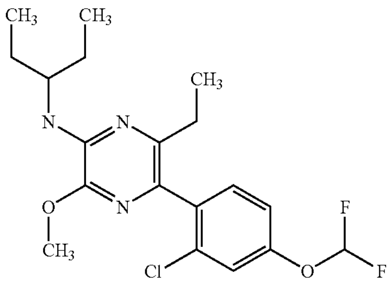 | 5-[2-chloro-4-(difluoromethoxy)phenyl]-6-ethyl-N-(1-ethylpropyl)-3-methoxypyrazin-2-amine |
| 264 | 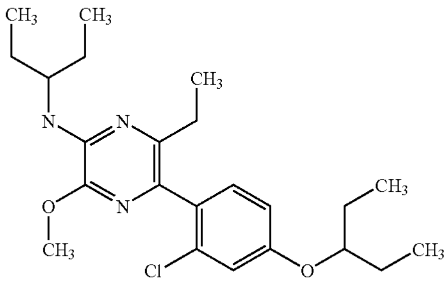 | 5-[2-chloro-4-(1-ethylpropoxy)phenyl]-6-ethyl-N-(1-ethylpropyl)-3-methoxypyrazin-2-amine |
| 265 | 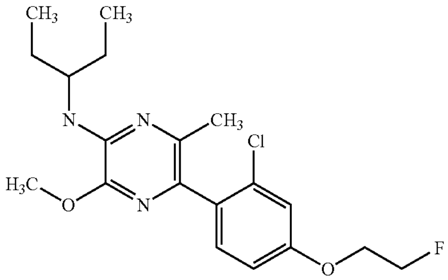 | 5-[2-chloro-4-(2-fluoroethoxy)phenyl]-N-(1-ethylpropyl)-3-methoxy-6-methylpyrazin-2-amine |
| 266 | 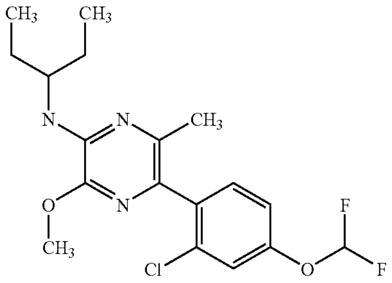 | 5-[2-chloro-4-(difluoromethoxy)phenyl]-N-(1-ethylpropyl)-3-methoxy-6-methylpyrazin-2-amine |
| 267 | 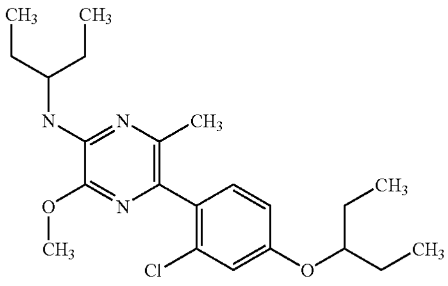 | 5-[2-chloro-4-(dimethylpropoxy)phenyl]-N-(1-ethylpropyl)-3-methoxy-6-methylpyrazin-2-amine |

-continued

| EX# | STRUCTURE | UPAC Name |
|---|---|---|
| 268 | 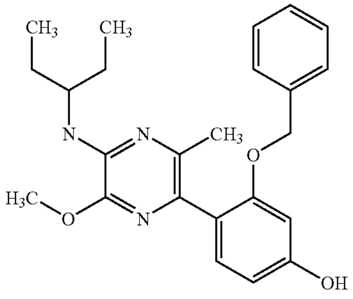 | 3-(benzyloxy)-4-{5-[(1-ethylpropyl)amino]-6-methoxy-3-methylpyrazin-2-yl}phenol |
| 269 | 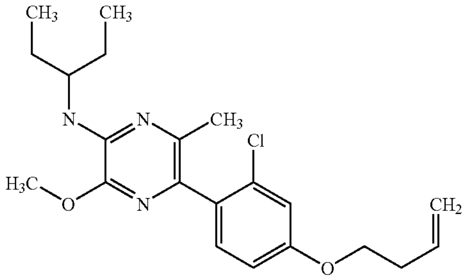 | 5-[4-(but-3-enyloxy)-2-chlorophenyl]-N-(1-ethylpropyl)-3-methoxy-6-methylpyrazin-2-amine |
| 270 | 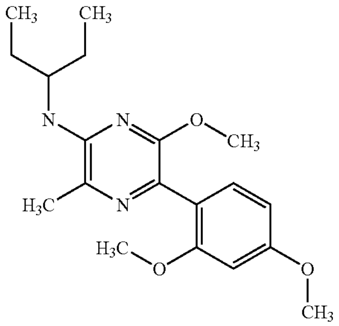 | 5-(2,4-dimethoxyphenyl)-N-(1-ethylpropyl)-6-methoxy-3-methylpyrazin-2-amine |
| 271 | 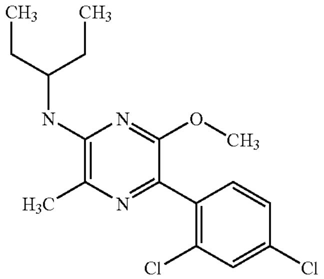 | 5-(2,4-dichlorophenyl)-N-(1-ethylpropyl)-6-methoxy-3-methylpyrazin-2-amine |
| 272 | 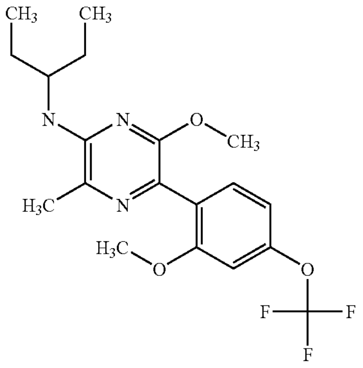 | N-(1-ethylpropyl)-6-methoxy-5-[2-methoxy-4-(trifluoromethoxy)phenyl]-3-methylpyrazin-2-amine |

-continued
| EX# | STRUCTURE | UPAC Name |
| --- | --- | --- |
| 273 | 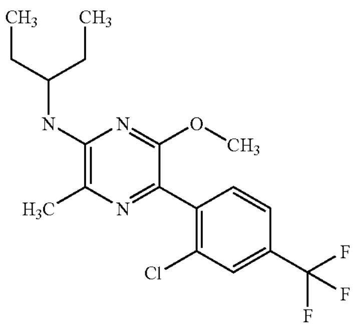 | 5-[2-chloro-4-(trifluoromethyl)phenyl]-N-(1-ethylpropyl)-6-methoxy-3-methylpyrazin-2-amine |
| 274 | 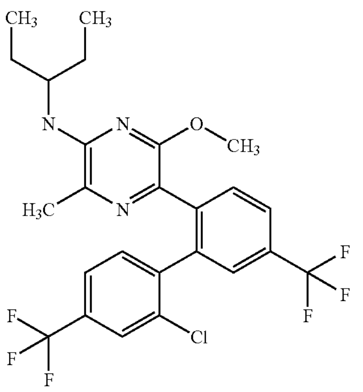 | 5-[2'-chloro-4',5-bis(trifluoromethyl)-1,1'-biphenyl-2-yl]-N-(1-ethylpropyl)-6-methoxy-3-methylpyrazin-2-amine |
| 275 | 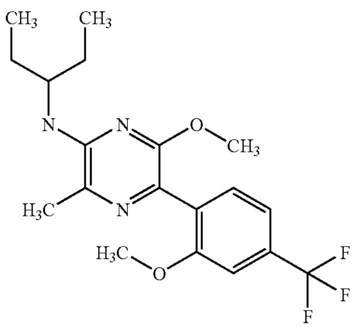 | N-(1-ethylpropyl)-6-methoxy-5-[2-methoxy-4-(trifluoromethyl)phenyl]-3-methylpyrazin-2-amine |
| 276 | 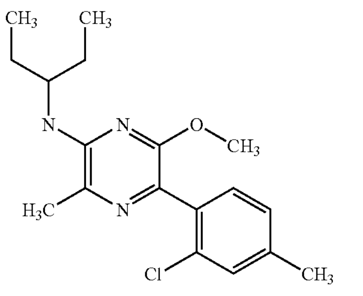 | 5-(2-chloro-4-methylphenyl)-N-(1-ethylpropyl)-6-methoxy-3-methylpyrazin-2-amine |

-continued

| EX# | STRUCTURE | UPAC Name |
|---|---|---|
| 277 | 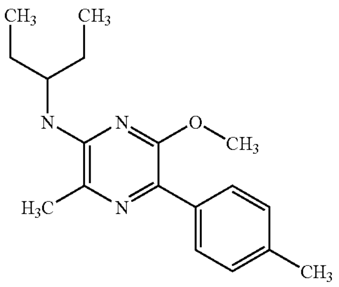 | N-(1-ethylpropyl)-6-methoxy-3-methyl-5-(4-methylphenyl)pyrazin-2-amine |
| 278 | 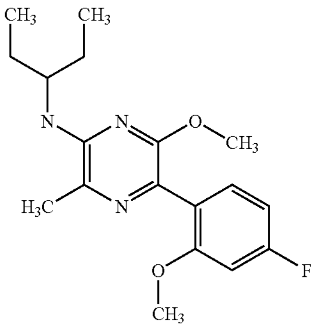 | N-(1-ethylpropyl)-5-(4-fluoro-2-methoxyphenyl)-6-methoxy-3-methylpyrazin-2-amine |
| 279 | 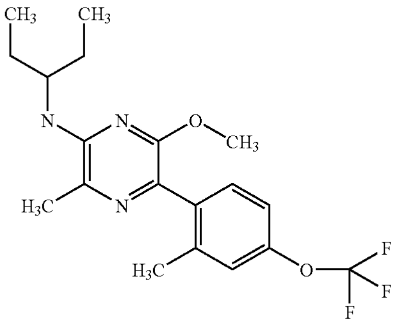 | N-(1-ethylpropyl)-6-methoxy-3-methyl-5-[2-methyl-4-(trifluoromethoxy)phenyl]pyrazin-2-amine |
| 280 | 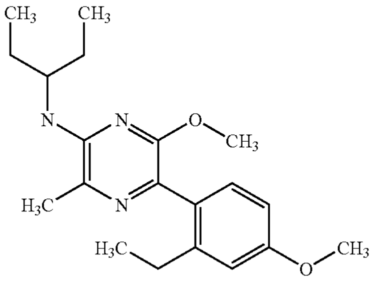 | 5-(2-ethyl-4-methoxyphenyl)-N-(1-ethylpropyl)-6-methoxy-3-methylpyrazin-2-amine |
| 281 | 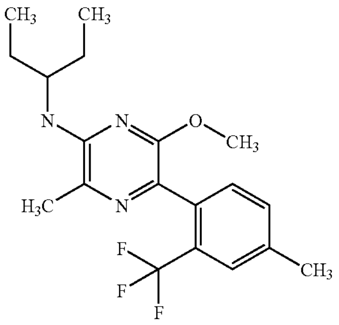 | N-(1-ethylpropyl)-6-methoxy-3-methyl-5-[4-methyl-2-(trifluoromethyl)phenyl]pyrazin-2-amine |

-continued
| EX# | STRUCTURE | UPAC Name |
| --- | --- | --- |
| 282 | 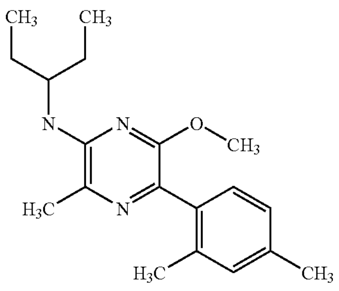 | 5-(2,4-dimethylphenyl)-N-(1-ethylpropyl)-6-methoxy-3-methylpyrazin-2-amine |
| 283 | 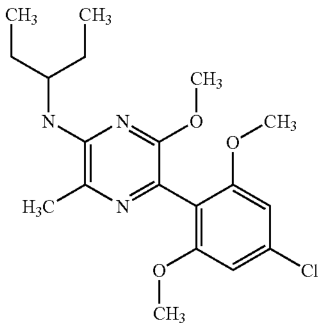 | 5-(4-chloro-2,6-dimethoxyphenyl)-N-(1-ethylpropyl)-6-methoxy-3-methylpyrazin-2-amine |
| 284 | 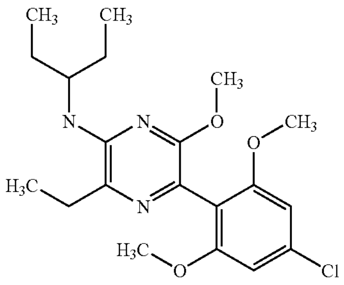 | 5-(4-chloro-2,6-dimethoxyphenyl)-3-ethyl-N-(1-ethylpropyl)-6-methoxypyrazin-2-amine |
| 285 | 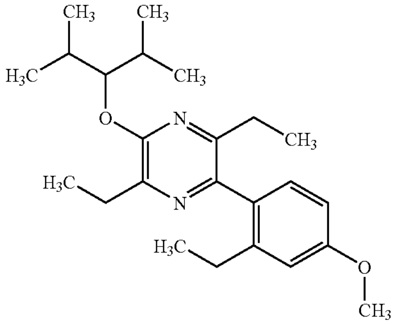 | 2,5-diethyl-3-methyl-4-methoxyphenyl)-6-(1-isopropyl-2-methylpropoxy)pyrazine |

-continued

| EX# | STRUCTURE | UPAC Name |
|---|---|---|
| 286 | 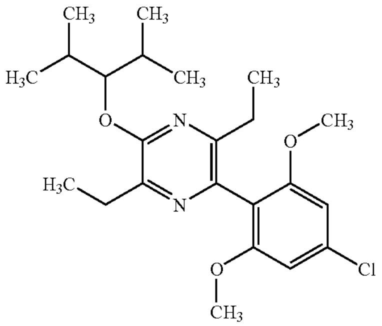 | 2-(4-chloro-2,6-dimethoxyphenyl)-3,6-diethyl-5-(1-isopropyl-2-methylpropoxy)pyrazine |
| 287 | 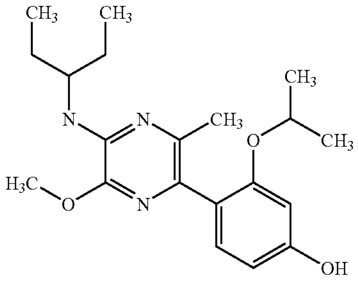 | 4-{5-[(1-ethylpropyl)amino]-6-methoxy-3-methylpyrazin-2-yl}-3-isopropoxyphenol |
| 288 | 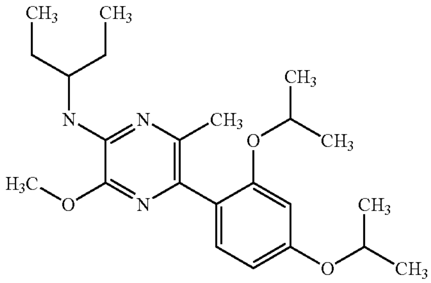 | 5-(2,4-diisopropoxyphenyl)-N-(1-ethylpropyl)-3-methoxy-6-methylpyrazin-2-amine |
| 289 | 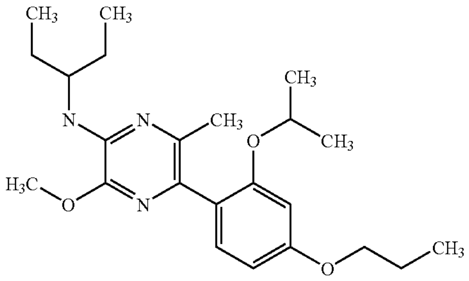 | N-(1-ethylpropyl)-5-(2-isopropoxy-4-propoxyphenyl)-3-methoxy-6-methylpyrazin-2-amine |
| 290 | 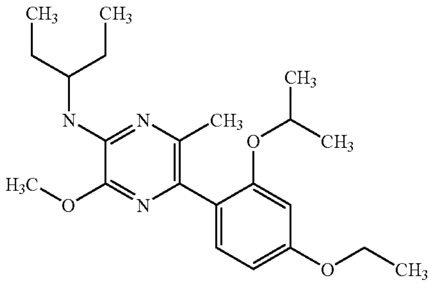 | 5-(4-ethoxy-2-isopropoxyphenyl)-N-(1-ethylpropyl)-3-methoxy-6-methylpyrazin-2-amine |

-continued

| EX# | STRUCTURE | UPAC Name |
|---|---|---|
| 291 | 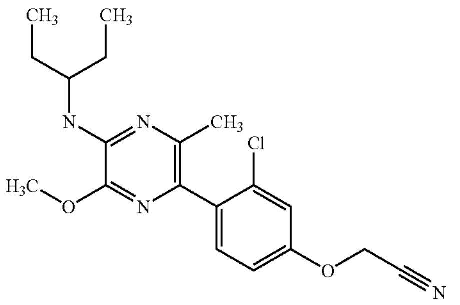 | (3-chloro-4-{5-[(1-ethylpropyl)amino]-6-methoxy-3-methylpyrazin-2-yl}phenoxy)acetonitrile |
| 292 | 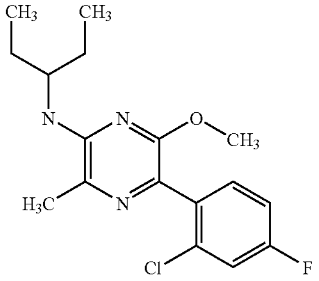 | 5-(2-chloro-4-fluorophenyl)-N-(1-ethylpropyl)-6-methoxy-3-methylpyrazin-2-amine |
| 293 | 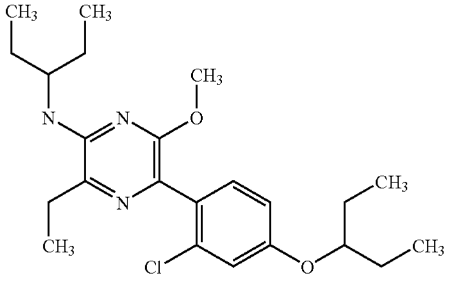 | 5-[2-chloro-4-(1-ethylpropoxy)phenyl]-3-ethyl-N-(1-ethylpropyl)-6-methoxypyrazin-2-amine |
| 294 | 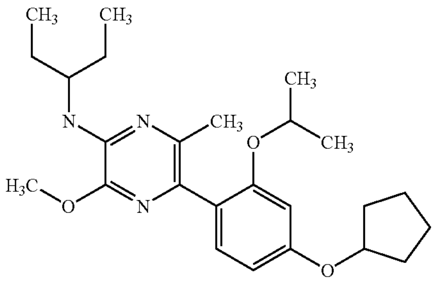 | 5-[4-(cyclopentyloxy)-2-isopropoxyphenyl]-N-(1-ethylpropyl)-3-methoxy-6-methylpyrazin-2-amine |
| 295 | 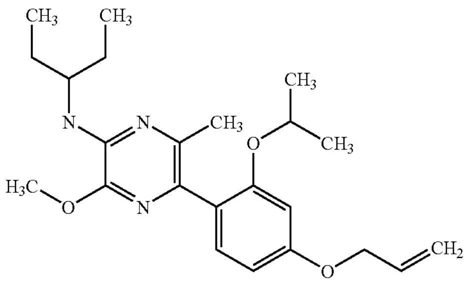 | 5-[4-(allyloxy)-2-isopropoxyphenyl]-N-(1-ethylpropyl)-3-methoxy-6-methylpyrazin-2-amine |

-continued

| EX# | STRUCTURE | UPAC Name |
|---|---|---|
| 296 | 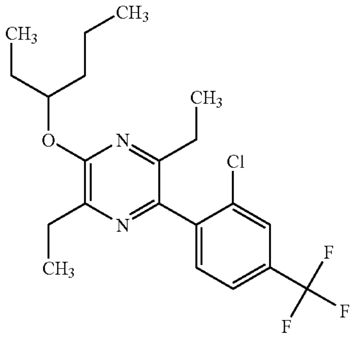 | 2-[2-chloro-4-(trifluoromethyl)phenyl]-3,6-diethyl-5-(1-ethylbutoxy)pyrazine |
| 297 | 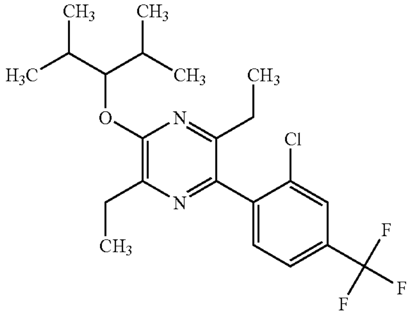 | 2-[2-chloro-4-(trifluoromethyl)phenyl]-3,6-diethyl-5-(1-isopropyl-2-methylpropoxy)pyrazine |
| 298 | 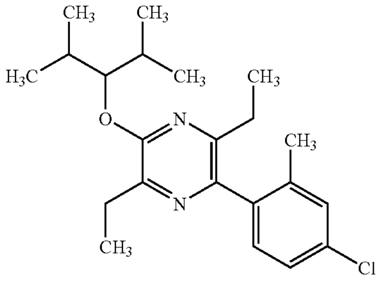 | 2-(4-chloro-2-methylphenyl)-3,6-diethyl-5-(1-isopropyl-2-methylpropoxy)pyrazine |
| 299 | 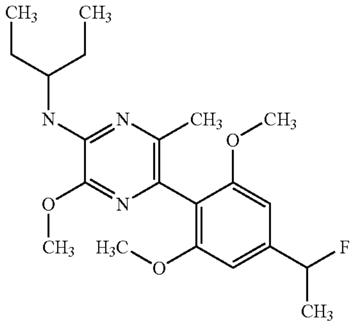 | N-(1-ethylpropyl)-5-[4-(1-fluoroethyl)-2,6-dimethoxyphenyl]-3-methoxy-6-methylpyrazin-2-amine |
| 300 | 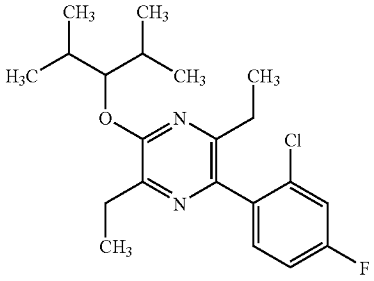 | 2-(2-chloro-4-fluorophenyl)-3,6-diethyl-5-(1-isopropyl-2-methylpropoxy)pyrazine |

-continued
| EX# | STRUCTURE | UPAC Name |
| --- | --- | --- |
| 301 | 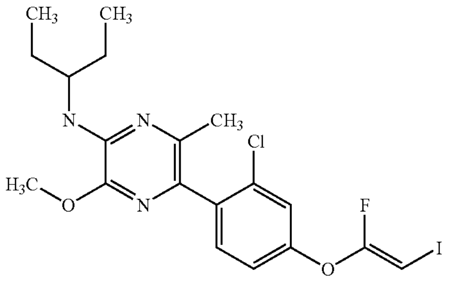 | 5-(2-chloro-4-{[(Z)-1-fluoro-2-iodoethenyl]oxy}phenyl)-N-(1-ethylpropyl)-3-methoxy-6-methylpyrazin-2-amine |
| 302 | 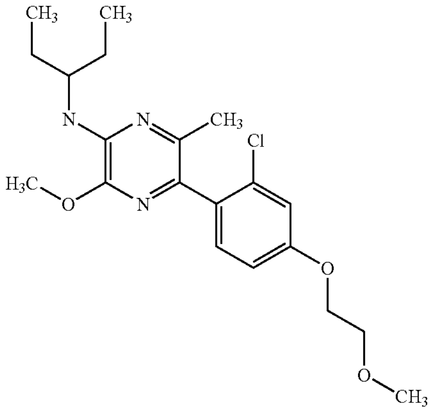 | 5-[2-chloro-4-(2-methoxyethoxy)phenyl]-N-(1-ethylpropyl)-3-methoxy-6-methylpyrazin-2-amine |
| 303 | 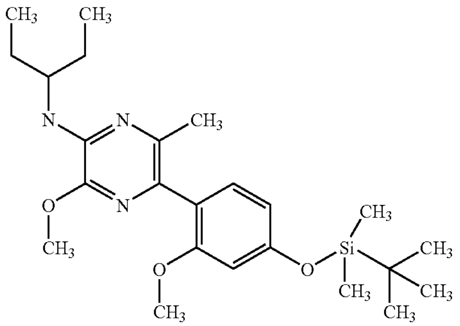 | 5-(4-{[tert-butyl(dimethyl)silyl]oxy}-2-methoxyphenyl)-N-(1-ethylpropyl)-3-methoxy-6-methylpyrazin-2-amine |
| 304 | 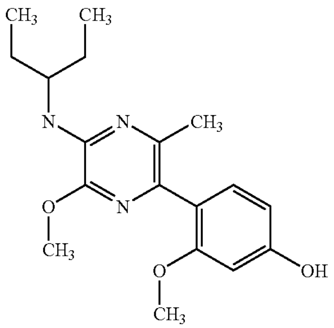 | 4-{5-[(1-ethylpropyl)amino]-6-methoxy-3-methylpyrazin-2-yl}-3-methoxyphenol |

-continued
| EX# | STRUCTURE | UPAC Name |
| --- | --- | --- |
| 305 | 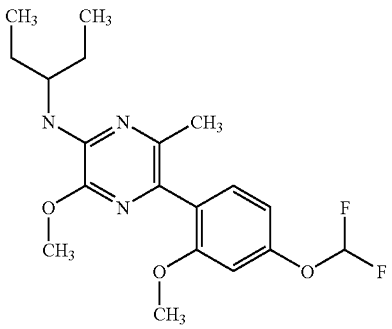 | 5-[4-(difluoromethoxy)-2-methoxyphenyl]-N-(1-ethylpropyl)-3-methoxy-6-methylpyrazin-2-amine |
| 306 | 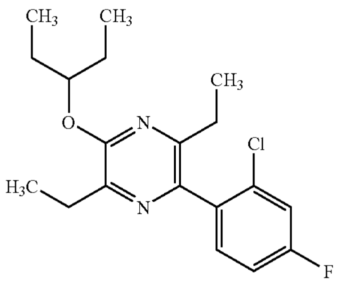 | 2-(2-chloro-4-fluorophenyl)-3,6-diethyl-5-(1-ethylpropoxy)pyrazine |
| 307 | 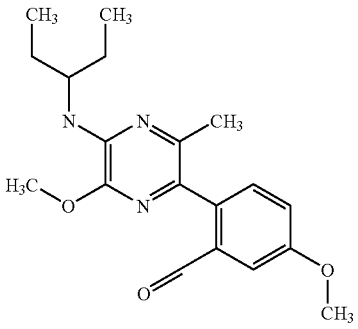 | 2-{5-[(1-ethylpropyl)amino]-6-methoxy-3-methylpyrazin-2-yl}-5-methoxybenzaldehyde |
| 308 | 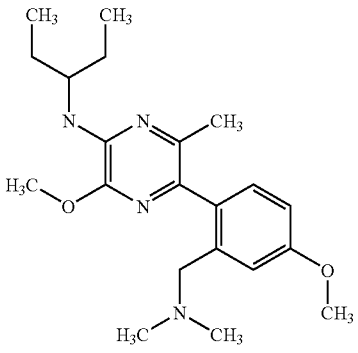 | 5-{2-[(dimethylamino)methyl]-4-methoxyphenyl}-N-(1-ethylpropyl)-3-methoxy-6-methylpyrazin-2-amine |

-continued
| EX# | STRUCTURE | UPAC Name |
| --- | --- | --- |
| 309 | 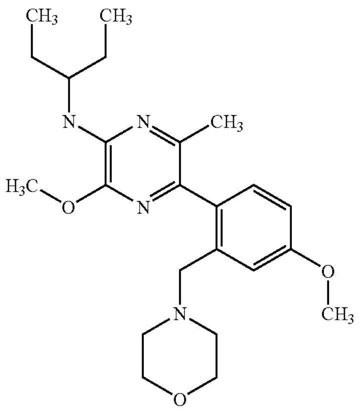 | N-(1-ethylpropyl)-3-methoxy-5-[4-methoxy-2-(morpholin-4-ylmethyl)phenyl]-6-methylpyrazin-2-amine |
| 310 | 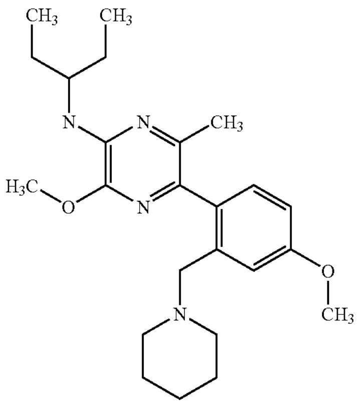 | N-(1-ethylpropyl)-3-methoxy-5-[4-methoxy-2-(piperidin-1-ylmethyl)phenyl]-6-methylpyrazin-2-amine |
| 311 | 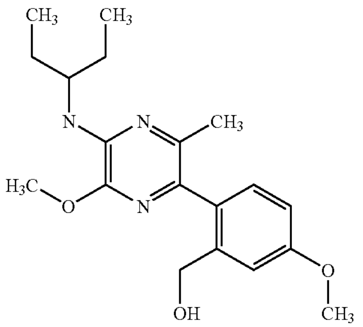 | (2-{5-[(1-ethylpropyl)amino]-6-methoxy-3-methylpyrazin-2-yl}-5-methoxyphenyl)methanol |
| 312 | 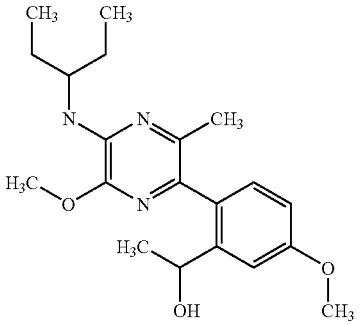 | 1-(2-{5-[(1-ethylpropyl)amino]-6-methoxy-3-methylpyrazin-2-yl}-5-methoxyphenyl)ethanol |

-continued
| EX# | STRUCTURE | UPAC Name |
|---|---|---|
| 313 | 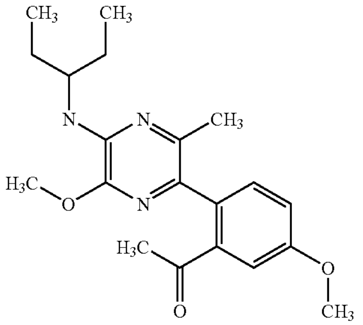 | 1-(2-{5-[(1-ethylpropyl)amino]-6-methoxy-3-methylpyrazin-2-yl}-5-methoxyphenyl)ethanone |
| 314 | 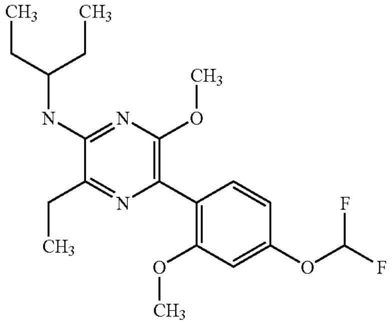 | 5-[4-(difluoromethoxy)-2-methoxyphenyl]-3-ethyl-N-(1-ethylpropyl)-6-methoxypyrazin-2-amine |
| 315 | 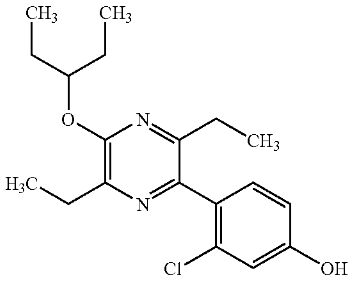 | 3-chloro-4-[3-diethyl-5-(1-ethylpropoxy)pyrazin-2-yl]phenol |
| 316 | 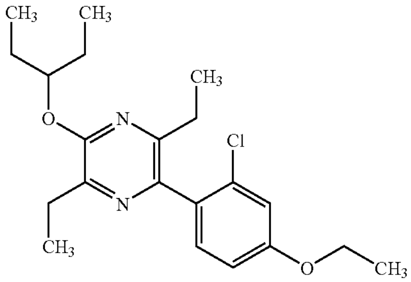 | 2-(2-chloro-4-ethoxyphenyl)-3,6-diethyl-5-(1-ethylpropoxy)pyrazine |
| 317 | 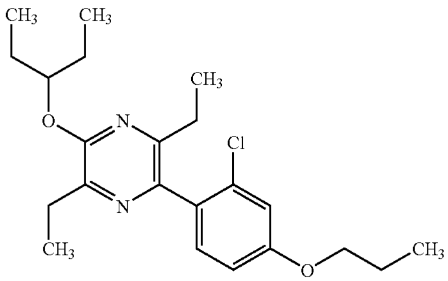 | 2-(2-chloro-4-propoxyphenyl)-3,6-diethyl-5-(1-ethylpropoxy)pyrazine |

-continued
| EX# | STRUCTURE | UPAC Name |
|---|---|---|
| 318 | 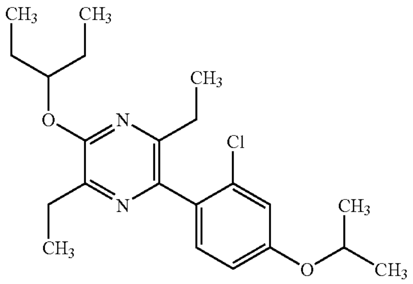 | 2-(2-chloro-4-isopropoxyphenyl)-3,6-diethyl-5-(1-ethylpropoxy)pyrazine |
| 319 | 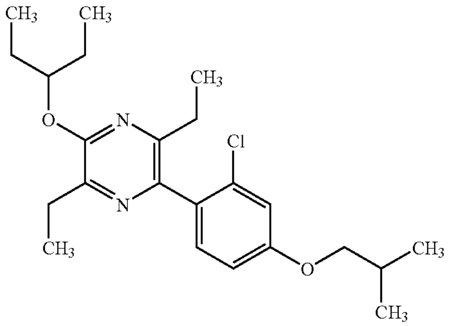 | 2-(2-chloro-4-isobutoxyphenyl)-3,6-diethyl-5-(1-ethylpropoxy)pyrazine |
| 320 | 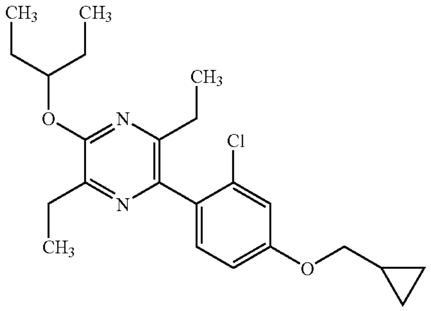 | 2-[2-chloro-4-(cyclopropylmethoxy)phenyl]-3,6-diethyl-5-(1-ethylpropoxy)pyrazine |
| 321 | 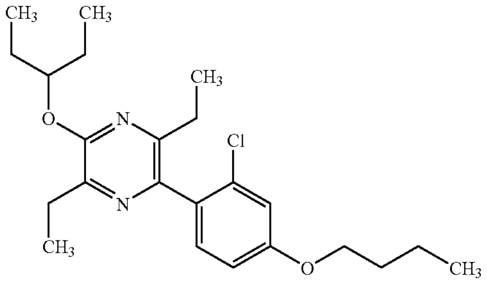 | 2-(4-butoxy-2-chlorophenyl)-3,6-diethyl-5-(1-ethylpropoxy)pyrazine |
| 322 | 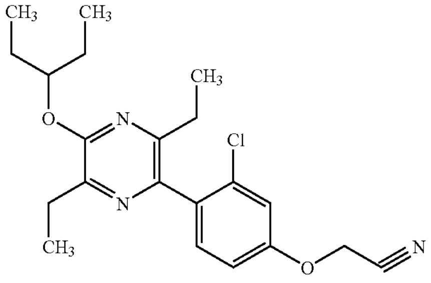 | {3-chloro-4-[3,6-diethyl-5-(1-ethylpropoxy)pyrazin-2-yl]phenoxy}acetonitrile |

-continued
| EX# | STRUCTURE | UPAC Name |
|---|---|---|
| 323 | 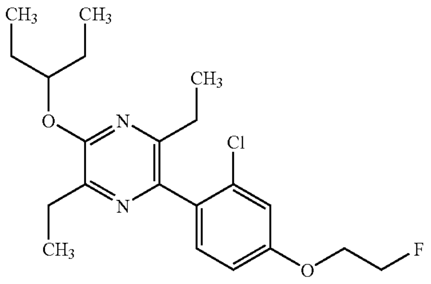 | 2-[2-chloro-4-(2-fluoroethoxy)phenyl]-3,6-diethyl-5-(1-ethylpropoxy)pyrazine |
| 324 | 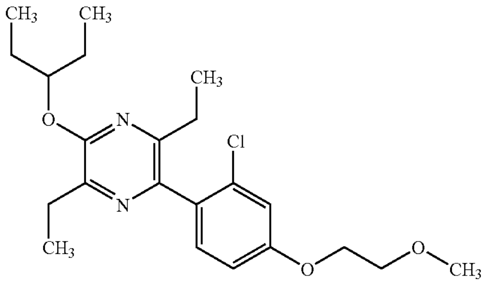 | 2-[2-chloro-4-(2-methoxyethoxy)phenyl]-3,6-diethyl-5-(1-ethylpropoxy)pyrazine |
| 325 | 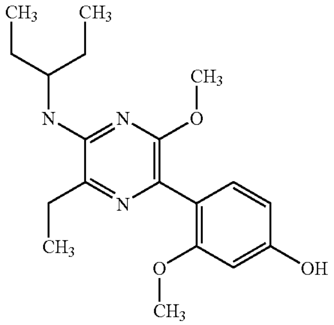 | 4-{6-ethyl-5-[(1-ethylpropyl)amino]-3-methoxypyrazin-2-yl}-3-methoxyphenol |
| 326 | 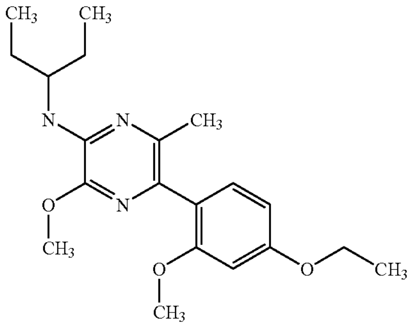 | 5-(4-ethoxy-2-methoxyphenyl)-N-(1-ethylpropyl)-3-methoxy-6-methylpyrazin-2-amine |
| 327 | 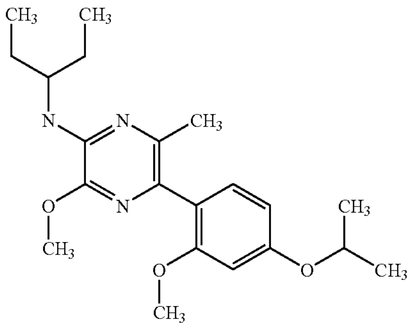 | N-(1-ethylpropyl-5-(4-isopropoxy-2-methoxyphenyl)-3-methoxy-6-methylpyrazin-2-amine |

-continued
| EX# | STRUCTURE | UPAC Name |
|---|---|---|
| 328 | 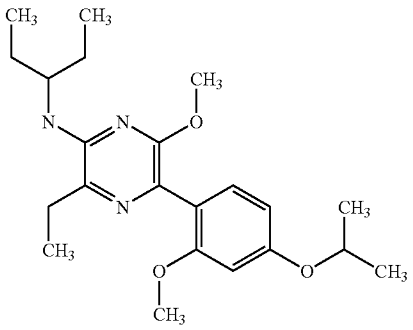 | 3-ethyl-N-(1-ethylpropyl)-5-(4-isopropoxy-2-methoxyphenyl)-6-methoxypyrazin-2-amine |
| 329 | 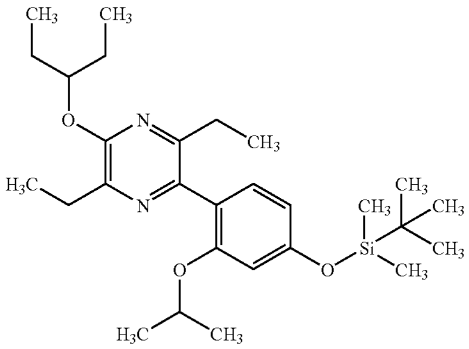 | 2-(4-{[tert-butyl(dimethyl)silyl]oxy}-2-isopropoxyphenyl)-3,6-diethyl-5-(1-ethylpropoxy)pyrazine |
| 330 | 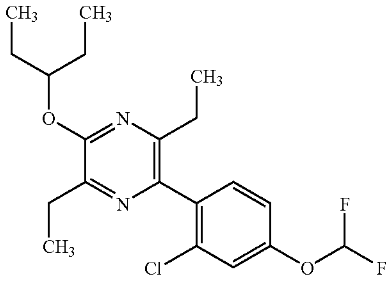 | 2-[2-chloro-4-(difluoromethoxy)phenyl]-3,6-diethyl-5-(1-ethylpropoxy)pyrazine |
| 331 | 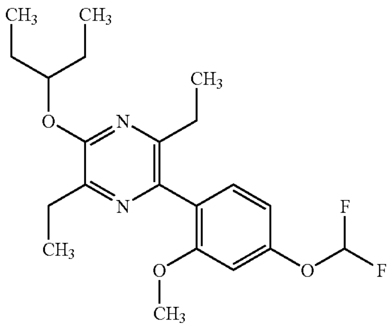 | 2-[4-(difluoromethoxy)-2-methoxyphenyl]-3,6-diethyl-5-(1-ethylpropoxy)pyrazine |

-continued
| EX# | STRUCTURE | UPAC Name |
| --- | --- | --- |
| 332 | 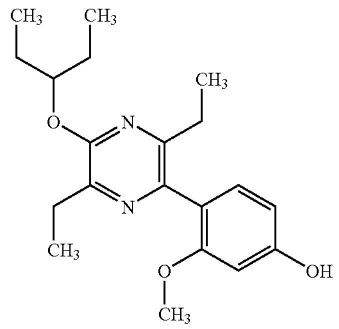 | 4-[3,6-diethyl-5-(1-ethylpropoxy)pyrazin-2-yl]-3-methoxyphenol |
| 333 | 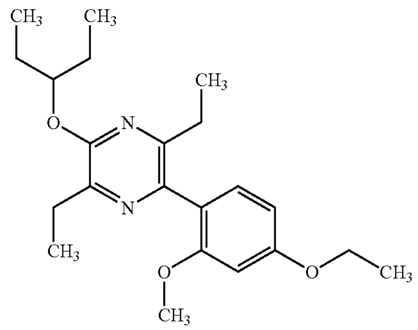 | 2-(4-ethoxy-2-methoxyphenyl)-3,6-diethyl-5-(1-ethylpropoxy)pyrazine |
| 334 | 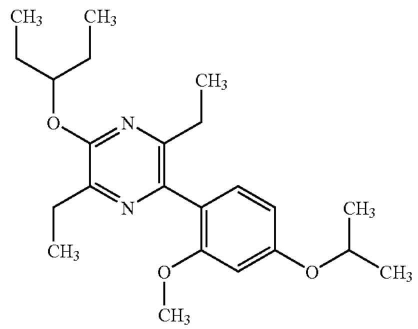 | 2,5-diethyl-3-(1-ethylpropoxy)-6-(4-isopropoxy-2-methoxyphenyl)pyrazine |
| 335 | 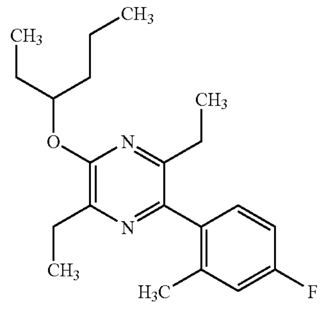 | 2,5-diethyl-3-(1-ethylbutoxy)-6-(4-fluoro-2-methylphenyl)pyrazine |

-continued
| EX# | STRUCTURE | UPAC Name |
|---|---|---|
| 336 | 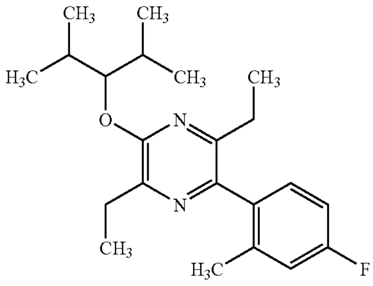 | 2,5-diethyl-3-(4-fluoro-2-methylphenyl)-6-(1-isopropyl-2-methylpropoxy)pyrazine |
| 337 | 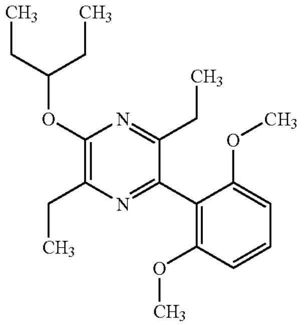 | 2-(2,6-dimethoxyphenyl)-3,6-diethyl-5-(1-ethylpropoxy)pyrazine |
| 338 | 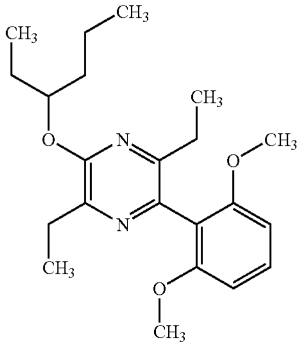 | 2-(2,6-dimethoxyphenyl)-3,6-diethyl-5-(1-ethylbutoxy)pyrazine |
| 339 | 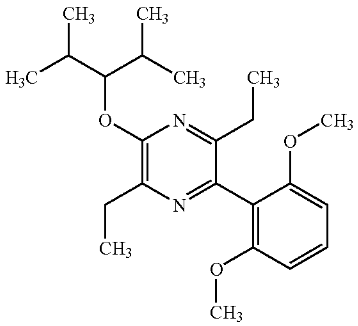 | 2-(2,6-dimethoxyphenyl)-3,6-diethyl-5-(1-isopropyl-2-methylpropoxy)pyrazine |

-continued
| EX# | STRUCTURE | UPAC Name |
|---|---|---|
| 340 | 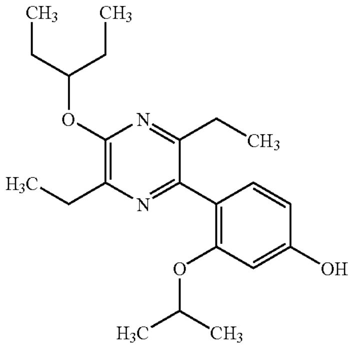 | 4-[3,6-diethyl-5-(1-ethylpropoxy)pyrazin-2-yl]-3-isopropoxyphenol |
| 341 | 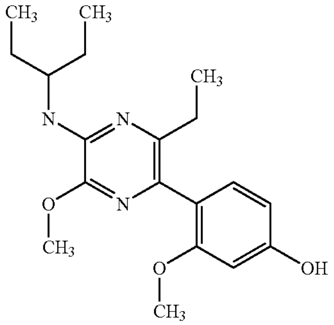 | 4-{3-ethyl-5-[(1-ethylpropyl)amino]-6-methoxypyrazin-2-yl}-3-methoxyphenol |
| 342 | 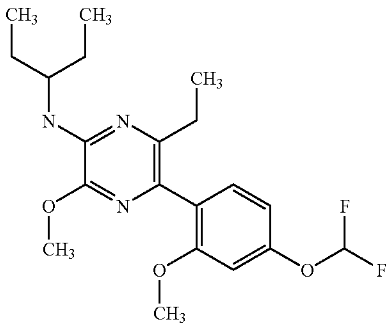 | 5-[4-(difluoromethoxy)-2-methoxyphenyl]-6-ethyl-N-(1-ethylpropyl)-3-methoxypyrazin-2-amine |
| 343 | 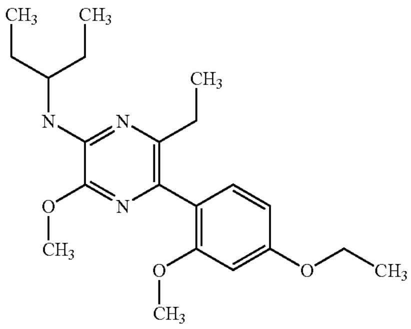 | 5-(4-ethoxy-2-methoxyphenyl)-6-ethyl-N-(1-ethylpropyl)-3-methoxypyrazin-2-amine |

-continued
| EX# | STRUCTURE | UPAC Name |
|---|---|---|
| 344 | 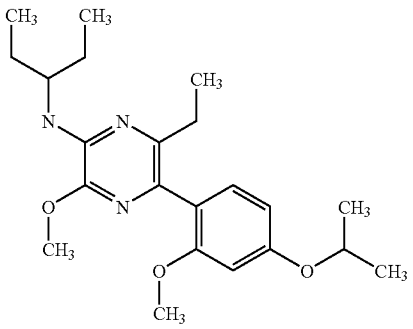 | 6-ethyl-N-(1-ethylpropyl)-5-(4-isopropoxy-2-methoxyphenyl)-3-methoxypyrazin-2-amine |
| 345 | 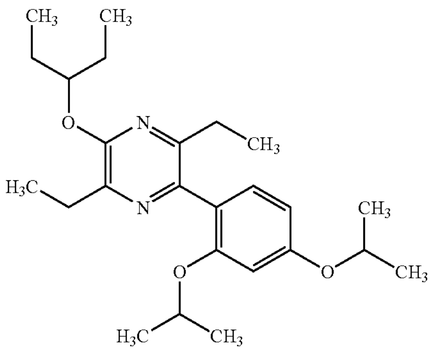 | 2-(2,4-diisopropoxyphenyl)-3,6-diethyl-5-(1-ethylpropoxy)pyrazine |
| 346 | 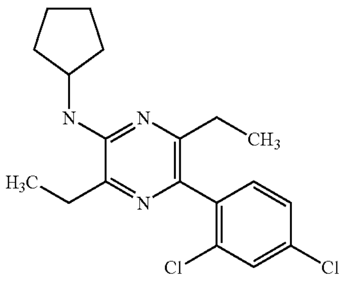 | N-cyclopentyl-5-(2,4-dichlorophenyl)-3,6-diethylpyrazin-2-amine |
| 347 | 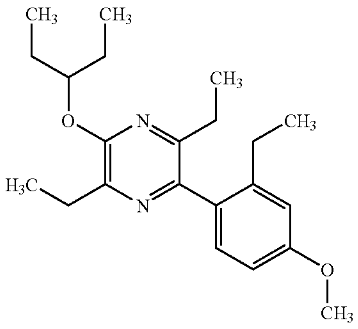 | 2,5-diethyl-3-(2-ethyl-4-methoxyphenyl)-6-(1-ethylpropoxy)pyrazine |
| 348 | 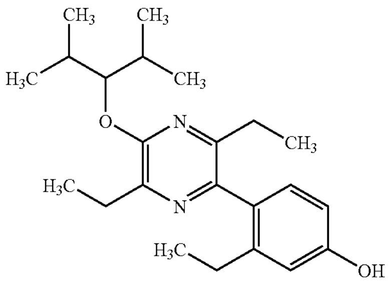 | 4-[3,6-diethyl-5-(1-isopropyl-2-methylpropoxy)pyrazin-2-yl]-3-ethylphenol |

-continued
| EX# | STRUCTURE | UPAC Name |
| --- | --- | --- |
| 349 | 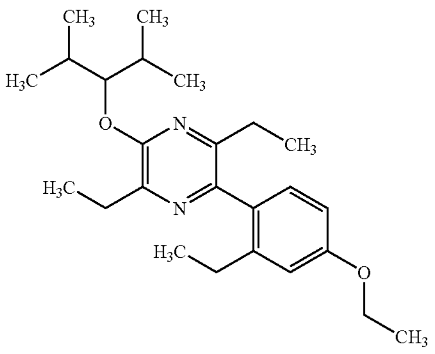 | 2-(4-ethoxy-2-ethylphenyl)-3,6-diethyl-5-(1-isopropyl-2-methylpropoxy)pyrazine |
| 350 | 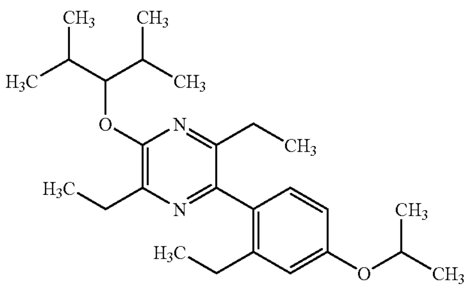 | 2,5-diethyl-3-(2-ethyl-4-isopropoxyphenyl)-6-(1-isopropyl-2-methylpropoxy)pyrazine |
| 351 | 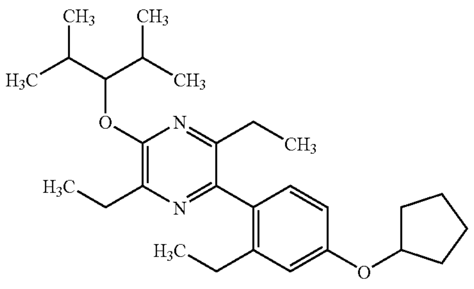 | 2-[4-(cyclopenproxy)-2-ethylphenyl]-3,6-diethyl-5-(1-isopropyl-2-methylpropoxy)pyrazine |
| 352 | 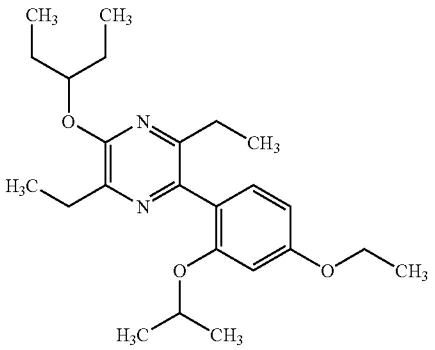 | 2-(4-ethoxy-2-isopropoxyphenyl)-3,6-diethyl-5-(1-ethylpropoxy)pyrazine |

-continued
| EX# | STRUCTURE | UPAC Name |
|---|---|---|
| 353 | 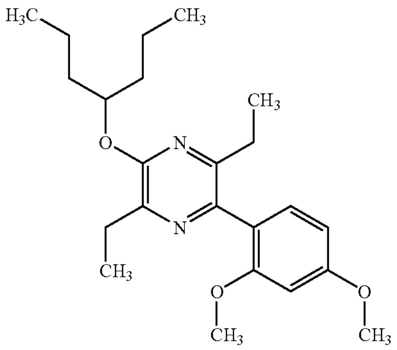 | 2-(2,4-dimethoxyphenyl)-3,6-diethyl-5-(1-propylbutoxy)pyrazine |
| 354 | 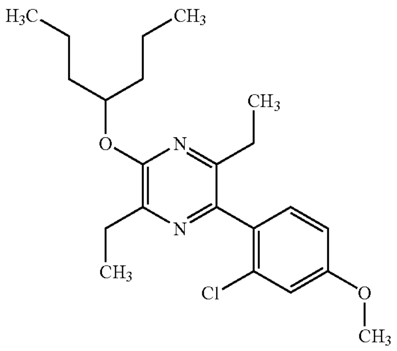 | 2-(2-chloro-4-methoxyphenyl)-3,6-diethyl-5-(1-propylbutoxy)pyrazine |
| 355 | 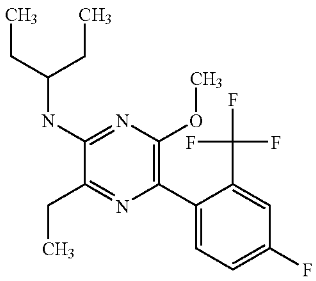 | 3-ethyl-N-(1-ethylpropyl)-5-[4-fluoro-2-(trifluoromethyl)phenyl]-6-methoxypyrazin-2-amine |
| 356 | 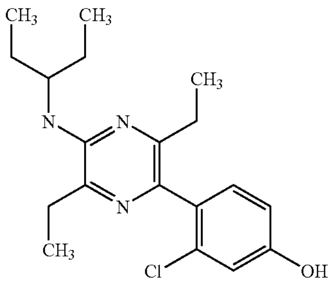 | 3-chloro-4-{3,6-diethyl-5-[(1-ethylpropyl)amino]pyrazin-2-yl}phenol |

-continued
| EX# | STRUCTURE | UPAC Name |
|---|---|---|
| 357 | 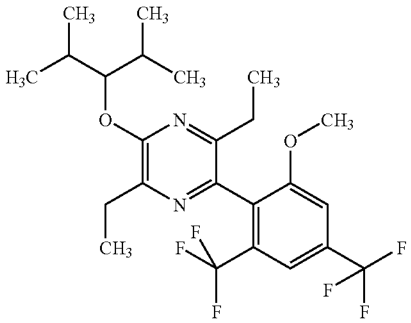 | 2,5-diethyl-3-(1-isopropyl-2-methylpropoxy)-6-[2-methoxy-4,6-bis(trifluoromethyl)phenyl]pyrazine |
| 358 | 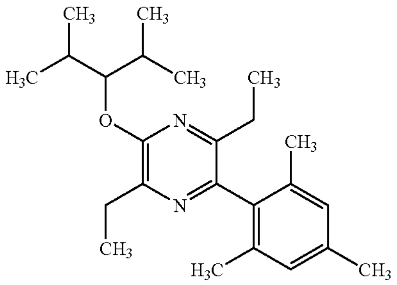 | 2,5-diethyl-3-(1-isopropyl-2-methylpropoxy)-6-mesitylpyrazine |
| 359 | 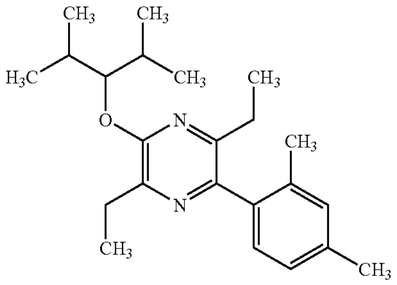 | 2-(2,4-dimethylphenyl)-3,6-diethyl-5-(1-isopropyl-2-methylpropoxy)pyrazine |
| 360 | 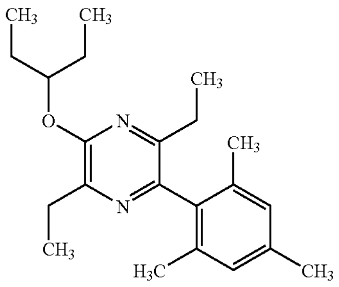 | 2,5-diethyl-3-(1-ethylpropoxy)-6-mesitylpyrazine |
| 361 | 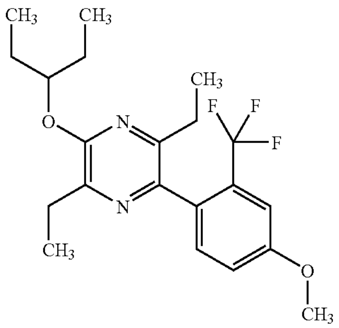 | 2,5-diethyl-3-(1-ethylpropoxy)-6-[4-methoxy-2-(trifluoromethyl)phenyl]pyrazine |

-continued
| EX# | STRUCTURE | UPAC Name |
|---|---|---|
| 362 | 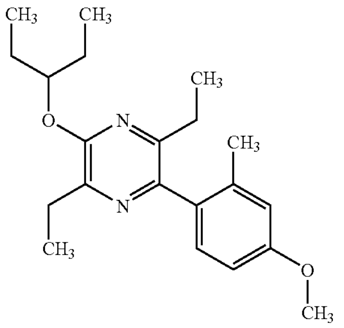 | 2,5-diethyl-3-(1-ethylpropoxy)-6-(4-methoxy-2-methylphenyl)pyrazine |
| 363 | 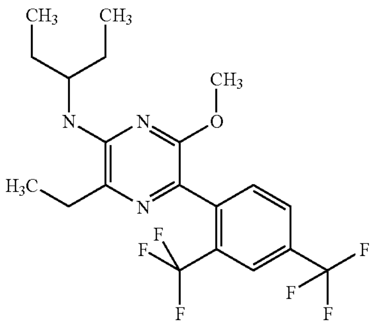 | 5-[2,4-bis(trifluoromethyl)phenyl]-3-ethyl-N-(1-ethylpropyl)-6-methoxypyrazin-2-amine |
| 364 | 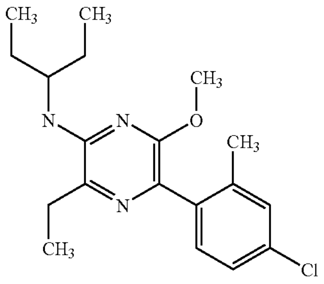 | 5-(4-chloro-2-methylphenyl)-3-ethyl-N-(1-ethylpropyl)-6-methoxypyrazin-2-amine |
| 365 | 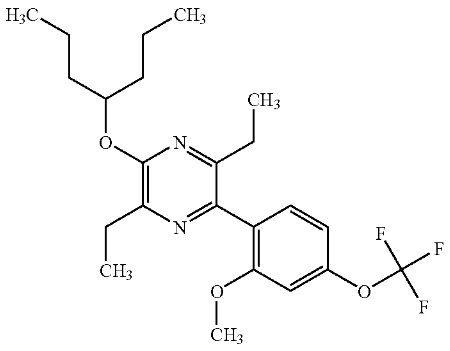 | 2,5-diethyl-3-[2-methoxy-4-(trifluoromethoxy)phenyl]-6-(1-propylbutoxy)pyrazine |

-continued
| EX# | STRUCTURE | UPAC Name |
|---|---|---|
| 366 | 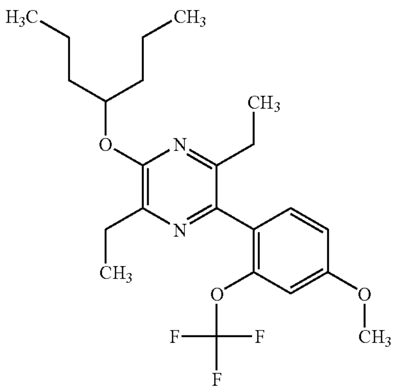 | 2,5-diethyl-3-(4-methoxy-2-(trifluoromethoxy)phenyl]-6-(1-propylbutoxy)pyrazine |
| 367 | 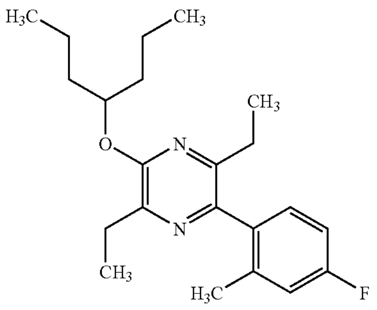 | 2,5-diethyl-3-(4-fluoro-2-methylphenyl)-6-(1-propylbutoxy)pyrazine |
| 368 | 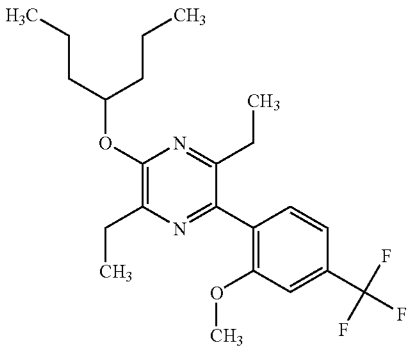 | 2,5-diethyl-3-[2-methoxy-4-(trifluoromethyl)phenyl]-6-(1-propylbutoxy)pyrazine |
| 369 | 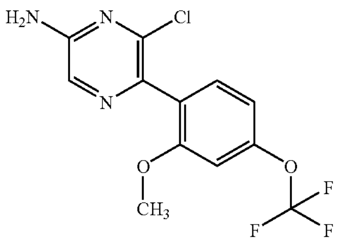 | 6-chloro-5-[2-methoxy-4-(trifluoromethoxy)phenyl]pyrazin-2-amine |

-continued
| EX# | STRUCTURE | UPAC Name |
|---|---|---|
| 370 | 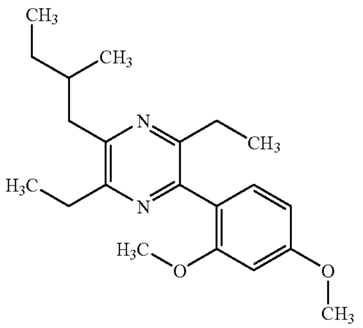 | 2-(2,4-dimethoxyphenyl)-3,6-diethyl-5-(2-methylbutyl)pyrazine |
| 371 | 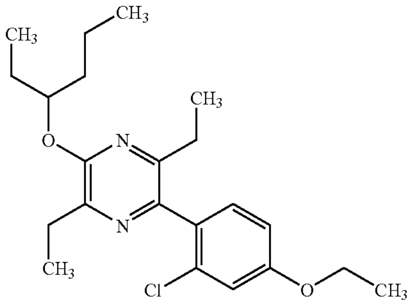 | 2-(2-chloro-4-ethoxyphenyl)-3,6-diethyl-5-(1-ethylbutoxy)pyrazine |
| 372 | 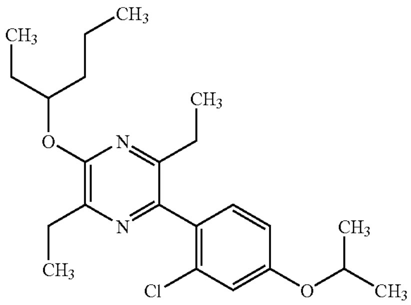 | 2-(2-chloro-4-isopropoxyphenyl)-3,6-diethyl-5-(1-ethylbutoxy)pyrazine |
| 373 | 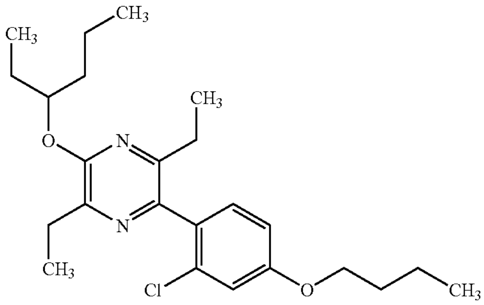 | 2-(4-butoxy-2-chlorophenyl)-3,6-diethyl-5-(1-ethylbutoxy)pyrazine |
| 374 | 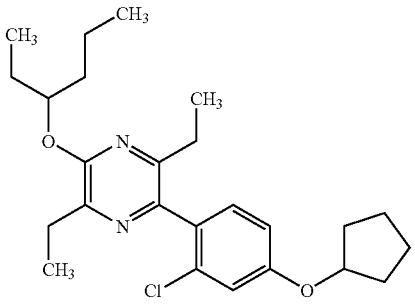 | 2-[2-chloro-4-(cyclopentyloxy)phenyl]-3,6-diethyl-5-(1-ethylbutoxy)pyrazine |

-continued

| EX# | STRUCTURE | UPAC Name |
|---|---|---|
| 375 | 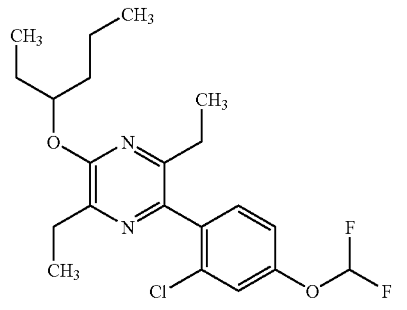 | 2-[2-chloro-4-(trifluoromethoxy)phenyl]-3,6-diethyl-5-(1-ethylbutoxy)pyrazine |
| 376 | 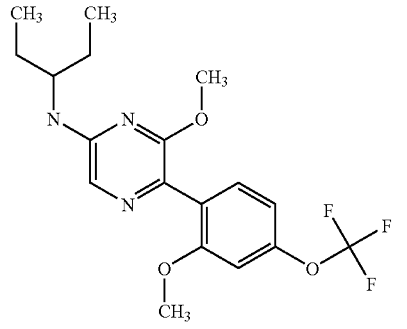 | N-(1-ethylpropyl)-6-methoxy-5-[2-methoxy-4-(trifluoromethoxy)phenyl]pyrazin-2-amine |
| 377 | 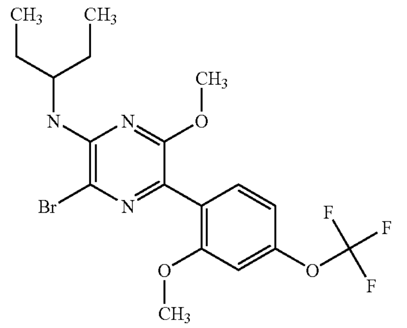 | 3-bromo-N-(1-ethylpropyl)-6-methoxy-5-[2-methoxy-4-(trifluoromethoxy)phenyl]pyrazin-2-amine |
| 378 | 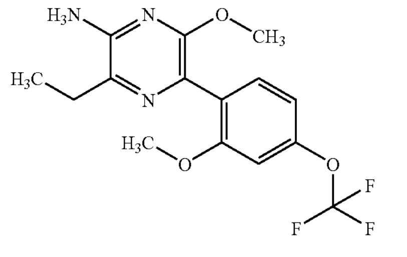 | 3-ethyl-6-methoxy-5-[2-methoxy-4-(trifluoromethoxy)phenyl]pyrazin-2-amine |
| 379 | 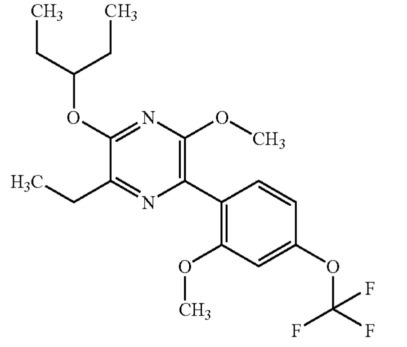 | 2-ethyl-3-(1-ethylpropoxy)-5-methoxy-6-(2-methoxy-4-(trifluoromethoxy)phenyl]pyrazine |

-continued
| EX# | STRUCTURE | UPAC Name |
|---|---|---|
| 380 | 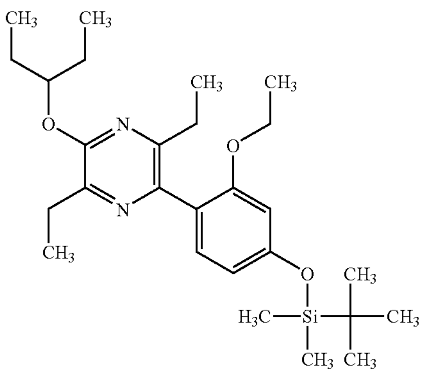 | 2-(4-{[tert-butyl(dimethyl)silyl]oxy}-2-ethoxyphenyl)-3,6-diethyl-5-(1-ethylpropoxy)pyrazine |
| 381 | 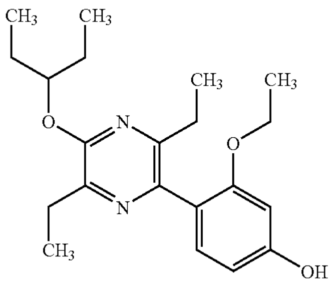 | 4-[3,6-diethyl-4-(1-ethylpropoxy)pyrazin-2-yl]-3-ethoxyphenol |
| 382 | 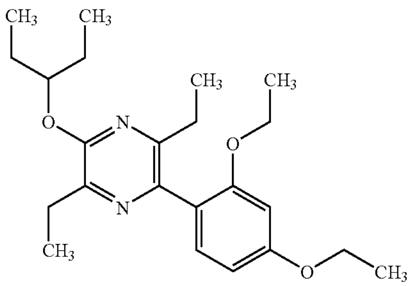 | 2-(2,4-diethoxyphenyl)-3,6-diethyl-5-(1-ethylpropoxy)pyrazine |
| 383 | 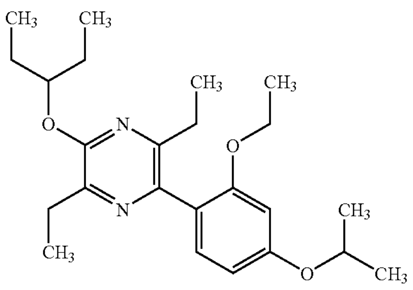 | 2-(2-ethoxy-4-isopropoxyphenyl)-3,6-diethyl-5-(1-ethylpropoxy)pyrazine |
| 384 | 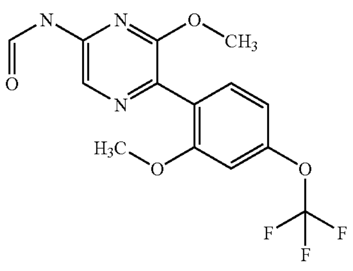 | 6-methoxy-5-[2-methoxy-4-(trifluoromethoxy)phenyl]pyrazin-2-ylformamide |

-continued
| EX# | STRUCTURE | UPAC Name |
|---|---|---|
| 385 | 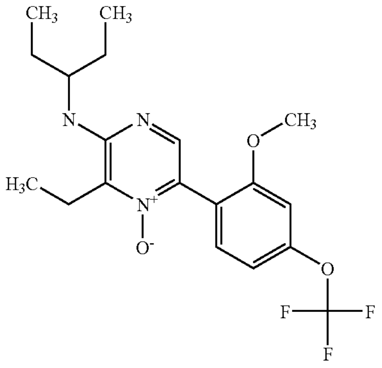 | 3-ethyl-N-(1-ethylpropyl)-5-[2-methoxy-4-(trifluoromethoxy)phenyl]pyrazin-2-amine 4-oxide |
| 386 | 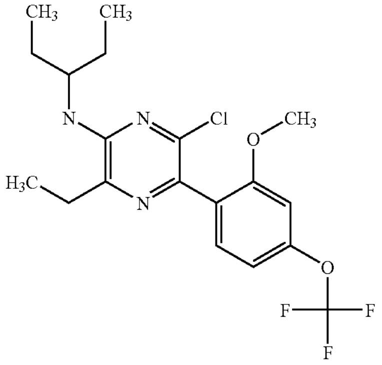 | 6-chloro-3-ethyl-N-(1-ethylpropyl)-5-[2-methoxy-4-(trifluoromethoxy)phenyl]-pyrazin-2-amine |
| 387 | 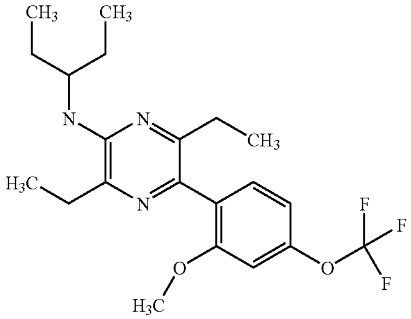 | 2,5-diethyl-3-(methylbutyl)-6-[2-methoxy-4-(trifluoromethoxy)phenyl]pyrazine |
| 388 | 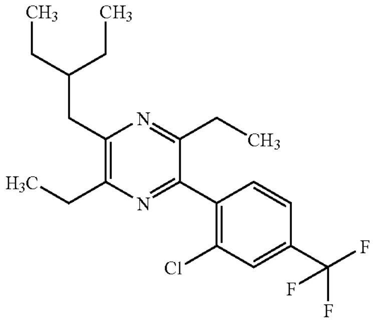 | 2-[2-chloro-4-(trifluoromethyl)phenyl]-3,6-diethyl-5-(2-ethylbutyl)pyrazine |

-continued
| EX# | STRUCTURE | UPAC Name |
| --- | --- | --- |
| 389 | 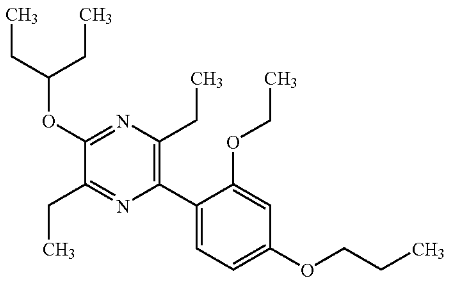 | 2-(2-ethoxy-4-propoxyphenyl)-3,6-diethyl-5-(1-ethylpropoxy)pyrazine |
| 390 | 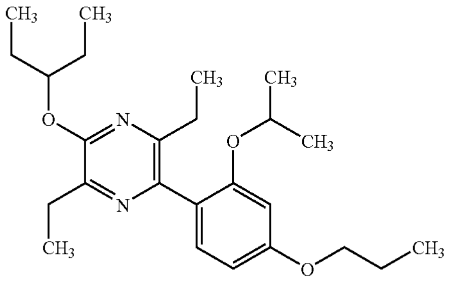 | 2,5-diethyl-3-(1-ethylpropoxy)-6-(2-isopropoxy-4-propoxyphenyl)pyrazine |
| 391 | 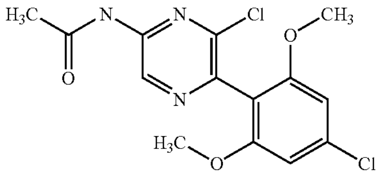 | N-[6-chloro-5-(4-chloro-2,6-dimethoxyphenyl)pyrazin-2-yl]acetamide |
| 392 | 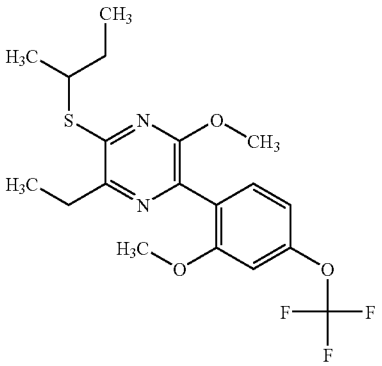 | 2-(sec-butylthio)-3-ethyl-6-methoxy-5-[2-methoxy-4-(trifluoromethoxy)phenyl]pyrazine |
| 393 | 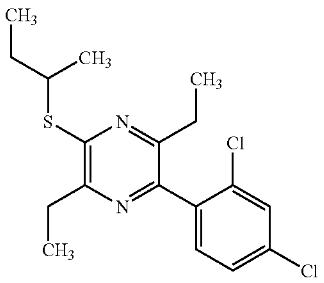 | 2-(sec-butylthio)-3-(2,4-dichlorophenyl)-3,6-diethylpyrazine |

-continued

| EX# | STRUCTURE | UPAC Name |
|---|---|---|
| 394 | 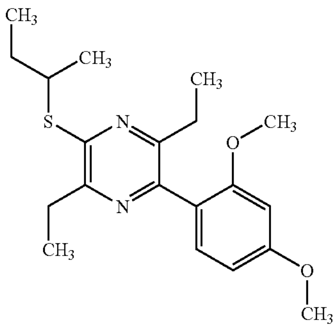 | 2-(sec-butylthio)-5-(2,4-dimethoxyphenyl)-3,6-diethylpyrazine |
| 395 | 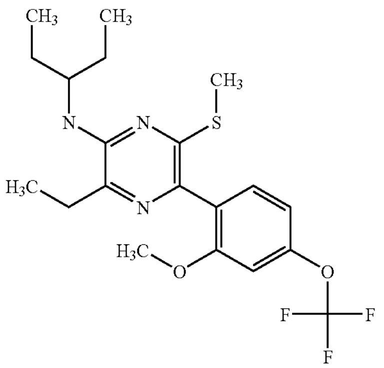 | 3-ethyl-N-(1-ethylpropyl)-5-[2-methoxy-4-(trifluoromethoxy)phenyl]-6-(methylthio)pyrazin-2-amine |
| 396 | 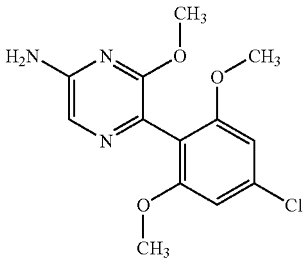 | 5-(4-chloro-2,6-dimethoxyphenyl)-6-methoxypyrazin-2-amine |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims include this specification.

What is claimed is:

1. A compound of the formula:

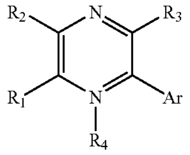

or a pharmaceutically acceptable salt thereof, wherein:

$R_1$ is selected from, $C_{1-4}$ alkyl, $C_{2-4}$ alkenyl, $C_{2-4}$ alkynyl, halogen, CN, $C_{1-4}$ haloalkyl, trifluoromethyl, trifluoromethoxy, —NH($C_{1-4}$ alkyl), —N($C_{1-4}$ alkyl)($C_{1-4}$ alkyl), —O($C_{1-4}$ alkyl), and S(O)$_n$($C_{1-4}$ alkyl);

$R_2$ is selected from the group consisting of —$OR_A$, —$NHR_A$, —$NR_AR_B$, —NHC —$NR_BC$(=O)$R_A$, —NHS(O)$_nR_A$, —$NR_B$S(O)$_nR_A$, $R_3$ is selected from the group consisting of hydrogen, halogen, $C_{1-4}$ alkyl, —O($C_{1-4}$ alkyl), —NH($C_{1-4}$ alkyl), —N($C_{1-4}$ alkyl)($C_{1-4}$ alkyl), and —S(O)$_n$($C_{1-4}$ alkyl), haloalkyl, trifluoromethyl, trifluoromethoxy, —$XR_A$ and Y;

$R_4$ is absent or an oxygen atom;

Ar is selected from the group consisting of: pyridyl, pyridonyl, pyrimidinyl, and thienyl, each of which is unsubstituted or mono-, di-, or tri-substituted with $R_C$;

$R_A$ and $R_B$, which may be the same or different, are independently selected at each occurrence from the group consisting of: hydrogen and straight, branched, or cyclic alkyl groups consisting of 1 to 8 carbon atoms, which may contain one or more double or triple bonds, each of which may be further substituted with one or more substituent(s) selected from oxo, hydroxy, halogen, —O($C_{1-4}$ alkyl), —NH($C_{1-4}$ alkyl), —N($C_{1-4}$ alkyl)($C_{1-4}$ alkyl), —NHC(O)($C_{1-4}$ alkyl), —N($C_{1-4}$ alkyl)C(=O)($C_{1-4}$ alkyl), —NHS(O)$_n$($C_{1-4}$ alkyl), —S(O)$_n$($C_{1-4}$ alkyl), —S(O)$_n$NH($C_{1-4}$ alkyl), —S(O)$_n$N($C_{1-4}$ alkyl)($C_{1-4}$ alkyl), and Z;

$R_C$ is independently selected at each occurrence from the group consisting of halogen, cyano, haloalkyl, trifluoromethyl, trifluoromethoxy, hydroxy, amino, and $C_{1-6}$ alkyl optionally substituted with 0–2 $R_D$, $C_{2-6}$ alkenyl substituted with 0–2 $R_D$, $C_{1-4}$ alkynyl substituted with 0–2 $R_D$, $C_{3-7}$ cycloalkyl substituted with 0–2 $R_D$, ($C_{3-7}$ cycloalkyl)$C_{1-4}$ alkyl substituted with 0–2 $R_D$, —O($C_{1-4}$ alkyl) substituted with 0–2 $R_D$, —NH($C_{1-4}$ alkyl) substituted with 0–2 $R_D$, —N($C_{1-4}$ alkyl)($C_{1-4}$ alkyl) each independently substituted with 0–2 $R_D$, —$XR_A$, and Y;

$R_D$ is independently selected at each occurrence the group consisting of halogen, hydroxy, cyano, $C_{1-4}$alkyl, —O($C_{1-4}$alkyl), —NH($C_{1-4}$alkyl), —N($C_{1-4}$alkyl)($C_{1-4}$ alkyl), morpholino, pyrrolidino, piperidino, thiomorpholino, piperazino, 4-hydroxypiperidino, —S(O)$_n$($C_{1-4}$ alkyl), trifluoromethyl, trifluoromethoxy, CO($C_{1-4}$ alkyl), CONH($C_{1-4}$alkyl), CON($C_{1-4}$alkyl)($C_{1-4}$alkyl), —$XR_A$ and Y;

X is independently selected at each occurrence from the group consisting of —$CH_2$—, —$CHR_B$—, —O—, —C(=O)—, —C(=O)O—, —S(O)$_n$—, —NH—, —$NR_B$—, —C(=O)NH—, —C(=O)$NR_B$—, —S(O)$_n$NH—, —S(O)$_n$$NR_B$—, —OC(=S)S—, —NHC(=O)—, —$NR_B$C(=O)—, —NHS(O)$_n$—, —OSiH$_n$($C_{1-4}$alkyl)$_{2-n}$-, and $NR_B$S(O)$_n$—; and Y and Z are independently selected at each occurrence from the group consisting of: 3- to 7-membered carbocyclic and heterocyclic groups, which are saturated, unsaturated, or aromatic, which may be substituted with one or more substituents selected from halogen, haloalkyl, oxo, hydroxy, amino, $C_{1-4}$ alkyl, —O($C_{1-4}$ alkyl), —NH($C_{1-4}$ alkyl), —N($C_{1-4}$ alkyl)($C_{1-4}$ alkyl), and —S(O)$_n$($C_{1-4}$ alkyl), and said 3- to 7-membered heterocyclic groups contain one or more heteroatom(s) selected from N, O, and S, with the point of attachment being either carbon or nitrogen; and n is independently selected at each occurrence from 0, 1, and 2.

2. A compound according to claim 1, $R_4$ is absent and Ar is 2-, 3-, or 4-pyridyl, mono-, di-, or tri-substituted with $R_C$.

3. A compound according to claim 1 wherein $R_4$ is absent and Ar is 2-, 3-, or 4-pyridyl, mono-, di-, or tri-substituted with $R_C$, and $R_1$ and $R_3$ are independently selected from the group consisting of hydrogen, halogen, methyl, ethyl, ethoxy and methoxy.

4. The compound of claim 1, wherein $R_2$ is selected from the group consisting of dipropylamino, 3-pentylamino, 4-heptylamino.

5. The compound of claim 1, wherein $R_1$ and $R_3$ are selected from the group consisting of methyl, ethyl, methoxy, ethoxy, and methylamino.

6. The compound of claim 1, wherein Ar is selected from 2-pyridyl, 3-pyridyl, 2-pyrimidinyl, and 4-pyrimidinyl, each of is mono-substituted or di-substituted with $R_C$, wherein at least one of the $R_C$ substituents is ortho or para to the point of attachment of Ar to the pyrazine ring.

7. The compound of claim 6, wherein $R_C$ is selected from the group consisting of halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$alkoxy), and mono- or di($C_{1-4}$ alkyl)amino.

8. The compound of claim 1, wherein $R_2$ is selected from the group consisting of dipropylamino, 3-pentylamino, 4-heptylamino;

$R_1$ and $R_3$ are selected from the group consisting of methyl, ethyl, methoxy, ethoxy, and methylamino;

Ar is selected from 2-pyridyl, 3-pyridyl, 2-pyrimidinyl, and 4-pyrimidinyl, each of is mono-substituted or di-substituted with $R_C$, wherein at least one of the $R_C$ substituents is ortho or para to the point of attachment of Ar to the pyrazine ring; and $R_C$ is selected from the group consisting of halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$alkoxy), and mono- or di($C_{1-4}$ alkyl)amino.

9. The compound of claim 8, wherein $R_2$ is selected from the group consisting of 3-penlylamino;

$R_1$ and $R_3$ are selected from the group consisting of methyl, ethyl, and methoxy; and Ar is selected from 3-pyridyl and 2-pyrimidinyl, each of which is mono-substituted or di-substituted with $R_C$, wherein at least one of the $R_C$ substituents is ortho or para to the point of attachment of Ar to the pyrazine ring.

10. The compound of claim 1, wherein

Ar is selected from the group consisting of: pyridyl, pyridonyl, pyrimidinyl, and thienyl, each or which is mono-, di-, or tri-substituted with $R_C$.

11. The compound of claim 1, wherein

Ar is selected from the group consisting of: pyridyl, pyridonyl, and pyrimidinyl, each of which is unsubstituted or mono-, di-, or tri-substituted with $R_C$.

12. A compound of the Formula:

Formula A

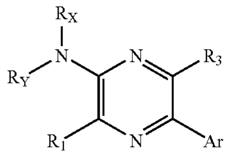

wherein $R_X$ and $R_Y$ are the same or different and are independently selected from the group consisting of hydrogen and straight, branched, or cyclic alkyl groups having from 1 to 8 carbon atoms, which may contain one or more double or triple bonds, each of which may be further substituted with one or more substituent(s) independently selected from hydroxy, halogen, —O($C_{1-4}$ alkyl), —NH($C_{1-4}$ alkyl), —N($C_{1-4}$ alkyl)($C_{1-4}$ alkyl), and optionally substituted phenyl;

$R_1$ is selected from H, $C_{1-4}$ alkyl, $C_{2-4}$ alkenyl, $C_{2-4}$ alkynyl, halogen, CN, $C_{1-4}$ haloalkyl, trifluoromethyl, trifluoromethoxy, —NH($C_{1-4}$ alkyl), —N($C_{1-4}$ alkyl)($C_{1-4}$ alkyl), —O($C_{1-4}$ alkyl), and S(O)$_n$($C_{1-4}$ alkyl);

$R_3$ is selected from the group consisting of hydrogen, halogen, $C_{1-4}$ alkyl, —O($C_{1-4}$ alkyl), —NH($C_{1-4}$ alkyl), —N($C_{1-4}$ alkyl)($C_{1-4}$ alkyl), and —S(O)$_n$($C_{1-4}$ alkyl), haloalkyl, trifluoromethyl, trifluoromethoxy, —$XR_A$ and Y;

Ar is selected from the group consisting of: 2-, 3-, or 4-pyridyl and 2-, 4-, or 5-pyrimidinyl, each of which is unsubstituted or mono- di- or tri-substituted with $R_C$;

$R_A$ and $R_B$, which may be the stone or different, are independently selected at each occurrence from the group consisting of: hydrogen and straight, branched, or cyclic alkyl groups consisting of 1 to 8 carbon atoms, which may contain one or more double or triple bonds, each of which may be further substituted with one or more substituent(s) selected from oxo, hydroxy, halogen, —O($C_{1-4}$ alkyl), —NH($C_{1-4}$ alkyl), —N($C_{1-4}$ alkyl)($C_{1-4}$ alkyl), —NHC(O)($C_{1-4}$ alkyl), —N($C_{1-4}$ alkyl)C(═O)($C_{1-4}$ alkyl), —NHS$(O)_n$($C_{1-4}$ alkyl), —S$(O)_n$($C_{1-4}$ alkyl), —S$(O)_n$NH($C_{1-4}$ alkyl), —S$(O)_n$N($C_{1-4}$ alkyl)($C_{1-4}$ alkyl), and Z;

$R_C$ is independently selected at each occurrence from the group consisting of halogen, cyano, haloalkyl, trifluoromethyl, trifluoromethoxy, hydroxy, amino, and $C_{1-6}$ alkyl optionally substituted with 0–2 $R_D$, $C_{2-6}$ alkenyl substituted with 0–2 $R_D$, $C_{1-4}$ alkenyl substituted with 0–2 $R_D$, $C_{3-7}$ cycloalkyl substituted with 0–2 $R_D$, ($C_{3-7}$ cycloalkyl)$C_{1-4}$ alkyl substituted with 0–2 $R_D$, —O($C_{1-4}$ alkyl) substituted with 0–2 $R_D$, —NH($C_{1-4}$ alkyl) substituted with 0–2 $R_D$, —N($C_{1-4}$ alkyl)($C_{1-4}$ alkyl) each independently substituted with 0–2 $R_D$, —$XR_A$, and Y;

$R_D$ is independently selected at each occurrence the group consisting of halogen, hydroxy, cyano, $C_{1-4}$alkyl, —O($C_{1-4}$alkyl), —NH($C_{1-4}$alkyl), —N($C_{1-4}$alkyl)($C_{1-4}$ alkyl), morpholino, pyrrolidino, piperidino, thiomorpholino, piperazino, 4-hydroxypiperidino, —S$(O)_n$($C_{1-4}$ alkyl), trifluoromethyl, trifluoromethoxy, CO($C_{1-4}$ alkyl), CONH($C_{1-4}$alkyl), CON($C_{1-4}$alkyl)($C_{1-4}$alkyl), —$XR_A$ and Y:

X is independently selected at each occurrence from the group consisting of —$CH_2$—, —$CHR_B$—, —O—, —C(═O)—, —C(═O)O—, —S$(O)_n$—, —NH—, —$NR_B$—, —C(═O)NH—, —C(═O)$NR_B$—, —S$(O)_n$NH—, —S$(O)_n$$NR_B$—, —OC(═S)S—, —NHC(═O)—, —$NR_B$C(═O)—, —NHS$(O)_n$—, —OSi$H_n$($C_{1-4}$alkyl)$_{2-n}$-, and —$NR_B$S$(O)_n$—; and Y and Z are independently selected at each occurrence from the group consisting of: 3- to 7-membered carbocyclic and heterocyclic groups, which are saturated, unsaturated, or aromatic, which may be substituted with one or more substituents selected from halogen, haloalkyl, oxo, hydroxy, amino, $C_{1-4}$ alkyl, —O($C_{1-4}$ alkyl), —NH($C_{1-4}$ alkyl), —N($C_{1-4}$ alkyl)($C_{1-4}$ alkyl), and —S$(O)_n$($C_{1-4}$ alkyl), and said 3- to 7-membered heterocyclic groups contain one or more heteroatom(s) selected from N, O, and S, with the point of attachment being either carbon or nitrogen; and n is independently selected at each occurrence from 0, 1, and 2.

13. A compound according to claim 12, wherein Ar is 2- or 3-pyridyl, mono-, di-, or tri-substituted with $R_C$; and $R_1$ and $R_3$ are independently selected from the group consisting of hydrogen, halogen, methyl, ethyl, ethoxy and methoxy.

14. A compound according to claim 12, wherein:

$R_X$ is hydrogen;

$R_Y$ is chosen from the group consisting of:

straight, branched, or cyclic alkyl groups having from 1 to 8 carbon atoms, which may contain one or more double or triple bonds;

$R_1$ and $R_3$ are independently chosen from halogen, $C_{1-4}$ alkyl, —O($C_{1-4}$ alkyl), —NH($C_{1-4}$ alkyl), —N($C_{1-4}$ alkyl)($C_{1-4}$ alkyl), haloalkyl, trifluoromethyl, and trifluoromethoxy; and Ar is 2- or 3-pyridyl, which is mono-substituted or di-substituted mono, with substituent(s) independently selected from: halogen, cyano, haloalkyl, trifluoromethyl, trifluoromethoxy, hydroxy, amino, and $C_{1-6}$ alkyl, $C_{1-4}$alkoxy, $C_{1-4}$alkoxy($C_{1-4}$alkoxy), mono- or di($C_{1-4}$)amino($C_{1-4}$alkoxy), and mono- or di($C_{1-4}$ alkyl) amino.

15. The compound of claim 12, wherein $R_X$ is hydrogen and $R_Y$ is 3-pentyl.

16. A pharmaceutical composition comprising a pharmaceutically acceptable carrier and a compound of a compound according to claim 1.

* * * * *